US011891387B2

(12) United States Patent
Ameriks et al.

(10) Patent No.: US 11,891,387 B2
(45) Date of Patent: Feb. 6, 2024

(54) MONOACYLGLYCEROL LIPASE MODULATORS

(71) Applicant: Janssen Pharmaceutica NV, Beerse (BE)

(72) Inventors: Michael K. Ameriks, San Diego, CA (US); Brian Ngo Laforteza, San Diego, CA (US); Suchitra Ravula, San Diego, CA (US); Jamie M. Schiffer, San Diego, CA (US); Brice M. Stenne, La Jolla, CA (US)

(73) Assignee: Janssen Pharmaceutica NV, Beerse (BE)

(*) Notice: Subject to any disclaimer, the term of this patent is extended or adjusted under 35 U.S.C. 154(b) by 198 days.

(21) Appl. No.: 17/212,377

(22) Filed: Mar. 25, 2021

(65) Prior Publication Data

US 2022/0372030 A1  Nov. 24, 2022

Related U.S. Application Data

(60) Provisional application No. 63/000,329, filed on Mar. 26, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .............. C07D 471/04; C07D 519/00
See application file for complete search history.

(56) References Cited

U.S. PATENT DOCUMENTS

| | | | |
|---|---|---|---|
| 4,812,462 A | 3/1989 | Blankley et al. |
| 4,816,463 A | 3/1989 | Blankley et al. |
| 5,338,744 A | 8/1994 | Dudley et al. |
| 8,431,704 B2 | 4/2013 | Love et al. |
| 8,513,248 B2 | 8/2013 | Dean et al. |
| 8,871,760 B2 | 10/2014 | Brotherton-pleiss et al. |
| 8,933,236 B2 | 1/2015 | Chowdhury et al. |
| 8,987,249 B2 | 3/2015 | Anderskewitz et al. |
| 9,056,874 B2 | 6/2015 | Adams et al. |
| 9,066,946 B2 | 6/2015 | Alcazar Vaca et al. |
| 9,156,824 B2 | 10/2015 | Dally et al. |
| 9,181,271 B2 | 11/2015 | Li et al. |
| 9,233,974 B2 | 1/2016 | Link et al. |
| 9,242,969 B2 | 1/2016 | Barsanti et al. |
| 9,273,047 B2 | 3/2016 | Hunt et al. |
| 9,273,947 B2 | 3/2016 | Kim et al. |
| 9,290,476 B2 | 3/2016 | Leonard et al. |
| 9,375,418 B2 | 6/2016 | Schmidt et al. |
| 9,434,715 B2 | 9/2016 | Conza et al. |
| 9,447,045 B2 | 9/2016 | Chen et al. |
| 9,464,084 B2 | 10/2016 | Alcazar Vaca et al. |
| 9,532,992 B2 | 1/2017 | Kuntz et al. |
| 9,561,228 B2 | 2/2017 | Haq et al. |
| 9,617,272 B2 | 4/2017 | Kumar et al. |
| 9,637,456 B2 | 5/2017 | Amans et al. |
| 10,112,937 B2 | 10/2018 | Alcazar Vaca et al. |
| 10,150,765 B2 | 12/2018 | Alcazar Vaca et al. |
| 10,150,766 B2 | 12/2018 | Letavic et al. |
| 2005/0096345 A1 | 5/2005 | Thompson et al. |
| 2006/0217448 A1 | 9/2006 | Kelly et al. |
| 2006/0293337 A1 | 12/2006 | Evans et al. |
| 2008/0275052 A1 | 11/2008 | Dhar et al. |
| 2010/0144758 A1 | 6/2010 | Dillon et al. |
| 2011/0252717 A1 | 10/2011 | Graf Fernandez |

(Continued)

FOREIGN PATENT DOCUMENTS

CN  101778850 A  7/2010
FR  2857363 A1  1/2005

(Continued)

OTHER PUBLICATIONS

Ahn et al., "Enzymatic Pathways That Regulate Endocannabinoid Signaling in the Nervous System", Chem Rev., 2008, p. 1687-1707, vol. 108, No. 5.
Alhouayek et al., "Increasing endogenous 2-arachidonoylglycerol levels counteracts colitis and related systemic Inflammation", Faseb J., Aug. 2011, 2711-2721, vol. 25, No. 8.
Bedse et al., "Functional Redundancy Between Canonical Endocannabinoid Signaling Systems in the Modulation of Anxiety", Biol Psychiatry, Oct. 1, 2017, 488-499, vol. 82, No. 7.
Bedse et al., "Therapeutic endocannabinoid augmentation for mood and anxiety disorders: comparative profiling of FAAH, MAGL and dual inhibitors", Transl Psychiatry, Apr. 26, 2018, 92, vol. 8, No. 1.
Benito et al., "Cannabinoid CB2 Receptors in Human Brain Inflammation", British Journal of Pharmacology, 2008, 277-285, vol. 153.
Berge, S.M. et al., "Pharmaceutical Salts", J. Pharm. Sci., 1977, 1-19, vol. 66.

(Continued)

*Primary Examiner* — Laura L Stockton

(57) ABSTRACT

Fused and bridged compounds of Formula (I), and pharmaceutically acceptable salts, isotopes, N-oxides, solvates, and stereoisomers thereof, pharmaceutical compositions containing them, methods of making them, and methods of using them including methods for treating disease states, disorders, and conditions associated with MGL modulation, such as those associated with pain, psychiatric disorders, neurological disorders (including, but not limited to major depressive disorder, treatment resistant depression, anxious depression, autism spectrum disorders, Asperger syndrome, bipolar disorder), cancers and eye conditions:

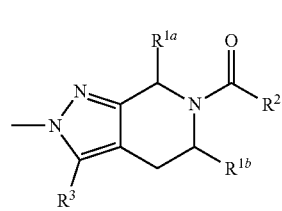

(I)

wherein $R^{1a}$, $R^{1b}$, $R^2$, and $R^3$, are defined herein.

19 Claims, No Drawings

(56) References Cited

U.S. PATENT DOCUMENTS

| | | |
|---|---|---|
| 2011/0294790 A1 | 12/2011 | Mantegani et al. |
| 2012/0190680 A1 | 7/2012 | Bakthavatchalam et al. |
| 2014/0213554 A1 | 7/2014 | Wu et al. |
| 2014/0251902 A1 | 9/2014 | Solheim et al. |
| 2014/0275015 A1 | 9/2014 | Alcazar Vaca et al. |
| 2014/0275056 A1 | 9/2014 | Letavic et al. |
| 2014/0275096 A1 | 9/2014 | Ameriks et al. |
| 2014/0275120 A1 | 9/2014 | Alcazar Vaca et al. |
| 2015/0290190 A1 | 10/2015 | Ameriks et al. |
| 2015/0322062 A1 | 11/2015 | Alcazar Vaca et al. |
| 2016/0016962 A1 | 1/2016 | Ameriks et al. |
| 2016/0024082 A1 | 1/2016 | Alcazar Vaca et al. |
| 2016/0039809 A1 | 2/2016 | Alcazar Vaca et al. |
| 2016/0039836 A1 | 2/2016 | Letavic et al. |
| 2016/0046596 A1 | 2/2016 | Banerjee et al. |
| 2017/0081342 A1 | 3/2017 | Cheung et al. |
| 2018/0118749 A1 | 5/2018 | Andres Gil et al. |

FOREIGN PATENT DOCUMENTS

| | | |
|---|---|---|
| JP | 2012525351 A | 10/2012 |
| JP | 2013/505220 A | 2/2013 |
| NO | 2014/152589 A1 | 9/2014 |
| WO | 2004/014374 A1 | 2/2004 |
| WO | 2004013144 A1 | 2/2004 |
| WO | 2006/023750 A2 | 3/2006 |
| WO | 2006/080884 A1 | 8/2006 |
| WO | 2006/110516 A1 | 10/2006 |
| WO | 2009/002423 A2 | 12/2008 |
| WO | 2009/023623 A1 | 2/2009 |
| WO | 2009095253 A1 | 8/2009 |
| WO | 2010/125101 A1 | 11/2010 |
| WO | 2010/125102 A1 | 11/2010 |
| WO | 2011050202 A1 | 4/2011 |
| WO | 2011/103715 A1 | 9/2011 |
| WO | 2011/121137 A1 | 10/2011 |
| WO | 2012/040048 A2 | 3/2012 |
| WO | 2012145581 A1 | 10/2012 |
| WO | 2014/152621 A1 | 9/2014 |
| WO | 2014152604 A1 | 9/2014 |
| WO | 2014/154897 A1 | 10/2014 |
| WO | 2015/025026 A1 | 2/2015 |
| WO | 2016/039977 A1 | 3/2016 |
| WO | 2016/039983 A1 | 3/2016 |
| WO | 2016040789 A1 | 3/2016 |
| WO | 2017087858 A1 | 5/2017 |
| WO | 2020065613 A1 | 4/2020 |
| WO | 2020065614 A1 | 4/2020 |
| WO | 2020211798 A1 | 10/2020 |
| WO | 2021064569 A1 | 4/2021 |
| WO | 2021/191359 A1 | 9/2021 |

OTHER PUBLICATIONS

Bernal-Chico et al., "Blockade of monoacylglycerol lipase inhibits oligodendrocyte excitotoxicity and prevents demyelination in vivo", Glia, Jan. 2015, 163-176, vol. 63, No. 1.

Buczynski and Parsons, "Quantification of brain endocannabinoid levels: methods, interpretations and pitfalls", Brit J Pharmacol, 2010, 423-442, vol. 160, No. 3.

Carroll et al., "Synthesis and Pharmacological Characterization of Nicotinic Acetylcholine Receptor Properties of (+)- and (-)-Pyrido-[3,4-b]homotropanes", Journal of Medicinal Chemistry, 2006, 3244-3250, vol. 49, No. 11.

Cavuoto et al., "The Expression of Receptors for Endocannabinoids in Human and Rodent Skeletal Muscle", Biochemical and Biophysical Research Communications, 2007, 105-110, vol. 364.

Chen et al., "Monoacylglycerol Lipase Is a Therapeutic Target for Alzheimer's Disease", Cell Rep., Nov. 29, 2012, 1329-1339, vol. 2, No. 5.

Chinnadurai et al., "Monoacylglycerol lipase inhibition as potential treatment for interstitial cystitis", Medical Hypotheses, Oct. 2019, 109321, vol. 131.

Christensen et al., "Efficacy and safety of the weight-loss drug rimonabant: a meta-analysis of randomised trials", The Lancet, 2007, 1706-1713, vol. 370.

Covey et al., "Inhibition of endocannabinoid degradation rectifies motivational and dopaminergic deficits in the Q175 mouse model of Huntington's disease", Neuropsychopharmacology, 2018, 2056-2063, vol. 43.

Curry et al., "Monoacylglycerol Lipase Inhibitors Reverse Paclitaxel-Induced Nociceptive Behavior and Proinflammatory Markers in a Mouse Model of Chemotherapy-Induced Neuropathy", J Pharmacol Exp Ther., Jul. 2018, 169-183, vol. 366, No. 1.

Devane et al., "Isolation and structure of a brain constituent that binds to the cannabinoid receptor", Science, 1992, 1946-1949, vol. 258.

Di Marzo et al., "Endocannabinoids and the regulation of their levels in health and disease", Curr Opin Lipidol, 2007, 129-140, vol. 18.

Di Marzo et al., "Plant, Synthetic, and Endogenous Cannabinoids in Medicine", Annu Rev Med., 2006, 553-574., vol. 57.

Dinh et al., "Brain monoglyceride lipase participating in endocannabinoid inactivation", Proc Natl Acad Sci USA, Aug. 6, 2002, 10819-10824, vol. 99, No. 16.

Folkes et al., "An endocannabinoid-regulated basolateral amygdala-nucleus accumbens circuit modulates sociability", J Clin Invest., 2020, 1728-1742., vol. 130, Issue 4.

Ghosh et al., "The monoacylglycerol lipase inhibitor JZL 184 suppresses inflammatory pain in the mouse carrageenan model", Life Sci., Mar. 19, 2013, 498-505, vol. 92, No. 8-9.

Greene et al., "Chapter 7 Protection for the Amino Group", Protective Groups in Organic Synthesis, Third Edition, John Wiley & Sons, 1999, pp. 518-525; 579-580; 620-621.

Guindon et al., "Peripheral antinociceptive effects of inhibitors of monoacylglycerol lipase in a rat model of inflammatory pain", Br J Pharmacol., 2011, 1464-1478, vol. 163.

Hajrasouliha et al., "Endogenous cannabinoids contribute to remote ischemic preconditioning via cannabinoid CB2 receptors in the rat heart", Eur J Pharmacol, 2008, 246-252, vol. 579.

Hauer et al., "Glucocorticoid-endocannabinoid interaction in cardiac surgical patients: relationship to early cognitive dysfunction and late depression", Rev Neurosci., 2012, 681-690, vol. 23, No. 5-6.

Herkenam et al., "Cannabinoid receptor localization in brain", Proc. Nat. Acad. Sci., 1990, 1932-1936, vol. 87, No. 5.

Hernandez-Torres et al., "A Reversible and Selective Inhibitor of Monoacylglycerol Lipase Ameliorates Multiple Sclerosis", Angew Chem Int Ed Engl., Dec. 8, 2014, 13765-13770, vol. 53, No. 50.

Hill et al., "Circulating endocannabinoids and N-acyl ethanolamines are differentially regulated in major depression and following exposure to social stress", Psychoneuroendocrinology, Sep. 3, 2009, 1257-1262, vol. 34, No. 8.

Hill et al., "Reductions in circulating endocannabinoid levels in individuals with post-traumatic stress disorder following exposure to the World Trade Center attacks", Psychoneuroendocrinology, 2013, 2952-2961, vol. 38, No. 12.

Hill et al., "Serum Endocannabinoid Content is Altered in Females with Depressive Disorders: A Preliminary Report", Pharmacopsychiatry, Mar. 2008, 48-53, vol. 41, No. 2.

International Search Report and Written Opinion for International Application No. PCT/IB2020/059099 dated Nov. 24, 2020.

International Search Report and Written Opinion for International Application No. PCT/EP2021/057764 dated Jun. 8, 2021.

International Search Report and Written Opinion for International Application No. PCT/IB2019/058240 dated Jan. 10, 2020.

International Search Report and Written Opinion for International Application No. PCT/IB2019/058241 dated Jan. 10, 2020.

Jung et al., "Uncoupling of the endocannabinoid signalling complex in a mouse model of fragile X syndrome", Nature Communications, 2012, 1080., vol. 3.

Katz et al., "Endocannabinoid Degradation Inhibition Improves Neurobehavioral Function, Blood-Brain Barrier Integrity, and Neuroinflammation following Mild Traumatic Brain Injury", J Neurotrauma, Mar. 1, 2015, 297-306, vol. 32, Issue 5.

(56) References Cited

OTHER PUBLICATIONS

Kinsey et al., "Blockade of Endocannabinoid-Degrading Enzymes Attenuates Neuropathic Pain", J Pharmacol Exp Ther., Sep. 2009, 902-910, vol. 330, No. 3.
Ligresti et al., "From endocannabinoid profiling to 'endocannabinoid therapeutics'", Curr Opin Chem Biol., Jun. 2009, 321-331, vol. 13, No. 3.
Long et al., "Characterization of Monoacylglycerol Lipase Inhibition Reveals Differences in Central and Peripheral Endocannabinoid Metabolism", Chem Biol., Jul. 31, 2009, 744-753, vol. 16, No. 7.
Long et al., "Selective blockade of 2-arachidonoylglycerol hydrolysis produces cannabinoid behavioral effects", Nat Chem Biol., Jan. 2009, 37-44, vol. 5, No. 1.
Manske, R.H.F. and Kulka, M., "The Skraup Synthesis of Quinolines", Org. Reaction, 1953, 59-98, vol. 7.
Matsuda et al., "Structure of a cannabinoid recepter and functional expresion of the cloned cDNA", Nature, 1990, 561-564, vol. 346.
Mechoulam et al., "Identification of an endogenous 2-monoglyceride, present in canine gut, that binds to cannabinoid receptors", Biochem Pharmacol, 1995, 83-90, vol. 50.
Miller et al., "Controlled-deactivation cb1 receptor ligands as a novel strategy to lower intraocular pressure", Pharmaceuticals, 2018, 1-8, vol. 11, No. 50.
Mulvihill et al., "Therapeutic potential of monoacylglycerol lipase inhibitors", Life Sci., Mar. 19, 2013, 492-497, vol. 92, No. 8-9.
Munro et al., "Molecular characterization of a peripheral receptor for cannabinoids", Nature, 1993, 61-65, vol. 365.
Nikitenko, A.A., et al., "Selective Hydrolysis of Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate as a Key Step in the Large-Scale Synthesis of Bicyclic Heteroaryl Carboxyaldehydes", Org. Process Res. Dev., 2006, 712-716, vol. 10, No. 4.
Nithipatikom et al., "2-Arachidonoylglycerol: a novel inhibitor of androgen-independent prostate cancer cell invasion", Cancer Res., Dec. 15, 2004, 8826-8830, vol. 64, No. 24.
Nithipatikom et al., "A new class of inhibitors of 2-arachidonoylglycerol hydrolysis and invasion of prostate cancer cells", Biochem Biophys Res Commun., Jul. 15, 2005, 1028-1033, vol. 332, No. 4.
Nithipatikom et al., "Anti-proliferative effect of a putative endocannabinoid, 2-arachidonylglyceryl ether in prostate carcinoma cells", Prostaglandins Other Lipid Mediat., Feb. 9, 2011, 34-43, vol. 94, No. 1-2.
Nomura et al., "Endocannabinoid Hydrolysis Generates Brain Prostaglandins That Promote Neuroinflammation", Science, Nov. 11, 2011, 809-813, vol. 334, No. 6057.
Pacher et al., "Pleiotropic effects of the CB2 cannabinoid receptor activation on human monocyte migration: Implications for atherosclerosis and inflammatory diseases", Amer J Physiol, 2008, H1133-H1134, vol. 294.
Pasquarelli et al., "Contrasting effects of selective MAGL and FAAH inhibition on dopamine depletion and GDNF expression in a chronic MPTP mouse model of Parkinson's disease", Neurochem Int., Nov. 2017, 14-24, vol. 110.
Pasquarelli et al., "Evaluation of monoacylglycerol lipase as a therapeutic target in a transgenic mouse model of ALS", Neuropharmacology, Sep. 15, 2017, 157-169, vol. 124.
Patel et al., "The endocannabinoid system as a target for novel anxiolytic drugs", Neurosci Biobehav Rev., May 2017, 56-66, vol. 76, Part A.
Piomelli, "The molecular logic of endocannabinoid signalling", Nat Rev Neurosci, 2003, 873-884, vol. 4.
Piro et al., "A Dysregulated Endocannabinoid-Eicosanoid Network Supports Pathogenesis in a Mouse Model of Alzheimer's Disease", Cell Rep., Jun. 28, 2012, 617-623, vol. 1, No. 6.
Ramesh et al., "Blockade of Endocannabinoid Hydrolytic Enzymes Attenuates Precipitated Opioid Withdrawal Symptoms in Mice", J Pharmacol Exp Ther., Oct. 2011, 173-185, vol. 339, No. 1.
Schlosburg et al., "Chronic monoacylglycerol lipase blockade causes functional antagonism of the endocannabinoid system", Nat Neurosci., Sep. 13, 2010, 1113-1119, vol. 9.

Sticht et al., "Inhibition of monoacylglycerol lipase attenuates vomiting in Suncus murinus and 2-arachidonoyl glycerol attenuates nausea in rats", Br J Pharmacol., Apr. 2012, 2425-2435, vol. 165, No. 8.
Straiker et al., "Monoacylglycerol Lipase Limits the Duration of Endocannabinoid-Mediated Depolarization-Induced Suppression of Excitation in Autaptic Hippocampal Neurons", Mol Pharmacol., Dec. 2009, 1220-1227, vol. 76, No. 6.
Sugiura et al., "2-Arachidonoylgylcerol: A Possible Endogenous Cannabinoid Receptor Ligand in Brain", Biochem Biophys Res Commun, 1995, 89-97, vol. 215.
Sugiura et al., "Biosynthesis and degradation of anandamide and 2-arachidonoylglycerol and their possible physiological significance", Prostaglandins Leukot Essent Fatty Acid, Feb.-Mar. 2002, 173-192, vol. 66, No. 2-3.
Suguira et al., "Biochemistry, pharmacology and physiology of 2-arachidonoylglycerol, an endogenous cannabinoid receptor ligand", Prog Lipid Res, 2006, 405-446, vol. 45, No. 5.
Terrone et al., "Inhibition of monoacylglycerol lipase terminates diazepam-resistant status epilepticus in mice and its effects are potentiated by a ketogenic diet", Epilepsia, Jan. 2018, 79-91, vol. 59, No. 1.
Tuo et al., "Therapeutic Potential of Fatty Acid Amide Hydrolase, Monoacylglycerol Lipase, and N-Acylethanolamine Acid Amidase Inhibitors", J Med Chem., Jan. 12, 2017, 4-46, vol. 60, No. 1.
Von Ruden et al., "Inhibition of monoacylglycerol lipase mediates a cannabinoid 1-receptor dependent delay of kindling progression in mice", Neurobiol Dis., May 2015, 238-245, vol. 77.
Walter et al., "ATP Induces a Rapid and Pronounced Increase in 2-Arachidonoylglycerol Production by Astrocytes, a Response Limited by Monoacylglycerol Lipase", J Neurosci., Sep. 15, 2004, 8068-8074, vol. 24, No. 37.
Wang et al., "Treating a novel plasticity defect rescues episodic memory in Fragile X model mice", Mol Psychiatry, 2018, 1798-1806, vol. 23, No. 8.
Wenzel et al., "Novel multi-target directed ligand-based strategies for reducing neuroinflammation in Alzheimer's disease", Life Sci., Aug. 15, 2018, 314-322, vol. 207.
Wilkerson et al., "The Selective Monoacylglycerol Lipase Inhibitor MJN110 Produces Opioid-Sparing Effects in a Mouse Neuropathic Pain Model", J Pharmacol Exp Ther., Apr. 2016, 145-156, vol. 357, No. 1.
Wilson et al., "A high-throughput-compatible assay for determining the activity of fatty acid amide hydrolase", Anal Biochem., Jul. 15, 2003, 270-275, vol. 318, No. 2.
Yi et al., "Reductions in circulating endocannabinoid 2-arachidonoylglycerol levels in healthy human subjects exposed to chronic stressors", Progress in Neuro-Psychopharmacology and Biological Psychiatry, 2016, 92-97, vol. 67, No. 3.
Zhang et al., "Inhibition of monoacylglycerol lipase prevents chronic traumatic encephalopathy-like neuropathology in a mouse model of repetitive mild closed head injury", J Cereb Blood Flow Metab., Mar. 31, 2015, 706, vol. 35, Issue No. 4.
Alekseev, et al., Use of the Graebe-Ullmann Reaction in the Synthesis of 8-Methyl-Y-Carboline and Isomeric Aromatic Aza-Y-Carbolines, Chemistry of Heterocyclic Compounds, 2012, pp. 1235-1250, vol. 48 Issue 8.
Arbeloa, et al., P2X7 receptor blockade prevents ATP excitotoxicity in neurons and reduces brain damage after schemia, Neurobiology of Disease, 2012, pp. 954-961, vol. 45.
Arulkumaran, et al., A potential therapeutic role for P2X7 receptor (P2X7R) antagonists in the treatment of Inflammatory diseases, Expert Opin Investig, 2011, pp. 897-915, vol. 20 Issue 7.
Avignone, et al., Status Epilepticus Induces a Particular Microglial Activation State Characterized by Enhanced Purinergic Signaling, The Journal of Neuroscience, Sep. 10, 2008, pp. 9133-9144, vol. 28 Issue 37, Society for Neuroscience.
Bagshawe, "Antibody-Directed Enzyme prodrug Therapy: A Review", Drug Development Research, , vol. 34; pp. 220-230 (1995).
Bartlett, et al., The P2X7 Receptor Channel: Recent Development and the use of P2X7 antagonists in model of Disease, Pharmacol Rev, 2014, pp. 638-675, vol. 66.

(56) References Cited

OTHER PUBLICATIONS

Basso, et al., Behavioral profile of P2X7 receptor knockout mice in animal models of depression and anxiety: Relevance for neuropsychiatric disorders, Behavioural Brain Research, Oct. 18, 2008, pp. 83-90, vol. 198, Elsevier B.V.
Bennet, et al. (EDITOR), "Part XIV Oncology", Cecil Textbook of Medicine, vol. 1, 20th Edition: pp. 1004-1010 (1996).
Bertolini, et al., "A New Rational Hypothesis for the Pharmacophore of the Active Metabolite of Leflunomide, a Potent Immunosuppressive Drug", Journal of Medicinal Chemistry, vol. 40 (13); pp. 2011-2016 (1997).
Bodor, Nicholas "Novel Approaches to the Design of Safer Drugs: Soft Drugs and Site-Specific Chemical Delivery Systems", Advances in Drug Research, vol. 13; pp. 256-331, (1984).
Bourzac, et al., Glucose Transporter 2 Expression is Down Regulated Following P2X7 Activation in Enterocytes, Journal of Cellular Physiology, 2013, pp. 120-129, vol. 228.
Bundgaard, Hans "Design of Products", Design of Products, pp. 1-3, (1985).
Capuron, et al., Immune system to brain signaling: Neuropsychopharmacological implications, Pharmacology & Therapeutics, 2011, pp. 226-238, vol. 130, Elsevier Inc.
Chessell, et al., Disruption of the P2X7 purinoceptor gene abolishes chronic inflammatory and neuropathic pain, Pain, Jan. 5, 2005, pp. 386-396, vol. 114, Elsevier B.V.
Chu, et al., Inhibition of P2X7 receptor ameliorates transient global cerebral ischemia/reperfusion injury via modulating inflammatory responses in the rat hippocampus, Journal of Neuroinflammation, 2012, pp. 1-10, vol. 9 Issue 69.
Considine, G.D., Van Nostrand's Encyclopedia of Chemistry,, Encyclopedia of Chemistry, 2005, p. 261, Chapter 5.
Dantzer, Robert, Cytokine, Sickness Behavior, and Depression, Immunol Allergy Clin N Am, 2009, pp. 247-264, vol. 29.
Database Chemcats Ambinter Stock Screening Collection Accession No. 2040381923, Feb. 13, 2008.
Database Chemcats Ambinter Stock Screening Collection Accession No. 2040548370, Feb. 13, 2008.
Database Chemcats Ambinter Stock Screening Collection Accession No. 2046454718, Feb. 13, 2008.
Database Chemcats Ambinter Stock Screening Collection Database Accession No. 2040033692, Feb. 13, 2008.
Database Chemcats Aurora Screening Library Accession No. 2037938546, Sep. 6, 2007.
Database Chemcats Enamine Screening Library Accession No. 2035772210, Jan. 17, 2008.
Database Chemcats Ryan Scientific Screening Library Accession No. 2042634059, Jan. 25, 2008.
Database Chemcats Ryan Scientific Screening Library Accession No. 2042637020, Jan. 25, 2008.
Database Chemcats Ryan Scientific Screening Library Accession No. 2042676574, Jan. 25, 2008.
Database Chemcats Ryan Scientific Screening Library Accession No. 2043876860, Jan. 25, 2008.
Database Chemcats Ukrorgsynthesis Screening Collection Accession No. 2033253463, Mar. 6, 2007.
Delarasse, et al., The Purinergic Receptor P2X7 Triggers—Secretasedependent Processing of the Amyloid Precursor Protein, The Journal of Biological Chemistry, Nov. 16, 2010, pp. 2596-2606, vol. 286 Issue 4.
Dermer, Gerald B., "Another Anniversary For the War on Cancer",, Nature Publishing Group, Mar. 12, 1994, p. 320, vol. 12 No 2.
Diaz-Hernandez, et al., Altered P2X7-receptor level and function in mouse models of Huntington's disease and therapeutic efficacy of antagonist administration, The FASEB Journal, 2009, pp. 1893-1906, vol. 23.
Diaz-Hernandez, et al., In vivo P2X7 inhibition reduces amyloid plaques in Alzheimer's disease through GSK3 and secretases, Neurobiology of Aging, 2012, pp. 1816-1828, vol. 33.
Donnelly-Roberts, et al., [3H]JA-804598 ([3H]2-cyano-1-[(1S)-1-phenylethyl]-3-quinolin-5-ylguanidine) is a novel, potent, and selective antagonist radioligand for P2X7 receptors, Neuropharmacology, 2009, pp. 223-229, vol. 56.
Duan, et al., P2X7 Receptors: Properties and Relevance to CNS Function, GLIA, 2006, pp. 738-746, vol. 54.
Dyatkin et al, Determination of the Absolute Configuration of a Key Tricyclic Component of a Novel Vasopressin Receptor Antagonist by Use of Vibrational Circular Dichroism, Chirality, 2002, pp. 215-219, vol. 14.
Engel, et al., Seizure suppression and neuroprotection by targeting the purinergic P2X7 receptor during status epilepticus in mice, The FASEB Journal, 2012, pp. 1616-1628, vol. 26.
Ferrari, et al., The P2X7 Receptor: A Key Player in IL-1 Processing and Release1, The Journal of Immunology,, 2006, pp. 3877-3883, vol. 176.
Fleisher, et al., "Improved oral drug delivery: solubility limitations overcome by the use of prodrugs", Advanced Drug Delivery Reviews, vol. 19; pp. 115-130 (1996).
Freshney, et al., Culture of Animal Cells, Manual of Basic Technique, 1983, pp. 1-6, Chapter 1.
Friedle, et al., Recent Patents on Novel P2X7 Receptor Antagonists and their Potential for Reducing Central Nervous System Inflammation, Recent Patents on CNS Drug Discovery, 2010, pp. 35-45, vol. 5.
Furlan-Freguia, et al., P2X7 receptor signaling contributes to tissue factor-dependent thrombosis in mice, The Journal of Clinical Investigation, 2011, pp. 2932-2944, vol. 121 Issue 7.
Golub, et al., Molecular Classification of cancer: Class Discovery and class prediction by gene expression monitoring, Science, 1999, pp. 531-537, vol. 286.
Grygorowicz, et al., Temporal expression of P2X7 purinergic receptor during the course of experimental autoimmune encephalomyelitis, Neurochemistry International, Sep. 9, 2010, pp. 823-829, vol. 57.
Guile, et al., Antagonists of the P2X7 Receptor. From Lead Identification to Drug Development, Journal of Medicinal Chemistry, May 28, 2009, pp. 3123-3141, vol. 52 Issue 10.
Gunosewoyo, et al., P2X purinergic receptor ligands recently patented compounds, Expert Opin. Ther Patents, 2010, pp. 625-646, vol. 20 Issue 5.
Hackam, et al, "Translation of Research Evidence From animals to Humans", JAMA, vol. 296 (14): pp. 1731-1732 (2006).
Hudson, Derek, Methodological Implications of Simultaneous Solid-Phase peptide Synthesis, J.Org.Chem, 1988, pp. 617-624, vol. 53.
Ji, et al., P2X7 deficiency attenuates hypertension and renal injury in deoxycorticosterone acetate-salt hypertension, Am J Physiol Renal Physiol, 2012, pp. F1207-F1215, vol. 303.
Jordan, "Tamoxifen: a Most Unlikely Pioneering Medicine", Nature Reviews, vol. 2: pp. 205-213, (Mar. 2003).
Keating, et al., P2X7 Receptor-Dependent Intestinal Afferent Hypersensitivity in a Mouse Model of Postinfectious Irritable Bowel Syndrome, The Journal of Immunology, Jun. 22, 2011, pp. 1467-1474, vol. 187.
Killeen, et al., Signaling through purinergic receptors for ATP induce human cutaneous innate and adaptive th17 responses implications in the pathogenesis of psoriasis, The Journal of Immunology, 2013, pp. 4324-4336, vol. 190.
Kim, et al., Blockade of P2X receptor prevents astroglial death in the dentate gyrus following pilocarpine-induced status epilepticus, Neurological research, 2009, pp. 982-988, vol. 31.
Larsen, et al., "A text book of Drug Design and Development", Index; pp. 1-18 (1991).
Marcellino, et al., On the role of P2X7 receptors in dopamine nerve cell degeneration in a rat model of Parkinson's disease: studies with the P2X7 receptor antagonist A-438079, J Neural Transm, Apr. 13, 2010, pp. 681-687, vol. 117.
Martins, et al., The role of P2X7 purinergic receptors in inflammatory and nociceptive changes accompanying cyclophosphamide-induced haemorrhagic cystitis in mice, British Journal of Pharmacology, 2012, pp. 183-196, vol. 165.

(56) References Cited

OTHER PUBLICATIONS

Muller, et al., Apotential role for P2X7r in allergic airway inflammation in mice and humans, American Journal of Respiratory Cell and molecular Biology, 2011, pp. 456-464, vol. 44.

Oyanguren-Desez, et al., Gain-of-function of P2X7 receptor gene variants in multiple sclerosis, Cell Calcium, Sep. 8, 2011, pp. 468-472, vol. 50.

Parvathenani, et al., P2X7 Mediates Superoxide Production in Primary Microglia and Is Up-regulated in a Transgenic Mouse Model of Alzheimer's Disease, The Journal of Biological Chemistry, Jan. 27, 2003, pp. 13309-13317, vol. 278 Issue 15.

Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.

Robinson, et al., "Discovery of the Hemifumarate and (r-L-Alanyloxy)methyl Ether as Prodrugs of an Antirheumatic Oxindole: Prodrugs for the Enolic OH Group", Journal of Medicinal Chemistry, vol. 39 (1); pp. 10-18 (1996).

Romagnoli, et al., The P2X 7 receptor as a therapeutic target, Expert Opin. Ther., 2008, pp. 647-661, vol. 15 Issue 5.

Rudolph, et al., Novel methyl substituted 1-(5,6-dihydro-[1,2,4]triazolo [4,3-a]pyrazin-7(8H)-yl)methanones are P2X7 antagonists, Bioorganic & Medicinal Chemistry Letters, Jun. 9, 2015, pp. 3157-3163, vol. 25.

Sanz, et al., Activation of Microglia by Amyloid Requires P2X7 Receptor Expression1, The Journal of Immunology, 2009, pp. 4378-4385, vol. 182.

Shan, et al., "Prodrug Strategies Based on Intramolecular Cyclization Reactions", Journal of Pharmaceutical Sciences, vol. 86 (7): pp. 765-767 (Jul. 1977).

Sharp, et al., P2x7 deficiency suppresses development of experimental autoimmune encephalomyelitis, Journal of Neuroinflammation, Aug. 8, 2008, pp. 1-13, vol. 5 Issue 33.

Simone, Part XIV—Oncology, Textbook of Medicine, 1996, 20th edition, pp. 1004-1010, vol. 1.

Skaper, et al., The P2X7 purinergic receptor: from physiology to neurological disorders, The FASEB Journal, 2010, pp. 337-345, vol. 24.

Solini, et al., Enhanced P2X7 Activity in Human Fibroblasts From Diabetic Patients A Possible Pathogenetic Mechanism for Vascular Damage in Diabetes, Arterioscler Thromb Vasc Biol., 2004, pp. 1240-1245, vol. 24.

Stahl, et al., "Handbook Of Pharmaceutical Salts", International Union Of pure And Applied Chemistry, Index; pp. 1-3, (2002).

Surprenant, et al., Signaling at Purinergic P2X Receptors, Annu. Rev. Physiol, Oct. 13, 2008, pp. 333-359, vol. 71.

Thiboutot, et al., Inflammasome Activation by propionibacterium acnes: the Story of IL-1 in Acne continues to unfold, Journal Of Investigative Dermatology, 2014, pp. 595-597, vol. 134.

Vergani, et al., Effects of the purinergic Inhibitor Oxidized ATP in a model of Islet Allograft rejection, Diabetes, 2013, pp. 1665-1675, vol. 62.

Vergani, et al., Long term Heart Transplant Survival by targeting the Ionotropic Purinergic receptor P2X7, Circulation, 2013, pp. 463-475, vol. 127.

Keller, et al., "Radiosynthesis and Preclinical Evaluation of [18F]F-DPA, A Novel Pyrazolo[1,5a]pyrimidine Acetamide TSPO Radioligand, in Healthy Sprague Dawley Rats", Molecular Imaging and Biology, 2017, pp. 736-745, vol. 19.

Pike, Victor W., "Hypervalent aryliodine compounds as precursors for radiofluorination", J. Label Compd Radiopharm., 2018, pp. 196-227, vol. 61.

MONOACYLGLYCEROL LIPASE MODULATORS

CROSS-REFERENCE TO RELATED APPLICATIONS

This application claims priority to U.S. Patent Application No. 63/000,329, filed on Mar. 26, 2020, which is incorporated herein in its entirety.

FIELD OF THE INVENTION

The present invention is related to certain aryl piperidine chemical entities having MGL modulating properties, pharmaceutical compositions comprising these chemical entities, chemical processes for preparing these chemical entities and their use in the treatment of diseases, disorders or conditions associated with MGL receptor activity in subjects, in particular humans.

BACKGROUND OF THE INVENTION

*Cannabis Sativa* and analogs of $\Delta^9$-tetrahydrocannabinol have been used since the days of folk medicine for therapeutic purposes. The endocannabinoid system consists of two G-protein coupled receptors, cannabinoid receptor type 1 (CB1) (Matsuda el al., *Nature*, 1990, 346, 561-4) and cannabinoid receptor type 2 (CB2) (Munro et al., *Nature*, 1993, 365, 61-5). CB1 receptor is one of the most abundant G-protein coupled receptor expressed in the brain (Herkenam et al., *Proc. Nat. Acad Sci.*, 1990, 87 (5), 1932-1936). CB1 is also expressed peripherally in the liver, gastrointestinal tract, pancreas, adipose tissue and skeletal muscles (Di Marzo et al., *Curr Opin Lipidol*, 2007, 18, 129-140). CB2 is predominantly expressed in immune cells such as monocytes (Pacher et al., *Amer J Physiol* 2008, 294, H1133-H1134) and under certain conditions (inflammation) in the brain (Benito et al, *Brit J Pharmacol* 2008, 153, 277-285) and in skeletal (Cavuoto et al., *Biochem Biophys Res Commun*, 2007, 364, 105-110) and cardiac muscles (Hajrasouliha et al, *Eur J Pharmacol* 2008, 579, 246-252).

In 1992, N-arachidonoylethanolamine (AEA or anandamide) was found to be an endogenous ligand for cannabinoid receptors (Devane et al., *Science*, 1992, 258, 1946-9). Subsequently, 2-arachidonoylglycerol (2-AG) was also identified as an additional endogenous ligand for the cannabinoid receptors (Mechoulam et al., *Biochem Pharmacol*, 1995, 50, 83-90; Sugiura et al., *Biochem Biophys Res Commun*, 1995, 215, 89-97). Concentrations of 2-AG were reported to be at least 100 times higher than these of anandamide in the rat brain (Buczynski and Parsons, *Brit J Pharmacol*, 2010, 160 (3), 423-42). Therefore 2-AG may play more essential physiological roles than anandamide in the brain endocannabinoid system (Sugiura et al. *Prostaglandins Leukot Essent Fatty Acids*., 2002, February-March, 66(2-3): 173-92). The endocannabinoid 2-AG is a full agonist for CB1 and CB2 receptors, while anandamide is a partial agonist for both receptors (Suguira et al., *Prog Lipid Res*, 2006, 45(5):405-46). Unlike many classical neurotransmitters, endocannabinoids signal through a retrograde mechanism. They are synthesized on demand in postsynaptic neurons and then rapidly degraded following binding to presynaptic cannabinoid receptors (Ahn et al., *Chem Rev.* 2008, 108(5): 1687-707). Monoacylglycerol lipase (MGLL, also known as MAG lipase and MGL) is the serine hydrolase responsible for the degradation of 2-AG into arachidonic acid and glycerol in the central nervous system (Mechoulam et al., *Biochem Pharmacol*, 1995, 50, 83-90; Sugiura et al., *Biochem Biophys Res Commun*, 1995, 215, 89-97; Long et al, *Nat Chem Biol.* 2009 January; 5(1):37-44; Schlosburg et al, *Nat Neurosci.*, 2010, September; 13(9): 1113-9) and peripheral tissues (Long et al., *Chem Biol.*, 2009 Jul. 31; 16(7):744-53). Anandamide is hydrolyzed by fatty acid amide hydrolase (FAAH) (Piomelli, *Nat Rev Neurosci*, 2003, 4, 873-884). MGL exists in both soluble and membrane bound forms (Dinh et al., *Proc Natl Acad Sci USA.*, 2002 Aug. 6; 99(16):10819-24). In the brain MGL is located in presynaptic neurons (Straiker et al, *Mol Pharmacol.*, 2009, December; 76(6): 1220-7) and astrocytes (Walter et al., *J Neurosci.*, 2004 Sep. 15; 24(37):8068-74) within regions associated with high CB1 receptor density. Compared to wild-type controls, genetic ablation of MGL expression produces 10-fold increase in brain 2-AG levels without affecting anandamide concentration (Schlosburg et al., *Nat Neurosci.*, 2010, September; 13(9): 1113-9).

Thus, MGL modulation offers an interesting strategy for potentiating the cannabinoid system. The primary advantage of this approach is that only brain regions where endocannabinoids are actively produced will be modulated, potentially minimizing the side effects associated with exogenous CB1 agonists. Pharmacological inactivation of MGL by covalent inhibitors in animals increase 2-AG content in brain and peripheral tissues and has been found to produce antinociceptive, anxiolytic and anti-inflammatory effects that are dependent on CB1 and/or CB2 receptors (Long et al., *Nat Chem Biol.*, 2009, January, 5(1):37-44; Ghosh et al., *Life Sci.*, 2013 Mar. 19, 92(8-9):498-505; Bedse et al., *Biol Psychiatry.*, 2017 Oct. 1, 82(7):488-499; Bernal-Chico et al., *Glia.*, 2015, January, 63(1):163-76; Patel et al. *Neurosci Biobehav Rev.*, 2017, May, 76(Pt A):56-66; Betse et al., *Transl Psychiatry.*, 2018 Apr. 26, 8(1):92). In addition to the role of MGL in terminating 2-AG signaling, MGL modulation, including MGL inhibition also promotes CB1/2-independent effects on neuroinflammation (Nomura et al., *Science.*, 2011 Nov. 11; 334(6057):809-13). MGL modulation, including MGL inhibition leads to reduction in proinflammatory prostanoid signaling in animal models of traumatic brain injury (Katz et al., *J Neurotrauma.*, 2015 Mar. 1; 32(5):297-306; Zhang et al., *J Cereb Blood Flow Metab.*, 2015 Mar. 31; 35(4):443-453), neurodegeneration including Alzheimer's disease (Piro et al., *Cell Rep.*, 2012 Jun. 28, 1(6):617-23; Wenzel et al., *Life Sci.*, 2018 Aug. 15, 207: 314-322; Chen et al., *Cell Rep.*, 2012 Nov. 29, 2(5):1329-39), Parkinson's disease (Nomura et al., *Science*, 2011 Nov. 11, 334(6057), 809-13; Pasquarelli et al., *Neurochem Int.*, 2017, November, 110:14-24), amyotrophic lateral sclerosis (Pasquarelli et al., *Neuropharmacology*, 2017 Sep. 15, 124: 157-169), multiple sclerosis (Hernadez-Torres et al., *Angew Chem Int Ed Engl.*, 2014 Dec. 8, 53(50):13765-70; Bernal-Chico et al., *Glia.*, 2015, January, 63(1):163-76), Huntington's disease (Covey et al., *Neuropsychopharmacology*, 2018, 43, 2056-2063), Tourette syndrome and status epilepticus (Terrone et al., *Epilepsia.*, 2018, January, 59(1), 79-91; von Ruden et al., *Neurobiol Dis.*, 2015, May; 77:238-45).

Therefore, by potentiating the cannabinoid system and attenuating proinflammatory cascades, MGL modulation, including MGL inhibition offers a compelling therapeutic approach for the treatment of a vast array of complex diseases. Importantly, MGL modulation, including MGL inhibition in animals does not produces the full spectrum of neurobehavioral effects observed with $\Delta^9$-tetrahydrocannabinol and other CB1 agonists (Tuo et al., *J Med Chem.*, 2017 Jan. 12, 60(1), 4-46; Mulvihill et al., *Life Sci.*, 2013 Mar. 19, 92(8-9), 492-7).

Endocannabinoid hypoactivity is a risk factor for the treatment of depression, anxiety, and post-traumatic stress disorders. Millennia of human use of *Cannabis sativa*, and a brief period in which humans were treated with the endocannabinoid antagonist, rimonabant, provide support for that hypothesis. 2-AG levels are decreased in individuals with major depression (Hill et al., *Pharmacopsychiatry.*, 2008, March; 41(2): 48-53; Hill et al., *Psychoneuroendocrinology.*, 2009, September; 34(8): 1257-1262.). Low circulating 2-AG levels predict rates of depression (Hauer et al., *Rev Neurosci.*, 2012, 23(5-6):681-90). Reduced circulating 2-AG has been found in patient with post-traumatic stress disorder (PTSD) (Hill et al., *Psychoneuroendocrinology*, 2013, 38 (12), 2952-2961). Healthy volunteers exposed to chronic stressors exhibited progressively diminished circulating 2-AG levels which correlated with the onset of reductions in measures of positive emotions (Yi et al., *Progress in Neuro-Psychopharmacology and Biological Psychiatry*, 2016, 67 (3), 92-97). The CB1 receptor inverse agonist/antagonist Rimonabant has been withdrawn from the market due to the high incidence of severe depression and suicidal ideation (Christensen et al., *The Lancet*, 2007, 370, 1706-1713). Therefore, MGL modulators are potentially useful for the treatment of mood disorders, anxiety, PTSD, autism spectrum disorders, and Asperger syndrome (Folkes et al., *J Clin Invest.* 2020; 130(4):1728-1742, Jung et al., *Nature Communications*, 2012, 3, 1080; Wang et al., *Mol Psychiatry*, 2018 August, 23(8): 1798-1806).

Cannabinoid receptor agonists are clinically used to treat pain, spasticity, emesis, and anorexia (Di Marzo, et al., *Annu Rev Med.*, 2006, 57:553-74; Ligresti et al., *Curr Opin Chem Biol.*, 2009, June; 13(3):321-31). Therefore, MGL modulators, including MGL inhibitors are also potentially useful for these indications. MGL exerts CB1-dependant antinociceptive effects in animal models of noxious chemical, inflammatory, thermal and neuropathic pain (Guindon et al., *Br J Pharmacol.*, 2011, August; 163(7):1464-78; Kinsey et al., *J Pharmacol Exp Ther.*, 2009, September; 330(3):902-10; Long et al., *Nat Chem Biol.*, 2009, January; 5(1):37-44). MGL blockade reduces mechanical and acetone induced cold allodynia in mice subjected to chronic constriction injury of the sciatic nerve (Kinsey et al., *J Pharmacol Exp Ther.*, 2009, September; 330(3):902-10). MGL inhibition produces opiate-sparing events with diminished tolerance, constipation, and cannabimimetic side effects (Wilkerson et al., *J Pharmacol Exp Ther.*, 2016, April; 357(1):145-56). MGL blockade is protective in model of inflammatory bowel disease (Alhouayek et al., *FASEB J.*, 2011, August; 25(8): 2711-21). MGL inhibition also reverse paclitaxel-induced nociceptive behavior and proinflammatory markers in a mouse model of chemotherapy-induced neuropathy (Curry et al., *J Pharmacol Exp Ther.*, 2018, July; 366(1):169-18). MGL inhibitors are also potentially useful for the treatment of chronic inflammatory condition of the urinary bladder like interstitial cystitis (Chinnadurai et al., *Med Hypotheses* 2019, October; 131: 109321).

Inhibition of 2-AG hydrolysis exerts anti-proliferative activity and reduction in prostate cancer cell invasiveness (Nithipatikom et al., *Cancer Res.*, 2004 Dec. 15, 64(24): 8826-30; Nithipatikom et al., *Biochem Biophys Res Commun.*, 2005 Jul. 15, 332(4):1028-33; Nithipatikom et al., *Prostaglandins Other Lipid Mediat.*, 2011, February, 94(1-2):34-43). MGL is upregulated in aggressive human cancer cells and primary tumors where it has a unique role of providing lipolytic sources of free fatty acids for synthesis of oncogenic signaling lipids that promote cancer aggressiveness. Thus, beyond the physiological roles of MGL in mediated endocannabinoid signaling, MGL in cancer plays a distinct role in modulating the fatty acid precursor pools for synthesis of protumorigenic signaling lipids in malignant human cancer cells.

MGL blockade shows anti-emetic and anti-nausea effects in a lithium chloride model of vomiting in shrews (Sticht et al., *Br J Pharmacol.*, 2012, April, 165(8):2425-35).

MGL modulators, including MGL inhibitors may have utility in modulating drug dependence of opiates. MGL blockade reduce the intensity of naloxone-precipitated morphine withdrawal symptoms in mice. MGL blockade also attenuated spontaneous withdrawal signs in morphine-dependent mice (Ramesh et al., *J Pharmacol Exp Ther.*, 2011, October, 339(1):173-85).

MGL modulators are also potentially useful for the treatment of eye conditions, including but not limited to, glaucoma and disease states arising from elevated intraocular pressure (Miller et al., Pharmaceuticals, 2018, 11, 50).

SUMMARY OF THE INVENTION

Embodiments of the present invention relate to chemical entities, pharmaceutical compositions containing them, methods of making and purifying them, and methods for using them the treatment of diseases, disorders, and conditions associated with the MGL modulation. An additional embodiment of the invention is a method of treating a subject suffering from or diagnosed with a disease, disorder, or condition associated with the MGL modulation using at least one chemical entity of the invention.

Additional embodiments, features, and advantages of the invention will be apparent from the following detailed description and through practice of the invention.

Described herein are compounds of Formula (I):

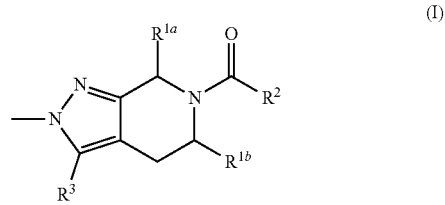

wherein
$R^{1a}$ is $C_{1-4}$alkyl;
$R^{1b}$ is H;
or $R^{1a}$ and $R^{1b}$ taken together form —$CH_2CH_2$— or —$CH_2CH_2CH_2$—;
$R^2$ is selected from:
  (a) phenyl or pyridyl, each optionally substituted with one or two substituents selected from halo, $C_{1-4}$alkyl, $C_{1-4}$haloalkyl, $OC_{1-4}$alkyl, $OC_{1-4}$haloalkyl, N-linked monocyclic or bicyclic heterocycloalkyl, monocyclic heteroaryl, and $C_{3-6}$cycloalkyl, or two adjacent ring substituents taken together with the carbons to which they are attached form a monocyclic cycloalkyl or hetercycloalkyl ring;
  (b) bicyclic heteroaryl optionally substituted with one or two substituents selected from halo, $C_{1-4}$alkyl, $C_{1-4}$haloalkyl, $OC_{1-4}$alkyl, $OC_{1-4}$haloalkyl, N-linked monocyclic or bicyclic heterocycloalkyl, monocyclic heteroaryl, and $C_{3-6}$cycloalkyl; and
$R^3$ is 1H—$C_{1-4}$alkyl-pyrazolyl, 1H—$C_{1-4}$haloalkyl-pyrazolyl, 1H-pyridyl-pyrazolyl, 1H—($C_{3-6}$cycloalkyl)-pyrazolyl, or 1H—(C$_{3-6}$cycloalkyl-methyl)-pyrazolyl, each pyrazolyl optionally substituted with halo, C$_{1-4}$alkyl, C$_{1-4}$haloalkyl, OC$_{1-4}$alkyl, or OC$_{1-4}$haloalkyl;

provided that when R$^2$ is phenyl or pyridyl, each optionally substituted with halo, C$_{1-4}$alkyl, or C$_{1-4}$haloalkyl, then (a) R$^{1a}$ and R$^{1b}$ are taken together form —CH$_2$CH$_2$— or —CH$_2$CH$_2$CH$_2$—; or (b) R$^3$ is not 1H—C$_{1-4}$alkyl-pyrazol-5-yl

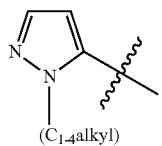

(C$_{1-4}$alkyl)

or 1H—C$_{1-4}$haloalkyl-pyrazol-5-yl

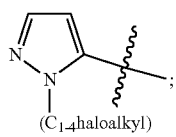

(C$_{1-4}$haloalkyl)

and pharmaceutically acceptable salts, isotopes, N-oxides, solvates, and stereoisomers thereof.

In some embodiments are compounds of Formula (I):

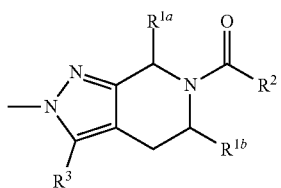

(I)

wherein
R$^{1a}$ is C$_{1-4}$alkyl;
R$^{1b}$ is H;
or R$^{1a}$ and R$^{1b}$ taken together form —CH$_2$CH$_2$— or —CH$_2$CH$_2$CH$_2$—;
R$^2$ is selected from:
(a)

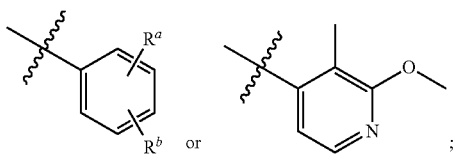

(b) a 5,6-fused or 6,5-fused heteroaryl selected from:

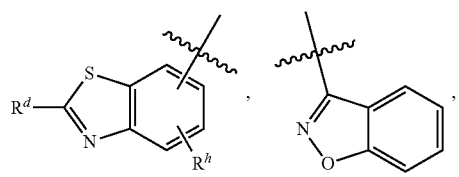

-continued

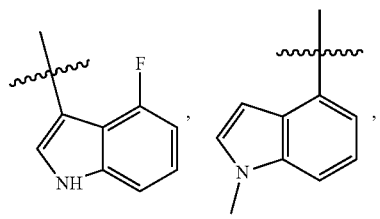

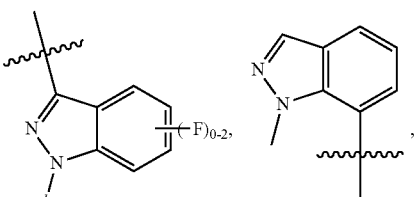

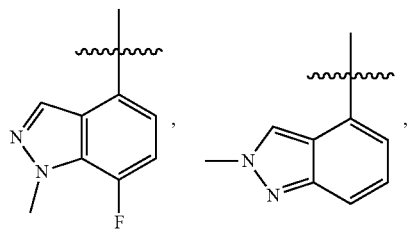

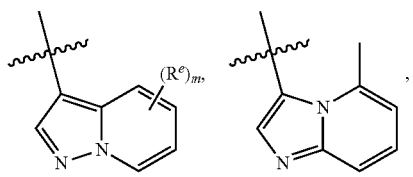

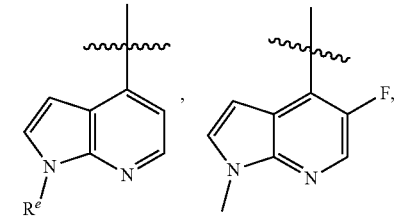

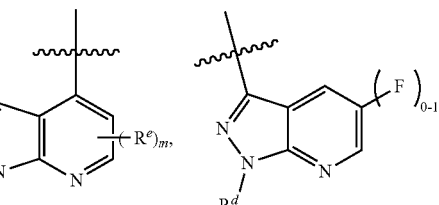

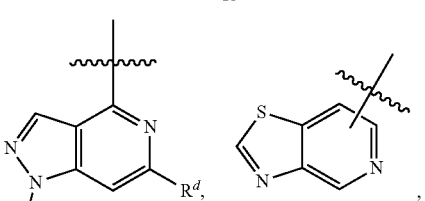

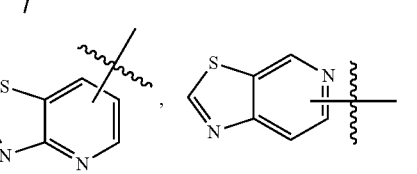

and

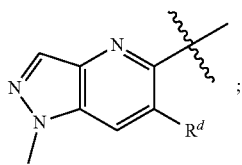

(c) a fused 6,6-heteroaryl selected from:

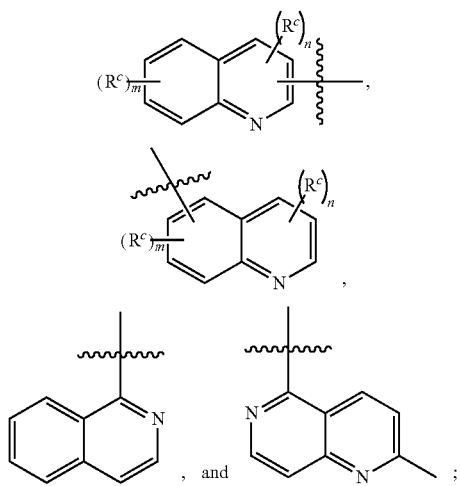

and (d)

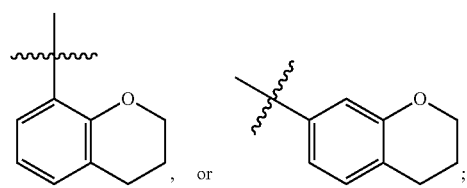 [SMILES: *c1cccc2c1OCCC2 ; *c1ccc2c(c1)OCCC2]

$R^3$ is a 5-membered heteroaryl ring selected from:

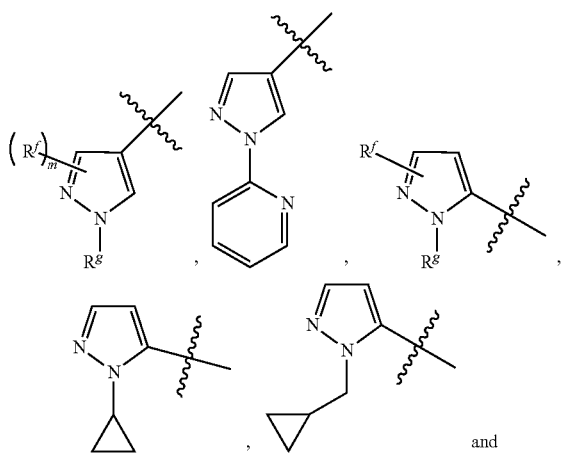

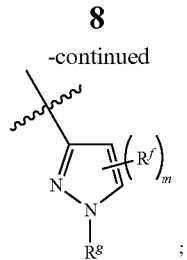

wherein
$R^a$ is selected from: H, halo, $C_{1-4}$alkyl, $C_{1-4}$haloalkyl, and $OC_{1-4}$alkyl;
$R^b$ is selected from: $C_{1-4}$alkyl, $C_{1-4}$haloalkyl, $OC_{1-4}$alkyl, $OC_{1-4}$haloalkyl,

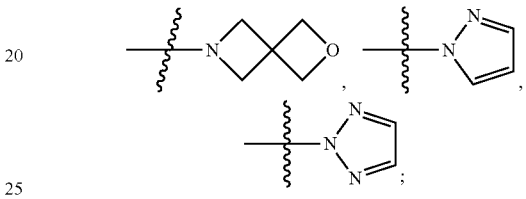

each $R^c$ is independently selected from: halo, $C_{1-4}$alkyl, and $OC_{1-4}$alkyl;
$R^d$ is H or $C_{1-4}$alkyl;
each $R^e$ is independently halo, $C_{1-4}$alkyl, or $C_{1-4}$haloalkyl;
each $R^f$ is independently selected from: $C_{1-4}$alkyl, $C_{1-4}$haloalkyl, and $OC_{1-4}$alkyl;
$R^g$ is $C_{1-4}$alkyl, or $C_{1-4}$haloalkyl; and
$R^h$ is selected from: H, $C_{1-4}$alkyl, $C_{1-4}$haloalkyl, and cycloalkyl;
n is 0, 1, or 2; and
m is 0, 1, or 2;
and pharmaceutically acceptable salts, isotopes, N-oxides, solvates, and stereoisomers thereof.

DETAILED DESCRIPTION OF THE INVENTION

As used herein, the terms "including", "containing" and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_{1-6}$alkyl" refers to straight- or branched-chain alkyl group having from 1 to 6 carbon atoms in the chain. "$C_{1-4}$alkyl" refers to straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

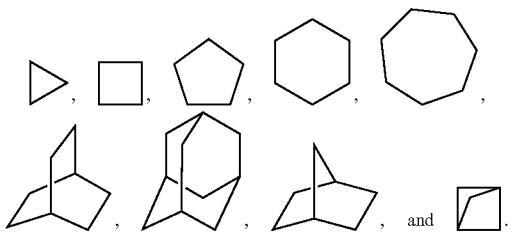

The term "halogen" or "halo" represents chlorine, fluorine, bromine, or iodine.

The term "haloalkyl" refers to a straight- or branched-chain alkyl group having from 1 to 6 carbon atoms in the chain optionally substituting hydrogens with halogens. The term "$C_{1-4}$ haloalkyl" as used here refers to a straight- or branched-chain alkyl group having from 1 to 4 carbon atoms in the chain, optionally substituting hydrogens with halogens. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "aryl" refers to a monocyclic, aromatic carbocycle (ring structure having ring atoms that are all carbon) having 6 atoms per ring (Carbon atoms in the aryl groups are sp2 hybridized.)

The term "phenyl" represents the following moiety:

The term "heteroaryl" as used herein, refers to an aromatic monocyclic or multicyclic ring system comprising 5 to 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring.

The term "5-membered heteroaryl" as used herein, refers to a heteroaryl group, as defined above, which has 5 ring atoms. Non-limiting examples of illustrative 5-membered heteroaryls include:

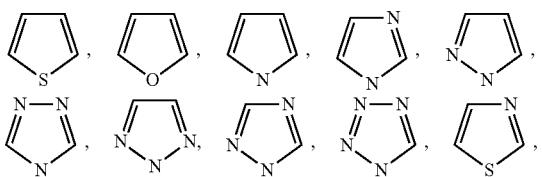

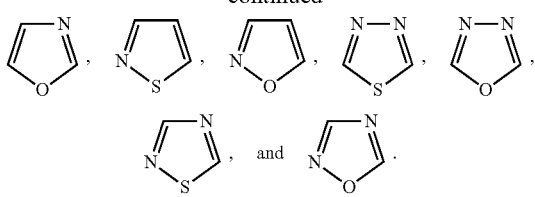

The term "6-membered heteroaryl" as used herein, refers to a heteroaryl group, as defined above, which has 6 ring atoms. Non-limiting examples of illustrative 6-membered heteroaryls include:

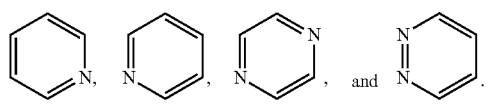

The term "5,6-fused bicyclic heteroaryl or 6,5-fused bicyclic heteroaryl" as used herein, refers to a heteroaryl group, as defined above, which has 9 ring atoms. Non-limiting examples of illustrative 5,6-fused bicyclic heteroaryl or 6,5-fused bicyclic heteroaryl include:

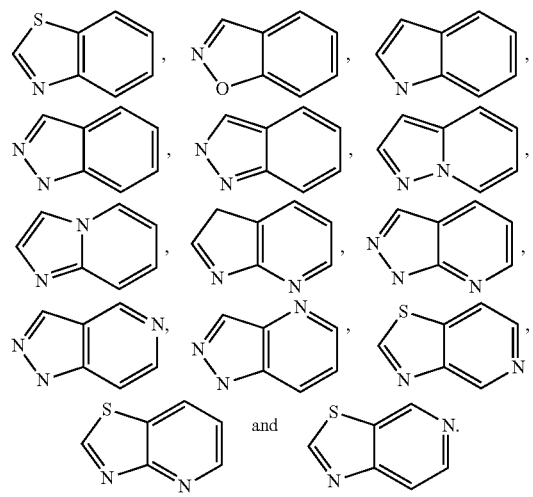

The term "6,6-fused bicyclic heteroaryl" as used herein, refers to a heteroaryl group, as defined above, which has 9 ring atoms. Non-limiting examples of illustrative 6,6-fused bicyclic heteroaryl include:

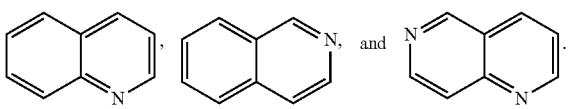

The term "heterocycloalkyl" as used herein, refers to a ring system which is non-aromatic, 1 to 4 of the ring atoms is independently O, N or S and the remaining ring atoms are carbon atoms, which may optionally be fused to another ring (aromatic or heteroaromatic). Non-limiting examples of illustrative heterocycloalkyl include:

Those skilled in the art will recognize that the species of heteroaryl, heterocycloalkyl, cycloalkyl, and aryl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "variable point of attachment" means that a group is allowed to be attached at more than one alternative position in a structure. The attachment will always replace a hydrogen atom on one of the ring atoms. In other words, all permutations of bonding are represented by the single diagram, as shown in the illustrations below.

the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of: hydrates, solvates, polymorphs and of such compounds, and mixtures thereof, even if such forms are not listed explicitly.

The term "R" at a stereocenter designates that the stereocenter is purely of the R-configuration as defined in the art; likewise, the term "S" means that the stereocenter is purely of the S-configuration. As used herein, the term "RS" refers to a stereocenter that exists as a mixture of the R- and S-configurations.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component

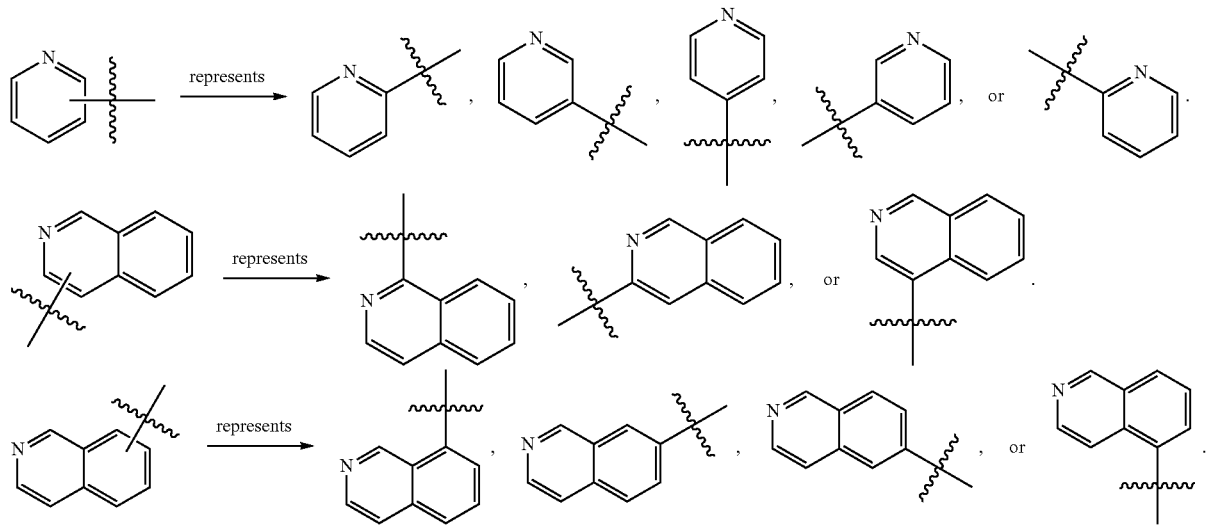

Those skilled in the art will recognize that that if more than one such substituent is present for a given ring, the bonding of each substituent is independent of all of the others. The groups listed or illustrated above are not exhaustive.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of mixture with relative stereochemistry as drawn. Unlabeled stereocenters drawn without stereo bond designations are a mixture of the R- and S-configurations. For unlabeled stereocenters drawn with stereo bond designations, the absolute stereochemistry is as depicted.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of: for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^2$H (or chemical symbol D), $^3$H (or chemical symbol T), $^{11}$C, $^{13}$C, $^{14}$C, $^{15}$N, $^{18}$O, $^{17}$O, $^{31}$P, $^{32}$P, $^{35}$S, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H, or D) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for such variable appearing elsewhere. In other words, where a variable appears more than once, the choice of the species from a specified list is independent of the choice of the species for the same variable elsewhere in the formula, unless stated otherwise.

The term $C_{n-m}$ alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from H and F".

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S^1$ and $S^2_{example}$ is $S_3$; $S^1_{example}$ is $S^1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$." is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" or "$C_{i-j}$" with j>i, when applied herein to a class of substituents, is meant to refer to embodiments of this invention for which each and every one of the number of carbon members, from i to j including i and j, is independently realized. By way of example, the term $C_1$-$C_3$ refers independently to embodiments that have one carbon member ($C_1$), embodiments that have two carbon members ($C_2$), and embodiments that have three carbon members ($C_3$).

A "pharmaceutically acceptable salt" is intended to mean a salt of an acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

The compounds of the invention, including their pharmaceutically acceptable salts, whether alone or in combination, (collectively, "active agent" or "active agents") of the present invention are useful as MGL-modulators in the methods of the invention. Such methods for modulating MGL comprise the use of a therapeutically effective amount of at least one chemical entity of the invention.

In some embodiments, the MGL modulator is an inhibitor and is used in a subject diagnosed with or suffering from a disease, disorder, or condition associated with MGL receptor activity, such as those described herein. Symptoms or disease states are intended to be included within the scope of "disease, disorders or conditions."

Accordingly, the invention relates to methods of using the active agents described herein to treat subjects diagnosed with or suffering from a disease, disorder, or condition associated with the MGL receptor activity. The term "treat" or "treating" as used herein is intended to refer to administration of an active agent or composition of the invention to a subject for the purpose of effecting a therapeutic or prophylactic benefit through modulation of MGL receptor activity.

Treating includes reversing, ameliorating, alleviating, inhibiting the progress of, lessening the severity of, or preventing a disease, disorder, or condition, or one or more symptoms of such disease, disorder or condition associated with the MGL modulation. The term "subject" refers to a mammalian patient in need of such treatment, such as a human.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme. The disclosure is directed to methods for treating, ameliorating and/or preventing diseases, conditions, or disorders associated with pain (including inflammatory pain), and also psychiatric disorders, neurological disorders, cancers and eye conditions by the administration of therapeutically effective amounts of MGL modulators to subjects in need thereof.

The term "modulators" include both inhibitors and activators, where "inhibitors" refer to compounds that decrease, prevent, inactivate, desensitize, or down-regulate the MGL expression or activity, and "activators" are compounds that increase, activate, facilitate, sensitize, or up-regulate MGL expression or activity.

As used herein, unless otherwise noted, the term "affect" or "affected" (when referring to a disease, condition or disorder that is affected by inhibition of MGL) includes a reduction in the frequency and/or severity of one or more symptoms or manifestations of said disease, condition or disorder; and/or include the prevention of the development of one or more symptoms or manifestations of said disease, condition or disorder or the development of the disease, condition or disorder.

In treatment methods according to the invention, a therapeutically effective amount of at least one active agent according to the invention is administered to a subject suffering from or diagnosed as having such a disease, disorder, or condition. A "therapeutically effective amount" means an amount or dose sufficient to generally bring about the desired therapeutic or prophylactic benefit in subjects in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units (e.g., BID, TID, QID or as required by modality).

Once improvement of the subject's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases associated with the MGL modulation, such as another MGL inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect MGL modulation.

The active agents of the invention are envisaged for use, alone or in combination with one or more additional active ingredients, to formulate pharmaceutical compositions of the invention. A pharmaceutical composition of the invention comprises a therapeutically effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents of the invention can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema, or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or condition associated with MGL modulation, comprising administering to the subject in need of such treatment a therapeutically effective amount of the active agent.

The compounds of Formula (I) are useful in methods for treating, ameliorating and/or preventing a disease, a condition or a disorder that is affected by the inhibition of MGL. Such methods comprise administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or pharmaceutically acceptable salts, isotopes, N-oxides, solvates and stereoisomers thereof, are useful for treating, ameliorating and/or preventing diseases, conditions, or disorders causing pain, psychiatric disorders, neurological disorders, cancers and eyes conditions. More particularly, the compounds of Formula (I), or pharmaceutically acceptable salts, isotopes, N-oxides, solvates and stereoisomers thereof, are useful for treating, ameliorating and/or preventing inflammatory pain, major depressive disorder, treatment resistant depression, anxious depression or bipolar disorder by administering to a subject in need thereof a therapeutically effective amount of a compound of Formula (I), or a pharmaceutically acceptable salt, isotope, N-oxide, solvate or stereoisomer thereof as herein defined.

1) Pain

Examples of inflammatory pain include, but are not limited to, pain due to a disease, condition, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, condition, disorder, or pain state including inflammation, osteoarthritis, rheumatoid arthritis, back pain, joint pain, abdominal pain, musculoskeletal diseases, skin diseases, post-operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In an embodiment, the present invention is directed to a method for treating, ameliorating and/or preventing inflammatory visceral hyperalgesia in which an enhanced visceral irritability exists, comprising, consisting of, and/or consisting essentially of the step of administering to a subject in need of such treatment a therapeutically effective amount of a compound of Formula (I) or a pharmaceutically acceptable salt, isotope, N-oxide, solvate or stereoisomer thereof. In a further embodiment, the present invention is directed to a method for treating inflammatory somatic hyperalgesia in which a hypersensitivity to thermal, mechanical and/or chemical stimuli exists, comprising administering to a subject in need of such treatment a therapeutically effective amount of a compound of Formula (I) or a pharmaceutically acceptable salt, isotope, N-oxide, solvate or stereoisomer thereof.

A further embodiment of the present invention is directed to a method for treating, ameliorating and/or preventing neuropathic pain. Examples of a neuropathic pain include pain due to a disease, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, vidian neuralgia or chemotherapy-induced neuropathy.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising administering to a subject in need of such treatment a therapeutically effective amount of a compound of Formula (I) or a pharmaceutically acceptable salt, isotope, N-oxide, solvate or stereoisomer thereof.

2) Psychiatric Disorders

Examples of psychiatric disorders include, but are not limited to, anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post-natal depression, manic depression, and bipolar depression, mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, anxious depression, bipolar disorder, depressive disorder with postpartum onset, depressive disorders with psychotic symptoms; persistent mood disorders, such as cyclothymia, dysthymia, euthymia; premenstrual dysphoric disorder; psychoses; and developmental disorders such as autism spectrum disorders, and Asperger syndrome.

3) Neurological Disorders

Examples of neurological disorder include, but are not limited to, tremors, dyskinesias, dystonias, spasticity, Tourette's Syndrome; neuromyelitis optica, Parkinson's disease; Alzheimer's disease; senile dementia; Huntington's disease; Epilepsy/seizure disorders and sleep disorders.

4) Cancers

Examples of cancers include, but are not limited to, benign skin tumors, prostate tumors, ovarian tumors and cerebral tumors (glioblastomas, medulloepitheliomas, medulloblastomas, neuroblastomas, tumors of embryonic origin, astrocytomas, astroblastomas, ependymomas, oligodendrogliomas, neuroepitheliomas, epiphyseal tumor, ependymoblastomas, malignant meningiomas, sarcomatosis, malignant melanomas, schwannomas).

5) Eye Conditions

Examples of eye conditions include, but are not limited to, ocular hypertension, glaucoma, degeneration, and apoptosis of retinal ganglion cells and neuroretinal cells.

Other embodiments of this invention provide for a method for modulating MGL receptor activity, including when such receptor is in a subject, comprising exposing MGL receptor to a therapeutically effective amount of at least one compound selected from compounds of the invention.

In some embodiments of Formula (I), $R^{1a}$ is $CH_3$ and $R^{1b}$ is H. In some embodiments, $R^{1a}$ and $R^{1b}$ come together to form —$CH_2CH_2$—. In some embodiments, $R^{1a}$ and $R^{1b}$ come together to form —$CH_2CH_2CH_2$—.

In some embodiments, $R^2$ is

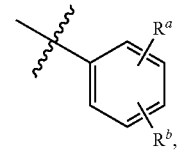

wherein $R^a$ is H, Cl, F, $C_{1-4}$alkyl or $C_{1-4}$haloalkyl; and $R^b$ is $C_{1-4}$alkyl, $C_{1-4}$haloalkyl, $OC_{1-4}$alkyl, or $OC_{1-4}$haloalkyl. In some embodiments, $R^2$ is

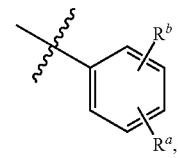

wherein $R^a$ is Cl, F, or $C_{1-4}$alkyl; and $R^b$ is

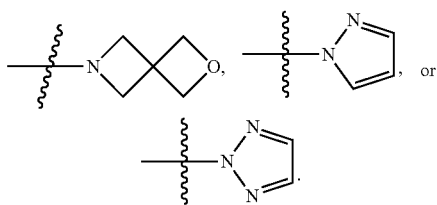

In some embodiments, $R^2$ is
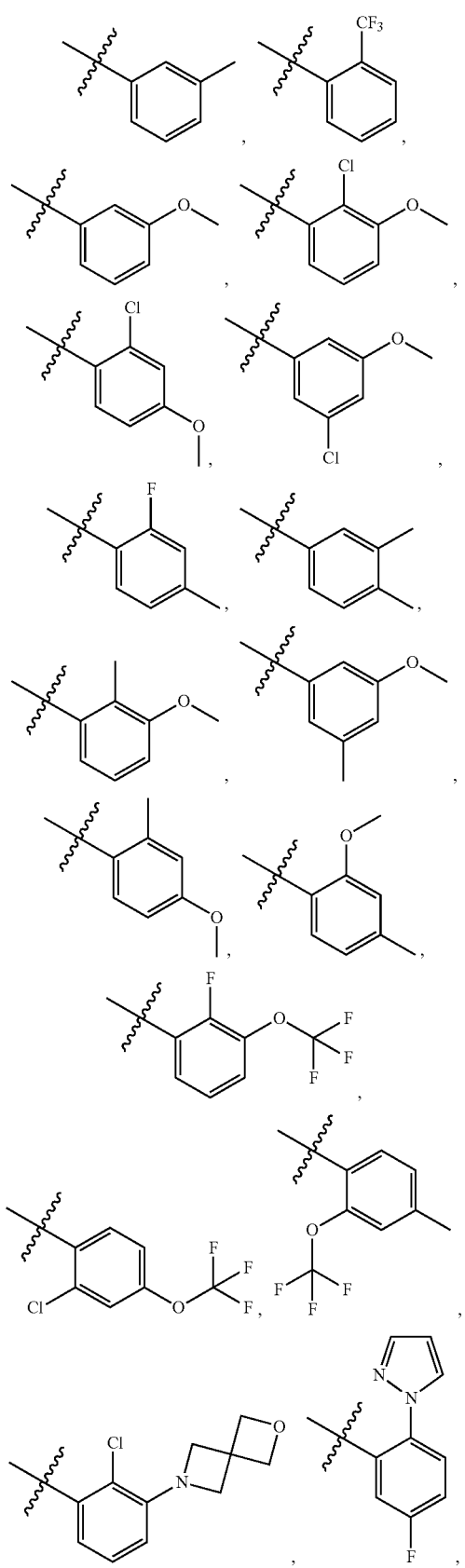
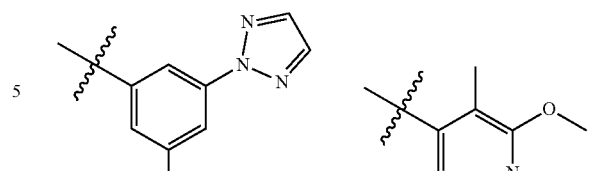
In some embodiments, $R^{1a}$ is $CH_3$ and $R^2$ is
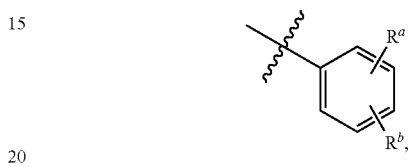
wherein $R^a$ is Cl, or F, and $R^b$ is $OC_{1-4}$alkyl. In some embodiments, $R^2$ is
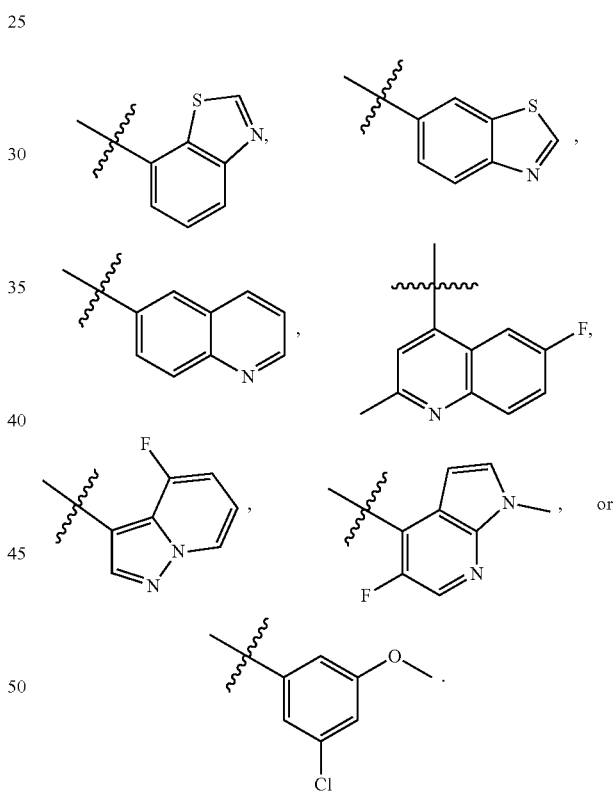
In some embodiments, $R^2$ is
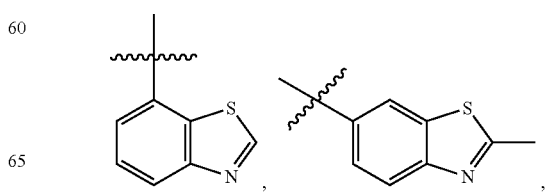

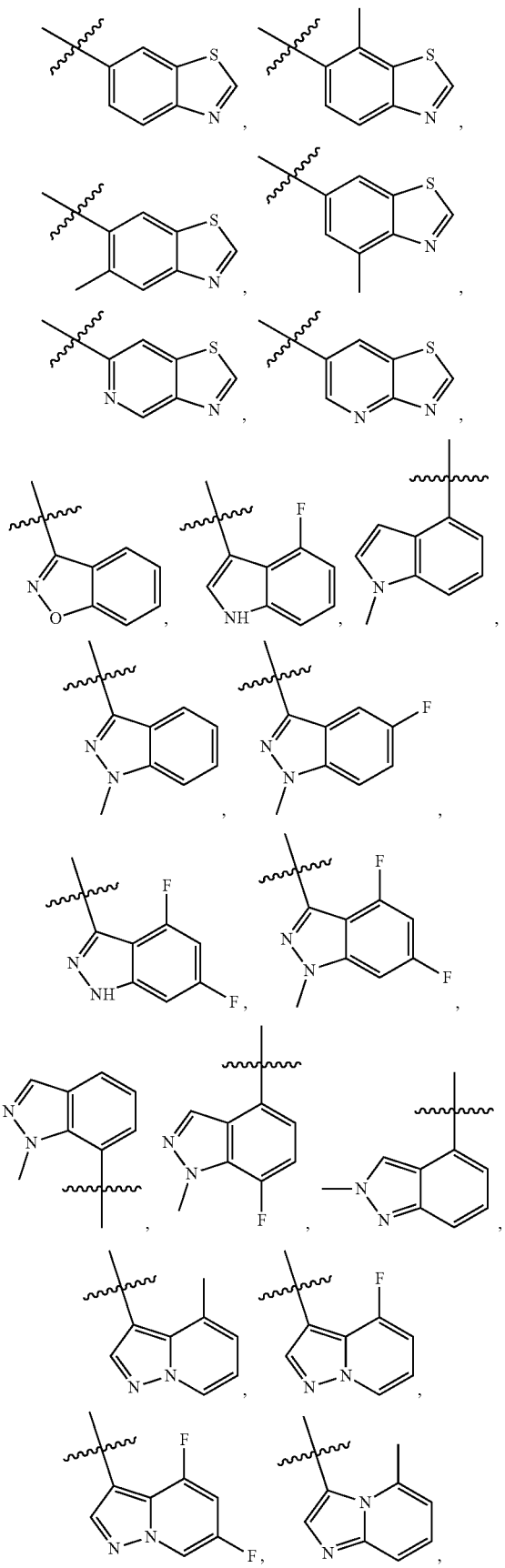
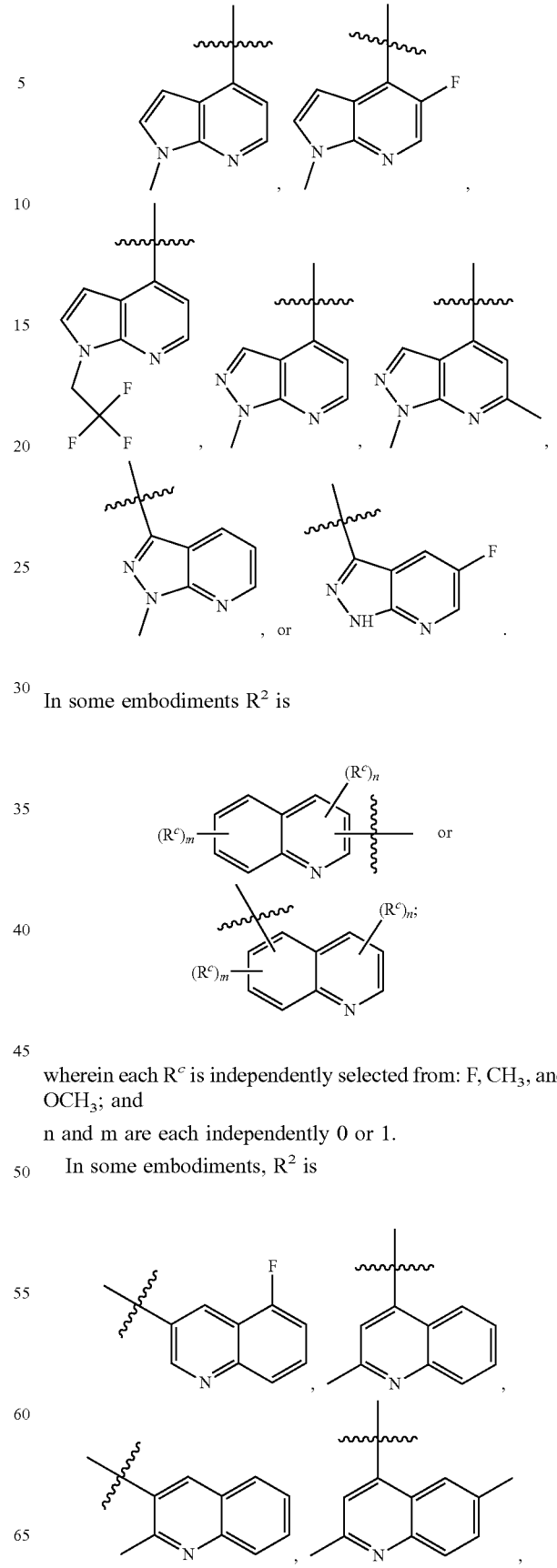
In some embodiments $R^2$ is
wherein each $R^c$ is independently selected from: F, $CH_3$, and $OCH_3$; and
n and m are each independently 0 or 1.
In some embodiments, $R^2$ is -continued

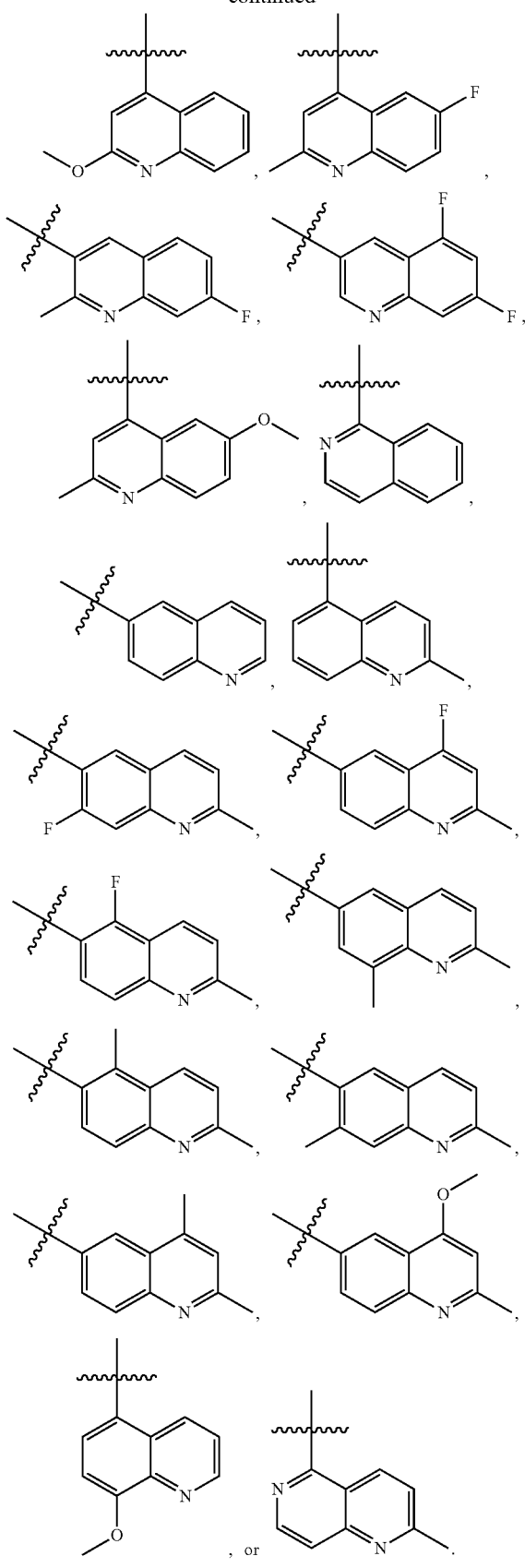

In some embodiments, $R^{1a}$ is $C_{1-4}$alkyl and $R^2$ is

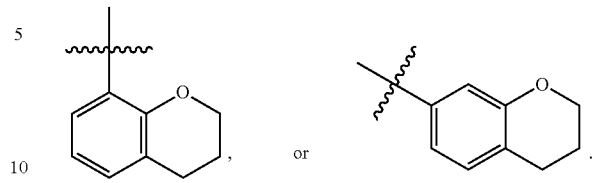

In some embodiments, $R^{1a}$ and $R^{1b}$ come together to form —$CH_2CH_2CH_2$—; and $R^2$ is

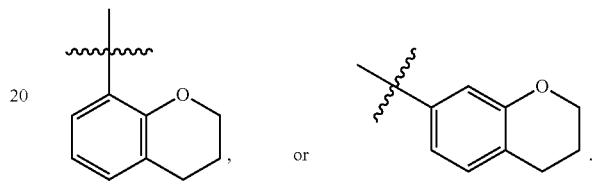

In some embodiments, $R^2$ is phenyl or pyridyl, each optionally substituted with one or two substituents selected from halo, $C_{1-4}$alkyl, $C_{1-4}$haloalkyl, $OC_{1-4}$alkyl, $OC_{1-4}$haloalkyl, N-linked monocyclic or bicyclic heterocycloalkyl, monocyclic heteroaryl, and $C_{3-6}$cycloalkyl, or two adjacent ring substituents taken together with the carbons to which they are attached form a monocyclic cycloalkyl or hetercycloalkyl ring. In some embodiments, $R^2$ is bicyclic heteroaryl optionally substituted with one or two substituents selected from halo, $C_{1-4}$alkyl, $C_{1-4}$haloalkyl, $OC_{1-4}$alkyl, $OC_{1-4}$haloalkyl, N-linked monocyclic or bicyclic heterocycloalkyl, monocyclic heteroaryl, and $C_{3-6}$cycloalkyl. In some embodiments, $R^2$ is bicyclic heteroaryl optionally substituted with one or two substituents selected from halo, $C_{1-4}$alkyl, $C_{1-4}$haloalkyl, $OC_{1-4}$alkyl, and $OC_{1-4}$haloalkyl. In some embodiments, $R^2$ is bicyclic heteroaryl optionally substituted with one or two substituents selected from halo and $C_{1-4}$alkyl.

In some embodiments, $R^3$ is

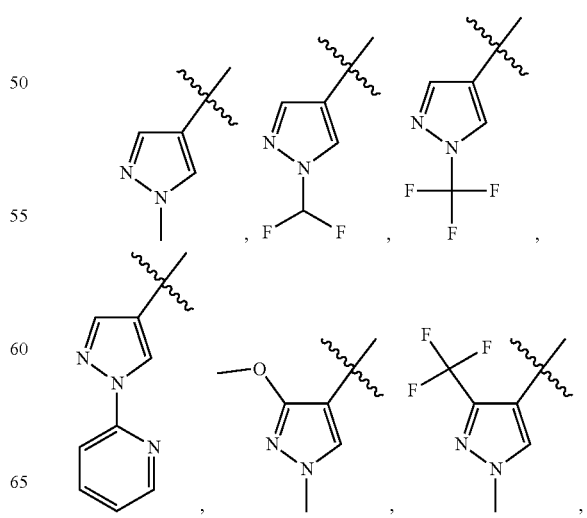

-continued

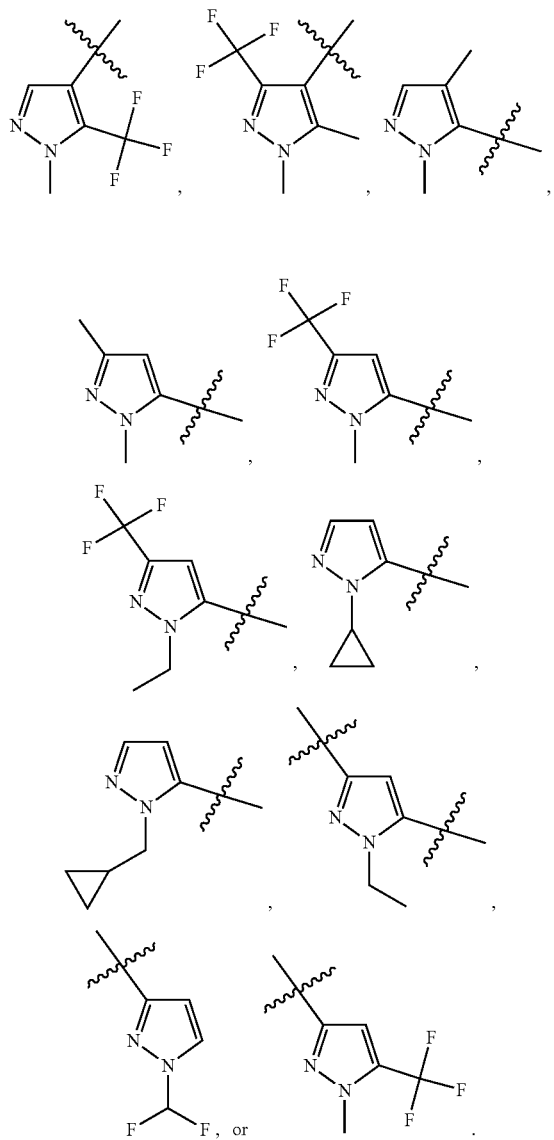

In some embodiments, R³ is

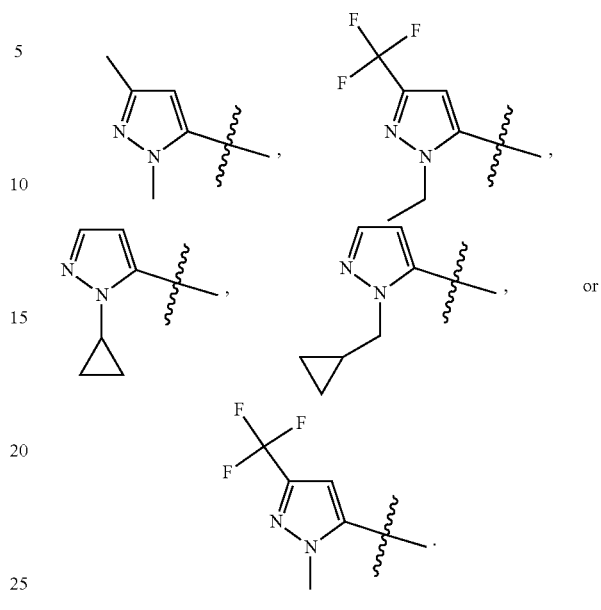

In some embodiments, R³ is

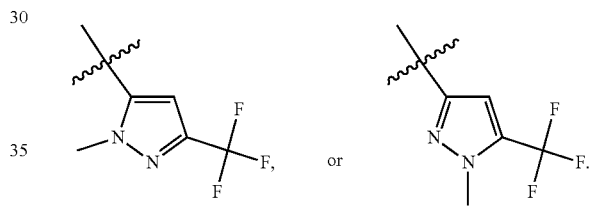

In some embodiments, R³ is 1H—C$_{1-4}$haloalkyl-pyrazolyl, 1H-pyridyl-pyrazolyl, 1H—(C$_{3-6}$cycloalkyl)-pyrazolyl, or 1H—(C$_{3-6}$cycloalkyl-methyl)-pyrazolyl, each pyrazolyl optionally substituted with halo, C$_{1-4}$alkyl, C$_{1-4}$haloalkyl, OC$_{1-4}$alkyl, or OC$_{1-4}$haloalkyl. In some embodiments, R³ is 1H—C$_{1-4}$alkyl-pyrazolyl, 1H—C$_{1-4}$haloalkyl-pyrazolyl, 1H-pyridyl-pyrazolyl, 1H—(C$_{3-6}$cycloalkyl)-pyrazolyl, or 1H—(C$_{3-6}$cycloalkyl-methyl)-pyrazolyl, each pyrazolyl optionally substituted with halo, C$_{1-4}$alkyl, C$_{1-4}$haloalkyl, OC$_{1-4}$alkyl, or OC$_{1-4}$haloalkyl; and R$^{1a}$ and R$^{1b}$ taken together form —CH$_2$CH$_2$— or —CH$_2$CH$_2$CH$_2$—. In some embodiments, R³ is 1H—C$_i$-4alkyl-pyrazolyl or 1H—C$_{1-4}$haloalkyl-pyrazolyl, each pyrazolyl substituted with halo, C$_{1-4}$alkyl, C$_{1-4}$haloalkyl, OC$_{1-4}$alkyl, or OC$_{1-4}$ haloalkyl. In some embodiments, R³ is 1H-pyridyl-pyrazolyl, 1H—(C$_{3-6}$cycloalkyl)-pyrazolyl, or 1H—(C$_{3-6}$cycloalkyl-methyl)-pyrazolyl, each pyrazolyl optionally substituted with halo, C$_{1-4}$alkyl, C$_{1-4}$haloalkyl, OC$_{1-4}$alkyl, or OC$_{1-4}$haloalkyl. In some embodiments, R³ is 1H-pyrazol-3-yl, 1H-pyrazol-4-yl, or 1H-pyrazol-5-yl, each optionally substituted as described herein. In some embodiments, R³ is 1H-pyrazol-3-yl or 1H-pyrazol-4-yl, each optionally substituted as described herein.

In some embodiments, n is 1 or 2. In some embodiments, m is 1 or 2. In some embodiments, m and n are each 1.

A further embodiment of the current invention is a compound as shown below in Table 1.

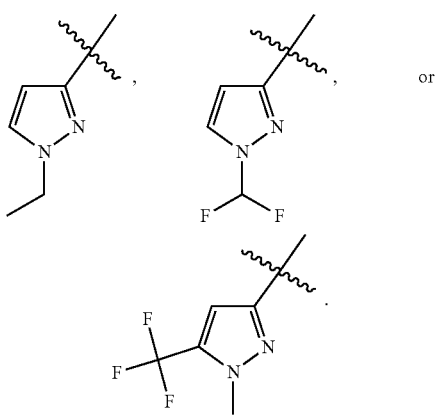

TABLE 1

| Ex # | Compound Name |
|---|---|
| 1 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-5-yl)methanone; |
| 2 | (S)-(3-(1,4-Dimethyl-1H-pyrazol-5-yl)-2,7-dimethyl-2,4,5,7-tetrahydro-6H-pyrazolo[3,4-c]pyridin-6-yl)(3-methoxy-2-methylphenyl)methanone; |
| 3 | (S)-(3-(1,5-Dimethyl-3-(trifluoromethyl)-1H-pyrazol-4-yl)-2,7-dimethyl-2,4,5,7-tetrahydro-6H-pyrazolo[3,4-c]pyridin-6-yl)(3-methoxy-2-methylphenyl)methanone; |
| 4 | (S)-(2-Chloro-3-(2-oxa-6-azaspiro[3.3]heptan-6-yl)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 5 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-1H-indol-3-yl)methanone; |
| 6 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indazol-3-yl)methanone; |
| 7 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylpyrazolo[1,5-a]pyridin-3-yl)methanone; |
| 8 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylimidazo[1,2-a]pyridin-3-yl)methanone; |
| 9 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-4-yl)methanone; |
| 10 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methylquinolin-4-yl)methanone; |
| 11 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoropyrazolo[1,5-a]pyridin-3-yl)methanone; |
| 12 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-(2,2,2-trifluoroethyl)-1H-pyrrolo[2,3-b]pyridin-4-yl)methanone; |
| 13 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-3-yl)methanone; |
| 14 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-methoxyquinolin-5-yl)methanone; |
| 15 | (S)-(1,6-Dimethyl-1H-pyrazolo[3,4-b]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 16 | (S)-(3-(3-Methoxy-1-methyl-1H-pyrazol-4-yl)-2,7-dimethyl-2,4,5,7-tetrahydro-6H-pyrazolo[3,4-c]pyridin-6-yl)(quinolin-6-yl)methanone; |
| 17 | (S)-(4,6-Difluoropyrazolo[1,5-a]pyridin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 18 | (S)-(5,7-Difluoroquinolin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 19 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-fluoropyrazolo[1,5-a]pyridin-3-yl)methanone; |
| 20 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxyquinolin-4-yl)methanone; |
| 21 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-1-methyl-1H-indazol-4-yl)methanone; |
| 22 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-indazol-3-yl)methanone; |
| 23 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-2H-indazol-4-yl)methanone; |
| 24 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-3-yl)methanone; |
| 25 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,6-dimethylquinolin-4-yl)methanone; |
| 26 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-methoxy-2-methylquinolin-4-yl)methanone; |
| 27 | (S)-(4,6-Difluoro-1-methyl-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 28 | (S)-(4,6-Difluoro-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 29 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-(trifluoromethyl)phenyl)methanone; |

TABLE 1-continued

| Ex # | Compound Name |
|---|---|
| 30 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-fluoro-4-methylphenyl)methanone; |
| 31 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-indazol-7-yl)methanone; |
| 32 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrazolo[3,4-b]pyridin-4-yl)methanone; |
| 33 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2,8-dimethylquinolin-6-yl)methanone; |
| 34 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(6-fluoro-2-methylquinolin-4-yl)methanone; |
| 35 | (S)-(2-Chloro-3-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 36 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxy-2-methylphenyl)methanone; |
| 37 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-(1H-pyrazol-1-yl)phenyl)methanone; |
| 38 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxyphenyl)methanone; |
| 39 | (S)-(3-Chloro-5-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 40 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylphenyl)methanone; |
| 41 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxy-4-methylphenyl)methanone; |
| 42 | (S)-(2-Chloro-4-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 43 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3,4-dimethylphenyl)methanone; |
| 44 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(isoquinolin-1-yl)methanone; |
| 45 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indol-4-yl)methanone; |
| 46 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrrolo[2,3-b]pyridin-4-yl)methanone; |
| 47 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-pyrrolo[2,3-b]pyridin-4-yl)methanone; |
| 48 | (S)-(2-Chloro-3-methoxyphenyl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 49 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrrolo[2,3-b]pyridin-4-yl)methanone; |
| 50 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(3-methyl-5-(2H-1,2,3-triazol-2-yl)phenyl)methanone; |
| 51 | (S)-(2-Chloro-3-methoxyphenyl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 52 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrrolo[2,3-b]pyridin-4-yl)methanone; |
| 53 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(3-methyl-5-(2H-1,2,3-triazol-2-yl)phenyl)methanone; |
| 54 | (S)-Chroman-8-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 55 | (S)-Chroman-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 56 | (S)-Benzo[d]thiazol-6-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 57 | (S)-Benzo[d]thiazol-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 58 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylbenzo[d]thiazol-6-yl)methanone; |
| 59 | (S)-Benzo[d]thiazol-6-yl(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 60 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-methoxy-3-methylpyridin-4-yl)methanone; |

TABLE 1-continued

| Ex # | Compound Name |
|---|---|
| 61 | (S)-Chroman-7-yl(2,7-dimethyl-3-(1-methyl-3-(trifluoromethyl)-1H-pyrazol-4-yl)-2,4,5,7-tetrahydro-6H-pyrazolo[3,4-c]pyridin-6-yl)methanone; |
| 62 | (S)-(2,7-Dimethyl-3-(1-methyl-1H-pyrazol-4-yl)-2,4,5,7-tetrahydro-6H-pyrazolo[3,4-c]pyridin-6-yl)(quinolin-6-yl)methanone; |
| 63 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(quinolin-6-yl)methanone; |
| 64 | (S)-(2,7-Dimethyl-3-(1-(trifluoromethyl)-1H-pyrazol-4-yl)-2,4,5,7-tetrahydro-6H-pyrazolo[3,4-c]pyridin-6-yl)(quinolin-6-yl)methanone; |
| 65 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(quinolin-6-yl)methanone; |
| 66 | (S)-(3-(1-Ethyl-1H-pyrazol-3-yl)-2,7-dimethyl-2,4,5,7-tetrahydro-6H-pyrazolo[3,4-c]pyridin-6-yl)(quinolin-6-yl)methanone; |
| 67 | (S)-(3-(1-(Difluoromethyl)-1H-pyrazol-3-yl)-2,7-dimethyl-2,4,5,7-tetrahydro-6H-pyrazolo[3,4-c]pyridin-6-yl)(quinolin-6-yl)methanone; |
| 68 | (S)-(3-(1-Cyclopropyl-1H-pyrazol-5-yl)-2,7-dimethyl-2,4,5,7-tetrahydro-6H-pyrazolo[3,4-c]pyridin-6-yl)(quinolin-6-yl)methanone; |
| 69 | (S)-(3-(1-(Difluoromethyl)-1H-pyrazol-4-yl)-2,7-dimethyl-2,4,5,7-tetrahydro-6H-pyrazolo[3,4-c]pyridin-6-yl)(quinolin-6-yl)methanone; |
| 70 | (S)-(2,7-Dimethyl-3-(1-(pyridin-2-yl)-1H-pyrazol-4-yl)-2,4,5,7-tetrahydro-6H-pyrazolo[3,4-c]pyridin-6-yl)(quinolin-6-yl)methanone; |
| 71 | (S)-(3-(1-(Cyclopropylmethyl)-1H-pyrazol-5-yl)-2,7-dimethyl-2,4,5,7-tetrahydro-6H-pyrazolo[3,4-c]pyridin-6-yl)(quinolin-6-yl)methanone; |
| 72 | ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(2-fluoro-4-methylphenyl)methanone; |
| 73 | ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(3-methoxy-2-methylphenyl)methanone; |
| 74 | (3-Methoxy-2-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 75 | Chroman-7-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 76 | ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(m-tolyl)methanone; |
| 77 | (3-Methoxy-5-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 78 | ((5R,9S)-3-(1-Ethyl-3-(trifluoromethyl)-1H-pyrazol-5-yl)-2-methyl-4,5,6,7,8,9-hexahydro-2H-5,9-epiminocycloocta[c]pyrazol-10-yl)(m-tolyl)methanone; |
| 79 | (3-Methoxy-2-methylphenyl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone; |
| 80 | ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(quinolin-6-yl)methanone; |
| 81 | (5-Fluoro-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 82 | (2-Methyl-1,6-naphthyridin-5-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 83 | (5-Fluoroquinolin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 84 | Benzo[d]isoxazol-3-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 85 | (1-Methyl-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 86 | (5-Fluoro-1-methyl-1H-indazol-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 87 | ((5R,9S)-2-Methyl-3-(1-methyl-5-(trifluoromethyl)-1H-pyrazol-3-yl)-4,5,6,7,8,9-hexahydro-2H-5,9-epiminocycloocta[c]pyrazol-10-yl)(quinolin-6-yl)methanone; |
| 88 | (6-Fluoro-2-methylquinolin-4-yl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone; |
| 89 | (3-Methoxy-2-methylphenyl)((5R,8S)-2-methyl-3-(1-methyl-3-(trifluoromethyl)-1H-pyrazol-5-yl)-2,4,5,6,7,8-hexahydro-5,8-epiminocyclohepta[c]pyrazol-9-yl)methanone; |
| 90 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-methylquinolin-6-yl)methanone; |
| 91 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-6-yl)methanone; |

TABLE 1-continued

| Ex # | Compound Name |
|---|---|
| 92 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,5-dimethylquinolin-6-yl)methanone; |
| 93 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,7-dimethylquinolin-6-yl)methanone; |
| 94 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,4-dimethylquinolin-6-yl)methanone; |
| 95 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylquinolin-6-yl)methanone; |
| 110 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methyl-2-(trifluoromethoxy)phenyl)methanone; |
| 112 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-fluoro-3-(trifluoromethoxy)phenyl)methanone; |
| 113 | (S)-(2-Chloro-4-(trifluoromethoxy)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 118 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrazolo[3,4-b]pyridin-4-yl)methanone; |
| 120 | (S)-Benzo[d]thiazol-6-yl(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 121 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxy-3-methylpyridin-4-yl)methanone; and |
| 122 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-6-yl)methanone; |
| 123 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-6-yl)methanone; |
| 132 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(6-fluoro-2-methylquinolin-4-yl)methanone; |
| 133 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methylbenzo[d]thiazol-6-yl)methanone; |
| 134 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylbenzo[d]thiazol-6-yl)methanone; and |
| 135 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylbenzo[d]thiazol-6-yl)methanone; | and pharmaceutically acceptable salts, isotopes, N-oxides, solvates, and stereoisomers thereof.

A further embodiment of the current invention is a compound as shown below in Table 2.

TABLE 2

| Ex # | Compound Name |
|---|---|
| 96 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-2-methylquinolin-6-yl)methanone; |
| 97 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxyquinolin-6-yl)methanone; |
| 98 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methoxy-2-methylquinolin-5-yl)methanone; |
| 99 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-fluoro-8-methoxyquinolin-4-yl)methanone; |
| 100 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-fluoro-8-methylquinolin-4-yl)methanone; |
| 101 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-fluoroisoquinolin-4-yl)methanone; |

TABLE 2-continued

| Ex # | Compound Name |
|---|---|
| 102 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methoxyquinolin-4-yl)methanone; |
| 103 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(5-fluoro-1-methyl-1H-pyrazolo[3,4-b]pyridin-4-yl)methanone; |
| 104 | (S)-(6-(Difluoromethyl)-1-methyl-1H-pyrazolo[3,4-b]pyridin-4-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 105 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrazolo[4,3-c]pyridin-4-yl)methanone; |
| 106 | (S)-(1,6-Dimethyl-1H-pyrazolo[4,3-c]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 107 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrazolo[4,3-b]pyridin-5-yl)methanone; |
| 108 | (S)-(1,6-Dimethyl-1H-pyrazolo[4,3-b]pyridin-5-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 109 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-(trifluoromethoxy)phenyl)methanone; |
| 111 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-3-(trifluoromethoxy)phenyl)methanone; |
| 114 | (S)-(4,6-Difluoro-1-methyl-1H-indazol-3-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 115 | (S)-(4,6-Difluoro-1H-indazol-3-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 116 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-fluoro-4-methylphenyl)methanone; |
| 119 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2,8-dimethylquinolin-6-yl)methanone; |
| 124 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-7-yl)methanone; |
| 125 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-7-yl)methanone; |
| 126 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[5,4-c]pyridin-4-yl)methanone; |
| 127 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-c]pyridin-6-yl)methanone; |
| 128 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-b]pyridin-6-yl)methanone; |
| 129 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-b]pyridin-7-yl)methanone; |
| 130 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-c]pyridin-7-yl)methanone; |
| 131 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[5,4-c]pyridin-4-yl)methanone; |
| 136 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(7-methylbenzo[d]thiazol-6-yl)methanone; |
| 137 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(5-methylbenzo[d]thiazol-6-yl)methanone; and |
| 138 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-methylbenzo[d]thiazol-6-yl)methanone; | and pharmaceutically acceptable salts, isotopes, N-oxides, solvates, and stereoisomers thereof.

A further embodiment of the current invention is a compound as shown below in Table 3.

TABLE 3

| Ex # | Compound Name |
|---|---|
| 1 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-5-yl)methanone; |
| 2 | (S)-(3-(1,4-Dimethyl-1H-pyrazol-5-yl)-2,7-dimethyl-2,4,5,7-tetrahydro-6H-pyrazolo[3,4-c]pyridin-6-yl)(3-methoxy-2-methylphenyl)methanone; |

TABLE 3-continued

| Ex # | Compound Name |
|---|---|
| 3 | (S)-(3-(1,5-Dimethyl-3-(trifluoromethyl)-1H-pyrazol-4-yl)-2,7-dimethyl-2,4,5,7-tetrahydro-6H-pyrazolo[3,4-c]pyridin-6-yl)(3-methoxy-2-methylphenyl)methanone; |
| 4 | (S)-(2-Chloro-3-(2-oxa-6-azaspiro[3.3]heptan-6-yl)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 5 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-1H-indol-3-yl)methanone; |
| 6 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indazol-3-yl)methanone; |
| 7 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylpyrazolo[1,5-a]pyridin-3-yl)methanone; |
| 8 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylimidazo[1,2-a]pyridin-3-yl)methanone; |
| 9 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-4-yl)methanone; |
| 10 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methylquinolin-4-yl)methanone; |
| 11 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoropyrazolo[1,5-a]pyridin-3-yl)methanone; |
| 12 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-(2,2,2-trifluoroethyl)-1H-pyrrolo[2,3-b]pyridin-4-yl)methanone; |
| 13 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-3-yl)methanone; |
| 14 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-methoxyquinolin-5-yl)methanone; |
| 15 | (S)-(1,6-Dimethyl-1H-pyrazolo[3,4-b]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 16 | (S)-(3-(3-Methoxy-1-methyl-1H-pyrazol-4-yl)-2,7-dimethyl-2,4,5,7-tetrahydro-6H-pyrazolo[3,4-c]pyridin-6-yl)(quinolin-6-yl)methanone; |
| 17 | (S)-(4,6-Difluoropyrazolo[1,5-a]pyridin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 18 | (S)-(5,7-Difluoroquinolin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 19 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-fluoropyrazolo[1,5-a]pyridin-3-yl)methanone; |
| 20 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxyquinolin-4-yl)methanone; |
| 21 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-1-methyl-1H-indazol-4-yl)methanone; |
| 22 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-indazol-3-yl)methanone; |
| 23 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-2H-indazol-4-yl)methanone; |
| 24 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-3-yl)methanone; |
| 25 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,6-dimethylquinolin-4-yl)methanone; |
| 26 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-methoxy-2-methylquinolin-4-yl)methanone; |
| 27 | (S)-(4,6-Difluoro-1-methyl-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 28 | (S)-(4,6-Difluoro-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 29 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-(trifluoromethyl)phenyl)methanone; |
| 30 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-fluoro-4-methylphenyl)methanone; |
| 31 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-indazol-7-yl)methanone; |

TABLE 3-continued

| Ex # | Compound Name |
|---|---|
| 32 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrazolo[3,4-b]pyridin-4-yl)methanone; |
| 33 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2,8-dimethylquinolin-6-yl)methanone; |
| 34 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(6-fluoro-2-methylquinolin-4-yl)methanone; |
| 35 | (S)-(2-Chloro-3-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 36 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxy-2-methylphenyl)methanone; |
| 37 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-(1H-pyrazol-1-yl)phenyl)methanone; |
| 38 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxyphenyl)methanone; |
| 39 | (S)-(3-Chloro-5-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 40 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylphenyl)methanone; |
| 41 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxy-4-methylphenyl)methanone; |
| 42 | (S)-(2-Chloro-4-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 43 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3,4-dimethylphenyl)methanone; |
| 44 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(isoquinolin-1-yl)methanone; |
| 45 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indol-4-yl)methanone; |
| 46 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrrolo[2,3-b]pyridin-4-yl)methanone; |
| 47 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-pyrrolo[2,3-b]pyridin-4-yl)methanone; |
| 48 | (S)-(2-Chloro-3-methoxyphenyl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 49 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrrolo[2,3-b]pyridin-4-yl)methanone; |
| 50 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(3-methyl-5-(2H-1,2,3-triazol-2-yl)phenyl)methanone; |
| 51 | (S)-(2-Chloro-3-methoxyphenyl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 52 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrrolo[2,3-b]pyridin-4-yl)methanone; |
| 53 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(3-methyl-5-(2H-1,2,3-triazol-2-yl)phenyl)methanone; |
| 54 | (S)-Chroman-8-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 55 | (S)-Chroman-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 56 | (S)-Benzo[d]thiazol-6-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 57 | (S)-Benzo[d]thiazol-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 58 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylbenzo[d]thiazol-6-yl)methanone; |
| 59 | (S)-Benzo[d]thiazol-6-yl(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; |
| 60 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-methoxy-3-methylpyridin-4-yl)methanone; |
| 61 | (S)-Chroman-7-yl(2,7-dimethyl-3-(1-methyl-3-(trifluoromethyl)-1H-pyrazol-4-yl)-2,4,5,7-tetrahydro-6H-pyrazolo[3,4-c]pyridin-6-yl)methanone; |
| 62 | (S)-(2,7-Dimethyl-3-(1-methyl-1H-pyrazol-4-yl)-2,4,5,7-tetrahydro-6H-pyrazolo[3,4-c]pyridin-6-yl)(quinolin-6-yl)methanone; |

TABLE 3-continued

| Ex # | Compound Name |
|---|---|
| 63 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(quinolin-6-yl)methanone; |
| 64 | (S)-(2,7-Dimethyl-3-(1-(trifluoromethyl)-1H-pyrazol-4-yl)-2,4,5,7-tetrahydro-6H-pyrazolo[3,4-c]pyridin-6-yl)(quinolin-6-yl)methanone; |
| 65 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(quinolin-6-yl)methanone; |
| 66 | (S)-(3-(1-Ethyl-1H-pyrazol-3-yl)-2,7-dimethyl-2,4,5,7-tetrahydro-6H-pyrazolo[3,4-c]pyridin-6-yl)(quinolin-6-yl)methanone; |
| 67 | (S)-(3-(1-(Difluoromethyl)-1H-pyrazol-3-yl)-2,7-dimethyl-2,4,5,7-tetrahydro-6H-pyrazolo[3,4-c]pyridin-6-yl)(quinolin-6-yl)methanone; |
| 68 | (S)-(3-(1-Cyclopropyl-1H-pyrazol-5-yl)-2,7-dimethyl-2,4,5,7-tetrahydro-6H-pyrazolo[3,4-c]pyridin-6-yl)(quinolin-6-yl)methanone; |
| 69 | (S)-(3-(1-(Difluoromethyl)-1H-pyrazol-4-yl)-2,7-dimethyl-2,4,5,7-tetrahydro-6H-pyrazolo[3,4-c]pyridin-6-yl)(quinolin-6-yl)methanone; |
| 70 | (S)-(2,7-Dimethyl-3-(1-(pyridin-2-yl)-1H-pyrazol-4-yl)-2,4,5,7-tetrahydro-6H-pyrazolo[3,4-c]pyridin-6-yl)(quinolin-6-yl)methanone; |
| 71 | (S)-(3-(1-(Cyclopropylmethyl)-1H-pyrazol-5-yl)-2,7-dimethyl-2,4,5,7-tetrahydro-6H-pyrazolo[3,4-c]pyridin-6-yl)(quinolin-6-yl)methanone; |
| 90 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-methylquinolin-6-yl)methanone; |
| 91 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-6-yl)methanone; |
| 92 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,5-dimethylquinolin-6-yl)methanone; |
| 93 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,7-dimethylquinolin-6-yl)methanone; |
| 94 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,4-dimethylquinolin-6-yl)methanone; |
| 95 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylquinolin-6-yl)methanone; |
| 110 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methyl-2-(trifluoromethoxy)phenyl)methanone; |
| 112 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-fluoro-3-(trifluoromethoxy)phenyl)methanone; |
| 113 | (S)-(2-Chloro-4-(trifluoromethoxy)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; |
| 118 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrazolo[3,4-b]pyridin-4-yl)methanone; |
| 120 | (S)-Benzo[d]thiazol-6-yl(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; |
| 121 | (S)-2-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxy-3-methylpyridin-4-yl)methanone; and |
| 122 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-6-yl)methanone; |
| 123 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-6-yl)methanone; |
| 132 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(6-fluoro-2-methylquinolin-4-yl)methanone; |
| 133 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methylbenzo[d]thiazol-6-yl)methanone; |
| 134 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylbenzo[d]thiazol-6-yl)methanone; and |
| 135 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylbenzo[d]thiazol-6-yl)methanone; | and pharmaceutically acceptable salts, isotopes, N-oxides, solvates, and stereoisomers thereof.

A further embodiment of the current invention is a compound as shown below in Table 4.

TABLE 4

| Ex # | Compound Name |
|---|---|
| 72 | ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(2-fluoro-4-methylphenyl)methanone; |
| 73 | ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(3-methoxy-2-methylphenyl)methanone; |
| 74 | (3-Methoxy-2-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 75 | Chroman-7-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 76 | ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(m-tolyl)methanone; |
| 77 | (3-Methoxy-5-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 78 | ((5R,9S)-3-(1-Ethyl-3-(trifluoromethyl)-1H-pyrazol-5-yl)-2-methyl-4,5,6,7,8,9-hexahydro-2H-5,9-epiminocycloocta[c]pyrazol-10-yl)(m-tolyl)methanone; |
| 79 | (3-Methoxy-2-methylphenyl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone; |
| 80 | ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(quinolin-6-yl)methanone; |
| 81 | (5-Fluoro-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 82 | (2-Methyl-1,6-naphthyridin-5-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 83 | (5-Fluoroquinolin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 84 | Benzo[d]isoxazol-3-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 85 | (1-Methyl-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 86 | (5-Fluoro-1-methyl-1H-indazol-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; |
| 87 | ((5R,9S)-2-Methyl-3-(1-methyl-5-(trifluoromethyl)-1H-pyrazol-3-yl)-4,5,6,7,8,9-hexahydro-2H-5,9-epiminocycloocta[c]pyrazol-10-yl)(quinolin-6-yl)methanone; |
| 88 | (6-Fluoro-2-methylquinolin-4-yl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone; and |
| 89 | (3-Methoxy-2-methylphenyl)((5R,8S)-2-methyl-3-(1-methyl-3-(trifluoromethyl)-1H-pyrazol-5-yl)-2,4,5,6,7,8-hexahydro-5,8-epiminocyclohepta[c]pyrazol-9-yl)methanone; | and pharmaceutically acceptable salts, isotopes, N-oxides, solvates, and stereoisomers thereof.

A further embodiment of the current invention is a compound selected from:

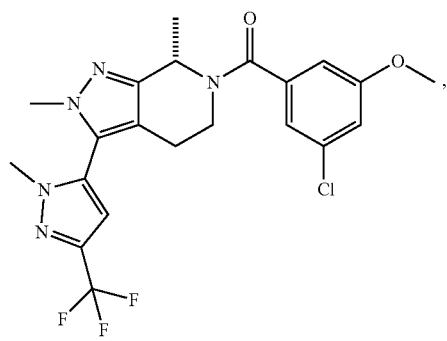

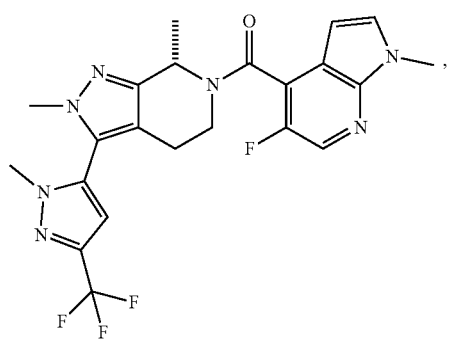

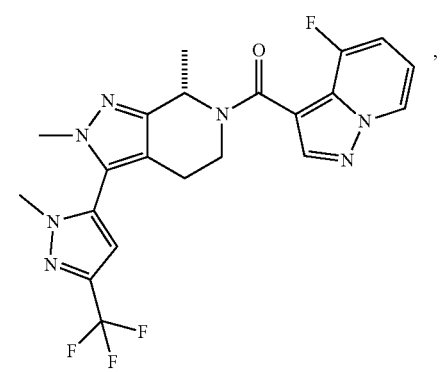

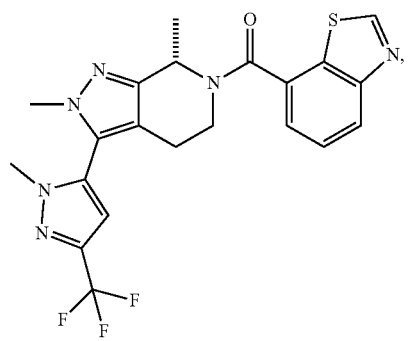

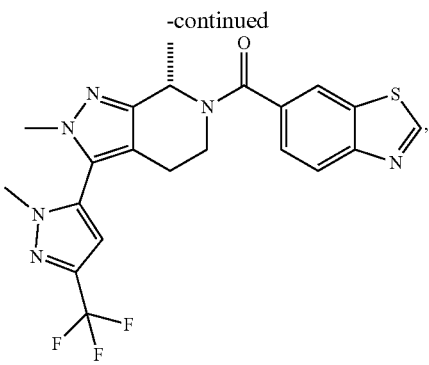

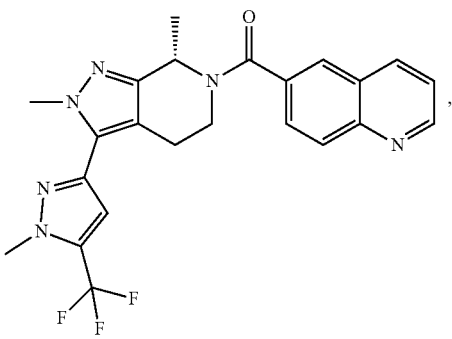

and

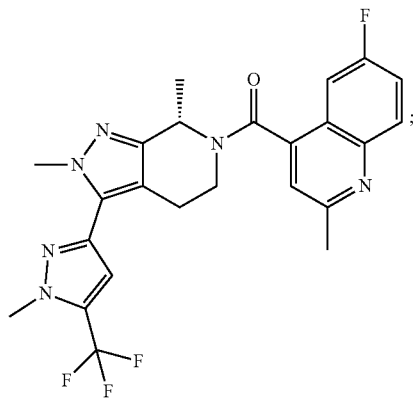

and pharmaceutically acceptable salts, isotopes, N-oxides, solvates, and stereoisomers thereof.

An additional embodiment of the invention is a compound of Formula (I) having the Formula (IA):

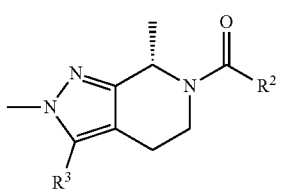

(IA)

wherein
R² is selected from:
(a)
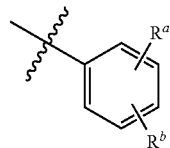 or 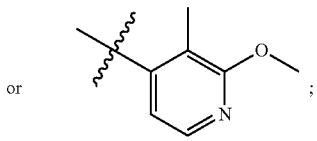;
(b) a 5,6-fused or 6,5-fused heteroaryl selected from:
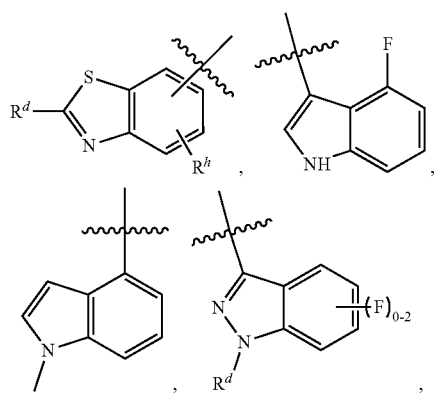
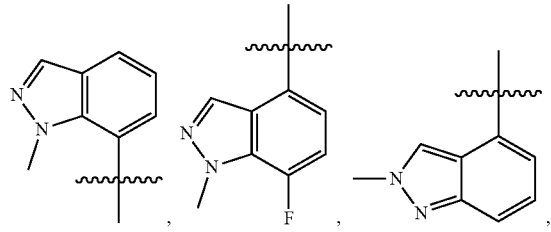
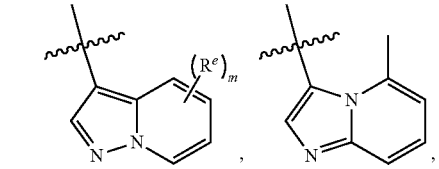
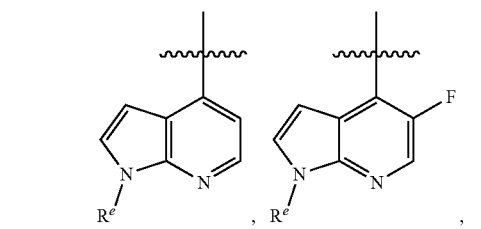
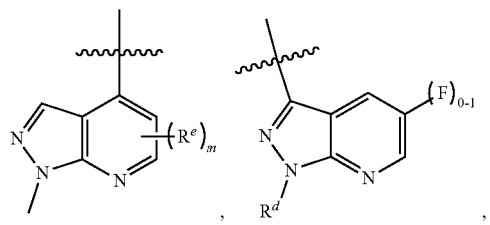
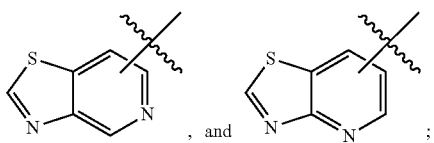, and ;
(c) a fused 6,6-heteroaryl selected from:
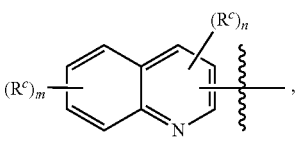
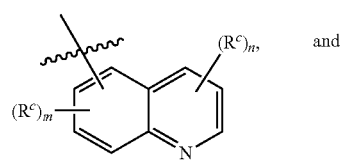 and
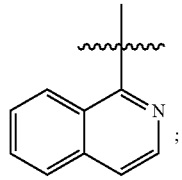;
and
(d)
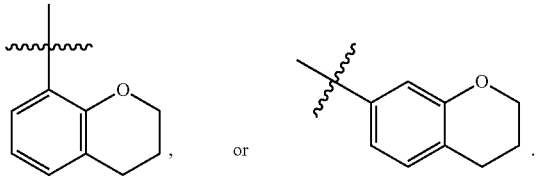 [SMILES: *c1cccc2c1OCCC2 ; *c1ccc2c(c1)OCCC2]
R³ is a 5-membered heteroaryl ring selected from:
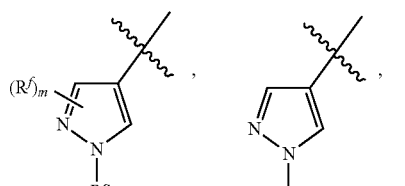
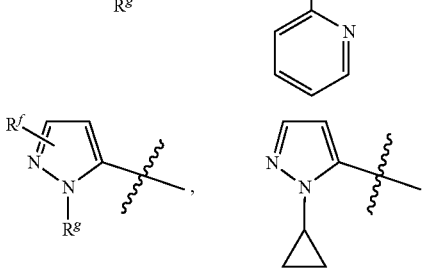

-continued

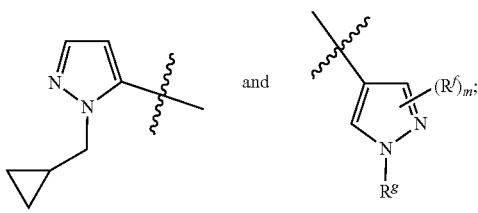

wherein
- $R^a$ is selected from: H, Cl, F, $C_{1-4}$alkyl, and $C_{1-4}$haloalkyl;
- $R^b$ is selected from: $C_{1-4}$alkyl, $C_{1-4}$haloalkyl, $OC_{1-4}$alkyl,

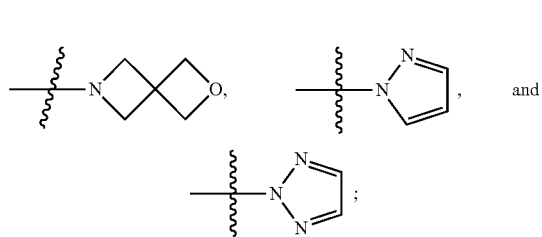

- each $R^c$ is independently selected from: halo, $C_{1-4}$alkyl, and $OCH_3$;
- $R^d$ is H or $CH_3$;
- each $R^e$ is independently F, $C_{1-4}$alkyl, or $C_{1-4}$haloalkyl;
- each $R^f$ is independently selected from: $C_{1-4}$alkyl, $C_{1-4}$haloalkyl, and $OCH_3$; and
- $R^g$ is $C_{1-4}$alkyl or $C_{1-4}$haloalkyl;

n is 0, 1, or 2; and
m is 0, 1, or 2;
or a pharmaceutically acceptable salt, isotope, N-oxide, solvate, or stereoisomer thereof.

In some embodiments of Formula (IA), $R^3$ is

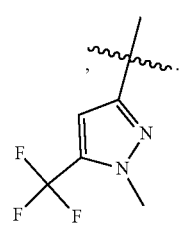

An additional embodiment of the invention is a compound of Formula (I) having the Formula (IB):

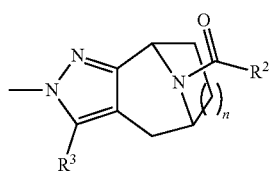

(IB)

wherein
n is 1 or 2;
$R^2$ is selected from:
(a)

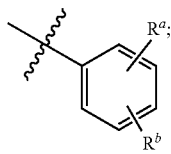

(b)

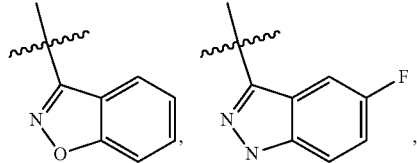

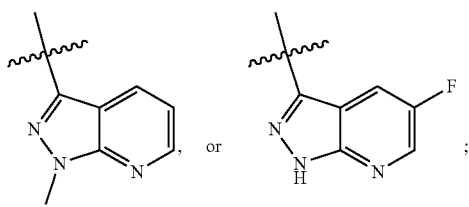

(c)

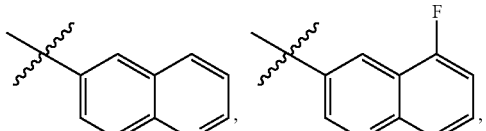

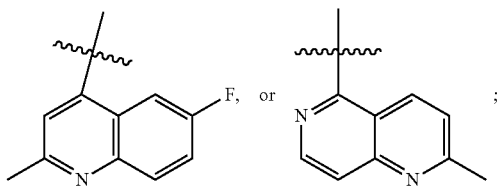

and
(d)

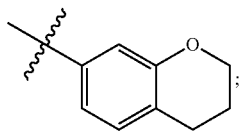 [SMILES: *c1ccc2c(c1)OCCC2]

and
R³ is

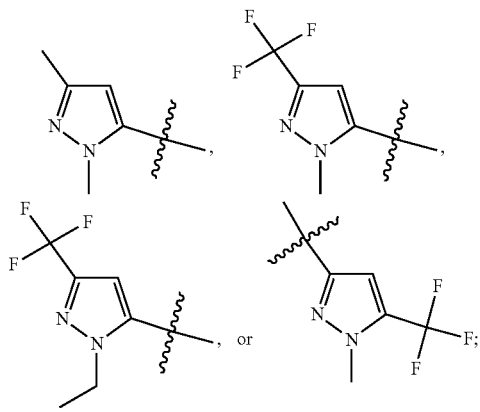

wherein
R^a is H, halo, or C_{1-4}alkyl; and
R^b is C_{1-4}alkyl or OC_{1-4}alkyl;
or a pharmaceutically acceptable salt, isotope, N-oxide, solvate, or stereoisomer thereof.

In some embodiments of Formula (IB), n is 2.

An additional embodiment of the invention is a compound selected from compounds of Formula (I), Formula (IA), and Formula (IB) or a combination thereof.

An additional embodiment of the invention is a pharmaceutical composition comprising:
(A) a therapeutically effective amount of at least one compound selected from compounds of Formula (I) and pharmaceutically acceptable salts, isotopes, N-oxides, solvates, and stereoisomers thereof, and
(B) at least one pharmaceutically acceptable excipient.

An additional embodiment of the invention is a pharmaceutical composition comprising a therapeutically effective amount of at least one compound selected from (a) the compounds in Table 1, (b) the compounds in Table 2, (c) the compounds in Table 3, and (d) the compounds in Table 4, including pharmaceutically acceptable salts, isotopes, N-oxides, solvates, and stereoisomers thereof, pharmaceutically acceptable prodrugs of such compounds, and pharmaceutically active metabolites of such compounds; and at least one pharmaceutically acceptable excipient.

An additional embodiment of the invention is a pharmaceutical composition comprising a therapeutically effective amount of at least one compound selected from compounds of Formula (IA), and pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising a therapeutically effective amount of at least one compound selected from compounds of Formula (IB), and pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

Also within the scope of the invention are enantiomers and diastereomers of the compounds of Formula (I) (as well as Formulas (IA) and (IB)). Also within the scope of the invention are the pharmaceutically acceptable salts, N-oxides or solvates of the compounds of Formula (I) (as well as Formulas (IA) and (IB)). Also within the scope of the invention are the pharmaceutically acceptable prodrugs of compounds of Formula (I) (as well as Formulas (IA) and (IB)), and pharmaceutically active metabolites of the compounds of Formula (I) (as well as Formulas (IA) and (IB)).

Also within the scope of the invention are isotopic variations of compounds of Formula (I) (as well as Formulas (IA) and (IB)), such as, e.g., deuterated compounds of Formula (I). Also within the scope of the invention are the pharmaceutically acceptable salts, N-oxides or solvates of the isotopic variations of the compounds of Formula (I) (as well as Formulas (IA) and (IB)). Also within the scope of the invention are the pharmaceutically acceptable prodrugs of the isotopic variations of the compounds of Formula (I) (Formula (I) (as well as Formulas (IA) and (IB)), and pharmaceutically active metabolites of the isotopic variations of the compounds of Formula (I) (as well as Formulas (IA) and (IB)).

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (I) (as well as Formulas (IA) and (IB)), and pharmaceutically acceptable salts, isotopes, N-oxides, solvates, and stereoisomers thereof, including enantiomers and diastereomers of the compounds of (Formula (I) (as well as Formulas (IA) and (IB)), isotopic variations of the compounds of Formula (I) (Formula (I) (as well as Formulas (IA) and (IB)), and pharmaceutically acceptable salts of all of the foregoing.

Also described herein is the use of a compound of Formula (I), (IA), or (IB), or a pharmaceutically acceptable salt, isotope, N-oxide, solvate, or stereoisomer thereof in the preparation of a medicament. In some embodiments, the medicament is for treatment of a disease, disorder, or condition mediated by MGL receptor activity. Also described herein is a compound of Formula (I), (IA), or (IB), or a pharmaceutically acceptable salt, isotope, N-oxide, solvate, or stereoisomer thereof, for use in a method of treating a disease, disorder, or condition mediated by MGL receptor activity.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following Table 5.

TABLE 5

| Acronym | Term |
|---|---|
| BOC | tert-butyloxycarbonyl |
| Boc₂O | di-tert-butyl dicarbonate |
| μL | Microliter |
| μmol | micromoles |
| ACN, MeCN | Acetonitrile |
| AcOH | Acetic acid |
| Aq, or Aq. | Aqueous |
| atm | Atmosphere |
| BOC | tert-butoxycarbonyl |
| (binaphthyl)P(t-Bu)₂, TrixiePhos | rac-2-(Di-tert-butylphosphino)-1,1'-binaphthyl |
| BOP | benzotriazol-1-yloxy-tris(dimethylamino)phosphonium hexafluorophosphate |
| br | Broad |
| Celite ® | Diatomaceous Earth |
| DCC | N,N'-dicyclohexylcarbodiimide |
| DCE | dichloroethane |
| DCM | dichloromethane |
| DIEA, DIPEA | N-ethyldiisopropylamine |
| DMAP | 4-dimethylaminopyridine |
| DME | dimethoxyethane |
| DMF | dimethylformamide |
| DMSO | Dimethylsulfoxide |
| DPPF | 1,1'-bis(diphenylphosphino)ferrocene |
| EDC, EDAC or EDCI | 1-ethyl-3-(3-dimethylaminopropyl)carbodiimide |
| ESI | Electrospray ionization |
| Ether, Et₂O | Diethyl ether |
| EtOAc, or EA | Ethyl Acetate |
| EtOH | Ethanol |
| FCC | Normal-phase silica gel chromatography |
| g | Grams |
| h, hr, hrs | Hours |
| HAL | Halogen |
| HATU | 1-[bis(dimethylamino)methylene]-1H-1,2,3-triazolo[4,5-b]pyridinium 3-oxid hexafluorophosphate |
| HBTU | N,N,N',N'-tetramethyl-(9-(1H-benzotriazol-1-yl)uronium hexafluorophosphate |
| Hex | hexanes |
| HOBt | hydroxybenzotriazole |
| HPLC | High-pressure liquid chromatography |
| Hz | Hertz |
| iPrOH, IPA | Isopropyl alcohol |
| Ir(ppy)₂(dtbbpy)PF₆ | [4,4'-Bis(1,1-dimethylethyl)-2,2'-bipyridine-N1,N1']bis[2-(2-pyridinyl-N)phenyl-C]iridium(III) hexafluorophosphate |
| Josiphos SL-J009-1 PD G3 | {(R)-1-[(Sp)-2-(Dicyclohexylphosphino)ferrocenyl]ethyldi-tert-butylphosphine}[2-(2'-amino-1,1'-biphenyl)]palladium(II) methanesulfonate |
| KOtBu | Potassium tert-Butoxide |
| LCMS | Liquid chromatography and mass spectrometry |
| LiHMDS/LHMDS | lithium bis(trimethylsilyl)amide |
| M | Molar |
| m/z | Mass to charge ratio |
| mCPBA | 3-chloroperoxybenzoic acid |
| Me | methyl |
| MeOH | Methanol |
| mg | Milligrams |
| min | Minute |
| mL | Milliliter |
| mmol | Millimoles |
| MS | Mass spectrometry |
| MTBE, or TBME | tert-butyl methyl ether |
| N | Normal |
| NMR | Nuclear magnetic resonance |
| NaOAc tri-hydrate | Sodium acetate trihydrate |
| OTf | CF₃SO₃— or triflate |
| PhenoFluor ™ | N,N'-,3-Bis(2,6-diisopropylphenyl)-2,2-difluoroimidazolidene |
| Pd(PPh₃)₂Cl₂ | palladium(II)bis(triphenylphosphine) dichloride |
| Pd(PPh₃)₄ | tetrakis(triphenylphosphine)palladium(0) |
| PdCl₂(dppf) | [1,1'-bis(diphenylphosphino)ferrocene]dichloropalladium(II) |
| PdCl₂(dtbpf) | [1,1'-bis(di-tert-butylphosphino)ferrocene]dichloropalladium(II) |
| Pd(TFA)₂ | trifluoroacetic acid palladium(II) salt |
| Pd₂(dba)₃ | tris(dibenzylidene)dipalladium(0) |
| Pd(t-Bu₃P)₂ | bis(tri-tert-butylphosphine)palladium(0) |
| PG | Protecting group |
| ppm | Parts per million |
| ppt | Precipitate |
| PTFE | Polytetrafluoroethylene |

TABLE 5-continued

| Acronym | Term |
|---|---|
| PyBroP ® | bromotripyrrolidinophosphonium hexafluorophosphate |
| RP | Reverse Phase |
| $R_t$ | Retention time |
| rt | Room temperature |
| sat | Saturated |
| SFC | Supercritical Fluid Chromatography |
| T | Temperature |
| T3P ® | 2,4,6-tripropyl-1,3,5,2,4,6-trioxatriphosphorinane-2,4,6-trioxide |
| TEA | triethylamine |
| Tf$_2$NPh | A-phenylbis(trifluoromethanesufonimide |
| Tf$_2$O | trifluoromethanesulfonic anhydride |
| TFA | trifluoroacetic acid |
| THF | tetrahydrofuran |
| TLC | Thin layer chromatography |
| triflate | trifluoromethanesulfonyl |
| V, or volumes | Volume in milliliters of solvent per gram of substrate |
| XPhos-Pd-G2 precatalyst | chloro(2-dicyclohexylphosphino-2',4',6'-triisopropyl-1,1'-biphenyl)[2-(2'-amino-1,1'-biphenyl)]palladium(II) |

PREPARATIVE EXAMPLES

Exemplary compounds useful in methods of the invention will now be described by reference to the illustrative synthetic schemes for their general preparation below and the specific examples to follow.

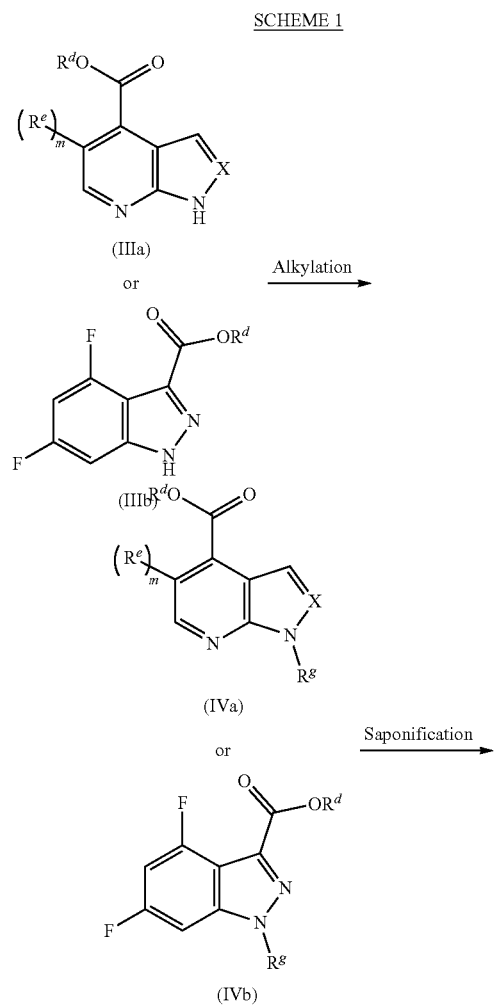

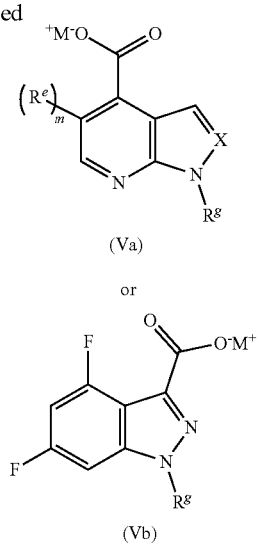

According to SCHEME 1 compounds of formula (IIIa) or (IIIb), where $R^e$ is F, m is 0 or 1, $R^d$ is H or C$_{1-4}$alkyl, and X is CH or N, are alkylated using a suitable reagent such as iodomethane, 2,2,2-trifluoroethyl trifluoromethanesulfonate, and the like; a suitable base such as NaH, potassium carbonate, and the like; in a suitable solvent such as DMF, and the like; at a suitable temperature such as 0° C. or rt to provide compounds of formula (IVa) or (IVb) where $R^g$ is C$_{1-4}$alkyl or C$_{1-4}$haloalkyl. Hydrolysis of the methyl ester is achieved employing conditions known to one skilled in the art, using a suitable base such as NaOH, LiOH, (CH$_3$)$_3$SiOK, and the like; in a suitable solvent such as THF; a suitable temperature of 60° C. for a period of 24 h; to provide compounds of formula (Va) or (Vb) where M is potassium, Na, or Li, preferably potassium.

SCHEME 2

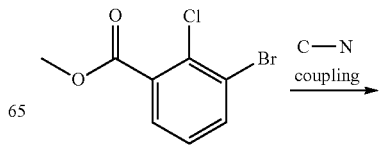

-continued

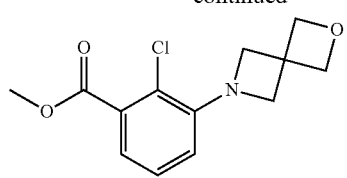

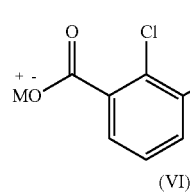

(VI)

According to SCHEME 2, a commercially available or synthetically accessible methyl 3-bromo-2-chlorobenzoate is reacted with a palladium precatalyst such as Josiphos SL-J009-1 PD G3 and the like; a base such as cesium carbonate, and the like; an amine such as 2-oxa-6-azaspiro [3.3]heptane, and the like, in a suitable solvent such as DME, at a temperature of 70° C., for a period of 1 h to provide methyl 2-chloro-3-(2-oxa-6-azaspiro[3.3]heptan-6-yl)benzoate. Hydrolysis of the methyl ester of methyl 2-chloro-3-(2-oxa-6-azaspiro[3.3]heptan-6-yl)benzoate employing conditions previously described provides a compound of formula (VI) where M is potassium.

SCHEME 3

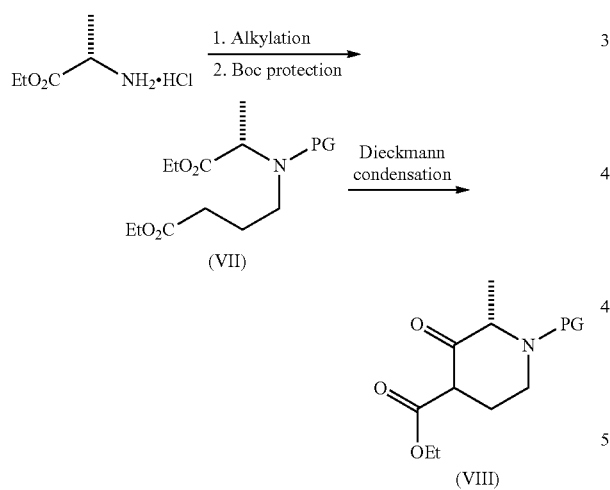

(VIII)

According to SCHEME 3, a compound of formula (VII) is prepared in two steps from ethyl L-alaninate hydrochloride. In a first step, ethyl L-alaninate hydrochloride is alkylated with ethyl 4-bromobutanoate; employing potassium iodide; a suitable base such as dibasic potassium phosphate. In a second step, BOC protection employing established methodologies, provides a compound of formula (VII). Cyclization under Dieckmann condensation conditions of a compound of formula (VII), where PG is BOC, using a suitable base such as LiHMDS or potassium tert-butoxide; in a suitable solvent such as tetrahydrofuran and the like; at temperatures between −40° C. to 20° C.; provides a keto-ester compound of formula (VIII).

SCHEME 4

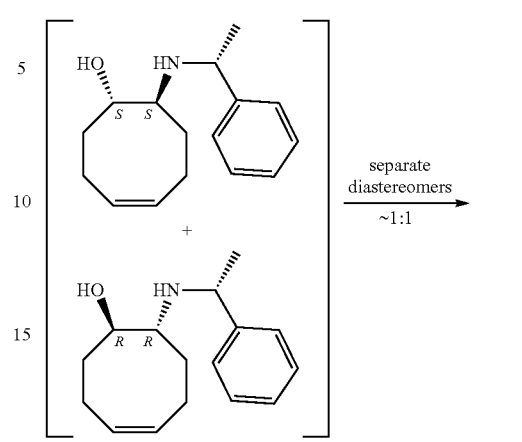

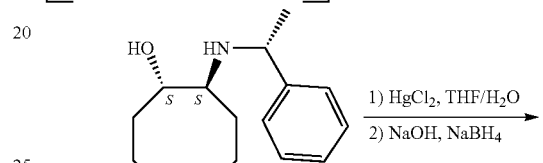

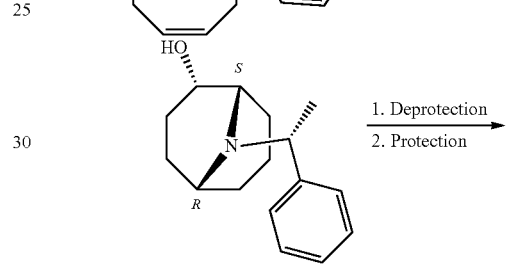

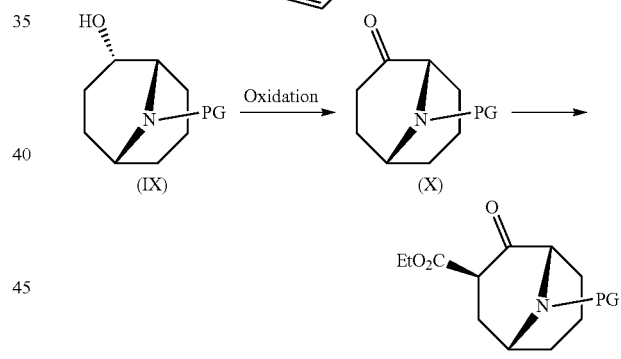

According to SCHEME 4, (1S,8S)-(+)-trans-8-[(R)-phenylethylamino)cyclooct-4-enol and (1R,8R)-(−)-trans-8-[(R)-phenylethylamino]cyclooct-4-enol are prepared according to methods as described in "Synthesis and Pharmacological Characterization of Nicotinic Acetylcholine Receptor Properties of (+)- and (−)-Pyrido-[3,4-b]homotropanes", Journal of Medicinal Chemistry, 49(11), 3244-3250; 2006.

(1S,8S,Z)-8-(((R)-1-phenylethyl)amino)cyclooct-4-en-1-ol is converted to (1S,2S,5R)-9-((R)-1-phenylethyl)-9-azabicyclo[3.3.1]nonan-2-ol in two steps. In a first step, reaction of (1S,8S,Z)-8-(((R)-1-phenylethyl)amino)cyclooct-4-en-1-ol with mercury(II) chloride, in a suitable solvent such as diethyl ether, tetrahydrofuran, dioxane, water, or a mixture thereof, at room temperature, for a period of 12-24 h, provides a mercurial chloride complex at the alkenyl moiety. In a second step, reduction of the aforementioned mercurial chloride complex is accomplished by reaction with 3 M sodium hydroxide, and a reducing agent such as sodium borohydride, at a temperature of about 0° C., to provide the cyclized (1S,2S,5R)-9-((R)-1-phenylethyl)-9-azabicyclo[3.3.1]nonan-2-ol product.

The chiral (R)-methylbenzyl is deprotected employing hydrogenation conditions known to one skilled in the art and employing established methodologies. For example, employing $H_2$ in the presence of a catalyst such as Pd/C, and the like, in a suitable solvent such as MeOH, and the like, to provide (1S,2S,5R)-9-azabicyclo[3.3.1]nonan-2-ol.

The amine moiety of (1S,2S,5R)-9-azabicyclo[3.3.1]nonan-2-ol is protected with a carbamate protecting group such as tert-butyloxycarbonyl (BOC). For example, reaction of (1S,2S,5R)-9-azabicyclo[3.3.1]nonan-2-ol, with BOC-anhydride, at room temperature, for a period of about 4-7 h, provides a compound of formula (IX), where PG is BOC.

A compound of formula (IX) is converted to compound of Formula (X) under oxidative conditions, such as Swern (Moffott-Swern) oxidation. For example, a compound of formula (IX) is treated with DMSO, oxalyl chloride, triethylamine, in a suitable solvent such as DCM, and the like, to provide a compound of formula (X). In a preferred method, the reaction is run initially at −78° C. and then warmed to room temperature and stirred overnight.

A compound of formula (X) is converted to compound (XI) by treatment with a strong base such as lithium bis(trimethylsilyl)amide (LiHMDS/LTHMDS), and the like, in a suitable solvent such as THF, and the like, at a temperature of about −78° C., for a period of about 30 minutes. The resulting lithium enolate is trapped by methyl or ethyl cyanoformate, at a temperature of about −78° C., for a period of 1-3 h, to furnish the β-keto ester compound of formula (XI), where PG is BOC.

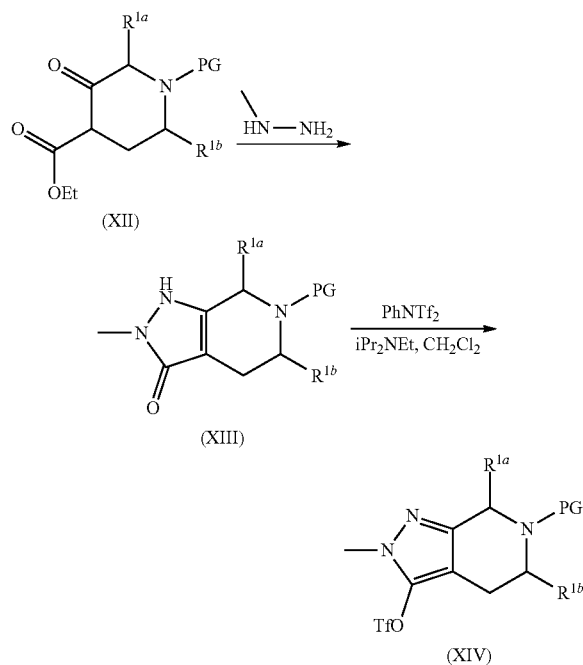

According to SCHEME 5, a commercially available or synthetically accessible compound of formula (XII) (which includes compounds of formula (VIII) and (XI)), where $R^{1a}$ is $CH_3$, or $R^{1a}$ and $R^{1b}$ come together to form —$CH_2CH_2CH_2$—, and PG is BOC (tert-butyloxycarbonyl); is reacted with methyl hydrazine in AcOH, at a temperature of about 80° C., to provide a compound of formula (XIII). Alternatively, a commercially available or synthetically accessible compound of formula (XII), where PG is BOC (tert-butyloxycarbonyl) is reacted with methyl hydrazine in a suitable solvent such as toluene or ethanol with a suitable base such as DIEA, at a temperature of between 80 and 110° C., to provide a compound of Formula (XIII).

Derivation of a compound of formula (XIII) with a sulfonate-based leaving group such as trifluoromethanesulfonyl (triflate) is achieved by is by reaction with a triflating agent such as trifluoromethanesulfonic anhydride ($Tf_2O$); a base such as triethylamine (TEA), pyridine, N-ethyldiisopropylamine (DIEA, DIPEA), and the like; in a suitable solvent such as DCM and the like. Milder triflating agents such as N-phenylbis(trifluoromethanesulfonimide) ($Tf_2NPh$), a base such as TEA, DIEA, and the like, in a suitable solvent such as DCM, and the like; are used for better selectivity, to provide a compound of formula (XIV).

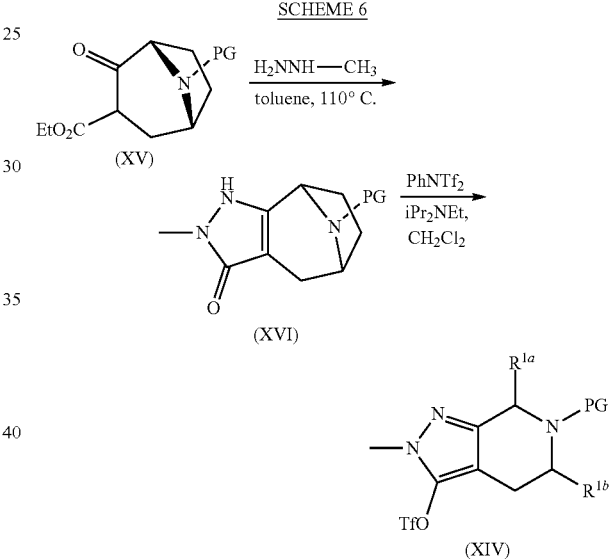

According to SCHEME 6, a compound of formula (XVI) is prepared in a manner as described in J. Org. Chem. 2002, 67, 3479-3486, where PG is BOC. A keto-ester compound of formula (XV), is reacted with a commercially available or synthetically accessible methylhydrazine, in an inert solvent such as toluene, and the like, at a temperature of about 100° C., to provide a compound of formula (XVI), where PG is Boc.

Derivation of a compound of formula (XVI), with a sulfonate-based leaving group such as trifluoromethanesulfonyl (triflate), is achieved by is by reaction with a triflating agent such as trifluoromethanesulfonic anhydride ($Tf_2O$), a base such as triethylamine (TEA), pyridine, and the like, in a suitable solvent such as DCM and the like. Milder triflating agents such as N-phenylbis(trifluoromethanesulfonimide) ($Tf_2NPh$), a base such as TEA, DIEA, and the like, in a suitable solvent such as DCM, and the like; are used for better selectivity, to provide a compound of formula (XIV), where $R^{1a}$ and $R^{1b}$ come together to form —$CH_2CH_2$—, and PG is BOC. Single enantiomers were isolated by Chiral SFC purification.

SCHEME 7

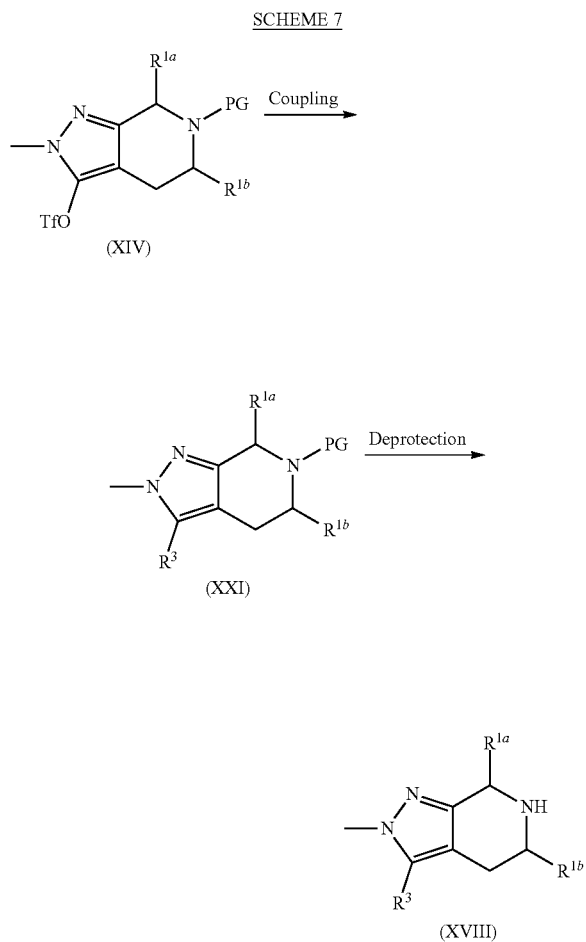

(XIV)

(XXI)

(XVIII)

According to SCHEME 7, a compound of formula (XIV) where $R^{1a}$ is $CH_3$, or $R^{1a}$ and $R^{1b}$ come together to form —$CH_2CH_2$—, or —$CH_2CH_2CH_2$—, and PG is BOC; is reacted in a metal mediated cross coupling reaction with a heteroaryl boronic acid, or boronate ester to provide a compound of formula (XVII) where PG is BOC. For example, a compound of formula (XIV), is reacted with a suitably substituted commercially available or synthetically accessible 5-membered heteroaryl boronic acid, boronate ester, and the like, in the presence of a palladium catalyst such as [1,1'-bis(di-tert-butylphosphino)ferrocene]dichloropalladium(II) (PdCl$_2$(dtbpf)), tetrakis(triphenylphosphine)palladium(0) (Pd(PPh$_3$)$_4$), [1,1'-bis(diphenylphosphino)ferrocene]dichloropalladium(II) (PdCl$_2$(dppf)), palladium(II) bis(triphenylphosphine) dichloride (Pd(PPh$_3$)$_2$Cl$_2$), XPhos-Pd-G2 precatalyst (chloro(2-dicyclohexylphosphino-2',4',6'-triisopropyl-1,1'-biphenyl)[2-(2'-amino-1,1'-biphenyl)]palladium(II)), and the like, a base such as K$_3$PO$_4$, aq. Na$_2$CO$_3$, Na$_2$CO$_3$, Cs$_2$CO$_3$, and the like, in a suitable solvent such as 1,2-dimethoxyethane, 1,4-dioxane, DMF, water, or a mixture thereof, at a temperature ranging from 60 to 180° C., employing microwave or conventional heating, for a period of about 30 min to 16 h, to provide a compound of formula (XVII).

Cleavage of the BOC protecting group on a compound of formula (XVII) is achieved according to procedures known to one skilled in the art and employing established methodologies. For example, under acidic conditions such as TFA/ CH$_2$Cl$_2$, HCl/Dioxane, and the like, to provide a compounds of formula (XVIII).

SCHEME 8

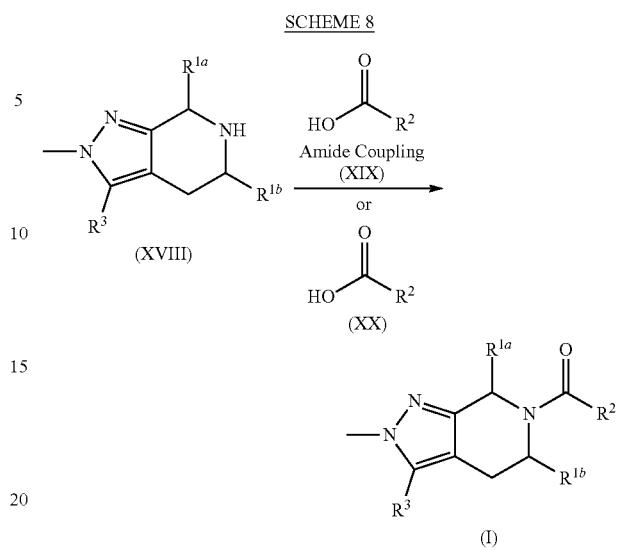

(XVIII)

(XX)

(I)

According to SCHEME 8, a compound of Formula (I) is prepared from a compound of Formula (XVIII), employing amide bond forming techniques known to one skilled in the art, such as coupling reactions with a suitably substituted commercially available or synthetically accessible aryl or heteroaryl carboxylic acid of formula (XIX), which are previously described, or by reaction of suitably substituted aryl or heteroaryl acid chlorides of formula (XX) (conversion of the acid to an acid chloride), employing a base such as TEA (triethylamine), and the like, in a suitable solvent such as DCM, THF, EtOAc, and the like. For example, conventional amide bond forming techniques such as coupling reactions which are well known to those skilled in the art (such as HATU (1-[bis(dimethylamino)methylene]-1H-1,2,3-triazolo[4,5-b]pyridinium 3-oxid hexafluorophosphate), BOP (benzotriazol-1-yloxy-tris(dimethylamino) phosphonium hexafluorophosphate), or conversion of the acid to an acid chloride). For example, reaction of a compound of formula (XVIII) with a commercially available or synthetically accessible (according to the schemes above) carboxylic acid of formula (XIX), where $R^3$ is a suitably substituted 5-membered heteroaryl ring as defined in Claim 1, where the acid is activated with an appropriate activating reagent, for example a carbodiimide, such as N,N'-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotrisaminophosphonium salt such as (benzotriazol-1-yloxy)tris (dimethylamino)phosphonium hexafluorophosphate (BOP), or bromotripyrrolidinophosphonium hexafluorophosphate (PyBroP®); a suitable pyridinium salt such as 2-chloro-1-methyl pyridinium chloride; or another suitable coupling agent such as N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5, 2,4,6-trioxatriphosphorinane-2,4,6-trioxide (T3P®) and the like. Coupling reactions are conducted in a suitable solvent such as DCM, THF, DMF and the like, optionally in the presence of a tertiary amine such as N-methylmorpholine, N-ethyldiisopropylamine (DIEA, DIPEA), or triethylamine (TEA), at a temperature ranging from about 0° C. to rt, to provide compound a of Formula (I).

SCHEME 9

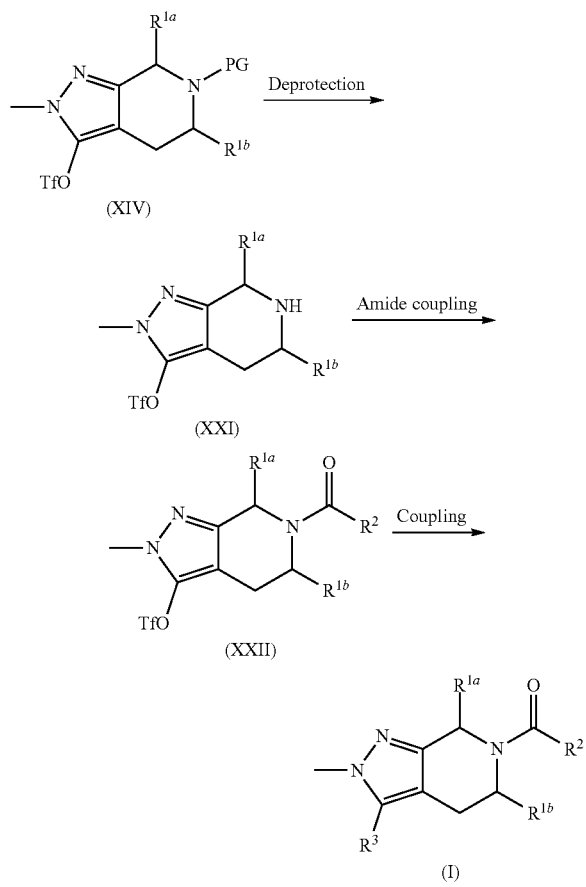

According to SCHEME 9, cleavage of the BOC protecting group on a compound of formula (XIV) according to methods previously described, provides a compound of formula (XXI). A compound of formula (XXII), where $R^2$ is a suitably substituted quinoline; is prepared by conventional amide bond forming techniques as previously described provides a compound of formula (XXII). A compound of formula (XXII) where $R^2$ is a suitably substituted quinoline; is reacted in a metal mediated cross coupling reaction as previously described to provide a compound of Formula (I). For example, a compound of formula (XXII) is reacted with a suitably substituted commercially available or synthetically accessible heteroaryl boronic acid, boronate ester, and the like, in the presence of a palladium catalyst such as [1,1'-bis(di-tert-butylphosphino)ferrocene]dichloropalladium(II) (PdCl$_2$(dtbpf)), tetrakis(triphenylphosphine)palladium(0) (Pd(PPh$_3$)$_4$), [1,1'-bis(diphenylphosphino)ferrocene]dichloropalladium(II) (PdCl$_2$(dppf)), palladium(II)bis(triphenylphosphine) dichloride (Pd(PPh$_3$)$_2$Cl$_2$), XPhos-Pd-G2 precatalyst (chloro(2-dicyclohexylphosphino-2',4',6'-triisopropyl-1,1'-biphenyl)[2-(2'-amino-1,1'-biphenyl)]palladium(II)), and the like, a base such as K$_3$PO$_4$, aq. Na$_2$CO$_3$, Na$_2$CO$_3$, Cs$_2$CO$_3$, and the like, in a suitable solvent such as 1,2-dimethoxyethane, 1,4-dioxane, DMF, water, or a mixture thereof, at a temperature ranging from 60 to 180° C., employing microwave or conventional heating, for a period of about 30 min to 16 h, to provide a compound of Formula (I).

SCHEME 10

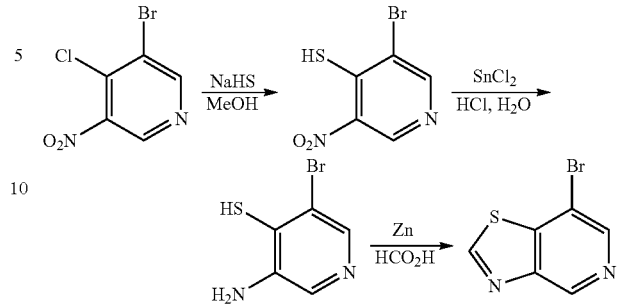

According to SCHEME 10, 7-bromothiazolo[4,5-c]pyridine may be prepared in three steps from commercially available or synthetically accessible 3-bromo-4-chloro-5-nitropyridine. For example, nucleophilic aromatic substitution of 3-bromo-4-chloro-5-nitropyridine with sodium hydrosulfide, in a suitable solvent such as MeOH and the like, at a temperature of 25° C., for a period of about 16 hours may provide 3-bromo-5-nitropyridine-4-thiol. Reduction of 3-bromo-5-nitropyridine-4-thiol may be achieved using stannous chloride and hydrochloric acid, in a suitable solvent such as water and the like, at a temperature of 25° C., for a period of about 3 hours to provide 3-amino-5-bromopyridine-4-thiol. Condensation of 3-amino-5-bromopyridine-4-thiol using zinc and formic acid, at a temperature of 100° C., for a period of about 1 hour may provide 7-bromothiazolo[4,5-c]pyridine.

SCHEME 11

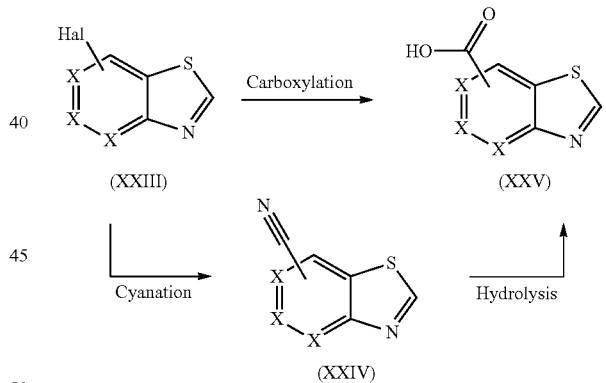

According to SCHEME 11, a compound of formula (XXIII), where Hal is Cl or Br; and X is CH or N, wherein only one X can be N; may undergo lithium-halogen exchange using a suitable base such as n-butyllithium; and react with a suitable source of carbon dioxide such as dry ice; in a suitable solvent such as tetrahydrofuran; at a temperature ranging from −78 to 25° C.; for a period of about 2 to 24 h, to provide a compound of the formula (XXV). In an alternate method, a compound of formula (XXIII) may undergo metal-mediated cyanation to provide a compound of formula (XXIV), where X is CH or N, wherein only one X can be N. For example, a compound of formula (XXIII), may react with zinc cyanide in the presence of zinc and a palladium catalyst such as tris(dibenzylidene)dipalladium(0) (Pd$_2$(dba)$_3$), trifluoroacetic acid palladium(II) salt (Pd(TFA)$_2$), bis(tri-tert-butylphosphine)

palladium(0) (Pd(t-Bu₃P)₂, and the like; with or without the addition of a ligand such as 1,1'-bis(diphenylphosphino)ferrocene (DPPF), (binaphthyl)P(t-Bu)₂, and the like; in a suitable solvent such as N,N-dimethylformamide, N,N-dimethylacetamide, and the like; at a temperature ranging from 90 to 120° C.; employing microwave or conventional heating; for a period of about 30 min to 16 h, to provide compounds of formula (XXIV).

Hydrolysis of the nitrile group on a compound of formula (XXIV) may be achieved employing conditions known to one skilled in the art, using a suitable base such as LiOH, NaOH, and the like; in a suitable solvent such as tetrahydrofuran or a mixture of tetrahydrofuran/water; at a temperature ranging from 25 to 100° C., for a period of about 16 h, to provide a compound of formula (XXV).

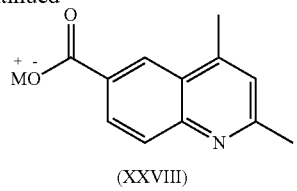

(XXVIII)

According to SCHEME 13, 6-bromo-2,4-dimethylquinoline is prepared under conditions known to one skilled in the art (Lindsley, C. W., et al, PCT Patent Publication No. WO 2018112312), by reacting commercially available 6-bromo-2-methylquinoline with ethyl 2-mercaptopropanoate in the

SCHEME 12

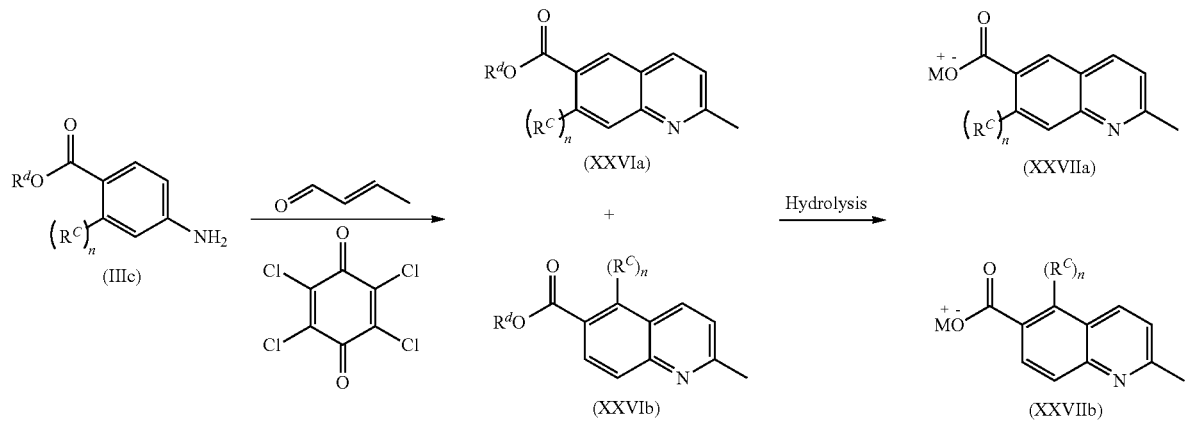

According to SCHEME 12, compounds of formulas (XXVIa) & (XXVIb), are prepared under conditions known to one skilled in the art (McDonald, A, et al, U.S. Pat. No. 9,611,252) by condensation of commercially available or synthetically accessible substituted methyl 4-aminobenzoates of formula (IIIc), where $R^c$ is F or CH₃, $R^d$ is methyl, and n is 0, or 1, with (E)-but-2-enal; in the presence of a suitable oxidant such as 2,3,5,6-tetrachlorocyclohexa-2,5-diene-1,4-dione; in a suitable solvent such as 6N HCl; at temperature of 100° C., for a period of about 10 minutes. Hydrolysis of the methyl ester is achieved employing conditions known to one skilled in the art, using a suitable base such as NaOH, LiOH, (CH₃)₃SiOK, and the like; in a suitable solvent such as tetrahydrofuran; at temperature of 60° C. for a period of 24 h; to provide compounds of formula (XXVIIa) and (XXVIIb) where M is potassium, Na, or Li.

presence of an iridium catalyst such as Ir(ppy)₂(dtbbpy)PF₆ and the like; and a suitable acid such as p-toluenesulfonic acid and the like; in a suitable solvent mixture such as dimethylsulfoxide and methanol. A compound of formula (XXVIII) is prepared in two steps from 6-bromo-2,4-dimethylquinoline. For example, palladium-catalyzed carbonylation of 6-bromo-2,4-dimethylquinoline using a suitable combination of palladium catalysts such as palladium(II) acetate and [1,1'-bis(diphenylphosphino)ferrocene]dichloropalladium(II) (PdCl₂(dppf)), and the like; in a suitable solvent such as methanol and the like; under an atmosphere of carbon monoxide; followed by hydrolysis of the resulting methyl ester employing conditions as shown above, provides a compound of formula (XXVIII), where M is K, Na, or Li.

SCHEME 13

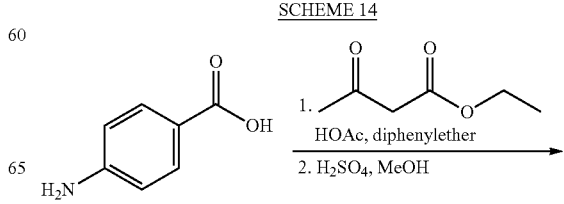

SCHEME 14

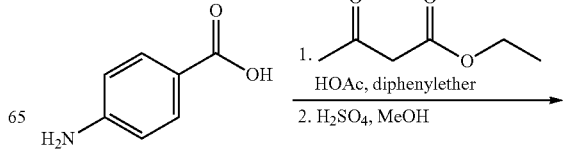

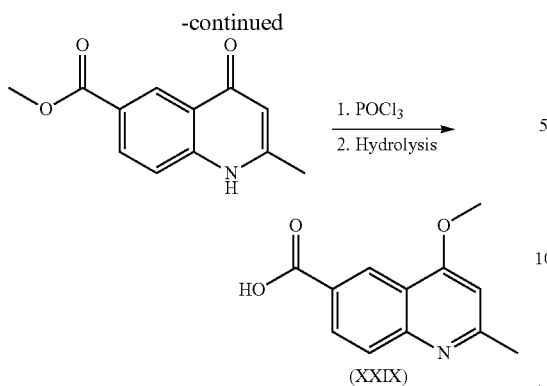

According to SCHEME 14, methyl 2-methyl-4-oxo-1,4-dihydroquinoline-6-carboxylate is prepared by reacting commercially available 4-aminobenzoic acid with ethyl 3-oxobutanoate and acetic acid in a suitable solvent such as toluene and the like; at a temperature of 120° C. for a period of 16 h and the resultant solid is further refluxed in a solvent such as diphenyl ether at 240° C. for a period of 3 h; followed by esterification with sulfuric acid in a suitable solvent such as methanol and the like; to provide corresponding methyl ester.

A compound of formula (XXIX) is prepared in two steps by heating methyl 2-methyl-4-oxo-1,4-dihydroquinoline-6-carboxylate with phosphorus oxychloride in presence of a catalytic amount of DMF, in a suitable solvent such as THF and the like; at 60° C. for a period of 6 h. Hydrolysis of the methyl ester is achieved employing conditions known to one skilled in the art, using a suitable base such as sodium methanolate, and the like; in a suitable solvent such as methanol; at temperature of 60° C. for a period of 16 h; to provide compound of formula (XXIX).

SCHEME 15

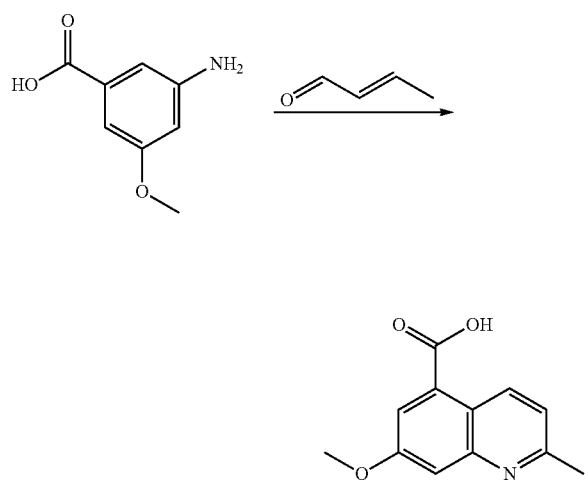

According to SCHEME 15, 7-methoxy-2-methylquinoline-5-carboxylic acid may be prepared by condensation of commercially available or synthetically accessible 3-amino-5-methoxybenzoic acid with an unsaturated aldehyde such as (E)-but-2-enal, using a suitable solvent such as 6N HCl, at a temperature of 100° C., for a period of about 1 h.

SCHEME 16

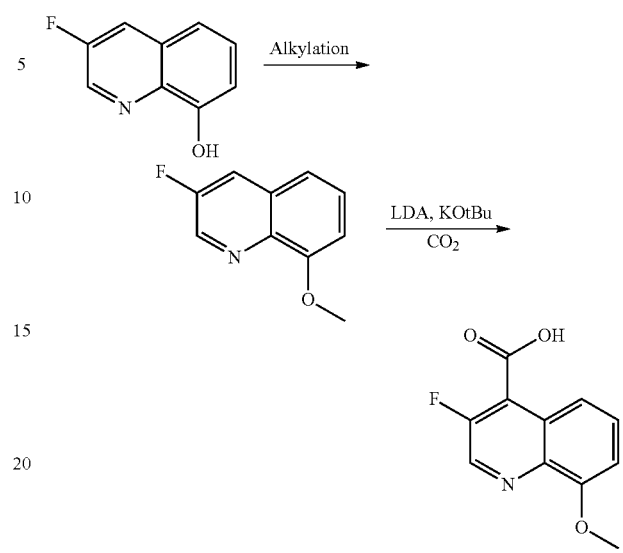

According to SCHEME 16, 3-fluoro-8-methoxyquinoline may be prepared by reacting commercially available or synthetically accessible 3-fluoroquinolin-8-ol with a suitable alkylating agent such as iodomethane, and the like; a suitable base such as potassium carbonate, and the like; in a suitable solvent such as N,N-dimethylformamide, and the like; at a suitable temperature range such as 0 to 25° C. 3-fluoro-8-methoxyquinoline-4-carboxylic acid may be prepared by metalation of 3-fluoro-8-methoxyquinoline in a manner described in Shi, G., et al, *Tetrahedron* Vol. 50, No. 4. 1129-1134, 1994 using a suitable base such as lithium diisopropylamide, activated by potassium tert-butoxide; in a suitable solvent such as tetrahydrofuran, and the like; at a temperature of −75° C., for a period of about 20 minutes; followed by quenching with a suitable source of carbon dioxide such as dry ice.

SCHEME 17

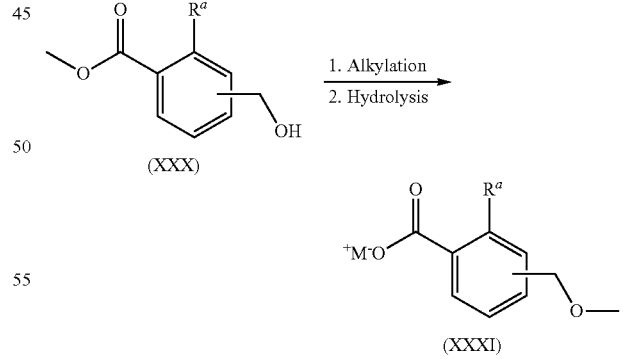

According to SCHEME 17, a compound of formula (XXXI) may be prepared by reacting a commercially available or synthetically accessible benzyl alcohol of formula (XXX), where $R^a$ is F or $CH_3$, with a suitable alkylating agent such as iodomethane, and the like; using a suitable base such as potassium carbonate, and the like; in a suitable solvent such as N,N-dimethylformamide, and the like; at a suitable temperature range such as 0 to 25° C.; followed by hydrolysis of the methyl ester employing conditions as shown above to provide a compound of formula (XXXI), where M is K, Na, or Li.

SCHEME 18

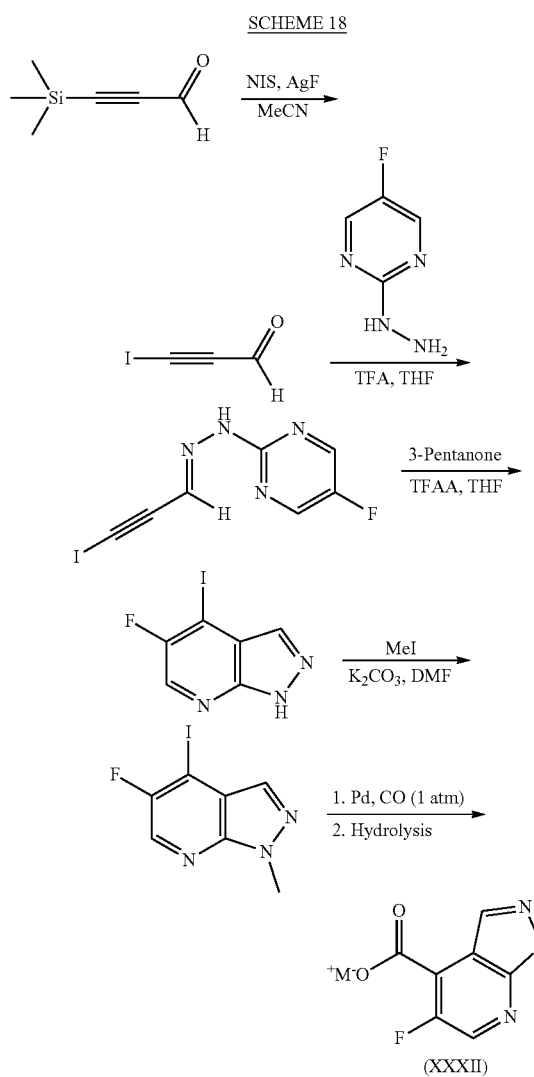

According to SCHEME 18, commercially available 3-(trimethylsilyl)propionaldehyde may be treated with a halogenating reagent such as N-iodosuccinimide, and the like; in the presence of silver fluoride; in a suitable solvent such as acetonitrile and the like; to afford 3-iodopropiolaldehyde. Condensation with commercially available 5-fluoro-2-hydrazineylpyrimidine with 3-iodopropiolaldehyde as described in Le Fouler, V., et al, *J. Am. Chem. Soc.* 2019, 141, 15901-15909 may provide (E)-5-fluoro-2-(2-(3-iodoprop-2-yn-1-ylidene)hydrazineyl)pyrimidine. The imine intermediate may then undergo intramolecular hetero-Diels-Alder cycloaddition using N-acetylating agents such as trifluoroacetic anhydride and the like; in presence of 3-pentanone; in a suitable solvent such as tetrahydrofuran, and the like; at a temperature of about 25° C. to afford 5-fluoro-4-iodo-1H-pyrazolo[3,4-b]pyridine. 5-fluoro-4-iodo-1H-pyrazolo[3,4-b]pyridine may be alkylated using a suitable reagent such as iodomethane, and the like; a suitable base such as, potassium carbonate, and the like; in a suitable solvent such as DMF, and the like; at a suitable temperature such as 0° C. or rt to provide 5-fluoro-4-iodo-1-methyl-1H-pyrazolo[3,4-b]pyridine. Palladium-catalyzed carbonylation of 5-fluoro-4-iodo-1-methyl-1H-pyrazolo[3,4-b]pyridine using a suitable combination of palladium catalysts such as palladium(II) acetate and [1,1'-bis(diphenylphosphino)ferrocene]dichloropalladium(II) (PdCl$_2$(dppf)), and the like; in a suitable solvent such as methanol and the like; under an atmosphere of carbon monoxide; followed by hydrolysis of the resulting methyl ester employing conditions as shown above, may provide compound of formula (XXXII), where M is K, Na, or Li.

SCHEME 19

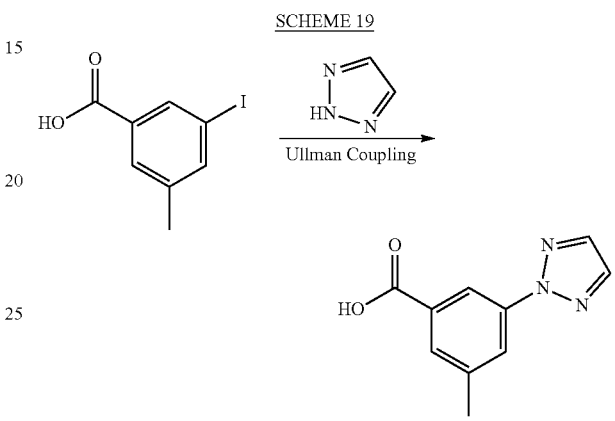

According to SCHEME 19, 3-methyl-5-(2H-1,2,3-triazol-2-yl)benzoic acid is prepared by reacting 3-iodo-5-methylbenzoic acid with 1H-1,2,3-triazole via an Ullman coupling reaction, utilizing a base such as cesium carbonate, a copper catalyst such as CuI, a ligand such as trans-N,N'-dimethylcyclohexane-1,2-diamine, in a suitable solvent such as DMF, at temperatures ranging from 100-140° C., under microwave irradiation.

SCHEME 20

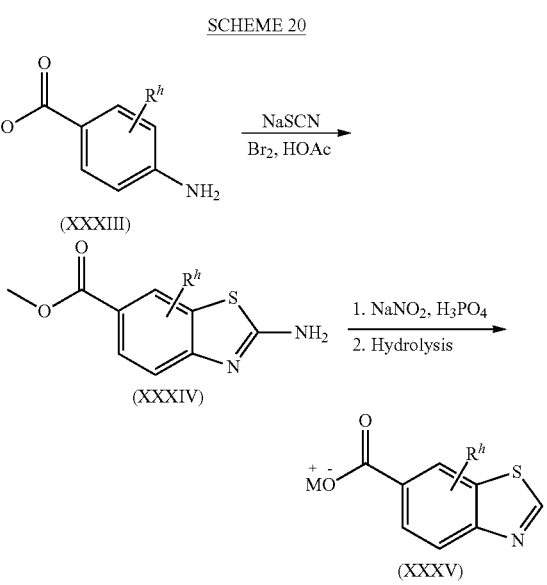

According to SCHEME 20, commercially available or synthetically accessible anilines of formula (XXXIII), where $R^h$ is CH$_3$, were treated with sodium thiocyanate and bromine in acetic acid at room temperature to provide corresponding 2-aminobenzo[d]thiazoles of formula (XXXIV) (Xu, Xiaodong, PCT Patent Publication No. WO 2018085148). Deamination of compounds of formula (XXXIV) is achieved by treatment with phosphoric acid in the presence of sodium nitrite or isoamyl nitrite, at a suitable temperature range such as −4° C. to 25° C. as described in Ismail, A., Sharp, E., and Chedeke, R., et al, *J. Org. Chem.*, Vol. 45, No. 11, 1980, 2243-2246. Subsequent hydrolysis of the methyl ester employing conditions as shown above provides a compound of formula (XXXV), where $R^b$ is $CH_3$ and M is K, Na, or Li.

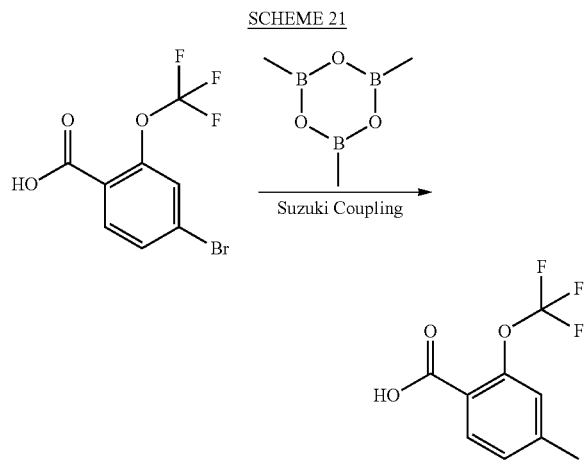

SCHEME 21

According to SCHEME 21, 4-methyl-2-(trifluoromethoxy)benzoic acid is prepared by reacting 4-bromo-2-(trifluoromethoxy)benzoic acid with trimethylboroxine, employing Suzuki cross-coupling conditions as previously described.

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via 1/16" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 μM, 30×100 or 50×150 mm) or an XBridge C18 OBD column (5 μM, 30×100, 50×100, or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 m, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

METHOD C. A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

METHOD D. A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

or

METHOD E. An ACCQ Prep HPLC with an XBridge C18 OBD column (5 μM, 30×100, or 50×100 mm), mobile phase of 5% ACN in $H_2O$ (both with 0.05% TFA) was held for 1 min, then a gradient of 5-95% ACN over 12 min, then held at 95% ACN for 2 min, with a flow rate of 80 mL/min.

or

METHOD F. An Agilent HPLC with an Xterra Prep RP18 column (5 μM, 30×100 or 50×150 mm) or an XBridge C18

OBD column (5 μM, 30×100, 50×100, or 50×150 mm), and a mobile phase of 5% ACN in H₂O (both with 0.05% TFA) was held for 2 min, then a gradient of 5-99% ACN over 15 min, then held at 99% ACN for 5 min, with a flow rate of 40 or 80 mL/min.

or

METHOD G. Boston Uni C18 150×40 mm×5 μm column (eluent: 1% to 31% (v/v) ACN and H₂O with 0.05% HCl))

Preparative supercritical fluid high performance liquid chromatography (SFC) was performed either on a Jasco preparative SFC system, an APS 1010 system from Berger instruments, or an SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad, dd=doublet of doublets, dt=doublet of triplets, td=triplet of doublets. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, MA) or OEMetaChem V1.4.0.4 (Open Eye).

Compounds designated as R* or S* are enantiopure compounds where the absolute configuration was not determined.

Intermediate 1: Potassium 2-chloro-3-(2-oxa-6-azaspiro[3.3]heptan-6-yl)benzoate

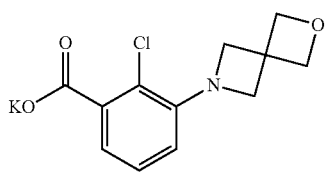

Step A: Methyl 2-chloro-3-(2-oxa-6-azaspiro[3.3]heptan-6-yl)benzoate. To a solution of methyl 3-bromo-2-chlorobenzoate (150 mg, 0.6 mmol) in 1,2-dimethoxyethane (5.0 mL) was added 2-oxa-6-azaspiro[3.3]heptane (66 mg, 0.67 mmol), cesium carbonate (587 mg, 1.8 mmol) and Josiphos SL-J009-1 PD G3 (56 mg, 0.06 mmol) under a nitrogen atmosphere. The reaction mixture was heated to 70° C. for 1 h and concentrated under reduced pressure. The residue was taken up in CH₂Cl₂ (10 mL), washed with H₂O (2×5.0 mL), brine (1×10 mL), dried over sodium sulfate, filtered and concentrated under reduced pressure. The resulting residue was purified by flash chromatography (SiO₂; 0-50% hexanes-EtOAc) to give the title compound as yellow solid (88.1 mg, 55%). MS (ESI): mass calcd. for $C_{13}H_{14}ClNO_3$, 267.1; m/z found, 268.1 [M+H]⁺. ¹H NMR (400 MHz, DMSO-d₆) δ 7.25 (dd, J=8.2, 7.6 Hz, 1H), 7.03 (dd, J=7.5, 1.5 Hz, 1H), 6.75 (dd, J=8.2, 1.5 Hz, 1H), 4.71 (s, 4H), 4.19 (s, 4H), 3.82 (s, 3H).

Step B: Potassium 2-chloro-3-(2-oxa-6-azaspiro[3.3]heptan-6-yl)benzoate. To a solution of methyl 2-chloro-3-(2-oxa-6-azaspiro[3.3]heptan-6-yl)benzoate (85 mg, 0.32 mmol) in THF (4.0 mL) was added potassium trimethylsilanolate (41 mg, 0.32 mmol) and the resulting mixture was heated to 60° C. for 5 h. The reaction mixture was then filtered and washed with THF to obtain the title compound as white solid which was taken on to the next step without purification. MS (ESI): mass calcd. for $C_{12}H_{11}ClKNO_3$, 291.0; m/z found, 254.1 [M-K+2+H]⁺.

Intermediate 2: Potassium 1-(2,2,2-trifluoroethyl)-1H-pyrrolo[2,3-b]pyridine-4-carboxylate

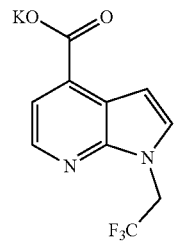

Step A: Methyl 1-(2,2,2-trifluoroethyl)-1H-pyrrolo[2,3-b]pyridine-4-carboxylate. To a cooled (0° C.) solution of methyl 1H-pyrrolo[2,3-b]pyridine-4-carboxylate (200 mg, 1.1 mmol) in DMF (4.0 mL) was added sodium hydride (60% in mineral oil, 68 mg, 1.7 mmol). The reaction mixture was warmed to rt and stirred for 1 h. After 1 h, the mixture was cooled to 0° C., then 2,2,2-trifluoroethyl trifluoromethanesulfonate (0.25 mL, 1.7 mmol) was added, and the reaction mixture was stirred for another hour. The reaction was then quenched with water, diluted with EtOAc (2×), and the combined organics washed with brine (4×), dried over Na₂SO₄, filtered, and concentrated. The resulting residue was taken to next step without further purification. MS (ESI): mass calcd. for $C_{11}H_9F_3N_2O_2$, 258.1; m/z found, 259.1 [M+H]⁺.

Step B: Potassium 1-(2,2,2-trifluoroethyl)-1H-pyrrolo[2,3-b]pyridine-4-carboxylate. The title compound was prepared in a manner analogous to Intermediate 1, Step B, using methyl 1-(2,2,2-trifluoroethyl)-1H-pyrrolo[2,3-b]pyridine-4-carboxylate instead of methyl 2-chloro-3-(2-oxa-6-azaspiro[3.3]heptan-6-yl)benzoate. MS (ESI): mass calcd. for $C_{10}H_7KF_3N_2O_2$, 282.0; m/z found, 245.1 [M-K+2+H]⁺.

Intermediate 3: Potassium 4,6-difluoropyrazolo[1,5-a]pyridine-3-carboxylate

The title compound was prepared in a manner analogous to Intermediate 1, Step B, using ethyl 4,6-difluoropyrazolo[1,5-a]pyridine-3-carboxylate instead of methyl 2-chloro-3-(2-oxa-6-azaspiro[3.3]heptan-6-yl)benzoate and the reaction mixture was heated for 24 hrs. MS (ESI): mass calcd. for $C_8H_3F_2KN_2O_2$, 235.9; m/z found, 199.1 [M-K+2+H]$^+$.

Intermediate 4: Lithium 5,7-difluoroquinoline-3-carboxylate

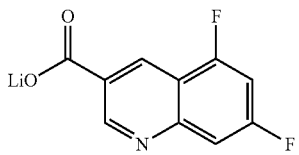

To a solution of ethyl 5,7-difluoroquinoline-3-carboxylate (75 mg, 0.32 mmol) in THF (2.5 mL) was added a solution of lithium hydroxide (15.0 mg, 0.63 mmol) in water (1.5 mL). The mixture was stirred at rt for 1 h, then concentrated under reduced pressure to afford the title compound as white solid which was further taken to next step without purification (quantitative yield). MS (ESI): mass calcd. for $C_{10}H_4F_2LiNO_2$, 215.0 m/z found, 210.1 [M-Li+2+H]$^+$.

Intermediate 5: Potassium 2-methyl-2H-indazole-4-carboxylate

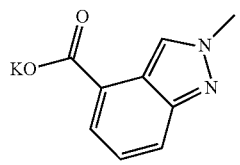

The title compound was prepared in a manner analogous to Intermediate 1, Step B, using methyl 2-methyl-2H-indazole-4-carboxylate instead of methyl 2-chloro-3-(2-oxa-6-azaspiro[3.3]heptan-6-yl)benzoate. MS (ESI): mass calcd. for $C_9H_7KN_2O_2$, 214.0; m/z found, 177.1 [M-K+2+H]$^+$.

Intermediate 6: Lithium 4,6-difluoro-1-methyl-1H-indazole-3-carboxylate

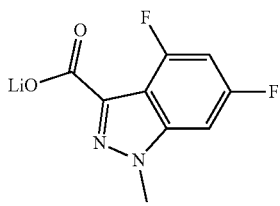

Step A: Methyl 4,6-difluoro-1-methyl-1H-indazole-3-carboxylate. The title compound was prepared in a manner analogous to Intermediate 2, Step A, using 4,6-difluoro-1H-indazole-3-carboxylic acid instead of methyl 1H-pyrrolo[2,3-b]pyridine-4-carboxylate and iodomethane instead of 2,2,2-trifluoroethyl trifluoromethanesulfonate. MS(ESI): mass calcd. for $C_{10}H_8F_2N_2O_2$, 226.1; m/z found, 226.9 [M+H]$^+$.
Step B: Lithium 4,6-difluoro-1-methyl-1H-indazole-3-carboxylate. To a solution of methyl 4,6-difluoro-1-methyl-1H-indazole-3-carboxylate (100 mg, 0.44 mmol) in THF (2.5 mL) was added a solution of lithium hydroxide (21.0 mg, 0.88 mmol) in water (1.5 mL). The mixture was stirred at rt for 1 h, then concentrated the solvent to afford the title compound as white solid which was further taken to next step without purification (quantitative yield). MS (ESI): mass calcd. for $C_9H_5F_2LiN_2O_2$, 218.05; m/z found, 213.0 [M-Li+2+H]$^+$.

Intermediate 7: Potassium 2-methyl-1,6-naphthyridine-5-carboxylate

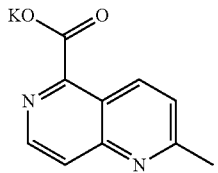

The title compound was prepared in a manner analogous to Intermediate 1, Step B, using ethyl 2-methyl-1,6-naphthyridine-5-carboxylate instead of methyl 2-chloro-3-(2-oxa-6-azaspiro[3.3]heptan-6-yl)benzoate. MS (ESI): mass calcd. for $C_{10}H_7KN_2O_2$, 226.0; m/z found, 189.1 [M-K+2+H]$^+$.

Intermediate 8: 5-Fluoro-1-methyl-1H-pyrrolo[2,3-b]pyridine-4-carboxylic Acid

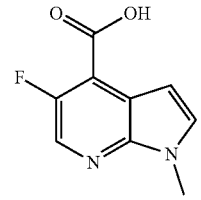

Step A: Methyl 5-fluoro-1-methyl-1H-pyrrolo[2,3-b]pyridine-4-carboxylate. Iodomethane (0.22 mL, 3.5 mmol) was added to a mixture of 5-fluoro-1H-pyrrolo[2,3-b]pyridine-4-carboxylic acid (250 mg, 1.4 mmol) and potassium carbonate (575 mg, 4.2 mmol) in DMF (4.8 mL) at room temperature. After 16 hours, a saturated aqueous solution of sodium bicarbonate (20 mL) was added and the mixture was extracted using EtOAc (3×30 mL). The combined organics were dried over MgSO$_4$, filtered and concentrated under reduced pressure to afford the title compound (85 mg, 29%). MS (ESI): mass calcd. for $C_{10}H_9FN_2O_2$, 208.1; m/z found, 209.1 [M+H]$^+$. $^1$H NMR (500 MHz, DMSO-d$_6$) δ 8.40-8.38 (m, 1H), 7.81 (d, J=3.4 Hz, 1H), 6.77 (d, J=3.4 Hz, 1H), 3.96 (s, 3H), 3.86 (s, 3H).
Step B: 5-Fluoro-1-methyl-1H-pyrrolo[2,3-b]pyridine-4-carboxylic acid. A mixture of methyl 5-fluoro-1-methyl-1H-pyrrolo[2,3-b]pyridine-4-carboxylate (85 mg, 0.4 mmol) and lithium hydroxide (4N in water, 0.51 mL, 2.0 mmol) in THF (3 mL) was stirred at room temperature. After 16 hours, the reaction mixture was concentrated under vacuum. Purification (METHOD F) afforded the title compound (94 mg, 79%). MS (ESI): mass calcd. for $C_9H_7FN_2O_2$, 194.1; m/z found, 195.1 [M+H]$^+$.

Intermediate 9: 1,5-Dimethyl-4-(4,4,5,5-tetramethyl-1,3,2-dioxaborolan-2-yl)-3-(trifluoromethyl)-1H-pyrazole

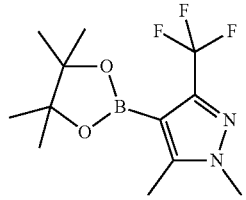

The title compound was prepared in a manner analogous to Intermediate 2, Step A, using 5-methyl-4-(4,4,5,5-tetramethyl-1,3,2-dioxaborolan-2-yl)-3-(trifluoromethyl)-1H-pyrazole instead of methyl 1H-pyrrolo[2,3-b]pyridine-4-carboxylate and iodomethane instead of 2,2,2-trifluoroethyl trifluoromethanesulfonate. MS (ESI): mass calcd. for $C_{12}H_{18}BF_3N_2O_2$, 290.1; m/z found, 291.1 [M+H]$^+$.

Intermediate 10: (S)-tert-Butyl 2,7-dimethyl-3-(((trifluoromethyl)sulfonyl) oxy)-2,4,5,7-tetrahydro-6H-pyrazolo[3,4-c]pyridine-6-carboxylate

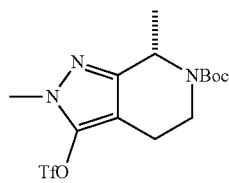 [SMILES: C[C@H]1c2nn(C)c(OS(=O)(=O)C(F)(F)F)c2CCN1C(=O)OC(C)(C)C]

Step A: Ethyl (S)-4-((1-ethoxy-1-oxopropan-2-yl) amino) butanoate. Into a 50 L reactor were added DMF (21 L, 6 V), ethyl L-alaninate hydrochloride (6.13 kg, 2.0 eq. 90% w/w), $K_2HPO_4$ (10.94 kg, 3.5 eq.) and KI (2.98 kg, 1.0 eq.) successively at 20-30° C. The resulting mixture was warmed to 50-55° C. and held at this temperature for 30 min. Then a solution of ethyl 4-bromobutanoate (3.50 kg, 1.0 eq.) in dimethylformamide (DMF) (7 L, 2 V) was added dropwise over 1 h while keeping the temperature at 50-55° C. The mixture was stirred at 50-55° C. for 3 h. After the completion of the reaction, the reaction mixture was cooled to 20-30° C. and transferred into another reactor followed by adding water (87.5 L, 25 V). The resulting mixture was extracted with tert-butyl methyl ether (MTBE) (17.5 L×4). The organic phase was collected and washed with brine (17.5 L). The organic phase was combined with the organic phases from other two batches (1.00 kg batch and 2.50 kg batch). Then the solution was concentrated under vacuum at 40-45° C. to give 6.8 kg of the title compound as a light-yellow oil (94% w/w assay by Q-NMR) in the yield of 82.2%. MS (ESI): mass calcd. for $C_{11}H_{21}NO_4$, 231.1; m/z found, 232.1 [M+H]$^+$.

Step B: Ethyl (S)-4-((tert-butoxycarbonyl)(1-ethoxy-1-oxopropan-2-yl)amino)butanoate. Into a 20 L reactor were added crude ethyl (S)-4-((1-ethoxy-1-oxopropan-2-yl) amino)butanoate (3.5 kg, 1.0 eq.), tetrahydrofuran (THF) (10 L, 3 V), and di-tert-butyl dicarbonate (3.5 kg, 1.05 eq.) at 20-30° C. The resulting mixture was warmed to 55-60° C. and held at this temperature for 3 h. After the completion of the reaction, the reaction mixture was concentrated under vacuum at 40-45° C. to give 5624 g of the title compound as a yellow oil with purity of 87.2% (GC) and 99.1% ee. The resulting residue was used in the next step without further purification.

Step C: 1-(tert-Butyl) 4-ethyl (2S)-2-methyl-3-oxopiperidine-1,4-dicarboxylate. Into a 10 L four-necked flask were added crude ethyl(S)-4-((tert-butoxycarbonyl)(1-ethoxy-1-oxopropan-2-yl)amino)butanoate (450 g, 87% pure, 1.9 mol, 1.0 eq.) and THF (2.25 L, 5 V) at 20-30° C. After the mixture was cooled to −40° C. to −30° C., lithium bis(trimethylsilyl) amide (LiHMDS) (1 M in THF, 2.9 L, 2.9 mol, 1.5 eq.) was added dropwise while keeping the temperature at −40° C. to −30° C. The resulting reaction mixture was warmed to 10-20° C. and held at this temperature for 1 h. After the completion of the reaction, the reaction mixture was combined with other two batches then poured into aq. citric acid (408.6 g in 2250 mL $H_2O$, 2.9 mol, 1.5 eq.). After phase separation, the aqueous layer was re-extracted with MTBE (12 L, 10 V), the combined organic layers were sequentially washed with brine (9 L×2). The organic phase was dried over $Na_2SO_4$, then concentrated under vacuum to give crude product. The resulting residue was purified by silica gel chromatography (petroleum ether/ethyl acetate=1/0 to 20/1) to give the title compound (1100 g) with 99% purity in the yield of 70% over two steps. $^1$H NMR (500 MHz, CDCl$_3$) δ 4.26-4.10 (m, 2H), 2.79 (s, 1H), 2.34-2.14 (m, 2H), 1.47 (d, J=27.0 Hz, 2H), 1.40 (s, 9H), 1.36 (s, 1H), 1.29 (d, J=6.9 Hz, 3H), 1.23 (t, J=7.1 Hz, 3H).

Step D: tert-Butyl (7S)-2,7-dimethyl-3-oxo-2,3,3a,4,5,7-hexahydro-6H-pyrazolo[3,4-c]pyridine-6-carboxylate. Into a 10 L four-necked flask were added methylhydrazine sulfate (360 g, 2.5 mol, 1.5 eq.), EtOH (5 L, 10.6 V) and DIEA (399 mL, 2.4 mol, 1.45 eq.) at 20-30° C. The resulting mixture was warmed to 75-80° C. over 30 min. Then a solution of 1-(tert-butyl) 4-ethyl (2S)-2-methyl-3-oxopiperidine-1,4-dicarboxylate (495 g crude, assay weight 470 g, 1.6 mol, 1.0 eq.) in EtOH (500 mL) was added dropwise over 20 min while keeping the temperature at 75-80° C. The resulting mixture was stirred at 75-80° C. for 4 h. After completion of the reaction, the reaction mixture was concentrated under vacuum. The resulting residue was combined with the residue from another 470 g batch. To the combined residues were diluted with DCM (8 L, 8.5 V), $H_2O$ (2 L, 2.7 V) and brine (2.5 L, 2.7 V). After phase separation, the aqueous layers were re-extracted with DCM (2 L×2). The combined organic layers were dried over $Na_2SO_4$, then concentrated under vacuum to give the title compound, which was used in the next step without further purification. MS (ESI): mass calcd. for $C_{13}H_{21}N_3O_3$, 267.2; m/z found, 268.1 [M+H]$^+$.

Step E: (S)-tert-Butyl 2,7-dimethyl-3-(trifluoromethylsulfonyloxy)-4,5-dihydro-2H-pyrazolo[3,4-c]pyridine-6 (7H)-carboxylate. Into a 10 L four-necked flask were added tert-butyl (7S)-2,7-dimethyl-3-oxo-2,3,3a,4,5,7-hexahydro-6H-pyrazolo[3,4-c]pyridine-6-carboxylate (940 g, 3.3 mol, 1.0 eq.), DCM (6 L, 6.4 V) and DIEA (550 mL, 3.3 mol, 1.0 eq.) at 20-30° C. After the mixture was cooled to 10-20° C., N-(5-chloro-2-pyridyl)bis(trifluoromethane-sulfonimide) (902 g, 2.3 mol, 0.7 eq.) was added batch-wise while keeping the temperature at 10-20° C. Additional N-(5-chloro-2-pyridyl)bis(trifluoromethanesulfonimide) (232 g, 0.6 mol, 0.18 eq.) was added. After stirring overnight, HPLC indicated the reaction was completed. Then the reaction mixture was concentrated under vacuum, followed by purification with silica gel chromatography (petroleum ether/ethyl acetate=1/0 to 8/1) to give 1106 g of the title compound with a purity of 99% (84% yield over two steps). $^1$H NMR (400 MHz, CDCl₃) δ 5.19 (br, 1H), 4.30 (br, 1H), 3.78 (s, 3H), 2.99-2.85 (m, 1H), 2.59-2.52 (m, 1H), 1.48 (s, 10H), 1.41 (d, J=6.4 Hz, 3H).

Intermediate 11: tert-Butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate

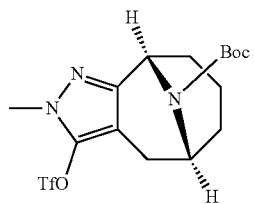 [SMILES: Cn1nc2c(c1OS(=O)(=O)C(F)(F)F)C[C@H]1CCC[C@H]2N1C(=O)OC(C)(C)C]

Step A: (4Z)-9-Oxabicyclo[6.1.0]non-4-ene. To a solution of 1,5-cyclooctadiene (125 g, 116 mmol) in tetrahydrofuran (175 mL) was added a solution of 3-chloroperoxybenzoic acid (mCPBA) (55%, 300 g, 956 mmol) in chloroform (1.75 L) dropwise, and the reaction was stirred at room temperature for 42 h. The reaction mixture was washed with 20% sodium bisulfite (4×1 L), saturated sodium bicarbonate (4×1 L) and brine (2×1 L). The organic layer was dried over sodium sulfate, filtered and evaporated. The mixture was distilled under vacuum (bp=40° C. at 2 mm Hg) to give the title compound (74.2 g, 51% yield) as a colorless liquid. MS (ESI): mass calcd. for C₈H₁₂O, 124.1; m/z found, 123.0 [M−H]⁻.

Step B: (1S,8S,Z)-8-(((R)-1-Phenylethyl)amino)cyclooct-4-en-1-ol. To a solution of ytterbium(III) trifluoromethanesulfonate hydrate (12.5 g, 20.2 mmol) in distilled tetrahydrofuran (200 mL) was added (R)-(+)-α-methylbenzyl amine (77 mL, 604 mmol, 0.95 g/mL) and 1,2-epoxy-5-cyclooctene (50 g, 403 mmol) in distilled tetrahydrofuran (300 mL). The reaction mixture was stirred in a sealed tube at 100° C. for 48 h, poured into water (500 mL), and the volatiles were evaporated. The aqueous layer was extracted with dichloromethane (3×500 mL) and the combined organic layers were dried over sodium sulfate, filtered, and evaporated to give the title compound (120 g, crude) as a yellow oil. The reaction was repeated on a 99 g scale (798 mmol). The resulting products from both reactions were combined and converted to the hydrochloride salt in 2 batches. To 20 g of The resulting residue was added hydrogen chloride (3.88 M in diethyl ether, 82 mL, 318 mmol). The precipitate was collected and the first crop (3.34 g, 11.8 mmol, 14%) was isolated as a white crystalline solid. To the remaining crude product (280 g, 114 mmol) in ethyl acetate (560 mL) was added hydrogen chloride (3.88 M in diethyl ether, 560 mL, 2173 mmol). The suspension was stirred at room temperature for 30 min and the precipitate was collected. The solid was suspended in ethyl acetate saturated with water (5.6 L) and stirred at 50° C. for 30 min. After cooling to room temperature, the precipitate was collected and the second crop (78 g, 277 mmol, 24% yield) was isolated as a white crystalline solid. MS (ESI): mass calcd. for C₁₆H₂₃NO, 245.2; m/z found, m/z=246.2 [M+H]⁺. ¹H NMR (400 MHz, CDCl₃) δ 7.46-7.18 (m, 6H), 4.33-4.09 (m, 2H), 3.88 (br. s., 4H), 3.42 (s, 1H), 3.02-2.82 (m, 1H), 2.05-1.85 (m, 2H), 1.79-1.60 (m, 2H), 1.50 (d, J=6.8 Hz, 2H), 1.38-1.27 (m, 2H).

Step C: (1S,2S,5R)-9-((R)-1-phenylethyl)-9-azabicyclo[3.3.1]nonan-2-ol. To a solution of mercury(II) chloride (104 g, 383 mmol) in tetrahydrofuran (750 mL) and water (320 mL) was added a solution of (1S,8S,Z)-8-[[(1R)-1-phenylethyl]amino]cyclooct-4-en-1-ol (98.0 g, 348 mmol) in tetrahydrofuran (350 mL) and sodium hydroxide (3 M, 116 mL, 348 mmol) and the reaction was stirred at room temperature for 1 d. To the reaction mixture was added sodium hydroxide (3 M, 280 mL, 840 mmol) and a solution of sodium borohydride (13.0 g, 344 mmol) in sodium hydroxide (3 M, 70 mL, 210 mmol) at 0° C. and the reaction was stirred at room temperature for 1 d to give the title compound (98 g), which was used in the next step without further purification. LCMS: 58%, $t_R$=2.019 min, MS (ESI): mass calcd. for C₁₆H₂₃NO, 245.2; m/z found, 246.1 [M+H]⁺.

Step D: tert-Butyl (1S,2S,5R)-2-hydroxy-9-azabicyclo[3.3.1]nonane-9-carboxylate. A mixture of (1R,2S,5R)-9-[(1R)-1-phenylethyl]-9-azabicyclo[3.3.1]nonan-4-ol (98.0 g, crude) and 10% palladium on carbon (42.5 g) in methanol (2.5 L) was stirred at room temperature for 2 h under hydrogen. To the reaction mixture was added di-tert-butyl dicarbonate (175 g, 802 mmol) and triethylamine (56 mL, 402 mmol) and the reaction was stirred at room temperature for 18 h. The reaction mixture was filtered through a pad of Celite©; and the Celite© was washed with methanol (2×500 mL). The combined filtrates were concentrated under reduced pressure and the residue was purified by silica gel column chromatography eluting with ethyl acetate. The residue was purified by gradient silica gel column chromatography eluting with heptane:ethyl acetate (100:0→3:1) to give a first crop of the title compound (43.4 g, 180 mmol, 44% yield) as a yellow oil. ¹H NMR (500 MHz, DMSO-d₆) δ 4.94-4.87 (m, 1H), 4.08-3.87 (m, 2H), 3.66-3.53 (m, 1H), 1.96-1.31 (m, 10H), 1.39 (s, 9H).

Step E: tert-Butyl (1R,5R)-2-oxo-9-azabicyclo[3.3.1]nonane-9-carboxylate. To a solution of oxalyl chloride (12.9 mL, 152 mmol) in dichloromethane (560 mL) was added dimethyl sulfoxide (21.5 mL, 303 mmol) dropwise at −78° C. To the reaction mixture was added a solution of tert-butyl (1R,2S,5R)-2-hydroxy-9-azabicyclo[3.3.1]nonane-9-carboxylate (24.5 g, 102 mmol) in dichloromethane (140 mL) and the reaction was stirred at −78° C. for 30 min. Triethylamine (TEA) (85 mL, 61 mmol) was added and the reaction was allowed to warm to room temperature and stirred for 2 h. The reaction mixture was washed with water (3×300 mL), dried over sodium sulfate, filtered and evaporated. The residue was purified by silica gel column chromatography eluting with heptane:ethyl acetate (4:1) to afford the title compound (19.5 g, 82 mmol, 80% yield) as a white crystalline solid. [α]$_D^{25}$ +116.0° (c 0.110, MeOH). MS (ESI): mass calcd. for C₁₃H₂₁NO₃, 239.2; m/z found, 262.1 [M+Na]⁺.

Step F: 9-(tert-Butyl) 3-ethyl (1S,5R)-2-oxo-9-azabicyclo[3.3.1]nonane-3,9-dicarboxylate. To a solution of tert-butyl (1R,5R)-2-oxo-9-azabicyclo[3.3.1]nonane-9-carboxylate (8.2 g, 34.3 mmol) in distilled tetrahydrofuran (180 mL) was added lithium bis(trimethylsilyl)amide (LiHMDS) (1 M in tetrahydrofuran, 41.2 mL, 41.2 mmol) at −78° C. and the reaction was stirred at −78° C. for 30 min. To the reaction mixture was added a solution of ethyl cyanoformate (4.4 mL, 44.5 mmol) in distilled tetrahydrofuran (20 mL) and the reaction was stirred at −78° C. for 1 h. The reaction was quenched with saturated ammonium chloride (200 mL). The aqueous layer was extracted with dichloromethane (2×200 mL). The combined organic layers were washed with water (2×150 mL), dried over sodium sulfate, filtered and evaporated. The residue was purified by silica gel column chromatography eluting with heptane:ethyl acetate (4:1) to afford the title compound (5.5 g, 18 mmol, 51% yield) as a pale-yellow oil. $[\alpha]_D^{25}$ −45.0° (c 0.185, MeOH). MS (ESI): mass calcd. for $C_{16}H_{25}NO_5$, 311.2; m/z found, 256.1 $[M+2H-tBu]^+$. $^1$H NMR (300 MHz, DMSO-$d_6$) δ 11.83 (s, 1H), 4.52-4.37 (m, 1H), 4.36-4.25 (m, 1H), 4.20 (q, J=7.1 Hz, 2H), 2.66-2.49 (m, 1H), 2.09 (d, J=16.5 Hz, 1H), 1.76-1.45 (m, 6H), 1.39 (s, 9H), 1.24 (t, J=7.1 Hz, 3H).

Step G: tert-Butyl (5R,9S)-2-methyl-3-oxo-2,3,4,5,6,7,8,9-octahydro-1H-5,9-epiminocycloocta[c]pyrazole-10-carboxylate. To a mixture of 9-(tert-butyl) 3-ethyl (1S,5R)-2-oxo-9-azabicyclo[3.3.1]nonane-3,9-dicarboxylate (20.4 g, 65.5 mmol) in acetic acid (AcOH) (260 mL) was added methylhydrazine (5.2 mL, 99.3 mmol, 0.88 g/mL) and the reaction was stirred at 80° C. for 8 h. The reaction mixture was evaporated, and the residue was purified by silica gel column chromatography eluting with ethyl acetate:methanol (10:1) to give the title compound (15.4 g, 52.5 mmol, 80% yield). MS (ESI): mass calcd. for $C_{15}H_{23}N_3O_3$, 293.2; m/z found, 294.2 $[M+H]^+$.

Step H: tert-Butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate. To a solution of tert-butyl (5R,9S)-2-methyl-3-oxo-2,3,4,5,6,7,8,9-octahydro-1H-5,9-epiminocycloocta[c]pyrazole-10-carboxylate (20.0 g, 68.2 mmol) in dichloromethane (300 mL) was added N,N-diisopropylethylamine (13 mL, 75.1 mmol), and N-phenyl-bis(trifluoromethanesulfonimide) (26.8 g, 75.0 mmol) and the reaction was stirred at room temperature for 18 h. The reaction mixture was washed with saturated sodium bicarbonate (2×200 mL), 10% potassium bisulfate (2×200 mL) and brine (1×200 mL), dried over sodium sulfate, filtered and evaporated. The residue was purified by gradient silica column chromatography eluting with heptane:ethyl acetate (6:1→4:1). The residue was dissolved in ethyl acetate (100 mL) and evaporated. The less pure fractions were combined and evaporated. The residue was dissolved in dichloromethane (100 mL), washed with saturated sodium bicarbonate (3×150 mL), dried over sodium sulfate, filtered, and evaporated. The products were combined to give the title compound (16.4 g, 39 mmol, 56% yield) as a colorless oil. MS (ESI): mass calcd. for $C_{16}H_{22}F_3N_3O_5S$, 425.1; m/z found, 370.1 $[M+2H-tbutyl]^+$. $^1$H NMR (500 MHz, DMSO-$d_6$) δ 5.06 (d, J=18.9 Hz, 1H), 4.48 (d, J=31.6 Hz, 1H), 3.73 (s, 3H), 2.84 (dd, J=16.3, 7.4 Hz, 1H), 2.44 (d, J=16.3 Hz, 1H), 1.78-1.61 (m, 3H), 1.59-1.41 (m, 2H), 1.38 (s, 9H), 1.27-1.16 (m, 1H). Optical rotation: $[\alpha]_D^{25}$ +10.0° (c 0.15, MeOH).

Intermediate 12: tert-Butyl (5R,8S)-2-methyl-3-(((trifluoromethyl)sulfonyl)oxy)-2,4,5,6,7,8-hexahydro-5,8-epiminocyclohepta[c]pyrazole-9-carboxylate

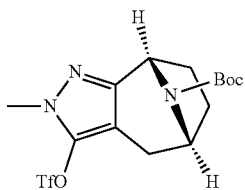 [SMILES: Cn1nc2c(c1OS(=O)(=O)C(F)(F)F)C[C@@H]1CC[C@H]2N1C(=O)OC(C)(C)C]

Step A: Ethyl 5-formyl-1H-pyrrole-2-carboxylate. A cooled (0° C.) solution of dichloroethane (DCE) (250 mL) and $POCl_3$ (18.7 mL, 201 mmol) was slowly charged with N,N-dimethylformamide (DMF) (17.7 mL, 230 mmol), this suspension was stirred at 0° C. for 15 min. Then the reaction mixture was charged with a solution of ethyl 1H-pyrrole-2-carboxylate (20 g, 144 mmol) dissolved in DCE (50 mL) and stirred at 0° C. for 30 min warming to rt overnight. The completed reaction was cooled to 0° C. and a 50 mL solution of NaOAc tri-hydrate (~43 g) was added. The resulting mixture was heated to 75° C. for 30 min and then cooled to rt. The aq. layer was extracted with methyl tert-butyl ether (MTBE, TBME) washed with aq. $NaHCO_3$, brine, dried over $Na_2SO_4$, filtered and concentrated. Purification (FCC, eluting with 0-10% EtOAc/Hex) afforded the title compound (18.1 g, 75%). MS (ESI): mass calcd. for $C_8H_9NO_3$, 167.1; m/z found, 168.1 $[M+H]^+$.

Step B: Ethyl (E)-5-(3-ethoxy-3-oxoprop-1-en-1-yl)-1H-pyrrole-2-carboxylate. A cooled (0° C.) solution of NaH (8.7 g, 217 mmol) in THF (200 mL) was charged with triethylphosphono acetate (61.7 g, 234 mmol). The reaction mixture was stirred at 0° C. for 3 hours, then ethyl 5-formyl-1H-pyrrole-2-carboxylate (27.9 g, 167 mmol) was added. The reaction mixture was stirred at rt overnight. The reaction mixture was quench with aq. $NH_4Cl$ (200 mL) and extracted into $Et_2O$ (×3), washed with brine, dried over $Na_2SO_4$, filtered and concentrated under reduced pressure. The resulting material was recrystallized form 10% EtOAc/Hex to give the title compound (39.5 g, 99.8%). MS (ESI): mass calcd. for $C_{12}H_{15}NO_4$, 237.1; m/z found, 238.1 $[M+H]^+$. $^1$H NMR (500 MHz, $CDCl_3$) δ 9.93 (s, 1H), 7.56 (d, J=16.0 Hz, 1H), 6.98-6.81 (m, 1H), 6.63-6.43 (m, 1H), 6.32 (d, J=16.0 Hz, 1H), 4.39 (q, J=7.1 Hz, 2H), 4.25 (q, J=7.1 Hz, 2H), 1.39 (t, J=7.1 Hz, 3H), 1.32 (t, J=7.2 Hz, 3H).

Step C: Ethyl 5-(3-ethoxy-3-oxopropyl)pyrrolidine-2-carboxylate. To a flask was added ethyl (E)-5-(3-ethoxy-3-oxoprop-1-en-1-yl)-1H-pyrrole-2-carboxylate (39.5 g, 167 mmol mmol) rhodium on alumina (27.4 g, 13.3 mmol) and this was suspended in acetic acid (80 mL) and was evacuated and back filled with $N_2$. The flask was then fitted with a $H_2$ bladder and evacuated and back filled with $H_2$ twice. The reaction mixture was stirred at rt for 48 hrs. The resulting reaction mixture was passed through a Celite©, washed with DCM, then concentrated under reduced pressure. Water (400 mL) was added to the reaction mixture, and the reaction mixture was extracted into DCM (×3). The organic layers were combined, washed with aq. $NaHCO_3$, brine, dried ($Na_2SO_4$), filtered and concentrated under reduced pressure to afford the title product as a tinted oil (38.6 g, 95%). MS (ESI): mass calcd. for $C_{12}H_{21}NO_4$, 243.1; m/z found, 244.1 $[M+H]^+$.

Step D: 1-(tert-Butyl) 2-ethyl 5-(3-ethoxy-3-oxopropyl)pyrrolidine-1,2-dicarboxylate. A solution of ethyl 5-(3-ethoxy-3-oxopropyl)pyrrolidine-2-carboxylate (38.6 g, 158 mmol) and Boc-anhydride (di-tert-butyl decarbonate) (38 g, 175 mmol) in DCM (317 mL) was slowly charged with TEA (44.1 mL, 317 mmol). The resulting reaction mixture was stirred at rt overnight. The reaction mixture was diluted with DCM (200 mL) and washed with water, brine, dried over $Na_2SO_4$, filtered and concentrated to give the title product (54.8 g, 100.6%). MS (ESI): mass calcd. for $C_{17}H_{29}NO_6$, 343.2; m/z found, 244.1 $[M+2H-CO_2tBu]^+$.

Step E: 8-(tert-Butyl) 3-ethyl 2-oxo-8-azabicyclo[3.2.1]octane-3,8-dicarboxylate. A solution of 1-(tert-butyl) 2-ethyl 5-(3-ethoxy-3-oxopropyl)pyrrolidine-1,2-dicarboxylate (54.8 g, 160 mmol) in THF (1.3 L) and KOtBu (21.5 g, 191 mmol) was heated at 60° C. for 3 h. The reaction mixture was cooled and concentrated under reduced pressure. The resulting residue was resuspended in DCM (800 mL) and washed with sat. NH₄Cl. The aq. layer was re-extracted with EtOAc (×2). The combined organic layers were washed with brine, dried over Na₂SO₄, filtered and concentrated under reduced pressure. Purification (FCC, SiO₂, eluting with 0-10% EtOAc/hex) afforded the title compound (37.8 g, 79.7%). MS (ESI): mass calcd. for $C_{15}H_{23}NO_5$, 297.2; m/z found, 242.1 [M+2H-tBu]⁺.

Step F: racemic-tert-Butyl 2-methyl-3-oxo-1,2,3,4,5,6,7,8-octahydro-5,8-epiminocyclohepta[c]pyrazole-9-carboxylate. A solution of 8-(tert-butyl) 3-ethyl 2-oxo-8-azabicyclo[3.2.1]octane-3,8-dicarboxylate (1.76 g, 5.9 mmol) in toluene (33 mL) was charged with methylhydrazine (467 mL). The resulting mixture was heated at 110° C. for 2 hours. The cooled reaction was concentrated under reduced pressure. Purification (FCC, SiO₂, eluting with 0-10% MeOH/DCM) afforded the title compound as a clear oil. MS (ESI): mass calcd. for $C_{14}H_{21}N_3O_3$, 279.2; m/z found, 280.2 [M+H]⁺.

Step G: tert-butyl (5R,8S)-2-Methyl-3-(((trifluoromethyl)sulfonyl)oxy)-2,4,5,6,7,8-hexahydro-5,8-epiminocyclohepta[c]pyrazole-9-carboxylate and tert-butyl (5S,8R)-2-Methyl-3-(((trifluoromethyl)sulfonyl)oxy)-2,4,5,6,7,8-hexahydro-5,8-epiminocyclohepta[c]pyrazole-9-carboxylate. To a solution of racemic-tert-butyl 2-methyl-3-oxo-1,2,3,4,5,6,7,8-octahydro-5,8-epiminocyclohepta[c]pyrazole-9-carboxylate (9.48 g, 34 mmol) in DCM (152 mL) was added N-phenyl-bis(trifluoromethansulfonimide) (13.5 g, 37 mmol) followed by DIEA (6.4 mL, 37 mmol). The resulting solution was stirred at rt for 18 h. The completed reaction was concentrated under reduced pressure. Purification (FCC, SiO₂, eluting with 0-20% EtOAc/Hex) afforded the title racemic mixture of compounds (11.2 g, 80%). MS (ESI): mass calcd. for $C_{15}H_{20}F_3N_3O_5S$, 411.1; m/z found, 356.0 [M+2H-tbutyl]⁺.

Single enantiomers were isolated by chiral SFC purification of racemic-tert-butyl 2-methyl-3-(((trifluoromethyl)sulfonyl)oxy)-2,4,5,6,7,8-hexahydro-5,8-epiminocyclohepta[c]pyrazole-9-carboxylate using stationary phase: Chiralpak IC 5 μm 250*30 mm, mobile phase: 93% CO₂, 7% iPrOH, giving tert-butyl (5R,8S)-2-methyl-3-(((trifluoromethyl)sulfonyl)oxy)-2,4,5,6,7,8-hexahydro-5,8-epiminocyclohepta[c]pyrazole-9-carboxylate (single enantiomer; 1.05 min retention time) MS (ESI): mass calcd. for $C_{15}H_{20}F_3N_3O_5S$, 411.1; m/z found, 356.0 [M+2H-t-butyl]⁺.

Intermediate 13: (S)-2,7-Dimethyl-3-(1-methyl-3-(trifluoromethyl)-1H-pyrazol-5-yl)-4,5,6,7-tetrahydro-2H-pyrazolo[3,4-c]pyridine

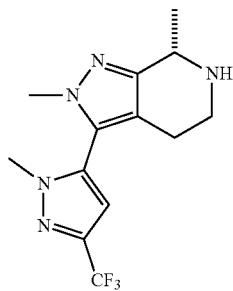 [SMILES: C[C@@H]1NCCc2c1nn(C)c2-c1cc(C(F)(F)F)nn1C]

Step A: tert-Butyl (S)-2,7-dimethyl-3-(1-methyl-3-(trifluoromethyl)-1H-pyrazol-5-yl)-2,4,5,7-tetrahydro-6H-pyrazolo[3,4-c]pyridine-6-carboxylate. To a solution of (S)-tert-butyl 2,7-dimethyl-3-(((trifluoromethyl)sulfonyl) oxy)-2,4,5,7-tetrahydro-6H-pyrazolo[3,4-c]pyridine-6-carboxylate (Intermediate 10, 500 mg, 1.25 mmol) in 1,4-dioxane (4.0 mL) was added (1-methyl-3-(trifluoromethyl)-1H-pyrazol-5-yl)boronic acid (291 mg, 1.5 mmol), aqueous sodium carbonate (2 M, 1.0 mL, 2.74 mmol) and XPhos-Pd-G2 (49.3 mg, 0.06 mmol) under a nitrogen atmosphere. The reaction mixture was heated to 90° C. for 2 h and concentrated under reduced pressure. The residue was taken up in ethyl acetate (EtOAc) (10 mL), washed with water (2×5.0 mL), brine (1×10 mL), dried over sodium sulfate, filtered, and concentrated under reduced pressure. The resulting residue was purified by flash chromatography (SiO₂; 0-40% hexanes-EtOAc) to give the title compound as an oil (390 mg, 0.50 mmol, 77%). MS (ESI): mass calcd. for $C_{18}H_{24}F_3N_5O_2$, 399.2; m/z found, 344.1 [M+2H-ᵗBu]⁺. ¹H NMR (400 MHz, DMSO-d₆) δ 7.08 (d, J=0.8 Hz, 1H), 5.11 (s, 1H), 4.22-4.04 (m, 1H), 3.78 (s, 3H), 3.69 (s, 3H), 3.05-2.83 (m, 1H), 2.50-2.41 (m, 1H), 2.37-2.22 (m, 1H), 1.44 (s, 9H), 1.37 (d, J=6.7 Hz, 3H).

Step B: (S)-2,7-Dimethyl-3-(1-methyl-3-(trifluoromethyl)-1H-pyrazol-5-yl)-4,5,6,7-tetrahydro-2H-pyrazolo[3,4-c]pyridine. To a mixture of tert-butyl (S)-2,7-dimethyl-3-(1-methyl-3-(trifluoromethyl)-1H-pyrazol-5-yl)-2,4,5,7-tetrahydro-6H-pyrazolo[3,4-c]pyridine-6-carboxylate (385 mg, 0.96 mmol) in dichloromethane (2 mL) was added trifluoroacetic acid (TFA) (2 mL, 26.1 mmol, 1.49 g/mL) at 0° C. and the reaction was stirred at room temperature for 30 minutes. The reaction mixture was concentrated with dichloromethane (25 mL), concentrated in vacuo, and the process repeated 3 additional times to afford the title compound as white solid which was taken to next step without purification. MS (ESI): mass calcd. for $C_{13}H_{16}F_3N_5$, 299.2; m/z found, 300.1 [M+H]⁺. ¹H NMR (500 MHz, Methanol-d₄) δ 6.86 (s, 1H), 4.61 (q, J=6.7 Hz, 1H), 3.81 (s, 3H), 3.75 (s, 3H), 3.67-3.60 (m, 1H), 3.41-3.33 (m, 1H), 2.88-2.67 (m, 2H), 1.70 (d, J=6.8 Hz, 3H).

Intermediate 14: (S)-2,7-Dimethyl-3-(1-methyl-5-(trifluoromethyl)-1H-pyrazol-3-yl)-4,5,6,7-tetrahydro-2H-pyrazolo[3,4-c]pyridine·trifluoroacetic Acid Salt

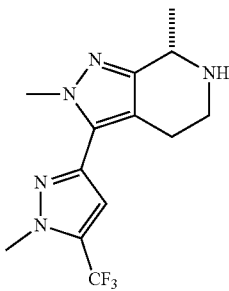 [SMILES: C[C@@H]1NCCc2c1nn(C)c2-c1cc(C(F)(F)F)n(C)n1]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using 1-methyl-3-(4,4,5,5-tetramethyl-1,3,2-dioxaborolan-2-yl)-5-(trifluoromethyl)-1H-pyrazole instead of (1-methyl-3-(trifluoromethyl)-1H- pyrazol-5-yl)boronic acid in Step A. The resulting mixture was carried on as the TFA salt without further purification. MS (ESI): mass calcd. for $C_{13}H_{16}F_3N_5$, 299.2; m/z found, 300.2 [M+H]$^+$. $^1$H NMR (500 MHz, CDCl$_3$) δ 6.71 (s, 1H), 4.16 (q, J=6.6 Hz, 1H), 4.05 (d, J=4.8 Hz, 6H), 3.64-3.24 (m, 1H), 3.07-2.97 (m, 2H), 2.83-2.63 (m, 2H), 1.55 (d, J=6.6 Hz, 3H).

Intermediate 15: (S)-2,7-Dimethyl-3-(1-methyl-5-(trifluoromethyl)-1H-pyrazol-4-yl)-4,5,6,7-tetrahydro-2H-pyrazolo[3,4-c]pyridine

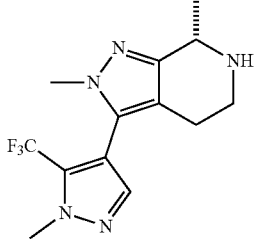

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using (1-methyl-5-(trifluoromethyl)-1H-pyrazol-4-yl)boronic acid instead of (1-methyl-3-(trifluoromethyl)-1H-pyrazol-5-yl)boronic acid in Step A. MS (ESI): mass calcd. for $C_{13}H_{16}F_3N_5$, 299.2; m/z found, 300.1 [M+H]$^+$. $^1$H NMR (600 MHz, CDCl$_3$) δ 7.45 (s, 1H), 4.08 (d, J=1.0 Hz, 3H), 4.04 (q, J=6.6 Hz, 1H), 3.65 (s, 3H), 3.28-3.20 (m, 1H), 2.95-2.86 (m, 1H), 2.51-2.41 (m, 1H), 2.36-2.27 (m, 1H), 1.49 (d, J=6.6 Hz, 3H).

Intermediate 16: (S)-3-(1,4-Dimethyl-1H-pyrazol-5-yl)-2,7-dimethyl-4,5,6,7-tetrahydro-2H-pyrazolo[3,4-c]pyridine

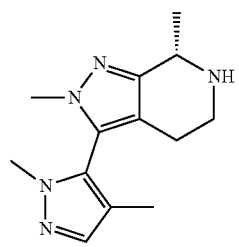 [SMILES: Cc1cnn(C)c1-c1c2c(nn1C)[C@H](C)NCC2]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using 1,4-dimethyl-5-(4,4,5,5-tetramethyl-1,3,2-dioxaborolan-2-yl)-1H-pyrazole instead of (1-methyl-3-(trifluoromethyl)-1H-pyrazol-5-yl)boronic acid in Step A. MS (ESI): mass calcd. for $C_{13}H_{19}N_5$, 245.2; m/z found, 246.1 [M+H]$^+$.

Intermediate 17: (S)-3-(1,5-Dimethyl-3-(trifluoromethyl)-1H-pyrazol-4-yl)-2,7-dimethyl-4,5,6,7-tetrahydro-2H-pyrazolo[3,4-c]pyridine

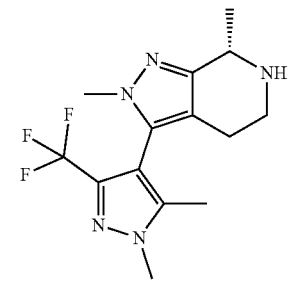 [SMILES: Cc1c(-c2c3c(nn2C)[C@H](C)NCC3)c(C(F)(F)F)nn1C]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using 1,5-dimethyl-4-(4,4,5,5-tetramethyl-1,3,2-dioxaborolan-2-yl)-3-(trifluoromethyl)-1H-pyrazole (Intermediate 9) instead of (1-methyl-3-(trifluoromethyl)-1H-pyrazol-5-yl)boronic acid in Step A. MS (ESI): mass calcd. for $C_{14}H_{18}F_3N_5$, 313.15; m/z found, 314.1 [M+H]$^+$.

Intermediate 18: (S)-3-(3-Methoxy-1-methyl-1H-pyrazol-4-yl)-2,7-dimethyl-4,5,6,7-tetrahydro-2H-pyrazolo[3,4-c]pyridine

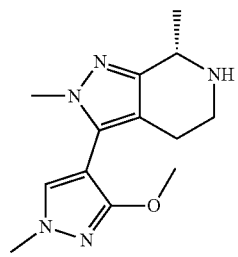 [SMILES: COc1nn(C)cc1-c1c2c(nn1C)[C@H](C)NCC2]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using 3-methoxy-1-methyl-4-(4,4,5,5-tetramethyl-1,3,2-dioxaborolan-2-yl)-1H-pyrazole instead of (1-methyl-3-(trifluoromethyl)-1H-pyrazol-5-yl)boronic acid in Step A. MS (ESI): mass calcd. for $C_{13}H_{19}N_5O$, 261.2; m/z found, 262.3 [M+H]$^+$.

Intermediate 19: (S)-2,7-Dimethyl-3-(1-methyl-3-(trifluoromethyl)-1H-pyrazol-4-yl)-4,5,6,7-tetrahydro-2H-pyrazolo[3,4-c]pyridine·HCl Salt

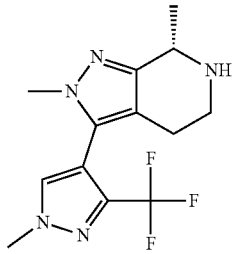 [SMILES: C[C@@H]1NCCc2c1nn(C)c2-c1cn(C)nc1C(F)(F)F]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using 1-methyl-4-(4,4,5,5-tetramethyl-1,3,2-dioxaborolan-2-yl)-3-(trifluoromethyl)-1H-pyrazole instead of (1-methyl-3-(trifluoromethyl)-1H-pyrazol-5-yl)boronic acid in Step A, and using HCl instead of TFA in Step B. EtOH was used instead of DCM in Step B. MS (ESI): mass calcd. for $C_{13}H_{16}F_3N_5$, 299.1; m/z found, 300.1 [M+H]$^+$.

Intermediate 20: (5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazole

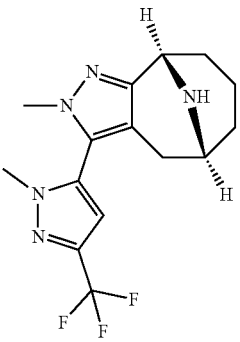 [SMILES: Cn1nc(C(F)(F)F)cc1-c1c2c(nn1C)[C@H]1CCC[C@H](C2)N1]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (Intermediate 11) instead of (S)-tert-butyl 2,7-dimethyl-3-(((trifluoromethyl)sulfonyl) oxy)-2,4,5,7-tetrahydro-6H-pyrazolo[3,4-c] pyridine-6-carboxylate in Step A. MS (ESI): mass calcd. for $C_{15}H_{18}F_3N_5$, 325.2; m/z found, 326.2 [M+H]$^+$.

Intermediate 21: (5R,9S)-2-Methyl-3-(1-methyl-5-(trifluoromethyl)-1H-pyrazol-3-yl)-4,5,6,7,8,9-hexahydro-2H-5,9-epiminocycloocta[c]pyrazole

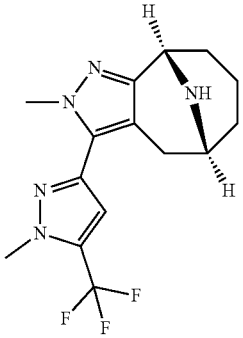 [SMILES: Cn1nc(-c2c3c(nn2C)[C@H]2CCC[C@H](C3)N2)cc1C(F)(F)F]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (Intermediate 11) instead of (S)-tert-butyl 2,7-dimethyl-3-(((trifluoromethyl)sulfonyl) oxy)-2,4,5,7-tetrahydro-6H-pyrazolo[3,4-c] pyridine-6-carboxylate and 1-methyl-3-(4,4,5,5-tetramethyl-1,3,2-dioxaborolan-2-yl)-5-(trifluoromethyl)-1H-pyrazole instead of (1-methyl-3-(trifluoromethyl)-1H-pyrazol-5-yl)boronic acid in Step A. MS (ESI): mass calcd. for $C_{15}H_{18}F_3N_5$, 325.2; m/z found, 326.1 [M+H]$^+$.

Intermediate 22: (5R,9S)-3-(1-Ethyl-3-(trifluoromethyl)-1H-pyrazol-5-yl)-2-methyl-4,5,6,7,8,9-hexahydro-2H-5,9-epiminocycloocta[c]pyrazole

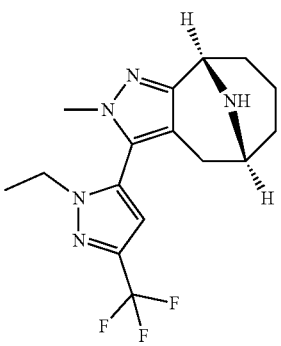 [SMILES: CCn1nc(C(F)(F)F)cc1-c1c2c(nn1C)[C@H]1CCC[C@H](C2)N1]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (Intermediate 11) instead of (S)-tert-butyl 2,7-dimethyl-3-(((trifluoromethyl)sulfonyl) oxy)-2,4,5,7-tetrahydro-6H-pyrazolo[3,4-c] pyridine-6-carboxylate and (1-ethyl-3-(trifluoromethyl)-1H-pyrazol-5-yl)boronic acid instead of (1-methyl-3-(trifluoromethyl)-1H-pyrazol-5-yl)boronic acid in Step A. MS (ESI): mass calcd. for $C_{16}H_{20}F_3N_5$, 339.2; m/z found, 340.3 $[M+H]^+$.

Intermediate 23: (5R,9S)-3-(1,3-Dimethyl-1H-pyrazol-5-yl)-2-methyl-4,5,6,7,8,9-hexahydro-2H-5,9-epiminocycloocta[c]pyrazole

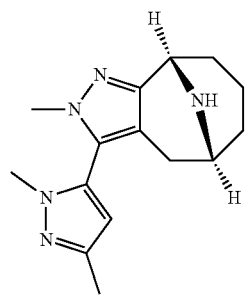 [SMILES: Cc1cc(-c2c3c(nn2C)[C@H]2CCC[C@H](C3)N2)n(C)n1]

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (Intermediate 11) instead of (S)-tert-butyl 2,7-dimethyl-3-(((trifluoromethyl)sulfonyl) oxy)-2,4,5,7-tetrahydro-6H-pyrazolo[3,4-c] pyridine-6-carboxylate and (1,3-dimethyl-1H-pyrazol-5-yl)boronic acid instead of (1-methyl-3-(trifluoromethyl)-1H-pyrazol-5-yl)boronic acid in Step A. MS (ESI): mass calcd. for $C_{15}H_{21}N_5$, 271.2; m/z found, 272.1 $[M+H]^+$.

Intermediate 24: (5R,8S)-2-Methyl-3-(1-methyl-3-(trifluoromethyl)-1H-pyrazol-5-yl)-2,4,5,6,7,8-hexahydro-5,8-epiminocyclohepta[c]pyrazole

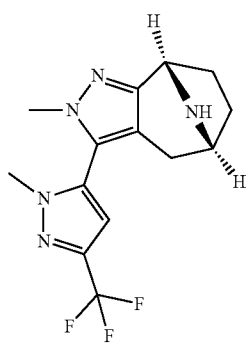

The title compound was prepared in a manner analogous to (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13) using tert-butyl (5R,8S)-2-methyl-3-(((trifluoromethyl)sulfonyl)oxy)-2,4,5,6,7,8-hexahydro-5,8-epiminocyclohepta[c]pyrazole-9-carboxylate (Intermediate 12) instead of (S)-tert-butyl 2,7-dimethyl-3-(((trifluoromethyl)sulfonyl) oxy)-2,4,5,7-tetrahydro-6H-pyrazolo[3,4-c] pyridine-6-carboxylate. MS (ESI): mass calcd. for $C_{14}H_{16}F_3N_5$, 311.1; m/z found, 312.2 $[M+H]^+$.

Intermediate 25: (S)-2,7-Dimethyl-6-(quinoline-6-carbonyl)-4,5,6,7-tetrahydro-2H-pyrazolo[3,4-c]pyridin-3-yl trifluoromethanesulfonate

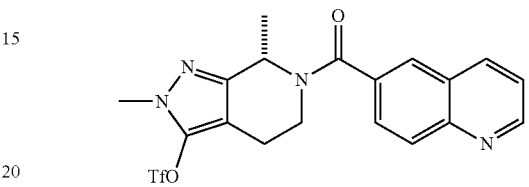

Step A: (S)-2,7-Dimethyl-4,5,6,7-tetrahydro-2H-pyrazolo[3,4-c]pyridin-3-yl trifluoromethanesulfonate. To a solution of (S)-tert-Butyl 2,7-dimethyl-3-(((trifluoromethyl)sulfonyl)oxy)-2,4,5,7-tetrahydro-6H-pyrazolo[3,4-c] pyridine-6-carboxylate (Intermediate 10, 2.0 g, 5.0 mmol) in $CH_2Cl_2$ (15 mL) was added trifluoroacetic acid (7.4 mL, 19.4 mmol) and the reaction stirred at room temperature for 30 min before concentrating in vacuo. The residue was taken up in EtOAc, sat. aq. $NaHCO_3$ carefully added, and the mixture stirred for 1 min. The layers were separated and the aqueous layer extracted with EtOAc followed by 20% iPrOH/$CHCl_3$. The combined organics were washed with brine, dried over $Na_2SO_4$, filtered, and concentrated in vacuo.

Step B: (S)-2,7-Dimethyl-6-(quinoline-6-carbonyl)-4,5,6,7-tetrahydro-2H-pyrazolo[3,4-c]pyridin-3-yl trifluoromethanesulfonate. To a solution of (S)-2,7-dimethyl-4,5,6,7-tetrahydro-2H-pyrazolo[3,4-c]pyridin-3-yl trifluoromethanesulfonate (1.5 g, 5.0 mmol) in $CH_2Cl_2$ (50 mL) was added quinoline-6-carboxylic acid (1.30 g, 7.51 mmol) and DIPEA (2.59 mL, 15.0 mmol), followed by propylphosphonic anhydride (50 wt % in EtOAc, 4.3 mL, 15.0 mmol). The reaction was stirred at room temperature for 30 min, and then quenched with $H_2O$. After stirring the mixture vigorously for 1-2 min, the layers were separated and the organic layer carefully washed with sat. aq. $NaHCO_3$ (caution: gas formation). The combined aqueous layers were transferred to a round bottom flask and stirred vigorously for 1-2 min until no further effervescence was observed, and then extracted with $CH_2Cl_2$. The two organic solutions were combined and washed once with brine, dried over $Na_2SO_4$, filtered, and concentrated in vacuo. The resulting residue was taken up in a mixture of $CH_2Cl_2$/hexanes, and the resulting precipitate collected via vacuum filtration, washing with hexanes, to afford the title compound as a tan solid (1.38 g). The filtrate was concentrated and purified by silica gel chromatography (0-20% MeOH in $CH_2Cl_2$) to afford a second batch of the title compound (0.52 g). Combined 83% yield. MS (ESI): mass calcd. for $C_{19}H_{17}F_3N_4O_4S$, 454.1; m/z found, 455.1 $[M+H]^+$. $^1H$ NMR (500 MHz, $CDCl_3$) δ 8.99 (dd, J=4.2, 1.7 Hz, 1H), 8.19 (dd, J=15.2, 8.6 Hz, 2H), 7.92 (d, J=1.9 Hz, 1H), 7.73 (dd, J=8.6, 1.9 Hz, 1H), 7.48 (dd, J=8.3, 4.2 Hz, 1H), 5.82 (br s, 0.51H), 4.91 (br s, 0.70H), 3.78 (s, 3.74H), 3.27 (br s, 1H), 2.94-2.44 (m, 2H), 1.58 (s, 3H).

Intermediate 26:
3-Methyl-5-(2H-1,2,3-triazol-2-yl)benzoic Acid

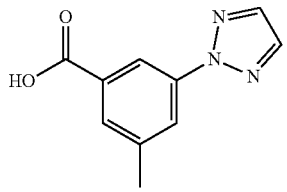

To a mixture of 3-iodo-5-methylbenzoic acid (200 mg, 0.76 mmol) in N,N-dimethylformamide (2.2 mL) was added 1H-1,2,3-triazole (199 μL, 3.44 mmol), cesium carbonate (423 mg, 1.30 mmol), trans-N,N'-dimethylcyclohexane-1,2-diamine (20 μL, 0.13 mmol) and copper(I) iodide (15 mg, 78.8 μmol). The reaction mixture was stirred at 140° C. for 60 min under microwave irradiation. The reaction mixture was filtered through a pad of Celite® and the Celite® was washed with ethyl acetate (2×5 mL). The combined filtrates were extracted with water (1×5 mL). The aqueous layer was acidified to pH 3 with 1 M hydrochloric acid. The aqueous layer was extracted with ethyl acetate (2×5 mL). The combined organic layers were dried over magnesium sulfate, filtered, and evaporated under reduced pressure. The resulting residue was purified by preparative HPLC to afford the title compound (51 mg, 32% yield) as an off-white powder. MS (ESI): mass calcd. for $C_9H_6FN_3O_2$, 203.1; m/z found, 204.1 [M+H]$^+$.

Intermediate 27:
5-Fluoro-2-methylquinoline-6-carboxylic Acid

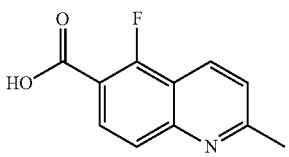

A mixture of 4-amino-2-fluorobenzoic acid (2.0 g, 13.0 mmol) and concentrated HCl (6M in water, 25.0 mL, 150 mmol) were stirred at 90° C. for 1 hour. To the reaction mixture was added (E)-but-2-enal (2.1 g, 30.0 mmol) at 90° C., and the reaction mixture was stirred for 45 minutes. The reaction mixture was cooled and poured into water (20 mL) and extracted with ethyl acetate (20 mL×3). The aqueous phase was concentrated to dryness under reduced pressure, the resulting residue was purified by preparative HPLC (METHOD G) to afford the title compound as a white solid (120 mg, 4.1% yield). MS (ESI): mass calcd. for $C_{11}H_8FNO_2$, 205.1; m/z found, 205.9 [M+H]$^+$. $^1$H NMR (400 MHz, DMSO-d$_6$) δ 8.91 (d, J=8.7 Hz, 1H), 8.32-8.24 (m, 1H), 8.13 (d, J=8.9 Hz, 1H), 7.88 (d, J=8.7 Hz, 1H), 2.91 (s, 3H).

Intermediate 28:
7-Fluoro-2-methylquinoline-6-carboxylic Acid

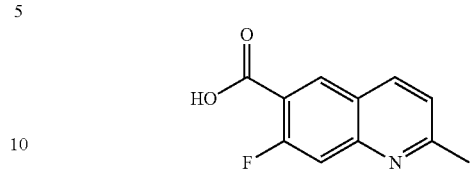

The title compound was prepared in a manner analogous to Intermediate 27. Purification by SFC over DAICEL CHIRALPAK AD-H (250 mm×30 mm×5 um (isocratic elution: EtOH (containing 0.1% of 25% aq. NH$_3$): supercritical CO$_2$, 25%: 75% to 25%: 75% (v/v)). MS (ESI): mass calcd. for $C_{11}H_8FNO_2$, 205.1; m/z found, 205.8 [M+H]$^+$. $^1$H NMR (400 MHz, DMSO-d$_6$) δ 8.36 (t, J=7.7 Hz, 2H), 7.61 (d, J=11.9 Hz, 1H), 7.42 (d, J=8.5 Hz, 1H), 2.66 (s, 3H).

Intermediate 29:
2,5-Dimethylquinoline-6-carboxylic Acid

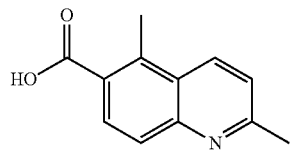

The title compound was prepared in a manner analogous to Intermediate 27 using 4-amino-2-methylbenzoic acid instead of 4-amino-2-fluorobenzoic acid. The resulting mixture of isomers was purified by SFC over DAICEL CHIRALPAK AD-H (250 mm×30 mm×5 um (isocratic elution: EtOH (containing 0.1% of 25% aq. NH$_3$): supercritical CO$_2$, 25%: 75% to 25%: 75% (v/v)) to afford the title compound as a white solid and 2,7-dimethylquinoline-6-carboxylic acid (Intermediate 30). MS (ESI): mass calcd. for $C_{12}H_{11}NO_2$, 201.2; m/z found, 202.2 [M+H]$^+$. $^1$H NMR (400 MHz, DMSO-d$_6$) δ 8.53 (d, J=8.5 Hz, 1H), 7.94 (d, J=8.8 Hz, 1H), 7.78 (d, J=8.8 Hz, 1H), 7.50 (d, J=8.8 Hz, 1H), 2.84 (s, 3H), 2.67 (s, 3H).

Intermediate 30:
2,7-Dimethylquinoline-6-carboxylic Acid

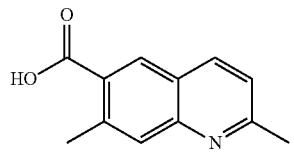

The title compound was isolated as the second product from the mixture described in Intermediate 29. MS (ESI): mass calcd. for $C_{12}H_{11}NO_2$, 201.2; m/z found, 202.2 [M+H]$^+$. $^1$H NMR (400 MHz, DMSO-d$_6$) δ 13.00 (br. s, 1H), 8.46 (s, 1H), 8.33 (d, J=8.3 Hz, 1H), 7.78 (s, 1H), 7.41 (d, J=8.5 Hz, 1H), 2.68 (s, 3H), 2.65 (s, 3H).

Intermediate 31:
2,4-Dimethylquinoline-6-carboxylic Acid

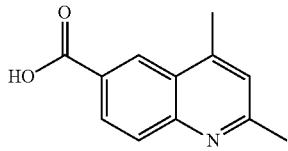

Step A: 6-Bromo-2,4-dimethylquinoline. To a mixture of 6-bromo-2-methylquinoline (555 mg, 2.5 mmol), ethyl 2-mercaptopropanoate (65 µL, 0.5 mmol) and 4-methylbenzenesulfonic acid (950 mg, 5.5 mmol) in DMSO (10 mL) and MeOH (20 mL) was added Ir(ppy)$_2$(dtbbpy)PF$_6$ catalyst (28 mg, 0.031 mmol) under nitrogen atmosphere. The resultant mixture was degassed with nitrogen for another 5 minutes and then irradiated with blue LEDs at room temperature. After 36 hours, 1N NaOH (10.0 mL) and DCM (100.0 mL) were added to the reaction mixture. The organic layer was separated, washed with brine (30 mL×3), dried over anhydrous sodium sulfate, filtered, and concentrated under reduced pressure. The resulting residue was purified by flash chromatography (SiO$_2$; 0-20% hexanes-EtOAc) to give the title compound as white solid (500 mg, 82%). MS (ESI): mass calcd. for C$_{11}$H$_{10}$BrN, 235.0; m/z found, 236.1 [M+H]$^+$. $^1$H NMR (400 MHz, CDCl$_3$) δ 8.07 (d, J=2.0 Hz, 1H), 7.87 (d, J=9.0 Hz, 1H), 7.72 (dd, J=2.2, 8.8 Hz, 1H), 7.14 (s, 1H), 2.67 (s, 3H), 2.62 (s, 3H).

Step B: Methyl 2,4-dimethylquinoline-6-carboxylate. To a solution of 6-bromo-2,4-dimethylquinoline (250 mg, 1.06 mmol) in DMF (6.0 mL) and MeOH (6.0 mL) was added triethylamine (482 mg, 4.8 mmol), Pd(dppf)Cl$_2$ (155 mg, 0.21 mmol) and Pd(OAc)$_2$ (24 mg, 0.11 mmol) under nitrogen atmosphere. The resultant mixture was saturated with CO and then heated to 80° C. for 12 hours. After cooling to room temperature, the reaction mixture was diluted with water (20 mL) and extracted with ethyl acetate (150 mL×3). The combined organic layers were dried over anhydrous sodium sulfate, filtered, and concentrated under reduced pressure. The resulting residue was purified by flash chromatography (SiO$_2$; 0-20% hexanes-EtOAc) to give the title compound as yellow solid (200 mg, 84%). MS (ESI): mass calcd. for C$_{13}$H$_{13}$NO$_2$, 215.1; m/z found, 216.1 [M+H]$^+$.

Step C: 2,4-Dimethylquinoline-6-carboxylic acid. To a solution of methyl 2,4-dimethylquinoline-6-carboxylate (200 mg, 0.93 mmol) in THF (4.0 mL) was added dropwise a solution of lithium hydroxide (110 mg, 4.6 mmol) in water (4.0 mL) and the resultant mixture was stirred at room temperature for 8 hours. 2M HCl solution was added to The resulting reaction to adjust to pH=3-4. The mixture was extracted with dichloromethane (3×50 mL) and the combined organic layers were dried over anhydrous sodium sulfate, filtered, and concentrated under reduced pressure to afford the title compound as a yellow solid. MS (ESI): mass calcd. for C$_{12}$H$_{11}$NO$_2$, 201.1; m/z found, 202.2 [M+H]$^+$.

Intermediate 32:
4-Methoxy-2-methylquinoline-6-carboxylic Acid

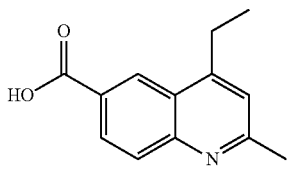 [SMILES: CCc1cc(C)nc2ccc(C(=O)O)cc12]

Step A: 2-Methyl-4-oxo-1,4-dihydroquinoline-6-carboxylic acid. To a solution of 4-aminobenzoic acid (3.5 g, 25.5 mmol) and acetic acid (731 µL, 12.8 mmol) in toluene (50.0 mL) was added ethyl 3-oxobutanoate (5.0 g, 38.4 mmol) and the mixture was heated to 120° C. for 16 hours. The reaction mixture was cooled to room temperature and the precipitate was filtered, washed with toluene (20 mL) and dried under reduced pressure. The resulting solid was then suspended in oxydibenzene (50.0 mL) and the mixture was stirred at 240° C. for 3 hours. The reaction mixture was cooled to room temperature and the suspension was filtered, washed with toluene (20.0 mL) to afford the title product as yellow solid (1.8 g, 17.3%). MS (ESI): mass calcd. for C$_{11}$H$_9$NO$_3$, 203.1; m/z found, 203.8 [M+H]$^+$. $^1$H NMR (400 MHz, DMSO-d$_6$) δ 12.78-12.63 (m, 1H), 11.82 (br s, 1H), 8.64 (d, J=2.0 Hz, 1H), 8.10 (dd, J=2.0, 8.8 Hz, 1H), 7.54 (d, J=8.5 Hz, 1H), 5.98 (s, 1H), 2.35 (s, 3H).

Step B: Methyl 2-methyl-4-oxo-1,4-dihydroquinoline-6-carboxylate. To a solution of 2-methyl-4-oxo-1,4-dihydroquinoline-6-carboxylic acid (1.8 g, 8.8 mmol) in methanol (20.0 mL) was added concentrated sulfuric acid (2.0 mL) and the resultant mixture was stirred at room temperature for 16 hours. The resulting reaction mixture was then poured into ice water (20.0 mL), then adjusted to pH=5 with 1M NaOH. The methanol was removed under reduced pressure and the aqueous layer extracted with ethyl acetate (20 mL×3). The combined organic layers were dried over anhydrous sodium sulfate, filtered, and concentrated under reduced pressure. The resulting residue was purified by flash chromatography (SiO$_2$; 0-50% hexanes-EtOAc) to give the title compound as yellow solid (650 mg, 33%). MS (ESI): mass calcd. for C$_{12}$H$_{11}$NO$_3$, 217.0; m/z found, 217.8 [M+H]$^+$. $^1$H NMR (400 MHz, DMSO-d$_6$) δ 12.13-11.64 (m, 1H), 8.65 (d, J=1.9 Hz, 1H), 8.11 (d, J=6.9 Hz, 1H), 7.57 (d, J=8.1 Hz, 1H), 5.99 (s, 1H), 3.87 (s, 3H), 2.35 (s, 3H).

Step C: Methyl 4-chloro-2-methylquinoline-6-carboxylate. Phosphorus oxychloride (750 mg, 4.9 mmol) was added to a mixture of methyl 2-methyl-4-oxo-1,4-dihydroquinoline-6-carboxylate (650 mg, 3.0 mmol), and THF (10.0 mL) in presence of catalytic amount of DMF (100 µL) at 0° C. The resultant mixture was stirred at 60° C. for 6 hours. After cooling to room temperature, the mixture was poured into water (10.0 mL), adjusted to pH=7-8 with 4M aqueous NaOH and concentrated to remove THF under reduced pressure. The resulting solid was filtered and washed with water (3 mL×3) to afford the title product as yellow solid (600 mg, 82%). MS (ESI): mass calcd. for C$_{12}$H$_{10}$ClNO$_2$, 235.0; m/z found, 235.8 [M+H]$^+$. $^1$H NMR (400 MHz, DMSO-d$_6$) δ 8.74 (s, 1H), 8.26 (d, J=8.6 Hz, 1H), 8.09 (d, J=8.8 Hz, 1H), 7.83 (s, 1H), 3.95 (s, 3H), 2.69 (s, 3H).

Step D: 4-Methoxy-2-methylquinoline-6-carboxylic acid. To a solution of methyl 4-chloro-2-methylquinoline-6-carboxylate (200 mg, 0.85 mmol) in methanol (2.0 mL) was added sodium methoxide (92 mg, 1.7 mmol). The reaction mixture was heated to 60° C. for 16 hours to provide a mixture of 4-methoxy-2-methylquinoline-6-carboxylic acid and 4-chloro-2-methylquinoline-6-carboxylic acid. Purification by HPLC (METHOD: Boston Green ODS 150*30 mm*5 um column (eluent: 10% to 40% (v/v) CH3CN and H2O with 0.225% HCOOH)) afforded the title compound, 4-methoxy-2-methylquinoline-6-carboxylic acid as yellow solid (20 mg, 10.3% yield). MS (ESI): mass calcd. for $C_{12}H_{11}NO_3$, 217.1; m/z found, 217.9 [M+H]$^+$. $^1$H NMR (400 MHz, DMSO-d$_6$) δ 8.72 (d, J=2.0 Hz, 1H), 8.17 (dd, J=2.3, 9.0 Hz, 1H), 7.84 (d, J=9.0 Hz, 1H), 6.13 (s, 1H), 3.75 (s, 3H), 2.49 (s, 3H).

Intermediate 33: 4-Methyl-2-(trifluoromethoxy) benzoic Acid

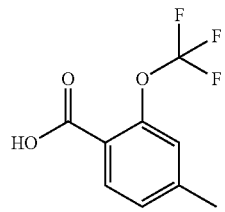

To a solution of 4-bromo-2-(trifluoromethoxy)benzoic acid (1 g, 3.5 mmol) in dioxane:water (15:3 mL) were added 2,4,6-trimethyl-1,3,5,2,4,6-trioxatriborinane (880 mg, 7.0 mmol), cesium carbonate (3.4 g, 10.53 mmol) and Pd(dppf)Cl$_2$ (260 mg, 0.35 mmol) under nitrogen atmosphere. The resultant mixture was purged with nitrogen for 5 minutes and heated to 100° C. for 16 hours. The resulting reaction mixture was filtered through a pad of Celite© and washed with ethyl acetate (5 mL×4). The filtrate was concentrated under reduced pressure and purified by HPLC (METHOD: Boston Uni C18 150×40 mm×5 μm column (eluent: 33% to 63% (v/v) CH$_3$CN and H2O with 0.225% FA)) to afford the title compound as yellow solid (100 mg, 13% yield). MS (ESI): mass calcd. for $C_9H_7F_3O_3$, 220.1; m/z found, 220.9 [M+H]$^+$. $^1$H NMR (400 MHz, DMSO-d$_6$) δ 13.24 (br s, 1H), 7.83 (d, J=7.8 Hz, 1H), 7.33 (d, J=8.0 Hz, 1H), 7.30 (s, 1H), 2.40 (s, 3H).

Intermediate 34: 7-Methylbenzo[d]thiazole-6-carboxylic Acid

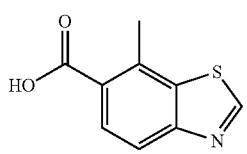

Step A: Methyl 2-amino-7-methylbenzo[d]thiazole-6-carboxylate and Methyl 2-amino-5-methylbenzo[d]thiazole-6-carboxylate. To an ice cold solution (0° C.) of methyl 4-amino-2-methylbenzoate (1 g, 6.0 mmol), sodium thiocyanate (1.75 g, 21.6 mmol) and acetic acid (15.0 mL) was added dropwise bromine (0.3 mL, 6.0 mmol) in acetic acid (1.0 mL) at 0° C. The resultant mixture was stirred at 0° C. for 30 minutes, warmed to room temperature and stirred for 16 hours. The resulting suspension was filtered through a pad of Celite© and the filtrate was diluted with water (20 mL). The mixture was quenched with 1M NaOH until pH=4 to obtain precipitation. The precipitate was filtered and washed with MeOH (5 mL×2). The resulting product mixture was purified by SFC over DAICEL CHIRALPAK AD-H (250 mm×30 mm×10 um (isocratic elution: EtOH (containing 0.1% of 25% aq. NH$_3$): supercritical CO$_2$, 30%: 70% to 30%: 70% (v/v)) to afford the two title products: methyl 2-amino-7-methylbenzo[d]thiazole-6-carboxylate (220 mg, 16%); MS (ESI): mass calcd. for $C_{10}H_{10}N_2O_2S$, 222.2; m/z found, 222.8 [M+H]$^+$. $^1$H NMR (400 MHz, DMSO-d$_6$) δ 7.87 (s, 2H), 7.77 (d, J=8.5 Hz, 1H), 7.22 (d, J=8.5 Hz, 1H), 3.80 (s, 3H), 2.61 (s, 3H).

methyl 2-amino-5-methylbenzo[d]thiazole-6-carboxylate (220 mg, 16%); MS (ESI): mass calcd. for $C_{10}H_{10}N_2O_2S$, 222.2; m/z found, 222.8 [M+H]$^+$. $^1$H NMR (400 MHz, DMSO-d$_6$) δ 8.18 (s, 1H), 7.84 (s, 2H), 7.22 (s, 1H), 3.79 (s, 3H), 2.54-2.54 (m, 3H).

Step B: Methyl 7-methylbenzo[d]thiazole-6-carboxylate. To a solution of methyl 2-amino-7-methylbenzo[d]thiazole-6-carboxylate (200 mg, 0.9 mmol) in THF (5 mL) was added isopentyl nitrite (232 mg, 2.0 mmol) and the mixture was stirred at 65° C. for 14 hours. The resulting mixture was concentrated to dryness under reduced pressure to afford the title product as brown solid, which was used in the next step without purification. MS (ESI): mass calcd. for $C_{10}H_9NO_2S$, 207.1; m/z found, 207.8 [M+H]$^+$.

Step C: 7-Methylbenzo[d]thiazole-6-carboxylic acid. To a solution of methyl 7-methylbenzo[d]thiazole-6-carboxylate (180 mg, 0.87 mmol) in dioxane:water (1:1, 5 mL) was added lithium hydroxide monohydrate (180 mg, 4.3 mmol). The resultant mixture was stirred at room temperature for 14 hours. The resulting reaction was diluted with water and extracted with ethyl acetate (10 mL×3). The aqueous phase was quenched with 3M HCl until pH=4.0 and then extracted with ethyl acetate (10 mL×3). The combined organic layers were dried over anhydrous sodium sulfate, filtered, and concentrated under reduced pressure to afford the title compound as yellow solid (170 mg). MS (ESI): mass calcd. for $C_9H_7NO_2S$, 193.0; m/z found, 193.8 [M+H]$^+$.

Intermediate 35: 5-Methylbenzo[d]thiazole-6-carboxylic Acid

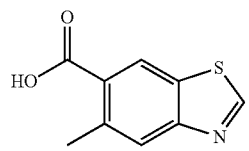

The title compound was prepared in a manner analogous to Intermediate 34, Steps B and C, using methyl 2-amino-5-methylbenzo[d]thiazole-6-carboxylate (Intermediate 34, Step A) instead of methyl 2-amino-7-methylbenzo[d]thiazole-6-carboxylate. MS (ESI): mass calcd. for $C_9H_7NO_2S$, 193.0; m/z found, 193.8 [M+H]$^+$.

Intermediate 36: 5-Methylbenzo[d]thiazole-6-carboxylic Acid

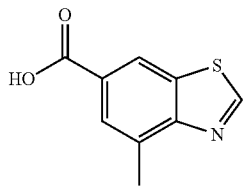

The title compound was prepared in a manner analogous to Intermediate 34, using methyl 4-amino-3-methylbenzoate in Step A instead of methyl 4-amino-2-methylbenzoate. MS (ESI): mass calcd. for $C_9H_7NO_2S$, 193.0; m/z found, 193.8 $[M+H]^+$.

Example 1: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-5-yl)methanone

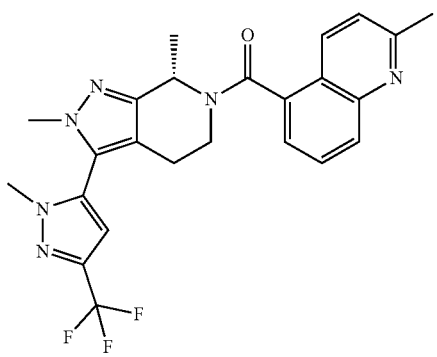

To a solution of (S)-2,7-dimethyl-3-(1-methyl-3-(trifluoromethyl)-1H-pyrazol-5-yl)-4,5,6,7-tetrahydro-2H-pyrazolo[3,4-c]pyridine (Intermediate 13, 25 mg, 83.5 μmol) in $CH_2Cl_2$ (2.0 mL) was added 2-methylquinoline-5-carboxylic acid (17.2 mg, 0.092 mmol), HATU (41.3 mg, 0.11 mmol), and N,N-diisopropylethylamine (43.2 μL, 0.25 mmol). After stirring at room temperature for 30 min, the mixture was concentrated in vacuo and purified by preparative HPLC (METHOD A) to afford the title compound as a white powder (13 mg, 33% yield). MS (ESI): mass calcd. for $C_{24}H_{23}F_3N_6O$, 468.2; m/z found, 469.0 $[M+H]^+$. $^1H$ NMR (400 MHz, DMSO-$d_6$) δ 8.12-7.71 (m, 3H), 7.66-7.29 (m, 2H), 7.10 (d, J=16.6 Hz, 1H), 5.96-5.68 (m, 1H), 4.92-4.27 (m, 1H), 3.89-3.59 (m, 6H), 2.74-2.58 (m, 4H), 2.31-2.13 (m, 2H), 1.67-1.30 (m, 3H).

Example 2: (S)-(3-(1,4-Dimethyl-1H-pyrazol-5-yl)-2,7-dimethyl-2,4,5,7-tetrahydro-6H-pyrazolo[3,4-c]pyridin-6-yl)(3-methoxy-2-methylphenyl)methanone

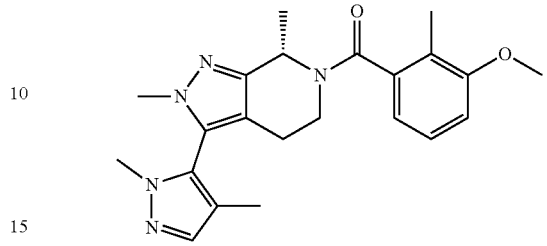

The title compound was prepared in a manner analogous to Example 1, using (S)-3-(1,4-dimethyl-1H-pyrazol-5-yl)-2,7-dimethyl-4,5,6,7-tetrahydro-2H-pyrazolo[3,4-c]pyridine (Intermediate 16) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-2-methylbenzoic acid instead of 2-methylquinoline-5-carboxylic acid. MS (ESI): mass calcd. for $C_{22}H_{27}N_5O_2$, 393.2; m/z found, 394.1 $[M+H]^+$. $^1H$ NMR (500 MHz, DMSO-$d_6$) δ 7.49-7.36 (m, 1H), 7.36-7.18 (m, 1H), 7.10-6.95 (m, 1H), 6.91-6.70 (m, 1H), 5.77-5.52 (m, 1H), 4.76-4.32 (m, 1H), 3.86-3.78 (m, 3H), 3.65-3.49 (m, 6H), 3.28-3.12 (m, 1H), 2.42-1.96 (m, 4H), 1.92-1.75 (m, 4H), 1.54-1.31 (m, 3H).

Example 3: (S)-(3-(1,5-Dimethyl-3-(trifluoromethyl)-1H-pyrazol-4-yl)-2,7-dimethyl-2,4,5,7-tetrahydro-6H-pyrazolo[3,4-c]pyridin-6-yl)(3-methoxy-2-methylphenyl)methanone The title compound was prepared in a manner analogous to Example 1, using (S)-3-(1,5-dimethyl-3-(trifluoromethyl)-1H-pyrazol-4-yl)-2,7-dimethyl-4,5,6,7-tetrahydro-2H-pyrazolo[3,4-c]pyridine (Intermediate 17) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-2-methylbenzoic acid instead of 2-methylquinoline-5-carboxylic acid. MS (ESI): mass calcd. for $C_{23}H_{26}F_3N_5O_2$, 461.2; m/z found, 462.0 $[M+H]^+$. $^1H$ NMR (500 MHz, CDCl$_3$) δ 7.25-7.13 (m, 1H), 6.90-6.63 (m, 2H), 6.09-5.78 (m, 1H), 5.06-4.81 (m, 1H), 4.72-4.64 (m, 1H), 3.91 (d, J=13.1 Hz, 3H), 3.88-3.78 (m, 3H), 3.63-3.45 (m, 4H), 3.29-2.96 (m, 1H), 2.75-2.37 (m, 1H), 2.29-2.20 (m, 1H), 2.06-1.97 (m, 1H), 1.92 (s, 1H), 1.62 (dd, J=8.5, 6.7 Hz, 3H), 1.46-0.99 (m, 2H).

Example 4: (S)-(2-Chloro-3-(2-oxa-6-azaspiro[3.3]heptan-6-yl)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

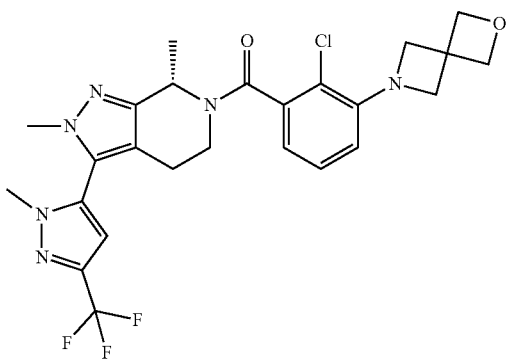 [SMILES: C[C@H]1c2nn(C)c(-c3cc(C(F)(F)F)nn3C)c2CCN1C(=O)c1cccc(N2CC3(COC3)C2)c1Cl]

The title compound was prepared in a manner analogous to Example 1, using potassium 2-chloro-3-(2-oxa-6-azaspiro[3.3]heptan-6-yl)benzoate (Intermediate 1) instead of 2-methylquinoline-5-carboxylic acid. MS (ESI): mass calcd. for $C_{25}H_{26}ClF_3N_6O_2$, 534.2; m/z found, 535.0 [M+H]$^+$. $^1$H NMR (500 MHz, DMSO-d$_6$) δ 7.36-7.04 (m, 2H), 6.86-6.48 (m, 2H), 5.63 (td, J=7.1, 3.3 Hz, 1H), 4.80-4.64 (m, 4H), 4.30-4.10 (m, 4H), 3.85-3.62 (m, 6H), 3.29-2.95 (m, 2H), 2.47-2.16 (m, 2H), 1.52-1.22 (m, 3H).

Example 5: (S)-(2,7-dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-1H-indol-3-yl)methanone

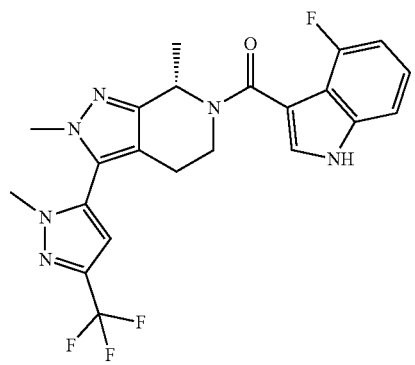 [SMILES: C[C@H]1c2nn(C)c(-c3cc(C(F)(F)F)nn3C)c2CCN1C(=O)c1c[nH]c2cccc(F)c12]

The title compound was prepared in a manner analogous to Example 1, using 4-fluoro-1H-indole-3-carboxylic acid instead of 2-methylquinoline-5-carboxylic acid. MS (ESI): mass calcd. for $C_{22}H_{20}F_4N_6O$, 460.2; m/z found, 461.1 [M+H]$^+$. $^1$H NMR (500 MHz, DMSO-d$_6$) δ 11.75 (s, 1H), 7.63 (s, 1H), 7.30 (d, J=8.2 Hz, 1H), 7.21-7.04 (m, 2H), 6.83 (dd, J=11.0, 7.8 Hz, 1H), 5.92-5.26 (m, 1H), 3.79 (s, 3H), 3.71 (s, 3H), 3.20-3.15 (m, 1H), 2.63-2.54 (m, 2H), 2.44-2.18 (m, 1H), 1.46 (d, J=6.8 Hz, 3H).

Example 6: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indazol-3-yl)methanone

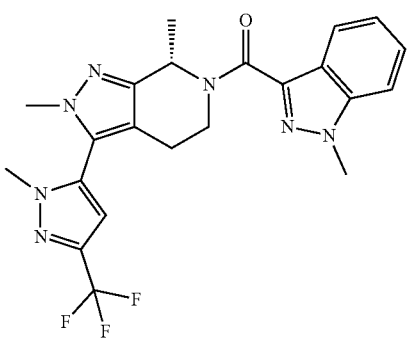 [SMILES: C[C@H]1c2nn(C)c(-c3cc(C(F)(F)F)nn3C)c2CCN1C(=O)c1nn(C)c2ccccc12]

The title compound was prepared in a manner analogous to Example 1, using 1-methyl-1H-indazole-3-carboxylic acid instead of 2-methylquinoline-5-carboxylic acid. MS (ESI): mass calcd. for $C_{22}H_{22}F_3N_7O$, 457.2; m/z found, 458.1 [M+H]$^+$. $^1$H NMR (600 MHz, DMSO-d$_6$) δ 7.96 (d, J=8.2 Hz, 1H), 7.73 (d, J=8.5 Hz, 1H), 7.47 (t, J=7.7 Hz, 1H), 7.25 (t, J=7.6 Hz, 1H), 5.92-5.47 (m, 1H), 4.85-4.61 (m, 1H), 4.18-4.09 (m, 3H), 3.76-3.62 (m, 4H), 2.78-2.56 (m, 4H), 1.74-1.66 (m, 2H), 1.51-1.43 (m, 3H).

Example 7: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylpyrazolo[1,5-a]pyridin-3-yl)methanone

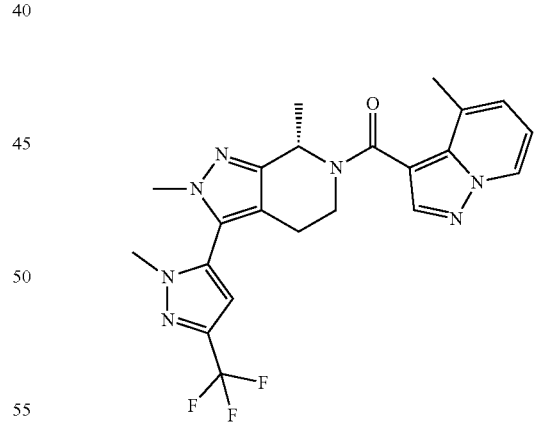

The title compound was prepared in a manner analogous to Example 1, using 4-methylpyrazolo[1,5-a]pyridine-3-carboxylic acid instead of 2-methylquinoline-5-carboxylic acid. MS (ESI): mass calcd. for $C_{22}H_{22}F_3N_7O$, 457.2; m/z found, 458.2 [M+H]$^+$. $^1$H NMR (400 MHz, Methanol-d$_4$) δ 7.87 (s, 1H), 7.57 (d, J=9.0 Hz, 1H), 7.42 (dd, J=9.0, 6.9 Hz, 1H), 6.96-6.84 (m, 2H), 5.83-5.59 (m, 1H), 4.30-4.10 (m, 1H), 3.82 (s, 3H), 3.77-3.66 (m, 3H), 3.60-3.48 (m, 1H), 2.90-2.74 (m, 1H), 2.68-2.41 (m, 4H), 1.64 (d, J=6.8 Hz, 3H).

Example 8: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylimidazo[1,2-a]pyridin-3-yl)methanone

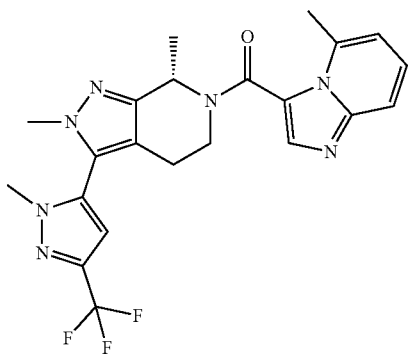 [SMILES: Cc1cccc2ncc(C(=O)N3CCc4c(nn(C)c4-c4cc(C(F)(F)F)nn4C)[C@@H]3C)n12]

The title compound was prepared in a manner analogous to Example 1, using lithium 5-methylimidazo[1,2-a]pyridine-3-carboxylate instead of 2-methylquinoline-5-carboxylic acid. MS (ESI): mass calcd. for $C_{22}H_{22}F_3N_7O$, 457.2; m/z found, 458.2 [M+H]$^+$. $^1$H NMR (400 MHz, DMSO-$d_6$) δ 8.65-8.53 (m, 1H), 8.36-8.04 (m, 1H), 7.17-7.03 (m, 2H), 7.00-6.82 (m, 1H), 5.81-5.54 (m, 1H), 5.08-4.40 (m, 1H), 3.80 (s, 3H), 3.75-3.63 (m, 3H), 3.29-3.09 (m, 1H), 2.84-2.56 (m, 2H), 2.36 (s, 3H), 1.49 (d, J=6.8 Hz, 3H).

Example 9: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-4-yl)methanone

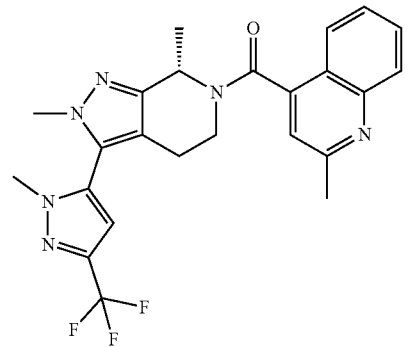 [SMILES: Cc1cc(C(=O)N2CCc3c(nn(C)c3-c3cc(C(F)(F)F)nn3C)[C@@H]2C)c2ccccc2n1]

The title compound was prepared in a manner analogous to Example 1, using 2-methylquinoline-4-carboxylic acid instead of 2-methylquinoline-5-carboxylic acid. MS (ESI): mass calcd. for $C_{24}H_{23}F_3N_6O$, 468.2; m/z found, 469.2 [M+H]$^+$. $^1$H NMR (400 MHz, DMSO-$d_6$) δ 8.08-7.92 (m, 1H), 7.82-7.38 (m, 4H), 7.19-7.01 (m, 1H), 5.93-5.60 (m, 1H), 4.97-4.44 (m, 1H), 3.87-3.55 (m, 6H), 3.24-3.14 (m, 1H), 2.75-2.66 (m, 3H), 2.66-2.54 (m, 1H), 2.36-2.13 (m, 1H), 1.66-1.39 (m, 3H).

Example 10: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methylquinolin-4-yl)methanone

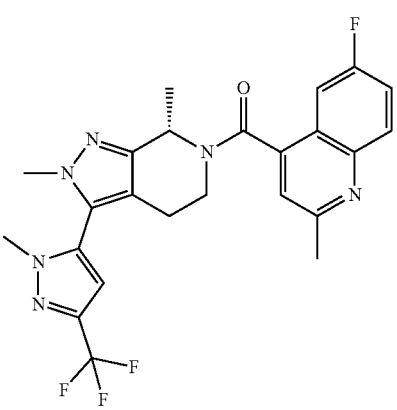 [SMILES: Cc1cc(C(=O)N2CCc3c(nn(C)c3-c3cc(C(F)(F)F)nn3C)[C@@H]2C)c2cc(F)ccc2n1]

The title compound was prepared in a manner analogous to Example 1, using 6-fluoro-2-methylquinoline-4-carboxylic acid instead of 2-methylquinoline-5-carboxylic acid. MS (ESI): mass calcd. for $C_{24}H_{22}F_4N_6O$, 486.2; m/z found, 487.2 [M+H]$^+$. $^1$H NMR (400 MHz, DMSO-$d_6$) δ 8.13-7.95 (m, 1H), 7.77-7.55 (m, 1H), 7.55-7.26 (m, 2H), 7.22-7.02 (m, 1H), 5.93-5.69 (m, 1H), 4.96-4.27 (m, 1H), 3.86-3.57 (m, 6H), 3.25-3.08 (m, 1H), 2.96-2.56 (m, 4H), 2.29-2.17 (m, 1H), 1.69-1.39 (m, 3H).

Example 11: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoropyrazolo[1,5-a]pyridin-3-yl)methanone

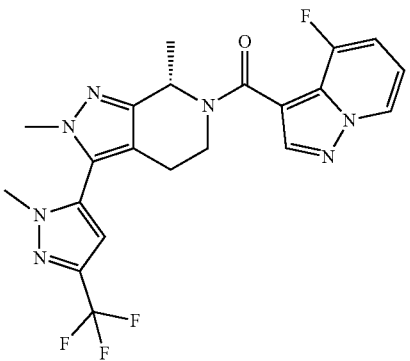 [SMILES: C[C@H]1c2nn(C)c(-c3cc(C(F)(F)F)nn3C)c2CCN1C(=O)c1cnn2cccc(F)c12]

The title compound was prepared in a manner analogous to Example 1, using 4-fluoropyrazolo[1,5-a]pyridine-3-carboxylic acid instead of 2-methylquinoline-5-carboxylic acid. MS (ESI): mass calcd. for $C_{21}H_{19}F_4N_7O$, 461.2; m/z found, 462.2 [M+H]$^+$. $^1$H NMR (400 MHz, DMSO-$d_6$) δ 8.69 (d, J=6.8 Hz, 1H), 8.27 (s, 1H), 7.26 (dd, J=10.7, 7.7 Hz, 1H), 7.10 (s, 1H), 7.05-6.92 (m, 1H), 5.86-5.44 (m, 1H), 3.79 (s, 3H), 3.71 (s, 3H), 3.17 (s, 2H), 2.71-2.55 (m, 1H), 2.32 (d, J=15.0 Hz, 1H), 1.48 (d, J=6.7 Hz, 3H).

Example 12: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-(2,2,2-trifluoroethyl)-1H-pyrrolo[2,3-b]pyridin-4-yl)methanone

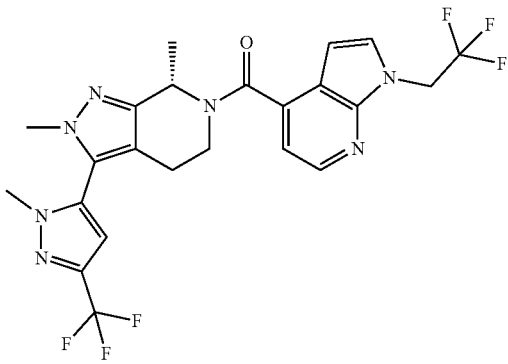 [SMILES: C[C@H]1c2nn(C)c(-c3cc(C(F)(F)F)nn3C)c2CCN1C(=O)c1ccnc2c1ccn2CC(F)(F)F]

The title compound was prepared in a manner analogous to Example 1, using potassium 1-(2,2,2-trifluoroethyl)-1H-pyrrolo[2,3-b]pyridine-4-carboxylate (Intermediate 2) instead of 2-methylquinoline-5-carboxylic acid. MS (ESI): mass calcd. for $C_{23}H_{21}F_6N_7O$, 525.2; m/z found, 526.2 [M+H]$^+$. $^1$H NMR (400 MHz, DMSO-d$_6$) δ 8.41 (d, J=4.8 Hz, 1H), 7.76-7.61 (m, 1H), 7.21 (d, J=4.8 Hz, 1H), 7.17-7.04 (m, 1H), 6.58-6.36 (m, 1H), 5.81-5.69 (m, 1H), 5.36-5.15 (m, 2H), 4.86-4.51 (m, 1H), 3.86-3.58 (m, 6H), 3.52-3.38 (m, 1H), 2.87-2.55 (m, 1H), 2.45-2.17 (m, 1H), 1.64-1.29 (m, 3H).

Example 13: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-3-yl)methanone

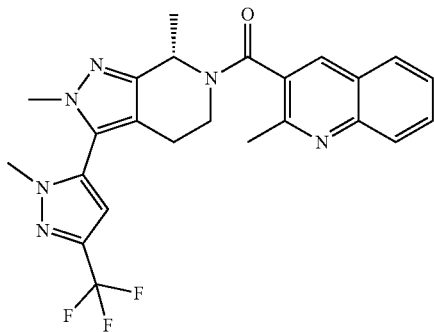 [SMILES: Cc1nc2ccccc2cc1C(=O)N1CCc2c(nn(C)c2-c2cc(C(F)(F)F)nn2C)[C@@H]1C]

The title compound was prepared in a manner analogous to Example 1, using 2-methylquinoline-3-carboxylic acid instead of 2-methylquinoline-5-carboxylic acid. MS (ESI): mass calcd. for $C_{24}H_{23}F_3N_6O$, 468.2; m/z found, 469.2 [M+H]$^+$. $^1$H NMR (400 MHz, DMSO-d$_6$) δ 8.29 (s, 1H), 7.97 (d, J=8.7 Hz, 2H), 7.87-7.73 (m, 1H), 7.68-7.53 (m, 1H), 7.11 (d, J=17.8 Hz, 1H), 5.81-5.60 (m, 1H), 4.85-4.47 (m, 1H), 3.09-3.02 (m, 1H), 3.85-3.77 (m, 3H), 3.75-3.64 (m, 3H), 3.44-3.36 (m, 1H), 2.60 (s, 3H), 2.34-2.19 (m, 1H), 1.56 (d, J=6.7 Hz, 3H).

Example 14: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-methoxyquinolin-5-yl)methanone

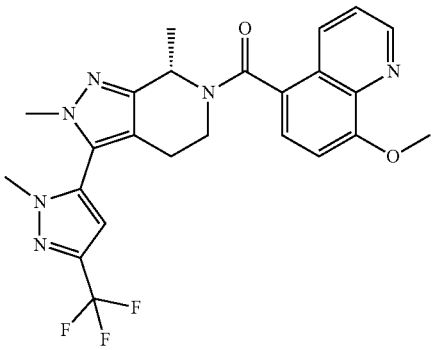

The title compound was prepared in a manner analogous to Example 1, using 8-methoxyquinoline-5-carboxylic acid instead of 2-methylquinoline-5-carboxylic acid. MS (ESI): mass calcd. for $C_{24}H_{23}F_3N_6O_2$, 484.2; m/z found, 485.2 [M+H]$^+$. $^1$H NMR (400 MHz, DMSO-d$_6$) δ 8.91 (s, 1H), 8.12 (d, J=8.5 Hz, 1H), 7.72-7.45 (m, 2H), 7.34-7.01 (m, 2H), 5.89-5.60 (m, 1H), 4.99-4.69 (m, 1H), 4.02 (s, 3H), 3.87-3.61 (m, 6H), 3.51-3.36 (m, 1H), 2.76-2.60 (m, 1H), 2.24 (d, J=16.7 Hz, 1H), 1.73-1.38 (m, 3H).

Example 15: (S)-(1,6-Dimethyl-1H-pyrazolo[3,4-b]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

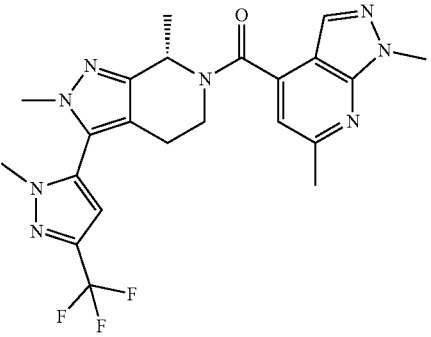

The title compound was prepared in a manner analogous to Example 1, using 1,6-dimethyl-1H-pyrazolo[3,4-b]pyridine-4-carboxylic acid instead of 2-methylquinoline-5-carboxylic acid. MS (ESI): mass calcd. for $C_{22}H_{23}F_3N_8O$, 472.2; m/z found, 473.2 [M+H]$^+$. $^1$H NMR (400 MHz, DMSO-d$_6$) δ 8.11-7.78 (m, 1H), 7.23-7.01 (m, 2H), 5.85-5.53 (m, 1H), 4.89-4.52 (m, 1H), 4.11-3.95 (m, 3H), 3.90-3.59 (m, 6H), 3.56-3.43 (m, 1H), 3.18-3.09 (m, 1H), 2.52 (s, 3H), 2.36-2.18 (m, 1H), 1.68-1.33 (m, 3H).

Example 16: (S)-(3-(3-Methoxy-1-methyl-1H-pyrazol-4-yl)-2,7-dimethyl-2,4,5,7-tetrahydro-6H-pyrazolo[3,4-c]pyridin-6-yl)(quinolin-6-yl)methanone

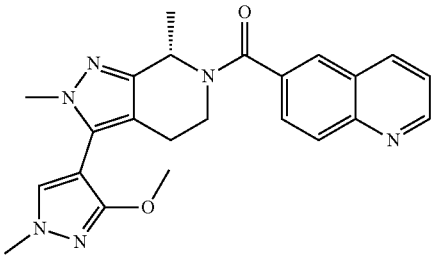 [SMILES: COc1nn(C)cc1-c1c2c(nn1C)[C@H](C)N(C(=O)c1ccc3ncccc3c1)CC2]

The title compound was prepared in a manner analogous to Example 1, using (S)-3-(3-methoxy-1-methyl-1H-pyrazol-4-yl)-2,7-dimethyl-4,5,6,7-tetrahydro-2H-pyrazolo[3,4-c]pyridine (Intermediate 18) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and quinoline-6-carboxylic acid instead of 2-methylquinoline-5-carboxylic acid. MS (ESI): mass calcd. for $C_{23}H_{24}N_6O_2$, 416.2; m/z found, 417.2 [M+H]+. 1H NMR (400 MHz, DMSO-$d_6$) δ 8.97 (dd, J=4.2, 1.7 Hz, 1H), 8.53-8.40 (m, 1H), 8.15-8.03 (m, 2H), 7.84-7.72 (m, 2H), 7.61 (dd, J=8.3, 4.2 Hz, 1H), 5.68-5.43 (m, 1H), 4.78-4.55 (m, 1H), 3.84 (s, 3H), 3.76-3.67 (m, 6H), 3.22-3.10 (m, 1H), 2.69-2.57 (m, 1H), 2.41-2.26 (m, 1H), 1.48 (s, 3H).

Example 17: (S)-(4,6-Difluoropyrazolo[1,5-a]pyridin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

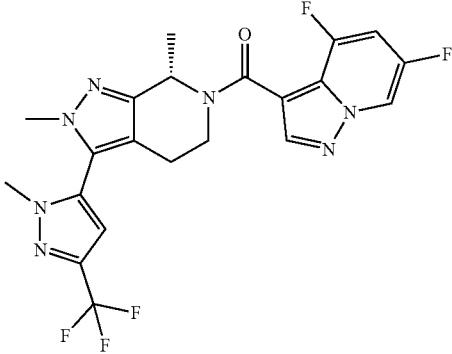 [SMILES: C[C@H]1c2nn(C)c(-c3cc(C(F)(F)F)nn3C)c2CCN1C(=O)c1cnn2cc(F)cc(F)c12]

The title compound was prepare in a manner analogous to Example 1, using potassium 4,6-difluoropyrazolo[1,5-a]pyridine-3-carboxylate (Intermediate 3) instead of 2-methylquinoline-5-carboxylic acid. MS (ESI): mass calcd. for $C_{21}H_{18}F_5N_7O$, 479.2; m/z found, 480.1 [M+H]+. 1H NMR (600 MHz, DMSO-$d_6$) δ 9.22-9.06 (m, 1H), 8.43-8.24 (m, 1H), 7.74-7.58 (m, 1H), 7.20-6.95 (m, 1H), 5.74-5.42 (m, 1H), 4.38-4.10 (m, 1H), 3.82-3.76 (m, 3H), 3.74-3.60 (m, 3H), 3.23-2.73 (m, 1H), 2.74-2.58 (m, 1H), 2.42-2.25 (m, 1H), 1.60-1.40 (m, 3H).

Example 18: (S)-(5,7-Difluoroquinolin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

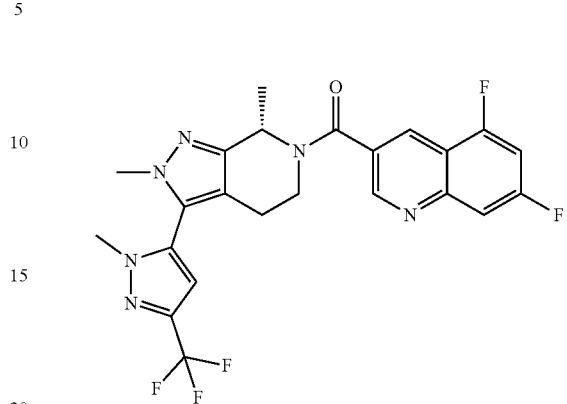

The title compound was prepared in a manner analogous to Example 1, using lithium 5,7-difluoroquinoline-3-carboxylate (Intermediate 4) instead of 2-methylquinoline-5-carboxylic acid. MS (ESI): mass calcd. for $C_{23}H_{19}F_5N_6O$, 490.15; m/z found, 491.1 [M+H]+. 1H NMR (600 MHz, DMSO-$d_6$) δ 9.14-9.00 (m, 1H), 8.66-8.48 (m, 1H), 7.90-7.60 (m, 2H), 7.16-7.05 (m, 1H), 5.77-5.57 (m, 1H), 4.75 (d, J=75.1 Hz, 1H), 3.90-3.78 (m, 3H), 3.77-3.64 (m, 3H), 2.82-2.58 (m, 2H), 2.32 (d, J=14.6 Hz, 1H), 1.66-1.31 (m, 3H).

Example 19: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-fluoropyrazolo[1,5-a]pyridin-3-yl)methanone

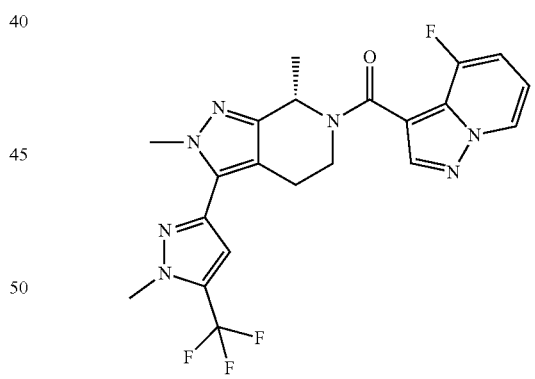

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and 4-fluoropyrazolo[1,5-a]pyridine-3-carboxylic acid instead of 2-methylquinoline-5-carboxylic acid. MS (ESI): mass calcd. for $C_{21}H_{19}F_4N_7O$, 461.2; m/z found, 462.2 [M+H]+. 1H NMR (600 MHz, DMSO-$d_6$) δ 8.70 (dd, J=6.9, 1.4 Hz, 1H), 8.27 (d, J=1.5 Hz, 1H), 7.33-7.14 (m, 2H), 7.09-6.96 (m, 1H), 5.77-5.46 (m, 1H), 4.95-4.51 (m, 1H), 4.05 (s, 3H), 3.98 (s, 3H), 3.24-3.11 (m, 1H), 2.82-2.72 (m, 1H), 2.68-2.55 (m, 1H), 1.51-1.39 (m, 3H).

Example 20: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxyquinolin-4-yl)methanone

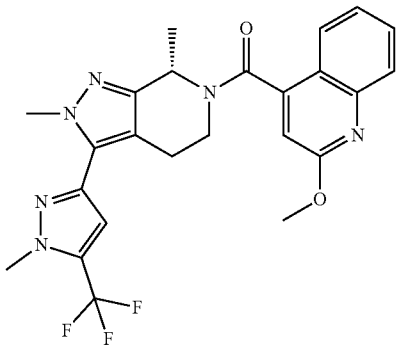 [SMILES: COc1cc(C(=O)N2CCc3c(nn(C)c3-c3cc(C(F)(F)F)n(C)n3)[C@@H]2C)c2ccccc2n1]

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-methoxyquinoline-4-carboxylic acid instead of 2-methylquinoline-5-carboxylic acid. MS (ESI): mass calcd. for $C_{24}H_{23}F_3N_6O_2$, 484.2; m/z found, 485.1 [M+H]$^+$. $^1$H NMR (600 MHz, DMSO-$d_6$) δ 7.92-7.79 (m, 1H), 7.79-7.32 (m, 3H), 7.32-6.95 (m, 2H), 5.83-5.65 (m, 1H), 5.05-4.27 (m, 1H), 4.12-3.84 (m, 9H), 3.48-3.37 (m, 1H), 3.30-3.10 (m, 1H), 3.03-2.63 (m, 1H), 1.71-1.32 (m, 3H).

Example 21: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-1-methyl-1H-indazol-4-yl)methanone

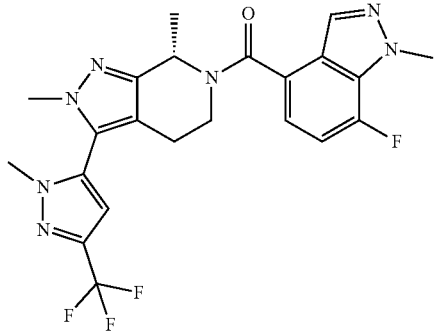

The title compound was prepared in a manner analogous to Example 1, using 7-fluoro-1-methyl-1H-indazole-4-carboxylic acid instead of 2-methylquinoline-5-carboxylic acid. MS (ESI): mass calcd. for $C_{22}H_{21}F_4N_7O$, 475.2; m/z found, 476.1 [M+H]$^+$. $^1$H NMR (400 MHz, DMSO-$d_6$) δ 8.01 (s, 1H), 7.29 (dd, J=12.0, 7.8 Hz, 1H), 7.22-7.06 (m, 2H), 5.84-5.54 (m, 1H), 4.92-4.44 (m, 1H), 4.28-4.13 (m, 3H), 3.80 (s, 3H), 3.71 (s, 3H), 3.18 (d, J=4.8 Hz, 1H), 2.61 (d, J=54.6 Hz, 1H), 2.41-2.18 (m, 1H), 1.53 (s, 3H).

Example 22: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-indazol-3-yl)methanone

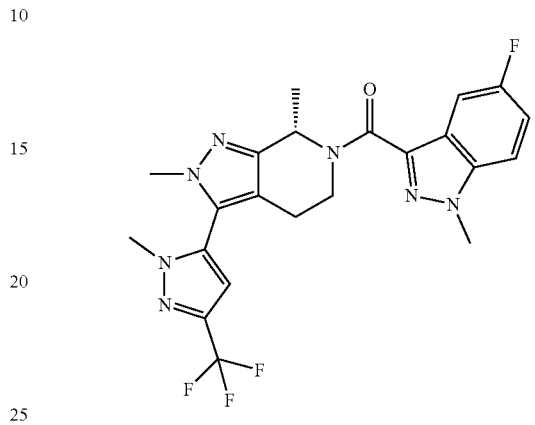

The title compound was prepared in a manner analogous to Example 1, using 5-fluoro-1-methyl-1H-indazole-3-carboxylic acid instead of 2-methylquinoline-5-carboxylic acid. MS (ESI): mass calcd. for $C_{22}H_{21}F_4N_7O$, 475.2; m/z found, 476.1 [M+H]$^+$. $^1$H NMR (400 MHz, DMSO-$d_6$) δ 7.86-7.62 (m, 2H), 7.47-7.33 (m, 1H), 7.11 (s, 1H), 6.26-5.62 (m, 1H), 5.12-4.63 (m, 1H), 4.13 (d, J=15.4 Hz, 3H), 3.85-3.77 (m, 3H), 3.74-3.63 (m, 3H), 3.20-3.11 (m, 1H), 2.78-2.64 (m, 1H), 2.46-2.35 (m, 1H), 1.57 (d, J=27.2 Hz, 3H).

Example 23: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-2H-indazol-4-yl)methanone

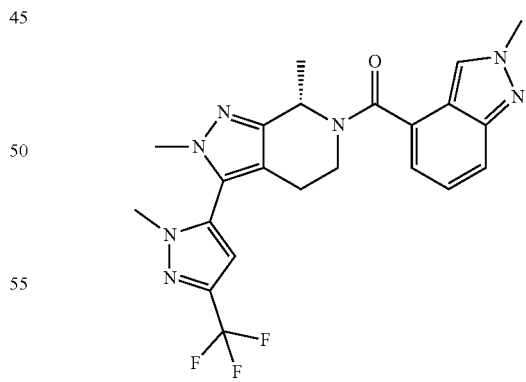

The title compound was prepared in a manner analogous to Example 1, using potassium 2-methyl-2H-indazole-4-carboxylate (Intermediate 5) instead of 2-methylquinoline-5-carboxylic acid. MS (ESI): mass calcd. for $C_{22}H_{22}F_3N_7O$, 457.2; m/z found, 458.1 [M+H]$^+$. $^1$H NMR (600 MHz, DMSO-$d_6$) δ 8.33 (s, 1H), 7.75-7.64 (m, 1H), 7.30 (dd, J=8.7, 6.7 Hz, 1H), 7.17-7.04 (m, 2H), 5.86-5.50 (m, 1H), 4.96-4.47 (m, 1H), 4.18 (s, 3H), 3.81 (s, 3H), 3.77-3.65 (m, 3H), 2.69-2.53 (m, 1H), 2.64-2.55 (m, 1H), 2.42-2.24 (m, 1H), 1.53 (s, 3H).

Example 24: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-3-yl)methanone

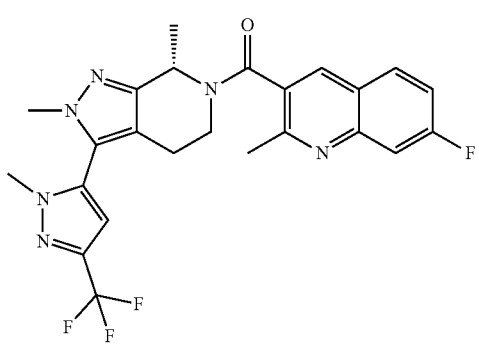 [SMILES: Cc1nc2cc(F)ccc2cc1C(=O)N1CCc2c(nn(C)c2-c2cc(C(F)(F)F)nn2C)[C@@H]1C]

The title compound was prepared in a manner analogous to Example 1, using 7-fluoro-2-methylquinoline-3-carboxylic acid instead of 2-methylquinoline-5-carboxylic acid. MS (ESI): mass calcd. for $C_{24}H_{22}F_4N_6O$, 486.2; m/z found, 487.1 [M+H]$^+$. $^1$H NMR (400 MHz, DMSO-d$_6$) δ 8.35 (s, 1H), 8.18-8.00 (m, 1H), 7.73 (dd, J=10.5, 2.6 Hz, 1H), 7.64-7.47 (m, 1H), 7.18-6.98 (m, 1H), 5.90-5.56 (m, 1H), 4.85-4.38 (m, 1H), 3.80 (s, 3H), 3.74 (s, 3H), 3.67 (s, 1H), 3.29 (s, 1H), 2.60 (s, 3H), 2.34-2.19 (m, 1H), 1.66-1.47 (m, 3H).

Example 25: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,6-dimethylquinolin-4-yl)methanone

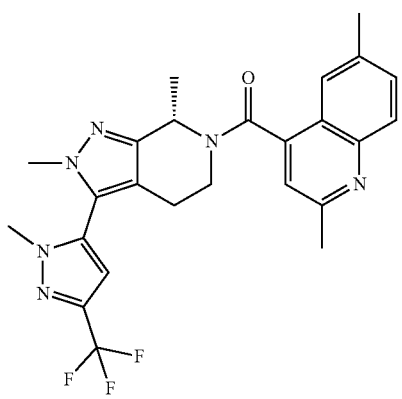 [SMILES: Cc1ccc2nc(C)cc(C(=O)N3CCc4c(nn(C)c4-c4cc(C(F)(F)F)nn4C)[C@@H]3C)c2c1]

The title compound was prepare in a manner analogous to Example 1, using 2,6-dimethylquinoline-4-carboxylic acid instead of 2-methylquinoline-5-carboxylic acid. MS (ESI): mass calcd. for $C_{25}H_{25}F_3N_6O$, 482.2; m/z found, 483.2 [M+H]$^+$. $^1$H NMR (400 MHz, DMSO-d$_6$) δ 7.90 (dd, J=8.7, 4.1 Hz, 1H), 7.69-7.20 (m, 3H), 7.17-7.02 (m, 1H), 5.93-5.74 (m, 1H), 4.88-4.28 (m, 1H), 3.87-3.60 (m, 6H), 3.27- 3.14 (m, 1H), 3.04-2.72 (m, 1H), 2.73-2.63 (m, 4H), 2.42 (s, 1H), 2.35-2.14 (m, 2H), 1.69-1.39 (m, 3H).

Example 26: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-methoxy-2-methylquinolin-4-yl)methanone

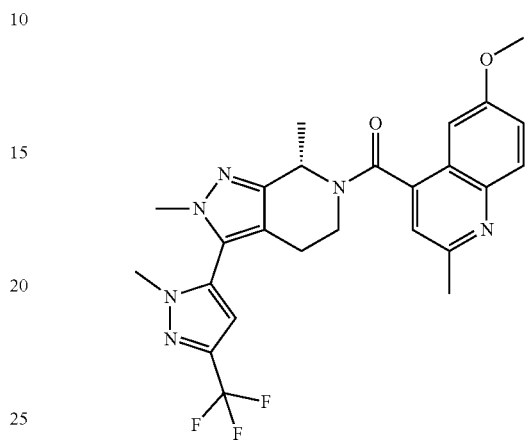

The title compound was prepared in a manner analogous to Example 1, using 6-methoxy-2-methylquinoline-4-carboxylic acid instead of 2-methylquinoline-5-carboxylic acid. MS (ESI): mass calcd. for $C_{25}H_{25}F_3N_6O_2$, 498.2; m/z found, 499.2 [M+H]$^+$. $^1$H NMR (400 MHz, DMSO-d$_6$) δ 7.92 (d, J=9.1 Hz, 1H), 7.54-7.26 (m, 2H), 7.13-6.87 (m, 2H), 5.98-5.68 (m, 1H), 4.97-4.30 (m, 1H), 3.85-3.73 (m, 6H), 3.72-3.43 (m, 3H), 3.21-3.14 (m, 1H), 2.71-2.59 (m, 3H), 2.60-2.55 (m, 1H), 2.24 (d, J=14.5 Hz, 1H), 1.72-1.35 (m, 3H).

Example 27: (S)-(4,6-Difluoro-1-methyl-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone

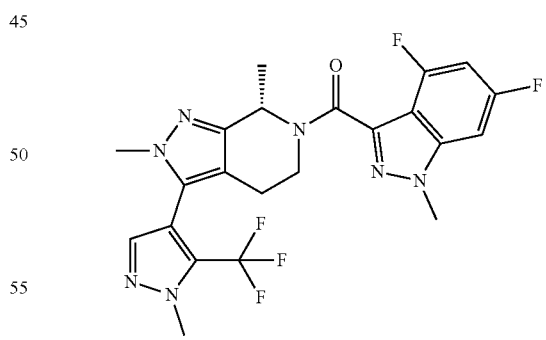

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and lithium 4,6-difluoro-1-methyl-1H-indazole-3-carboxylate (Intermediate 6) instead of 2-methylquinoline-5-carboxylic acid. MS (ESI): mass calcd. for $C_{22}H_{20}F_5N_7O$, 494.2; m/z found, 495.2 [M+H]+. 1H NMR (400 MHz, DMSO-d6) δ 7.90-7.79 (m, 1H), 7.55 (t, J=9.3, 2.7 Hz, 1H), 7.15-6.97 (m, 1H), 5.65 (q, J=6.7 Hz, 1H), 5.10-4.61 (m, 1H), 4.13-4.01 (m, 6H), 3.92-3.83 (m, 1H), 3.61 (d, J=28.2 Hz, 3H), 3.18-3.02 (m, 1H), 2.33-2.13 (m, 1H), 1.47 (dd, J=24.0, 6.7 Hz, 3H).

Example 28: (S)-(4,6-Difluoro-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone

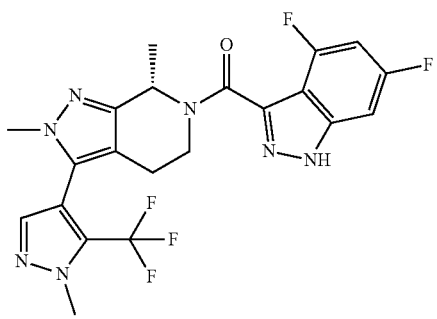 [SMILES: C[C@H]1c2nn(C)c(-c3cnn(C)c3C(F)(F)F)c2CCN1C(=O)c1n[nH]c2cc(F)cc(F)c12]

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 4,6-difluoro-1H-indazole-3-carboxylic acid instead of 2-methylquinoline-5-carboxylic acid. MS (ESI): mass calcd. for $C_{21}H_{18}F_5N_7O$, 479.2; m/z found, 480.1 [M+H]+. 1H NMR (400 MHz, DMSO-d6) δ 7.85 (d, J=5.4 Hz, 1H), 7.30 (dd, J=9.1, 2.1 Hz, 1H), 7.11-6.91 (m, 1H), 5.65 (q, J=6.6 Hz, 1H), 4.87 (dd, J=127.6, 9.1 Hz, 1H), 4.11-4.02 (m, 3H), 3.95-3.80 (m, 1H), 3.67-3.52 (m, 3H), 3.20-2.96 (m, 2H), 2.45-2.16 (m, 1H), 1.48 (dd, J=19.5, 6.7 Hz, 3H).

Example 29: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-(trifluoromethyl)phenyl)methanone

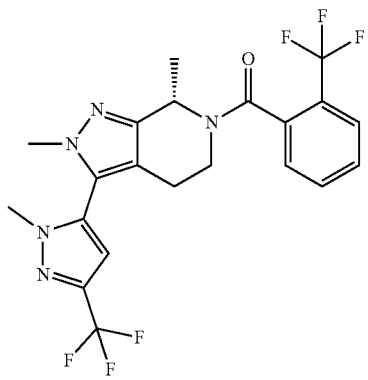 [SMILES: C[C@H]1c2nn(C)c(-c3cc(C(F)(F)F)nn3C)c2CCN1C(=O)c1ccccc1C(F)(F)F]

The title compound was prepared in a manner analogous to Example 1, using 2-(trifluoromethyl)benzoic acid instead of 2-methylquinoline-5-carboxylic acid. MS (ESI): mass calcd. for $C_{21}H_{19}F_6N_5O$, 471.2; m/z found, 472.1 [M+H]+. 1H NMR (400 MHz, DMSO-d6) δ 7.87-7.46 (m, 4H), 7.18-6.94 (m, 1H), 5.76-5.42 (m, 1H), 4.66-4.30 (m, 1H), 3.84-3.60 (m, 6H), 3.27-3.17 (m, 1H), 2.65-2.52 (m, 1H), 2.37-2.16 (m, 1H), 1.56-1.34 (m, 3H).

Example 30: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-fluoro-4-methylphenyl)methanone

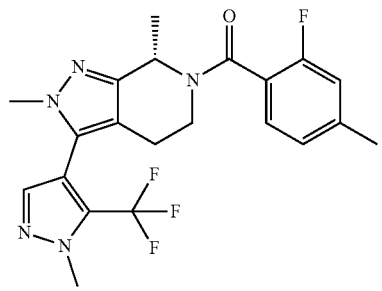

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-fluoro-4-methylbenzoic acid instead of 2-methylquinoline-5-carboxylic acid. MS (ESI): mass calcd. for $C_{21}H_{21}F_4N_5O$, 435.2; m/z found, 436.2 [M+H]+. 1H NMR (400 MHz, DMSO-d6) δ 7.84 (d, J=10.7 Hz, 1H), 7.36-7.02 (m, 3H), 5.58 (q, J=6.7 Hz, 1H), 4.74-4.50 (m, 1H), 4.10-4.02 (m, 3H), 3.68-3.53 (m, 3H), 3.49 (dd, J=13.9, 5.0 Hz, 1H), 3.25-2.97 (m, 1H), 2.36 (s, 3H), 2.26-2.18 (m, 1H), 1.54-1.30 (m, 3H).

Example 31: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-indazol-7-yl)methanone

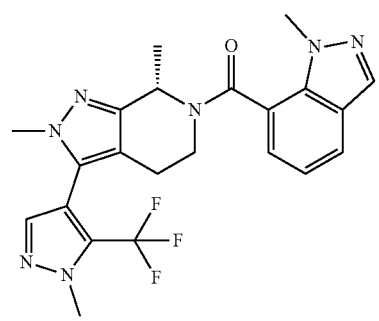 [SMILES: C[C@H]1c2nn(C)c(-c3cnn(C)c3C(F)(F)F)c2CCN1C(=O)c1cccc2cnn(C)c12]

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-indazole-7-carboxylic acid instead of 2-methylquinoline-5-carboxylic acid. MS (ESI): mass calcd. for C$_{22}$H$_{22}$F$_3$N$_7$O, 457.2; m/z found, 458.2 [M+H]$^+$. $^1$H NMR (400 MHz, DMSO-d$_6$) δ 8.21-8.09 (m, 1H), 7.99-7.76 (m, 2H), 7.44-7.15 (m, 2H), 5.92-5.50 (m, 1H), 4.86-4.38 (m, 1H), 4.12-3.78 (m, 6H), 3.65 (s, 3H), 3.54-3.43 (m, 1H), 2.43-2.03 (m, 2H), 1.49 (dd, J=47.5, 6.7 Hz, 3H).

Example 32: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrazolo[3,4-b]pyridin-4-yl)methanone

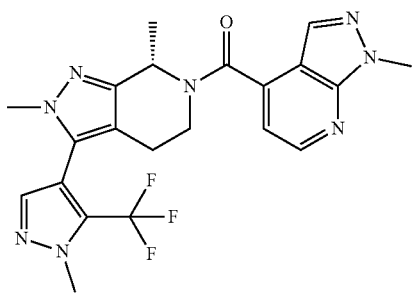

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-pyrazolo[3,4-b]pyridine-4-carboxylic acid instead of 2-methylquinoline-5-carboxylic acid. MS (ESI): mass calcd. for C$_{21}$H$_{21}$F$_3$N$_8$O, 458.2; m/z found, 459.2 [M+H]$^+$. $^1$H NMR (400 MHz, DMSO-d$_6$) δ 8.66 (d, J=4.7 Hz, 1H), 8.07 (s, 1H), 7.88-7.77 (m, 1H), 7.25 (d, J=4.6 Hz, 1H), 5.73-5.59 (m, 1H), 4.82-4.45 (m, 1H), 4.15-3.98 (m, 6H), 3.68-3.51 (m, 3H), 3.50-3.38 (m, 1H), 2.44-2.28 (m, 1H), 2.23-2.08 (m, 1H), 1.60-1.30 (m, 3H).

Example 33: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2,8-dimethylquinolin-6-yl)methanone

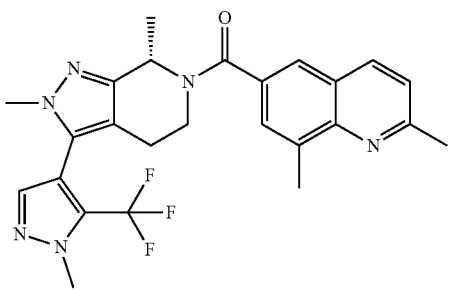

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2,8-dimethylquinoline-6-carboxylic acid instead of 2-methylquinoline-5-carboxylic acid. MS (ESI): mass calcd. for C$_{25}$H$_{25}$F$_3$N$_6$O, 482.2; m/z found, 483.2 [M+H]$^+$. $^1$H NMR (400 MHz, DMSO-d$_6$) δ 8.31 (d, J=8.4 Hz, 1H), 7.93-7.76 (m, 2H), 7.64-7.38 (m, 2H), 5.74-5.44 (m, 1H), 4.85-4.53 (m, 1H), 4.10-3.99 (m, 3H), 3.75-3.54 (m, 3H), 3.18 (d, J=5.1 Hz, 1H), 2.76-2.68 (m, 6H), 2.55 (d, J=6.9 Hz, 1H), 2.37-2.17 (m, 1H), 1.50 (d, J=6.7 Hz, 3H).

Example 34: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(6-fluoro-2-methylquinolin-4-yl)methanone

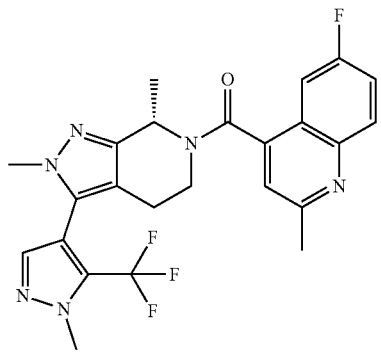 [SMILES: Cc1cc(C(=O)N2CCc3c(nn(C)c3-c3cnn(C)c3C(F)(F)F)[C@@H]2C)c2cc(F)ccc2n1]

The title compound was prepared in a manner analogous to Example 1, using (S)-2,7-Dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 6-fluoro-2-methylquinoline-4-carboxylic acid instead of 2-methylquinoline-5-carboxylic acid. MS (ESI): mass calcd. for C$_{24}$H$_{22}$F$_4$N$_6$O, 486.2; m/z found, 487.2 [M+H]$^+$. $^1$H NMR (500 MHz, DMSO-d$_6$) δ 8.08 (s, 1H), 7.84 (d, J=24.8 Hz, 1H), 7.65 (d, J=61.9 Hz, 1H), 7.48 (s, 1H), 7.37-7.14 (m, 1H), 5.88-5.58 (m, 1H), 4.87-4.27 (m, 1H), 4.11-3.98 (m, 3H), 3.71-3.54 (m, 4H), 2.71-2.62 (m, 3H), 2.47-2.04 (m, 2H), 1.69-1.34 (m, 3H).

Example 35: (S)-(2-Chloro-3-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

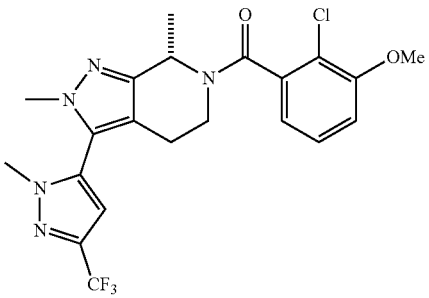 [SMILES: COc1cccc(C(=O)N2CCc3c(nn(C)c3-c3cc(C(F)(F)F)nn3C)[C@@H]2C)c1Cl]

The title compound was prepared in a manner analogous to Example 1, using 2-chloro-3-methoxybenzoic acid instead of 2-methylquinoline-5-carboxylic acid. MS (ESI): mass calcd. for $C_{21}H_{21}ClF_3N_5O_2$, 467.1; m/z found, 468.1 [M+H]$^+$. $^1$H NMR (600 MHz, CDCl$_3$) δ 7.37-7.21 (m, 0.9H), 7.00-6.86 (m, 2H), 6.77 (dd, J=7.6, 1.3 Hz, 0.1H), 6.63-6.56 (m, 1H), 5.99-5.89 (m, 0.60H), 5.03-4.65 (m, 0.73H), 3.97-3.88 (m, 3H), 3.84-3.67 (m, 6H), 3.60-3.50 (m, 0.70H), 3.41-3.20 (m, 0.69H), 3.15-2.98 (m, 0.43H), 2.87-2.68 (m, 0.66H), 2.48-2.36 (m, 0.80H), 2.26-2.16 (m, 0.62H), 1.66-1.60 (m, 1.83H), 1.51-1.39 (m, 1.38H).

Example 36: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxy-2-methylphenyl)methanone

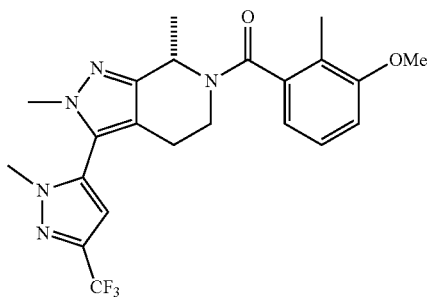

The title compound was prepared in a manner analogous to Example 1, using 3-methoxy-2-methylbenzoic acid instead of 2-methylquinoline-5-carboxylic acid. MS (ESI): mass calcd. for $C_{22}H_{24}F_3N_5O_2$, 447.2; m/z found, 448.2 [M+H]$^+$. $^1$H NMR (600 MHz, CDCl$_3$) δ 7.26-7.13 (m, 1H), 6.88-6.75 (m, 2H), 6.67-6.57 (m, 1H), 6.01-5.93 (m, 0.57H), 5.04-4.91 (m, 0.52H), 4.70 (q, J=6.8 Hz, 0.26H), 3.89-3.54 (m, 10H), 3.27-3.01 (m, 1H), 2.79-2.69 (m, 0.41H), 2.50-2.39 (m, 1H), 2.27-2.13 (m, 2.85H), 1.97 (s, 0.84H), 1.66-1.60 (m, 1.70H), 1.46-1.35 (m, 1.30H).

Example 37: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-(1H-pyrazol-1-yl)phenyl)methanone

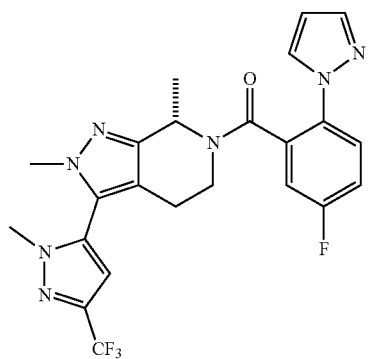 [SMILES: C[C@H]1c2nn(C)c(-c3cc(C(F)(F)F)nn3C)c2CCN1C(=O)c1cc(F)ccc1-n1cccn1]

The title compound was prepared in a manner analogous to Example 1, using 5-fluoro-2-(1H-pyrazol-1-yl)benzoic acid instead of 2-methylquinoline-5-carboxylic acid. MS (ESI): mass calcd. for $C_{23}H_{21}F_4N_7O$, 487.2; m/z found, 488.1 [M+H]$^+$. $^1$H NMR (600 MHz, CDCl$_3$) δ 7.85-7.46 (m, 3H), 7.26-7.08 (m, 2H), 6.62-6.17 (m, 2H), 5.79-5.72 (m, 0.81H), 4.86-4.64 (m, 0.59H), 3.82-3.64 (m, 7H), 3.56-3.42 (m, 0.83H), 3.16-2.90 (m, 1H), 2.53-2.35 (m, 0.79H), 2.29-2.17 (m, 0.71H), 1.96-1.90 (m, 0.33H), 1.52-1.34 (m, 2.34H).

Example 38: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxyphenyl)methanone

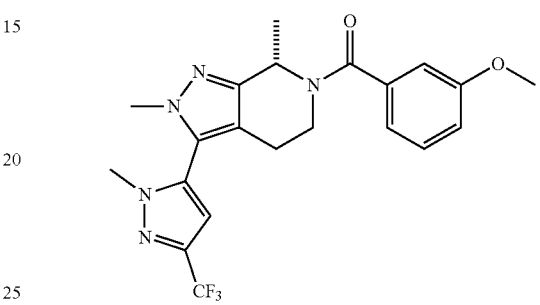

The title compound was prepared in a manner analogous to Example 1, using 3-methoxybenzoic acid instead of 2-methylquinoline-5-carboxylic acid. MS (ESI): mass calcd. for $C_{21}H_{22}F_3N_5O_2$, 433.2; m/z found, 434.1 [M+H]$^+$. $^1$H NMR (600 MHz, CDCl$_3$) δ 7.33 (t, J=7.7 Hz, 1H), 7.00-6.94 (m, 3H), 6.59 (d, J=0.6 Hz, 1H), 5.86 (br s, 0.37H), 5.09-4.76 (m, 0.58H), 3.84-3.80 (m, 7H), 3.72 (br s, 3H), 3.34-3.00 (m, 1H), 2.81-2.47 (m, 1H), 2.34 (br s, 1H), 1.59 (br s, 3H).

Example 39: (S)-(3-Chloro-5-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

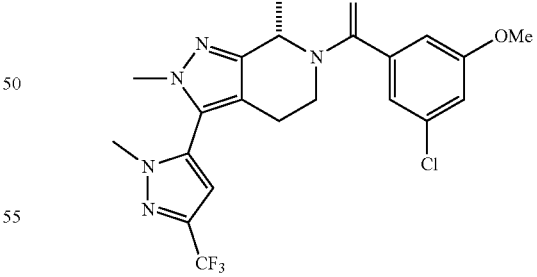

The title compound was prepared in a manner analogous to Example 1, using 3-chloro-5-methoxybenzoic acid instead of 2-methylquinoline-5-carboxylic acid. MS (ESI): mass calcd. for $C_{21}H_{21}ClF_3N_5O_2$, 467.1; m/z found, 468.0 [M+H]$^+$. $^1$H NMR (600 MHz, CDCl$_3$) δ 6.99-6.94 (m, 2H), 6.83 (s, 1H), 6.60 (s, 1H), 5.83 (s, 0.40H), 5.03-4.73 (m, 0.63H), 3.86-3.65 (m, 10H), 3.38-3.01 (m, 1H), 2.81-2.47 (m, 1H), 2.35 (s, 1H), 1.56 (s, 3H).

Example 40: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylphenyl)methanone

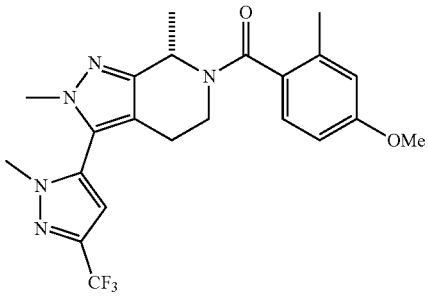

The title compound was prepared in a manner analogous to Example 1, using 4-methoxy-2-methylbenzoic acid instead of 2-methylquinoline-5-carboxylic acid. MS (ESI): mass calcd. for $C_{22}H_{24}F_3N_5O_2$, 447.2; m/z found, 448.2 [M+H]$^+$. $^1$H NMR (600 MHz, CDCl$_3$) δ 7.22-7.06 (m, 1H), 6.80-6.69 (m, 2H), 6.63-6.56 (m, 1H), 5.94 (br s, 0.54H), 5.01-4.66 (m, 0.60H), 3.85-3.56 (m, 10H), 3.28-2.98 (m, 1H), 2.79-2.66 (m, 0.36H), 2.50-2.06 (m, 4.77H), 1.61 (d, J=6.8 Hz, 1.53H), 1.41 (br s, 1.41H).

Example 41: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxy-4-methylphenyl)methanone

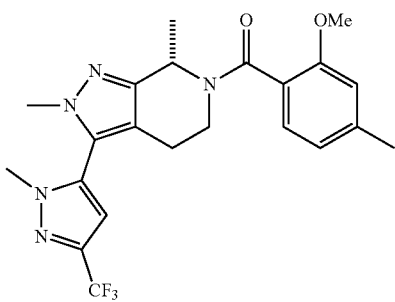

The title compound was prepared in a manner analogous to Example 1, using 2-methoxy-4-methylbenzoic acid instead of 2-methylquinoline-5-carboxylic acid. MS (ESI): mass calcd. for $C_{22}H_{24}F_3N_5O_2$, 447.2; m/z found, 448.2 [M+H]$^+$. $^1$H NMR (600 MHz, CDCl$_3$) δ 7.19-6.96 (m, 1H), 6.88-6.66 (m, 2H), 6.62-6.53 (m, 1H), 5.93 (q, J=6.7 Hz, 0.60H), 5.03-4.73 (m, 0.67H), 3.90-3.54 (m, 10H), 3.31-2.95 (m, 0.90H), 2.79-2.60 (m, 0.65H), 2.44-2.33 (m, 4H), 2.25-2.15 (m, 0.62H), 1.63-1.58 (m, 1.68H), 1.50-1.36 (m, 1.29H).

Example 42: (S)-(2-Chloro-4-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

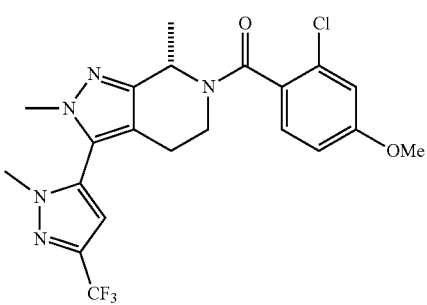 [SMILES: COc1ccc(C(=O)N2CCc3c(nn(C)c3-c3cc(C(F)(F)F)nn3C)[C@@H]2C)c(Cl)c1]

The title compound was prepared in a manner analogous to Example 1, using 2-chloro-4-methoxybenzoic acid instead of 2-methylquinoline-5-carboxylic acid. MS (ESI): mass calcd. for $C_{21}H_{21}ClF_3N_5O_2$, 467.1; m/z found, 468.1 [M+H]$^+$. $^1$H NMR (600 MHz, CDCl$_3$) δ 7.30-7.18 (m, 1H), 7.09-6.78 (m, 2H), 6.62-6.57 (m, 1H), 5.97-5.90 (m, 0.61H), 5.00-4.70 (m, 0.71H), 3.87-3.68 (m, 9.86H), 3.63-3.54 (m, 0.63H), 3.42-2.97 (m, 0.90H), 2.80-2.68 (m, 0.60H), 2.46-2.35 (m, 0.77H), 2.27-2.20 (m, 0.62H), 1.65-1.59 (m, 1.83H), 1.43-1.39 (m, 0.81H).

Example 43: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3,4-dimethylphenyl)methanone The title compound was prepared in a manner analogous to Example 1, using 3,4-dimethylbenzoic acid instead of 2-methylquinoline-5-carboxylic acid. MS (ESI): mass calcd. for $C_{22}H_{24}F_3N_5O$, 431.2; m/z found, 432.1 [M+H]$^+$. $^1$H NMR (600 MHz, CDCl$_3$) δ 7.20 (s, 1H), 7.18-7.12 (m, 2H), 6.61-6.58 (m, 1H), 5.85 (br s, 0.23H), 5.15-4.70 (m, 0.24H), 4.01-3.61 (m, 7H), 3.37-2.99 (m, 0.58H), 2.83-2.51 (m, 0.65H), 2.39-2.22 (m, 7.79H), 1.57 (br s, 3H).

Example 44: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(isoquinolin-1-yl)methanone

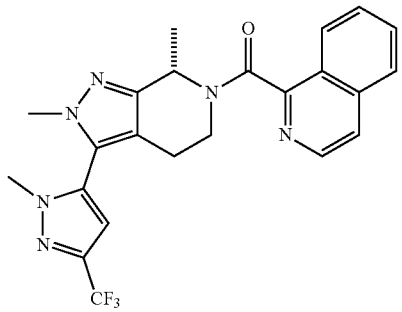 [SMILES: C[C@H]1c2nn(C)c(-c3cc(C(F)(F)F)nn3C)c2CCN1C(=O)c1nccc2ccccc12]

The title compound was prepared in a manner analogous to Example 1, using isoquinoline-1-carboxylic acid instead of 2-methylquinoline-5-carboxylic acid. MS (ESI): mass calcd. for $C_{23}H_{21}F_3N_6O$, 454.2; m/z found, 455.2 [M+H]$^+$. $^1$H NMR (500 MHz, CDCl$_3$) δ 8.56-8.50 (m, 1H), 8.07-7.98 (m, 1H), 7.91-7.86 (m, 1H), 7.77-7.68 (m, 2H), 7.66-7.56 (m, 1H), 6.63-6.55 (m, 1H), 6.09 (q, J=6.8 Hz, 0.62H), 5.18-5.11 (m, 0.36H), 4.81 (q, J=6.7 Hz, 0.35H), 3.85-3.73 (m, 4.87H), 3.65 (s, 1H), 3.53-3.45 (m, 0.63H), 3.33-3.15 (m, 1H), 2.92-2.64 (m, 1H), 2.55-2.47 (m, 0.34H), 2.21-2.14 (m, 0.64H), 1.75 (d, J=6.8 Hz, 1.88H), 1.46 (d, J=6.8 Hz, 1.04H).

Example 45: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indol-4-yl)methanone

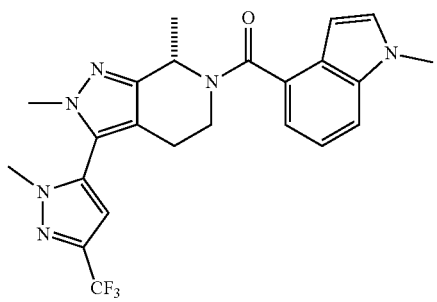

The title compound was prepared in a manner analogous to Example 1, using 1-methyl-1H-indole-4-carboxylic acid instead of 2-methylquinoline-5-carboxylic acid. MS (ESI): mass calcd. for $C_{23}H_{23}F_3N_6O$, 456.2; m/z found, 457.3 [M+H]$^+$. $^1$H NMR (500 MHz, CDCl$_3$) δ 7.38 (dd, J=8.3, 1.0 Hz, 1H), 7.28-7.22 (m, 1H), 7.15-7.06 (m, 2H), 6.59 (s, 1H), 6.43 (br s, 1H), 6.04 (br s, 0.51H), 5.07 (br s, J=44.6 Hz, 0.60H), 3.91-3.61 (m, 10H), 3.22 (br s, 1H), 2.90-2.07 (m, 2H), 1.76-1.38 (m, 3H).

Example 46: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrrolo[2,3-b]pyridin-4-yl)methanone

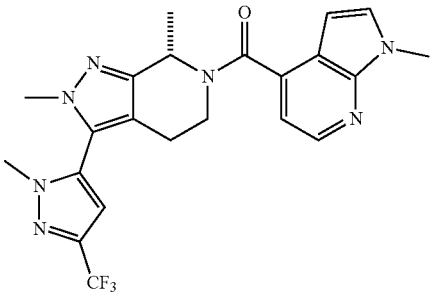

The title compound was prepared in a manner analogous to Example 1, using 1-methyl-1H-pyrrolo[2,3-b]pyridine-4-carboxylic acid instead of 2-methylquinoline-5-carboxylic acid. MS (ESI): mass calcd. for $C_{23}H_{23}F_3N_6O$, 457.2; m/z found, 458.3 [M+H]$^+$. $^1$H NMR (500 MHz, CDCl$_3$) δ 8.40 (d, J=4.8 Hz, 1H), 7.29-7.20 (m, 1H), 7.05 (d, J=4.8 Hz, 1H), 6.66-6.57 (m, 1H), 6.48-6.32 (m, 1H), 6.05-5.96 (m, 0.54H), 5.07-4.86 (m, 0.75H), 3.92 (s, 3H), 3.87-3.62 (m, 7H), 3.34-3.06 (m, 1H), 2.88-2.16 (m, 2H), 1.68 (d, J=6.7 Hz, 2H), 1.43 (br s, 1H).

Example 47: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-pyrrolo[2,3-b]pyridin-4-yl)methanone

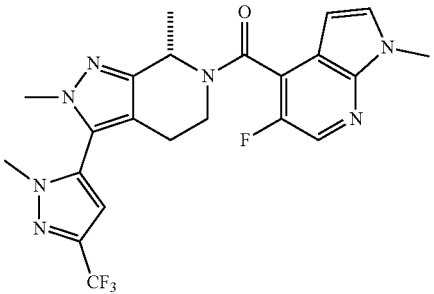

The title compound was prepared in a manner analogous to Example 1, using 5-fluoro-1-methyl-1H-pyrrolo[2,3-b]pyridine-4-carboxylic acid (Intermediate 8) instead of 2-methylquinoline-5-carboxylic acid. MS (ESI): mass calcd. for $C_{22}H_{21}F_4N_7O$, 475.2; m/z found, 476.2 [M+H]$^+$. $^1$H NMR (500 MHz, CDCl$_3$) δ 8.26 (s, 1H), 7.31 (s, 1H), 6.60 (d, J=19.2 Hz, 1H), 6.46-5.98 (m, 1H), 5.10-4.78 (m, 0.74H), 3.96-3.60 (m, 10H), 3.47-3.09 (m, 1H), 2.86-2.65 (m, 0.71H), 2.54-2.15 (m, 1.27H), 1.69 (d, J=6.7 Hz, 2H), 1.52-1.33 (m, 1H).

Example 48: (S)-(2-Chloro-3-methoxyphenyl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone

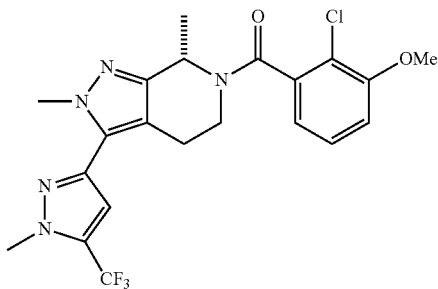 [SMILES: COc1cccc(C(=O)N2CCc3c(nn(C)c3-c3cc(C(F)(F)F)n(C)n3)[C@@H]2C)c1Cl]

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-chloro-3-methoxybenzoic acid instead of 2-methylquinoline-5-carboxylic acid. MS (ESI): mass calcd. for $C_{21}H_{21}ClF_3N_5O_2$, 467.1; m/z found, 468.2 [M+H]$^+$. $^1$H NMR (600 MHz, CDCl$_3$) δ 7.35-7.17 (m, 1.20H), 7.00-6.87 (m, 1.80H), 6.78-6.64 (m, 1H), 5.96-5.85 (m, 0.55H), 5.06-4.96 (m, 0.39H), 4.86-4.78 (m, 0.11H), 4.69-4.62 (m, 0.24H), 4.10-4.00 (m, 6H), 3.96-3.88 (m, 3H), 3.61-3.50 (m, 0.56H), 3.42-3.22 (m, 0.54H), 3.18-3.02 (m, 0.37H), 2.97-2.85 (m, 0.61H), 2.74-2.46 (m, 1.35H), 1.67-1.58 (m, 1.80H), 1.48 (d, J=6.8 Hz, 0.45H), 1.39 (d, J=6.7 Hz, 0.81H).

Example 49: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrrolo[2,3-b]pyridin-4-yl)methanone

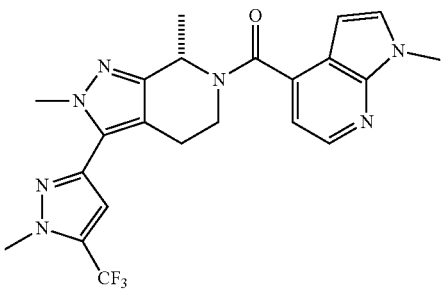

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-pyrrolo[2,3-b]pyridine-4-carboxylic acid instead of 2-methylquinoline-5-carboxylic acid. MS (ESI): mass calcd. for $C_{22}H_{22}F_3N_7O$, 457.2; m/z found, 458.2 [M+H]$^+$. $^1$H NMR (600 MHz, CDCl$_3$) δ 8.39 (s, 1H), 7.29-7.14 (m, 1H), 7.05 (s, 1H), 6.71 (d, J=55.2 Hz, 1H), 6.39 (d, J=81.9 Hz, 1H), 5.98 (d, J=7.0 Hz, 0.52H), 5.10-4.81 (m, 0.68H), 4.14-3.87 (m, 9.56H), 3.67 (d, J=13.5 Hz, 0.56H), 3.36-3.11 (m, 1H), 3.03-2.44 (m, 2H), 1.66 (d, J=6.8 Hz, 1.75H), 1.40 (d, J=6.7 Hz, 1.22H).

Example 50: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(3-methyl-5-(2H-1,2,3-triazol-2-yl)phenyl)methanone

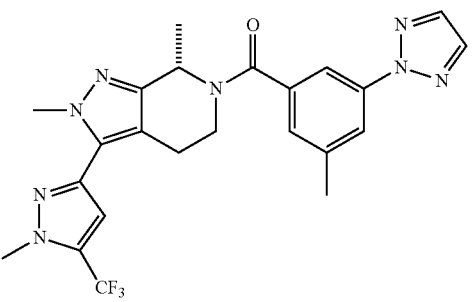 [SMILES: Cc1cc(C(=O)N2CCc3c(nn(C)c3-c3cc(C(F)(F)F)n(C)n3)[C@@H]2C)cc(-n2nccn2)c1]

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methyl-5-(2H-1,2,3-triazol-2-yl)benzoic acid (Intermediate 26) instead of 2-methylquinoline-5-carboxylic acid. MS (ESI): mass calcd. for $C_{23}H_{23}F_3N_8O$, 484.2; m/z found, 485.3 [M+H]$^+$. $^1$H NMR (600 MHz, CDCl$_3$) δ 8.00-7.95 (m, 2H), 7.81 (s, 2H), 7.22 (s, 1H), 6.72 (s, 1H), 5.86 (br s, 0.4H), 5.06-4.83 (m, 0.69H), 4.13-3.97 (m, 6.56H), 3.91-3.83 (m, 0.39H), 3.41-3.08 (m, 0.83H), 3.00-2.55 (m, 2H), 2.47 (s, 3.32H), 1.60 (s, 3H).

Example 51: (S)-(2-Chloro-3-methoxyphenyl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone

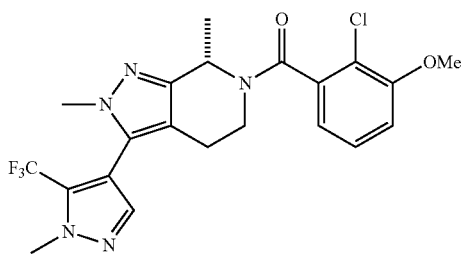 [SMILES: COc1cccc(C(=O)N2CCc3c(nn(C)c3-c3cnn(C)c3C(F)(F)F)[C@@H]2C)c1Cl]

The title compound was prepare in a manner analogous to Example 1, using (S)-2,7-dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-chloro-3-methoxybenzoic acid instead of 2-methylquinoline-5-carboxylic acid. MS (ESI): mass calcd. for $C_{21}H_{21}ClF_3N_5O_2$, 467.1; m/z found, 468.1 [M+H]$^+$. $^1$H NMR (500 MHz, CDCl₃) δ 7.50-7.44 (m, 1H), 7.33-7.20 (m, 1H), 6.97-6.86 (m, 1H), 5.95-5.86 (m, 0.58H), 4.99-4.90 (m, 0.46H), 4.81 (q, J=6.7 Hz, 0.15H), 4.65 (q, J=6.8 Hz, 0.30H), 4.11-4.06 (m, 3H), 3.96-3.88 (m, 3H), 3.70-3.61 (m, 3H), 3.56-3.44 (m, 0.59H), 3.38-3.30 (m, 0.37H), 3.27-3.18 (m, 0.18H), 3.14-2.97 (m, 0.41H), 2.78-2.63 (m, 0.61H), 2.42-2.31 (m, 0.84H), 2.21-2.15 (m, 0.57H), 1.67-1.58 (m, 2.27H), 1.48 (d, J=6.8 Hz, 0.45H), 1.40 (d, J=6.8 Hz, 0.87H).

Example 52: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrrolo[2,3-b]pyridin-4-yl)methanone

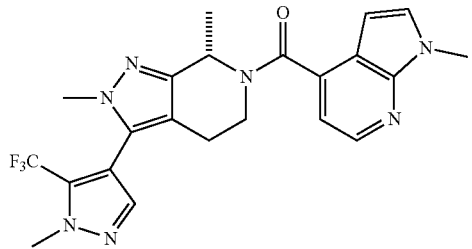

The title compound was prepared in a manner analogous to Example 1, using (S)-2,7-dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-pyrrolo[2,3-b]pyridine-4-carboxylic acid instead of 2-methylquinoline-5-carboxylic acid. MS (ESI): mass calcd. for $C_{22}H_{22}F_3N_7O$, 457.2; m/z found, 458.2 [M+H]⁺. ¹H NMR (500 MHz, CDCl₃) δ 8.39 (d, J=4.8 Hz, 1H), 7.52-7.43 (m, 1H), 7.25-7.18 (m, 1H), 7.04 (d, J=4.8 Hz, 1H), 6.47-6.24 (m, 1H), 6.03-5.92 (m, 0.69H), 5.04-4.81 (m, 1.16H), 4.13-4.05 (m, 2.36), 3.91 (s, 3H), 3.73-3.57 (m, 3.45H), 3.33-3.06 (m, 1.29), 2.83-2.67 (m, 0.49), 2.50-2.38 (m, 1.13H), 2.23-2.12 (m, 0.62H), 1.67 (d, J=6.8 Hz, 1.8H), 1.57 (s, 3.80H), 1.40 (d, J=6.8 Hz, 1.15H).

Example 53: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(3-methyl-5-(2H-1,2,3-triazol-2-yl)phenyl)methanone

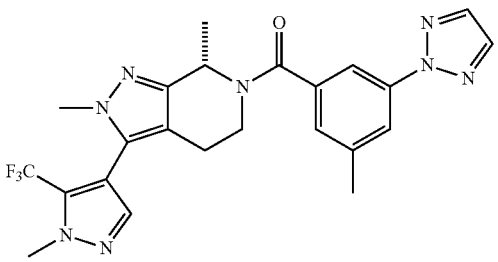 [SMILES: Cc1cc(C(=O)N2CCc3c(nn(C)c3-c3cnn(C)c3C(F)(F)F)[C@@H]2C)cc(-n2nccn2)c1]

The title compound was prepared in a manner analogous to Example 1, using (S)-2,7-dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methyl-5-(2H-1,2,3-triazol-2-yl)benzoic acid (Intermediate 26) instead of 2-methylquinoline-5-carboxylic acid instead of 2-methylquinoline-5-carboxylic acid. MS (ESI): mass calcd. for $C_{23}H_{23}F_3N_8O$, 484.2; m/z found, 485.3 [M+H]⁺. ¹H NMR (500 MHz, CDCl₃) δ 8.00-7.93 (m, 2H), 7.81 (s, 2H), 7.48 (s, 1H), 7.22 (s, 1H), 5.84 (br s, 0.50H), 5.05-4.76 (m, 1H), 4.09 (s, 3H), 3.88-3.56 (m, 4H), 3.39-3.03 (m, 1H), 2.78-2.52 (m, 1H), 2.47 (s, 3H), 2.42-2.21 (m, 1H), 1.60 (br s, 3H).

Example 54: (S)-Chroman-8-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

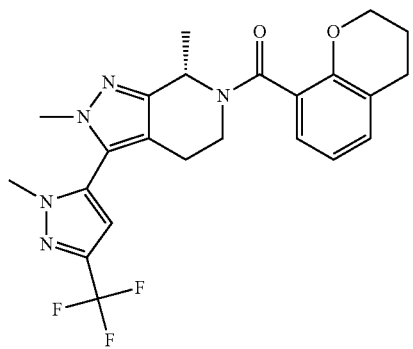 [SMILES: C[C@H]1c2nn(C)c(-c3cc(C(F)(F)F)nn3C)c2CCN1C(=O)c1cccc2c1OCCC2]

The title compound was prepared in a manner analogous to Example 1, using chromane-8-carboxylic acid instead of 2-methylquinoline-5-carboxylic acid. DMF was used instead of DCM. MS (ESI): mass calcd. for $C_{23}H_{24}F_3N_5O_2$, 459.2; m/z found, 460.3 [M+H]⁺. ¹H NMR (500 MHz, CDCl₃) δ 7.12-6.99 (m, 1.78H), 6.95-6.77 (m, 1.21H), 6.62-6.55 (m, 0.96H), 5.93 (p, J=7.0 Hz, 0.59H), 5.02-4.78 (m, 0.87H), 4.30-3.61 (m, 8.88H), 3.35-3.15 (m, 0.65H), 3.11-2.94 (m, 0.47H), 2.88-2.62 (m, 2.78H), 2.47-2.31 (m, 0.73H), 2.28-2.15 (m, 0.62H), 2.12-1.85 (m, 2.09H), 1.69-1.34 (m, 3H).

Example 55: (S)-Chroman-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

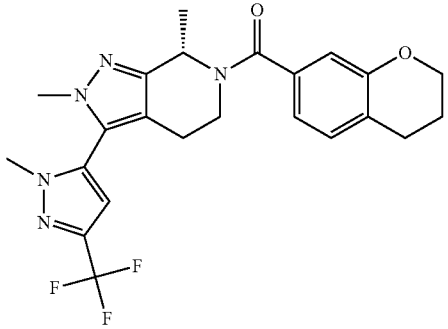 [SMILES: C[C@H]1c2nn(C)c(-c3cc(C(F)(F)F)nn3C)c2CCN1C(=O)c1ccc2c(c1)OCCC2]

The title compound was prepared in a manner analogous to Example 1, using chromane-7-carboxylic acid instead of 2-methylquinoline-5-carboxylic acid. DMF was used instead of DCM. MS (ESI): mass calcd. for $C_{23}H_{24}F_3N_5O_2$, 459.2; m/z found, 460.2 [M+H]$^+$. $^1$H NMR (600 MHz, DMSO-d$_6$) δ 7.13 (d, J=7.7 Hz, 1H), 7.09 (s, 1H), 6.84 (d, J=7.7 Hz, 1H), 6.74 (s, 1H), 5.54 (s, 0.65H), 4.92-4.42 (m, 0.34H), 4.20-4.10 (m, 2H), 3.83-3.59 (m, 7H), 3.26-2.98 (m, 1H), 2.77 (t, J=6.4 Hz, 2H), 2.64-2.56 (m, 1H), 2.38-2.22 (m, 1H), 1.98-1.88 (m, 2H), 1.53-1.36 (m, 3H).

Example 56: (S)-Benzo[d]thiazol-6-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

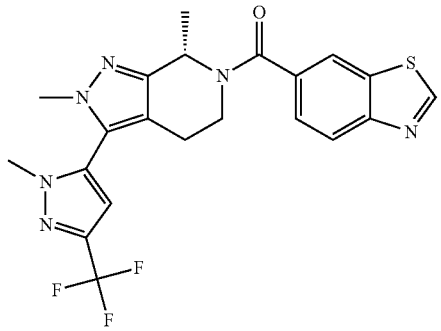 [SMILES: C[C@H]1c2nn(C)c(-c3cc(C(F)(F)F)nn3C)c2CCN1C(=O)c1ccc2ncsc2c1]

The title compound was prepared in a manner analogous to Example 1, using benzo[d]thiazole-6-carboxylic acid instead of 2-methylquinoline-5-carboxylic acid. DMF was used instead of DCM. MS (ESI): mass calcd. for $C_{21}H_{19}F_3N_6OS$, 460.1; m/z found, 461.1 [M+H]$^+$. $^1$H NMR (500 MHz, CDCl$_3$) δ 9.10 (s, 1H), 8.19 (d, J=8.3 Hz, 1H), 8.08 (s, 1H), 7.58 (d, J=8.1 Hz, 1H), 6.60 (s, 1H), 5.90 (br s, 0.43H), 5.18-4.69 (m, 0.74H), 4.00-3.55 (m, 6.75H), 3.44-3.04 (m, 1H), 2.89-2.23 (m, 2H), 1.80-1.41 (m, 3H).

Example 57: (S)-Benzo[d]thiazol-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

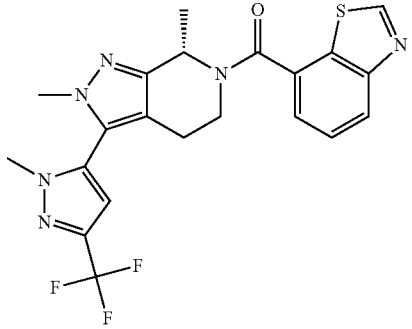 [SMILES: C[C@H]1c2nn(C)c(-c3cc(C(F)(F)F)nn3C)c2CCN1C(=O)c1cccc2ncsc12]

The title compound was prepared in a manner analogous to Example 1, using benzo[d]thiazole-7-carboxylic acid instead of 2-methylquinoline-5-carboxylic acid. DMF was used instead of DCM. MS (ESI): mass calcd. for $C_{21}H_{19}F_3N_6OS$, 460.1; m/z found, 461.2 [M+H]$^+$. $^1$H NMR (500 MHz, CDCl$_3$) δ 9.07 (s, 1H), 8.25-8.19 (m, 1H), 7.61-7.48 (m, 2H), 6.60 (s, 1H), 5.99-5.21 (m, 0.69H), 4.73-3.59 (m, 7.2H), 3.37-3.20 (m, 1H), 2.81-2.60 (m, 1H), 2.45-2.31 (m, 1H), 1.74-1.59 (m, 3H).

Example 58: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylbenzo[d]thiazol-6-yl)methanone

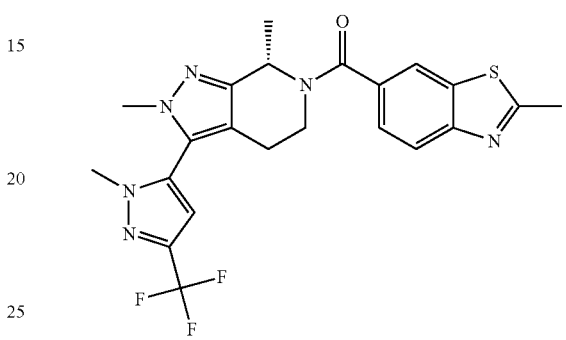

The title compound was prepare in a manner analogous to Example 1, using 2-methylbenzo[d]thiazole-6-carboxylic acid instead of 2-methylquinoline-5-carboxylic acid. DMF was used instead of DCM. MS (ESI): mass calcd. for $C_{22}H_{21}F_3N_6OS$, 474.1; m/z found, 475.2 [M+H]$^+$. $^1$H NMR (500 MHz, CDCl$_3$) δ 7.98 (d, J=8.3 Hz, 1H), 7.95-7.92 (m, 1H), 7.52-7.47 (m, 1H), 6.60 (s, 1H), 6.05-5.68 (m, 0.48H), 5.25-4.63 (m, 0.83H), 4.05-3.59 (m, 6.82H), 3.44-3.05 (m, 1H), 2.93-2.52 (m, 4H), 2.47-2.26 (m, 1H), 1.71-1.50 (m, 3H).

Example 59: (S)-Benzo[d]thiazol-6-yl(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone

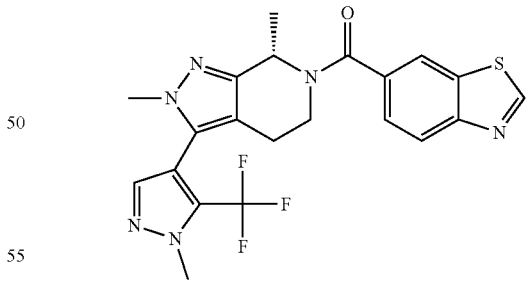

The title compound was prepared in a manner analogous to Example 1, using (S)-2,7-dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and benzo[d]thiazole-6-carboxylic acid instead of 2-methylquinoline-5-carboxylic acid. DMF was used instead of DCM. MS (ESI): mass calcd. for $C_{21}H_{19}F_3N_6OS$, 460.1; m/z found, 461.1 [M+H]$^+$. $^1$H NMR (500 MHz, CDCl$_3$) δ 9.08

(s, 1H), 8.17 (d, J=8.3 Hz, 1H), 8.08-8.05 (m, 1H), 7.57 (dd, J=8.4, 1.6 Hz, 1H), 7.48 (s, 1H), 5.86 (br s, 0.46H), 5.16-4.65 (m, 0.86H), 4.10 (s, 3H), 3.90-3.51 (m, 3.44H), 3.41-3.02 (m, 1H), 2.82-2.47 (m, 1H), 2.44-2.19 (m, 1H), 1.69-1.52 (m, 3H).

Example 60: (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-methoxy-3-methylpyridin-4-yl)methanone

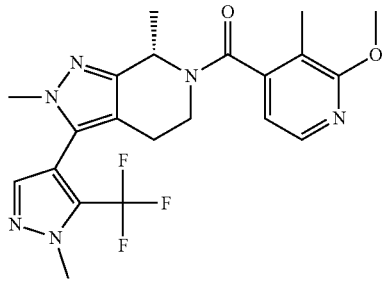

The title compound was prepared in a manner analogous to Example 1, using (S)-2,7-dimethyl-3-(1-methyl-5-(trifluoromethyl)-1H-pyrazol-4-yl)-4,5,6,7-tetrahydro-2H-pyrazolo[3,4-c]pyridine (Intermediate 15) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-methoxy-3-methylisonicotinic acid instead of 2-methylquinoline-5-carboxylic acid. DMF was used instead of DCM. MS (ESI): mass calcd. for $C_{21}H_{23}F_3N_6O_2$, 448.2; m/z found, 449.2 [M+H]$^+$. $^1$H NMR (500 MHz, CDCl$_3$) δ 8.11-7.96 (m, 1H), 7.51-7.42 (m, 1H), 6.81-6.55 (m, 1H), 5.94-5.85 (m, 1H), 4.95-4.87 (m, 0.45H), 4.84-4.77 (m, 0.12H), 4.62 (q, J=6.7 Hz, 0.30H), 4.12-4.04 (m, 3H), 4.01-3.91 (m, 3H), 3.72-3.59 (m, 3H), 3.56-3.44 (m, 0.59H), 3.30-3.20 (m, 0.55H), 3.04 (td, J=12.7, 4.0 Hz, 0.44H), 2.71-2.59 (m, 0.44H), 2.46-2.32 (m, 1H), 2.25-2.09 (m, 2.65H), 1.93 (s, 1H), 1.65-1.35 (m, 3H).

Example 61: (S)-Chroman-7-yl(2,7-dimethyl-3-(1-methyl-3-(trifluoromethyl)-1H-pyrazol-4-yl)-2,4,5,7-tetrahydro-6H-pyrazolo[3,4-c]pyridin-6-yl)methanone

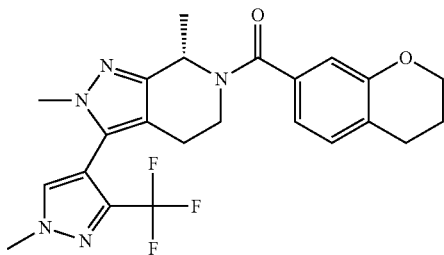 [SMILES: C[C@H]1c2nn(C)c(-c3cn(C)nc3C(F)(F)F)c2CCN1C(=O)c1ccc2c(c1)OCCC2]

The title compound was prepared in a manner analogous to Example 1, using (S)-2,7-dimethyl-3-(1-methyl-3-(trifluoromethyl)-1H-pyrazol-4-yl)-4,5,6,7-tetrahydro-2H-pyrazolo[3,4-c]pyridine HCl salt (Intermediate 19) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and chromane-7-carboxylic acid instead of 2-methylquinoline-5-carboxylic acid. DMF was used instead of DCM. MS (ESI): mass calcd. for $C_{23}H_{24}F_3N_5O_2$, 459.2; m/z found, 460.2 [M+H]$^+$. $^1$H NMR (500 MHz, CDCl$_3$) δ 7.44-7.42 (m, 1H), 7.07-7.02 (m, 1H), 6.89-6.84 (m, 1H), 6.82-6.80 (m, 1H), 5.79 (s, 0.48H), 5.11-4.65 (m, 1H), 4.23-4.14 (m, 2H), 4.03 (s, 3H), 3.92-3.74 (m, 0.52H), 3.63 (s, 3H), 3.30-2.95 (m, 1H), 2.79 (t, J=6.4 Hz, 2H), 2.71-2.43 (m, 1H), 2.38-2.17 (m, 1H), 2.04-1.97 (m, 2H), 1.64-1.44 (m, 3H).

Example 62: (S)-(2,7-Dimethyl-3-(1-methyl-1H-pyrazol-4-yl)-2,4,5,7-tetrahydro-6H-pyrazolo[3,4-c]pyridin-6-yl)(quinolin-6-yl)methanone

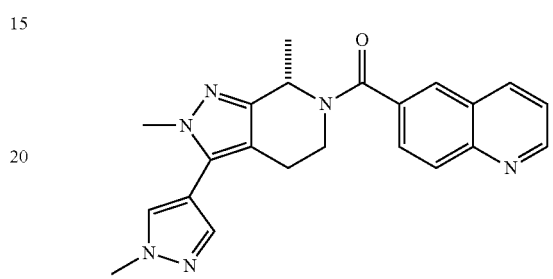

A microwave vial was charged with (S)-2,7-dimethyl-6-(quinoline-6-carbonyl)-4,5,6,7-tetrahydro-2H-pyrazolo[3,4-c]pyridin-3-yl trifluoromethanesulfonate (Intermediate 25, 15 mg, 33 μmol), 1-methyl-4-(4,4,5,5-tetramethyl-1,3,2-dioxaborolan-2-yl)-1H-pyrazole (8.2 mg, 39.6 μmol), XPhos-Pd-G2 precatalyst (1.3 mg, 1.65 μmol), saturated aqueous Na$_2$CO$_3$ (0.11 mL), and 1,4-dioxane (0.45 mL). The head space was evacuated under vacuum and refilled with N$_2$ (×3), and then the reaction stirred in a microwave reactor at 110° C. for 30 min. After cooling to room temperature, the mixture was diluted with DCM and H$_2$O, the layers separated, and the aqueous layer extracted with DCM (×2). The combined organics were washed with brine, dried over Na$_2$SO$_4$, filtered, and concentrated in vacuo. The residue was purified by preparative HPLC (METHOD A) to afford a white foam (7.3 mg, 57% yield). MS (ESI): mass calcd. for $C_{22}H_{22}N_6O$, 386.2; m/z found, 387.2 [M+H]$^+$. $^1$H NMR (600 MHz, CDCl$_3$) δ 8.98 (dd, J=4.2, 1.8 Hz, 1H), 8.23-8.13 (m, 2H), 7.93 (s, 1H), 7.75 (dd, J=8.6, 1.9 Hz, 1H), 7.60 (s, 1H), 7.49-7.44 (m, 2H), 5.89 (br s, 0.35H), 5.06-4.83 (m, 0.74H), 4.04-3.72 (m, 7H), 3.43-3.10 (m, 1H), 2.97-2.66 (m, 1H), 2.62-2.39 (m, 1H), 1.61 (br s, J=20.6 Hz, 3H).

Example 63: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(quinolin-6-yl)methanone

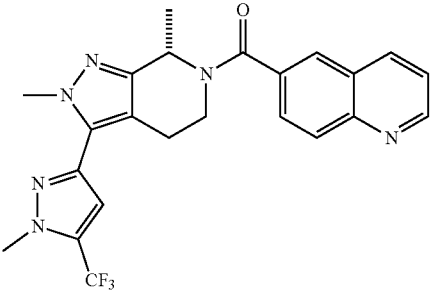 [SMILES: C[C@H]1c2nn(C)c(-c3cc(C(F)(F)F)n(C)n3)c2CCN1C(=O)c1ccc2ncccc2c1]

The title compound was prepared in a manner analogous to Example 62, using 1-methyl-3-(4,4,5,5-tetramethyl-1,3,2-dioxaborolan-2-yl)-5-(trifluoromethyl)-1H-pyrazole instead of 1-methyl-4-(4,4,5,5-tetramethyl-1,3,2-dioxaborolan-2-yl)-1H-pyrazole. MS (ESI): mass calcd. for C$_{23}$H$_{21}$F$_3$N$_6$O, 454.2; m/z found, 455.1 [M+H]$^+$. $^1$H NMR (600 MHz, CDCl$_3$) δ 8.98 (dd, J=4.2, 1.7 Hz, 1H), 8.25-8.12 (m, 2H), 7.93 (s, 1H), 7.75 (d, J=8.6 Hz, 1H), 7.46 (dd, J=8.3, 4.2 Hz, 1H), 6.73 (s, 1H), 5.89 (br s, 0.42H), 4.95 (br s, 0.66H), 4.12-3.78 (m, 7H), 3.45-3.10 (m, 1H), 3.05-2.53 (m, 2H), 1.58 (br s, 3H).

Example 64: (S)-(2,7-Dimethyl-3-(1-(trifluoromethyl)-1H-pyrazol-4-yl)-2,4,5,7-tetrahydro-6H-pyrazolo[3,4-c]pyridin-6-yl)(quinolin-6-yl)methanone

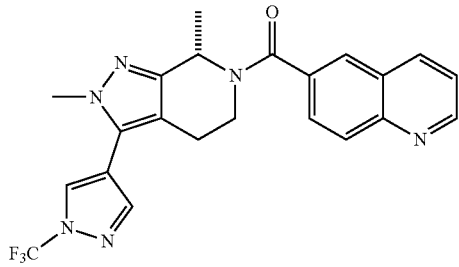 [SMILES: C[C@H]1c2nn(C)c(-c3cnn(C(F)(F)F)c3)c2CCN1C(=O)c1ccc2ncccc2c1]

The title compound was prepared in a manner analogous to Example 62, using 4-(4,4,5,5-tetramethyl-1,3,2-dioxaborolan-2-yl)-1-(trifluoromethyl)-1H-pyrazole instead of 1-methyl-4-(4,4,5,5-tetramethyl-1,3,2-dioxaborolan-2-yl)-1H-pyrazole. MS (ESI): mass calcd. for C$_{22}$H$_{19}$F$_3$N$_6$O, 440.2; m/z found, 441.2 [M+H]$^+$. $^1$H NMR (CDCl$_3$, 500 MHz): δ 9.00 (d, J=4.0 Hz, 1H), 8.21 (d, J=8.1 Hz, 1H), 8.17 (d, 1H), 7.93 (d, J=7.2 Hz, 2H), 7.90 (s, 1H), 7.76 (d, J=8.6 Hz, 1H), 7.49 (dd, J=8.2, 4.1 Hz, 1H), 6.01-5.79 (m, 1H), 5.05-4.85 (m, 1H), 3.97-3.73 (m, 3H), 3.37-3.17 (m, 1H), 3.01-2.80 (m, 1H), 2.58-2.38 (m, 1H), 1.64 (s, 3H).

Example 65: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(quinolin-6-yl)methanone

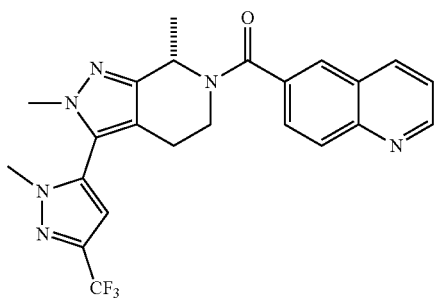 [SMILES: C[C@H]1c2nn(C)c(-c3cc(C(F)(F)F)nn3C)c2CCN1C(=O)c1ccc2ncccc2c1]

The title compound was prepared in a manner analogous to Example 62, using 1-methyl-5-(4,4,5,5-tetramethyl-1,3,2-dioxaborolan-2-yl)-3-(trifluoromethyl)-1H-pyrazole instead of 1-methyl-4-(4,4,5,5-tetramethyl-1,3,2-dioxaborolan-2-yl)-1H-pyrazole. MS (ESI): mass calcd. for C$_{23}$H$_{21}$F$_3$N$_6$O, 454.2; m/z found, 455.2 [M+H]$^+$. $^1$H NMR (DMSO-d$_6$, 500 MHz): δ 8.91 (d, J=3.3 Hz, 1H), 8.36 (d, J=8.1 Hz, 1H), 8.07 (d, J=8.6 Hz, 1H), 8.01 (s, 1H), 7.74 (d, J=8.5 Hz, 1H), 7.52 (dd, J=8.2, 4.2 Hz, 1H), 6.79 (s, 1H), 5.73-5.58 (m, 1H), 4.90-4.62 (m, 1H), 3.85 (s, 3H), 3.73 (s, 3H), 3.36-3.24 (m, 1H), 2.81-2.72 (m, 1H), 2.40-2.27 (m, 1H), 1.56 (d, J=5.9 Hz, 3H).

Example 66: (S)-(3-(1-Ethyl-1H-pyrazol-3-yl)-2,7-dimethyl-2,4,5,7-tetrahydro-6H-pyrazolo[3,4-c]pyridin-6-yl)(quinolin-6-yl)methanone

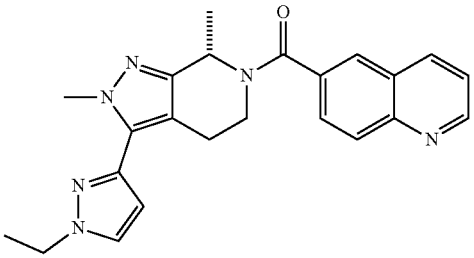 [SMILES: CCn1ccc(-c2c3c(nn2C)[C@H](C)N(C(=O)c2ccc4ncccc4c2)CC3)n1]

The title compound was prepared in a manner analogous to Example 62, using 1-ethyl-3-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole. MS (ESI): mass calcd. for C$_{23}$H$_{24}$N$_6$O, 400.2; m/z found, 401.2 [M+H]$^+$. $^1$H NMR (DMSO-d$_6$, 500 MHz): δ 8.91 (d, J=3.8 Hz, 1H), 8.36 (d, J=8.1 Hz, 1H), 8.07 (d, J=8.6 Hz, 1H), 8.00 (s, 1H), 7.76-7.66 (m, 2H), 7.52 (dd, J=8.2, 4.1 Hz, 1H), 6.38 (s, 1H), 5.68-5.49 (m, 1H), 4.22 (q, J=7.3, 7.3, 7.2 Hz, 2H), 4.09-3.73 (m, 4H), 3.38-3.16 (m, 1H), 2.90-2.81 (m, 1H), 2.68-2.54 (m, 1H), 1.53 (d, J=5.8 Hz, 3H), 1.49 (t, J=7.3, 7.3 Hz, 3H).

Example 67: (S)-(3-(1-(Difluoromethyl)-1H-pyrazol-3-yl)-2,7-dimethyl-2,4,5,7-tetrahydro-6H-pyrazolo[3,4-c]pyridin-6-yl)(quinolin-6-yl)methanone

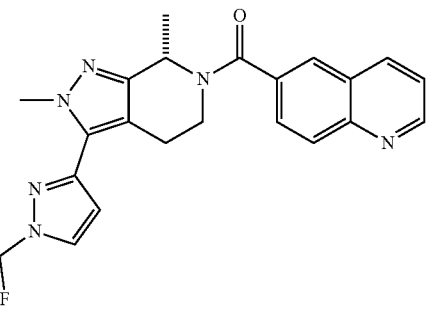

The title compound was prepared in a manner analogous to Example 62, using 1-(difluoromethyl)-3-(tetramethyl-1,3,2-dioxaborolan-2-yl)-1 h-pyrazole instead of 1-methyl-4-(4,4,5,5-tetramethyl-1,3,2-dioxaborolan-2-yl)-1H-pyrazole. MS (ESI): mass calcd. for C$_{22}$H$_{20}$F$_2$N$_6$O, 422.2; m/z found, 423.2 [M+H]$^+$. $^1$H NMR (400 MHz, CDCl$_3$) δ 8.98-8.92 (m, 1H), 8.20-8.10 (m, 2H), 7.92-7.84 (m, 2H), 7.76-7.69 (m, 1H), 7.48-7.42 (m, 1H), 7.23 (t, J=60.6, 60.6 Hz, 1H), 6.58 (s, 1H), 5.90-4.88 (m, 1H), 4.14-3.98 (m, 3H), 3.98-3.67 (m, 1H), 3.41-3.11 (m, 1H), 3.06-2.79 (m, 1H), 2.77-2.58 (m, 1H), 1.63-1.42 (m, 3H).

Example 68: (S)-(3-(1-Cyclopropyl-1H-pyrazol-5-yl)-2,7-dimethyl-2,4,5,7-tetrahydro-6H-pyrazolo[3,4-c]pyridin-6-yl)(quinolin-6-yl)methanone

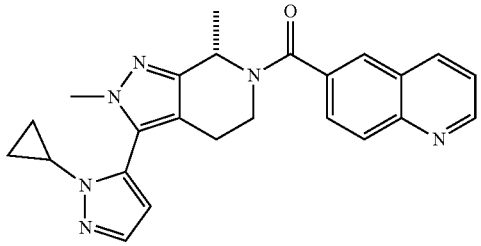 [SMILES: C[C@H]1c2nn(C)c(-c3ccnn3C3CC3)c2CCN1C(=O)c1ccc2ncccc2c1]

The title compound was prepared in a manner analogous to Example 62, using 1-cyclopropyl-5-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole. MS (ESI): mass calcd. for $C_{24}H_{24}N_6O$, 412.2; m/z found, 413.2 [M+H]$^+$. $^1$H NMR (500 MHz, MeOD) δ 8.96-8.92 (m, 1H), 8.48 (d, J=8.3 Hz, 1H), 8.15 (d, J=8.7 Hz, 1H), 8.09 (s, 1H), 7.87-7.79 (m, 1H), 7.66-7.60 (m, 1H), 7.57 (s, 1H), 6.47 (d, J=2.0 Hz, 1H), 5.91-5.73 (m, 1H), 3.97-3.78 (m, 1H), 3.78-3.59 (m, 3H), 3.55-3.49 (m, 1H), 3.49-3.36 (m, 1H), 2.84-2.71 (m, 1H), 2.59-2.37 (m, 1H), 1.70-1.55 (m, 3H), 1.09-1.01 (m, 1H), 1.01-0.91 (m, 3H).

Example 69: (S)-(3-(1-(Difluoromethyl)-1H-pyrazol-4-yl)-2,7-dimethyl-2,4,5,7-tetrahydro-6H-pyrazolo[3,4-c]pyridin-6-yl)(quinolin-6-yl)methanone

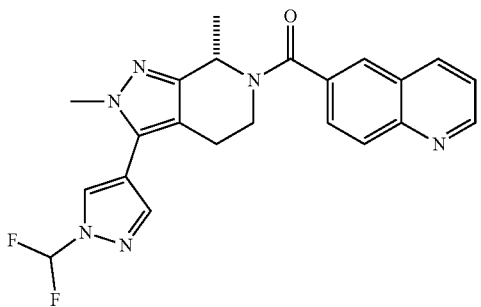 [SMILES: C[C@H]1c2nn(C)c(-c3cnn(C(F)F)c3)c2CCN1C(=O)c1ccc2ncccc2c1]

The title compound was prepared in a manner analogous to Example 62, using 1-(difluoromethyl)-4-(4,4,5,5-tetramethyl-1,3,2-dioxaborolan-2-yl)-1 h-pyrazole instead of 1-methyl-4-(4,4,5,5-tetramethyl-1,3,2-dioxaborolan-2-yl)-1H-pyrazole. MS (ESI): mass calcd. for $C_{22}H_{20}F_2N_6O$, 422.2; m/z found, 423.2 [M+H]$^+$. $^1$H NMR (400 MHz, DMSO-d$_6$) δ 9.01-8.95 (m, 1H), 8.63 (s, 1H), 8.51-8.44 (m, 1H), 8.14 (s, 1H), 8.13-8.08 (m, 2H), 8.05-7.74 (m, 2H), 7.65-7.57 (m, 1H), 5.68-4.66 (m, 1H), 3.98-3.79 (m, 3H), 3.79-3.61 (m, 1H), 3.32-3.04 (m, 1H), 2.92-2.80 (m, 1H), 2.49-2.36 (m, 1H), 1.57-1.41 (m, 3H).

Example 70: (S)-(2,7-Dimethyl-3-(1-(pyridin-2-yl)-1H-pyrazol-4-yl)-2,4,5,7-tetrahydro-6H-pyrazolo[3,4-c]pyridin-6-yl)(quinolin-6-yl)methanone

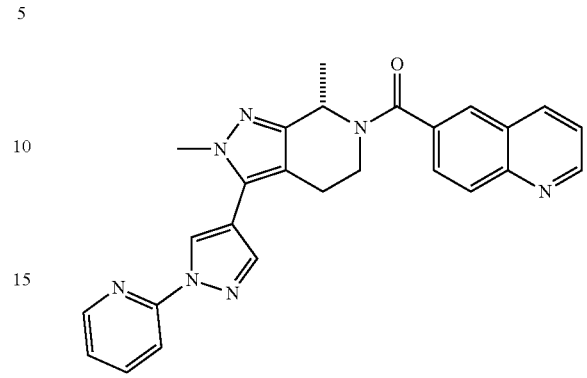

The title compound was prepared in a manner analogous Example 62, using 2-(4-(4,4,5,5-tetramethyl-1,3,2-dioxaborolan-2-yl)-1H-pyrazol-1-yl)pyridine instead of 1-methyl-4-(4,4,5,5-tetramethyl-1,3,2-dioxaborolan-2-yl)-1H-pyrazole. MS (ESI): mass calcd. for $C_{26}H_{23}N_7O$, 449.2; m/z found, 450.2 [M+H]$^+$. $^1$H NMR (500 MHz, CD$_3$OD) δ 8.97-8.93 (m, 1H), 8.87 (s, 1H), 8.52-8.46 (m, 2H), 8.17 (d, J=8.6 Hz, 1H), 8.13-8.07 (m, 1H), 8.04 (s, 1H), 8.04-7.96 (m, 2H), 7.90-7.82 (m, 1H), 7.64 (dd, 1H), 7.36 (t, 1H), 5.91-5.68 (m, 1H), 3.99 (s, 3H), 3.89-3.83 (m, 1H), 3.53-3.38 (m, 1H), 3.00-2.89 (m, 1H), 2.66-2.53 (m, 1H), 1.67-1.56 (m, 3H).

Example 71: (S)-(3-(1-(Cyclopropylmethyl)-1H-pyrazol-5-yl)-2,7-dimethyl-2,4,5,7-tetrahydro-6H-pyrazolo[3,4-c]pyridin-6-yl)(quinolin-6-yl)methanone

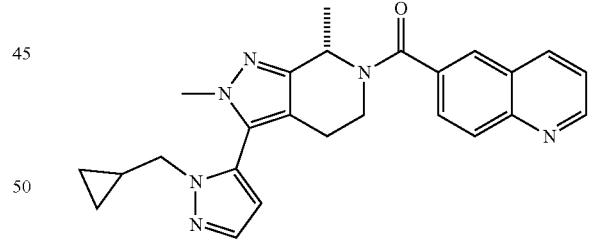

The title compound was prepared in a manner analogous to Example 62, using 1-(cyclopropylmethyl)-5-(tetramethyl-1,3,2-dioxaborolan-2-yl)-1 h-pyrazole instead of 1-methyl-4-(4,4,5,5-tetramethyl-1,3,2-dioxaborolan-2-yl)-1H-pyrazole. MS (ESI): mass calcd. for $C_{25}H_{26}N_6O$, 426.2; m/z found, 427.2 [M+H]$^+$. $^1$H NMR (500 MHz, CD$_3$OD) δ 8.97-8.92 (m, 1H), 8.48 (d, J=8.3 Hz, 1H), 8.16 (d, J=8.7 Hz, 1H), 8.09 (s, 1H), 7.91-7.80 (m, 1H), 7.67-7.60 (m, 2H), 6.50 (s, 1H), 6.01-5.63 (m, 1H), 4.00-3.92 (m, 1H), 3.92-3.77 (m, 2H), 3.77-3.57 (m, 3H), 3.50-3.34 (m, 1H), 2.82-2.64 (m, 1H), 2.56-2.27 (m, 1H), 1.70-1.54 (m, 3H), 1.11-1.03 (m, 1H), 0.56-0.45 (m, 2H), 0.29-0.10 (m, 1H), 0.10-0.02 (m, 1H).

Example 72: ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(2-fluoro-4-methylphenyl)methanone

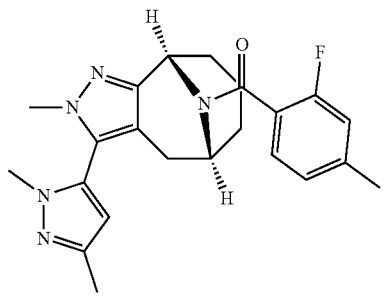

The title compound was prepared in a manner analogous to Example 1, using (5R,9S)-3-(1,3-dimethyl-1H-pyrazol-5-yl)-2-methyl-4,5,6,7,8,9-hexahydro-2H-5,9-epiminocycloocta[c]pyrazole (Intermediate 23) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-fluoro-4-methylbenzoic acid instead of 2-methylquinoline-5-carboxylic acid. MS (ESI): mass calcd. for $C_{23}H_{26}FN_5O$, 407.2; m/z found, 408.1[M+H]$^+$. $^1$H NMR (400 MHz, DMSO-d$_6$) δ 7.36-6.99 (m, 3H), 6.36-5.62 (m, 2H), 5.11-4.50 (m, 1H), 4.13-3.81 (m, 1H), 3.76-3.48 (m, 6H), 2.94-2.58 (m, 1H), 2.35 (d, J=9.6 Hz, 3H), 2.20 (d, J=5.8 Hz, 3H), 1.90-1.28 (m, 6H).

Example 73: ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(3-methoxy-2-methylphenyl)methanone

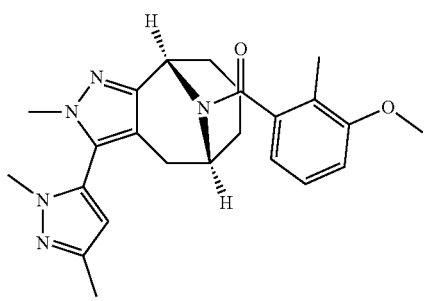

The title compound was prepared in a manner analogous to Example 1, using (5R,9S)-3-(1,3-dimethyl-1H-pyrazol-5-yl)-2-methyl-4,5,6,7,8,9-hexahydro-2H-5, 9-epiminocycloocta[c]pyrazole (Intermediate 23) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-2-methylbenzoic acid instead of 2-methylquinoline-5-carboxylic acid. MS (ESI): mass calcd. for $C_{24}H_{29}N_5O_2$, 419.2; m/z found, 420.1[M+H]$^+$. $^1$H NMR (400 MHz, DMSO-d$_6$) δ 7.35-7.15 (m, 1H), 7.07-6.40 (m, 2H), 6.33-6.19 (m, 1H), 5.80 (s, 1H), 4.54-4.39 (m, 1H), 3.86-3.77 (m, 3H), 3.74-3.51 (m, 6H), 2.98-2.83 (m, 1H), 2.72-2.53 (m, 1H), 2.44-2.26 (m, 1H), 2.23-2.10 (m, 5H), 1.80-1.34 (m, 6H).

Example 74: (3-Methoxy-2-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone

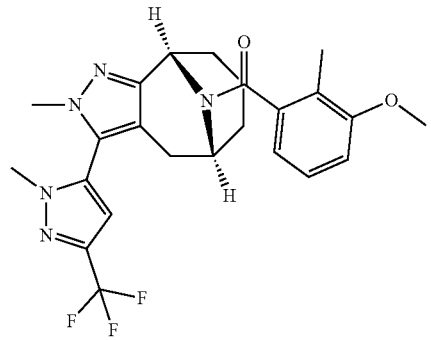

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-2-methylbenzoic acid instead of 2-methylquinoline-5-carboxylic acid. MS (ESI): mass calcd. for $C_{24}H_{26}F_3N_5O_2$, 473.2; m/z found, 474.2 [M+H]$^+$. $^1$H NMR (400 MHz, DMSO-d$_6$) δ 7.32-7.14 (m, 1H), 7.14-7.05 (m, 1H), 7.06-6.94 (m, 1H), 6.90-6.41 (m, 1H), 5.96-5.74 (m, 1H), 5.22-4.92 (m, 1H), 4.60-4.36 (m, 1H), 3.89-3.78 (m, 4H), 3.76-3.67 (m, 3H), 3.63 (d, J=7.3 Hz, 1H), 3.08-2.79 (m, 1H), 2.48-2.26 (m, 1H), 2.23-2.06 (m, 2H), 1.95-1.31 (m, 7H).

Example 75: Chroman-7-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone

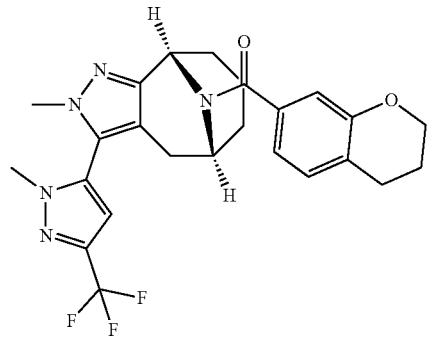 [SMILES: Cn1nc(C(F)(F)F)cc1-c1c2c(nn1C)[C@H]1CCC[C@@H](C2)N1C(=O)c1ccc2c(c1)OCCC2]

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and chromane-7-carboxylic acid instead of 2-methylquinoline-5-carboxylic acid. MS (ESI): mass calcd. for $C_{25}H_{26}F_3N_5O_2$, 485.2; m/z found, 486.1 [M+H]$^+$. $^1$H NMR (400 MHz, DMSO-d$_6$) δ 7.19-7.03 (m, 2H), 6.85-6.61 (m, 2H), 4.91 (d, J=34.2 Hz, 1H), 4.22-3.99 (m, 3H), 3.79 (s, 3H), 3.66 (d, J=23.5 Hz, 3H), 2.96-2.69 (m, 3H), 2.39 (dd, J=33.7, 16.4 Hz, 1H), 2.00-1.88 (m, 2H), 1.87-1.30 (m, 6H).

Example 76: ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(m-tolyl)methanone

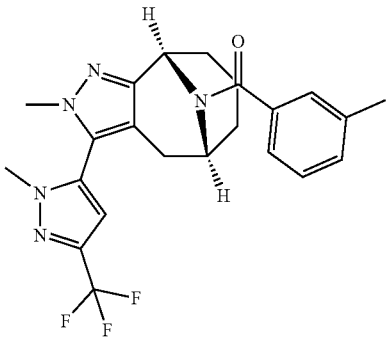

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methylbenzoic acid instead of 2-methylquinoline-5-carboxylic acid. MS (ESI): mass calcd. for C$_{23}$H$_{24}$F$_3$N$_5$O, 443.2; m/z found, 444.2 [M+H]$^+$. $^1$H NMR (400 MHz, DMSO-d$_6$) δ 7.43-7.02 (m, 5H), 5.80-5.56 (m, 1H), 5.04-4.73 (m, 1H), 3.80 (s, 3H), 3.72-3.49 (m, 3H), 3.00-2.69 (m, 1H), 2.39-2.30 (m, 4H), 1.98-1.30 (m, 6H).

Example 77: (3-Methoxy-5-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone

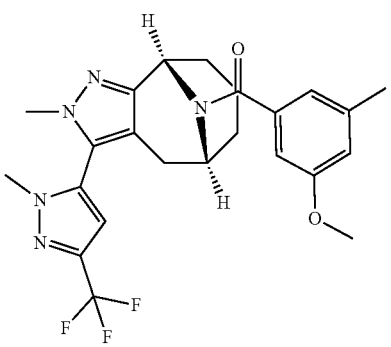

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-5-methylbenzoic acid instead of 2-methylquinoline-5-carboxylic acid. MS (ESI): mass calcd. for C$_{24}$H$_{26}$F$_3$N$_5$O$_2$, 473.2; m/z found, 474.3 [M+H]$^+$. $^1$H NMR (400 MHz, DMSO-d$_6$) δ 7.16-7.06 (m, 1H), 6.94-6.63 (m, 3H), 5.78-5.62 (m, 1H), 5.08-4.78 (m, 1H), 3.83-3.72 (m, 6H), 3.72-3.56 (m, 3H), 2.99-2.67 (m, 1H), 2.39-2.25 (m, 4H), 1.96-1.34 (m, 6H).

Example 78: ((5R,9S)-3-(1-Ethyl-3-(trifluoromethyl)-1H-pyrazol-5-yl)-2-methyl-4,5,6,7,8,9-hexahydro-2H-5,9-epiminocycloocta[c]pyrazol-10-yl)(m-tolyl)methanone

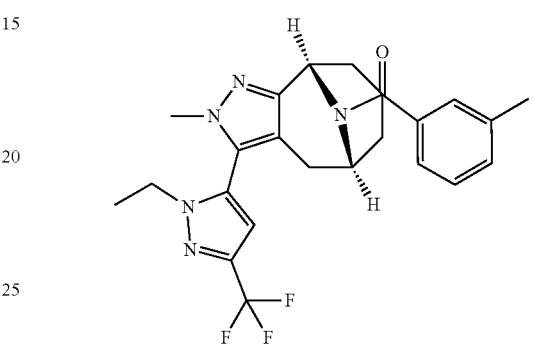

The title compound was prepared in a manner analogous to Example 1, using (5R,9S)-3-(1-ethyl-3-(trifluoromethyl)-1H-pyrazol-5-yl)-2-methyl-4,5,6,7,8,9-hexahydro-2H-5,9-epiminocycloocta[c]pyrazole (Intermediate 22) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methylbenzoic acid instead of 2-methylquinoline-5-carboxylic acid. MS (ESI): mass calcd. for C$_{24}$H$_{26}$F$_3$N$_5$O, 457.2; m/z found, 458.1 [M+H]$^+$. $^1$H NMR (400 MHz, DMSO-d$_6$) δ 7.45-6.98 (m, 5H), 5.83-5.59 (m, 1H), 5.08-4.76 (m, 1H), 4.07-3.99 (m, 2H), 3.72-3.56 (m, 3H), 2.97-2.67 (m, 1H), 2.45-2.26 (m, 4H), 2.02-1.38 (m, 6H), 1.35-1.26 (m, 3H).

Example 79: (3-Methoxy-2-methylphenyl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone

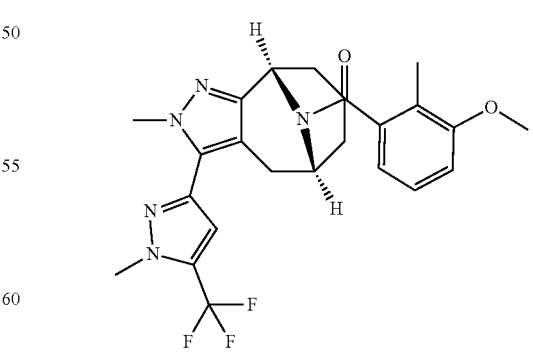

The title compound was prepared in a manner analogous to Example 1, using (5R,9S)-2-methyl-3-(1-methyl-5-(trifluoromethyl)-1H-pyrazol-3-yl)-4,5,6,7,8,9-hexahydro-2H-5, 9-epiminocycloocta[c]pyrazole (Intermediate 21) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-2-methylbenzoic acid instead of 2-methylquinoline-5-carboxylic acid. MS (ESI): mass calcd. for $C_{24}H_{26}F_3N_5O_2$, 473.2; m/z found, 474.1 [M+H]$^+$. $^1$H NMR (400 MHz, DMSO-d$_6$) δ 7.33-7.09 (m, 2H), 7.04-6.33 (m, 2H), 5.84-5.58 (m, 1H), 5.26-5.00 (m, 1H), 4.53-4.37 (m, 1H), 4.10-3.99 (m, 4H), 3.95-3.74 (m, 4H), 3.23-3.07 (m, 1H), 2.97-2.79 (m, 1H), 2.77-2.52 (m, 1H), 2.21-2.08 (m, 1H), 1.90-1.29 (m, 7H).

Example 80: ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(quinolin-6-yl)methanone

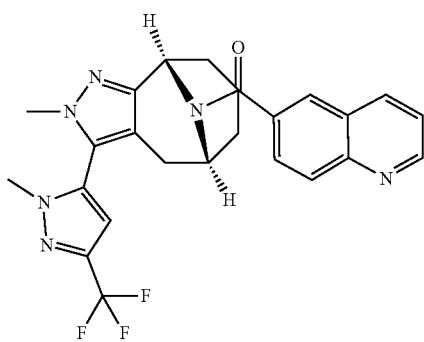

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and quinoline-6-carboxylic acid instead of 2-methylquinoline-5-carboxylic acid. MS (ESI): mass calcd. for $C_{25}H_{23}F_3N_6O$, 480.2; m/z found, 481.2 [M+H]$^+$. $^1$H NMR (500 MHz, DMSO-d$_6$) δ 9.04-8.86 (m, 1H), 8.48 (t, J=8.0 Hz, 1H), 8.19-8.01 (m, 2H), 7.84-7.67 (m, 1H), 7.70-7.48 (m, 1H), 7.20-7.05 (m, 1H), 5.91-5.59 (m, 1H), 4.21-4.00 (m, 1H), 3.82 (s, 3H), 3.67 (d, J=51.1 Hz, 3H), 3.02-2.80 (m, 1H), 2.37 (d, J=16.4 Hz, 1H), 2.10-1.33 (m, 6H).

Example 81: (5-Fluoro-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazol-10-yl)methanone

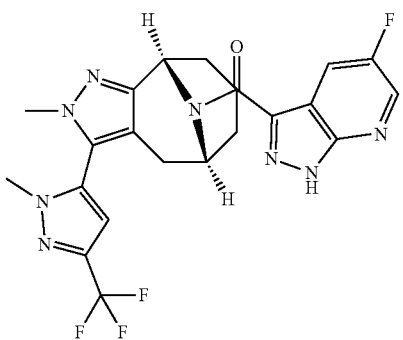

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 5-fluoro-1H-pyrazolo[3,4-b]pyridine-3-carboxylic acid instead of 2-methylquinoline-5-carboxylic acid. MS (ESI): mass calcd. for $C_{22}H_{20}F_4N_8O$, 488.2; m/z found, 489.2 [M+H]$^+$. $^1$H NMR (400 MHz, DMSO-d$_6$) δ 8.60 (s, 1H), 8.25-8.05 (m, 1H), 7.10 (s, 1H), 6.66-5.83 (m, 1H), 5.72-5.08 (m, 1H), 3.84-3.76 (m, 3H), 3.72-3.59 (m, 3H), 3.09-2.79 (m, 2H), 2.12-1.41 (m, 7H).

Example 82: (2-Methyl-1,6-naphthyridin-5-yl)((5R, 9S)-2-methyl-3-(1-methyl-3-(trifluoromethyl)-1H-pyrazol-5-yl)-4,5,6,7,8,9-hexahydro-2H-5, 9-epiminocycloocta[c]pyrazol-10-yl)methanone

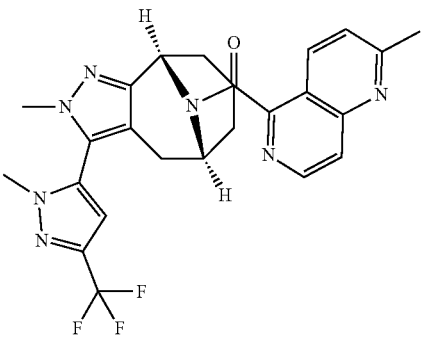

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and potassium 2-methyl-1,6-naphthyridine-5-carboxylate (Intermediate 7) instead of 2-methylquinoline-5-carboxylic acid. MS (ESI): mass calcd. for $C_{25}H_{24}F_3N_7O$, 495.2; m/z found, 496.2 [M+H]$^+$. $^1$H NMR (400 MHz, DMSO-d$_6$) δ 8.76-8.61 (m, 1H), 8.18 (dd, J=18.9, 8.6 Hz, 1H), 7.90 (dd, J=12.6, 5.9 Hz, 1H), 7.62-7.52 (m, 1H), 7.13 (d, J=11.4 Hz, 1H), 6.04-5.83 (m, 1H), 5.30-5.15 (m, 0.5H), 4.52-4.40 (m, 0.5H), 3.80 (d, J=15.9 Hz, 3H), 3.72 (d, J=1.2 Hz, 3H), 3.63-3.52 (m, 1H), 2.78-2.63 (m, 4H), 2.06-1.39 (m, 6H).

Example 83: (5-Fluoroquinolin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone

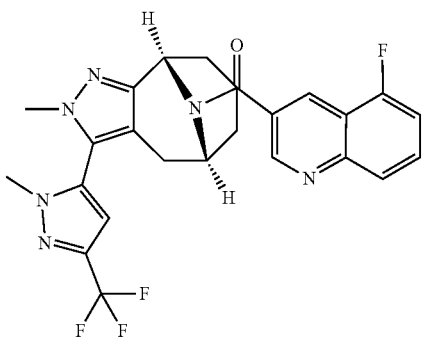

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 5-fluoroquinoline-3-carboxylic acid instead of 2-methylquinoline-5-carboxylic acid. MS (ESI): mass calcd. for $C_{25}H_{22}F_4N_6O$, 498.2; m/z found, 499.2 [M+H]$^+$. $^1$H NMR (400 MHz, DMSO-d$_6$) δ 9.06-8.87 (m, 1H), 8.57-8.34 (m, 1H), 8.00-7.80 (m, 2H), 7.55 (q, J=8.6 Hz, 1H), 7.13 (d, J=8.1 Hz, 1H), 5.86-5.73 (m, 1H), 4.31-4.08 (m, 1H), 3.85-3.76 (m, 3H), 3.74-3.59 (m, 3H), 3.05-2.81 (m, 1H), 2.36 (d, J=16.4 Hz, 1H), 2.10-1.35 (m, 6H).

Example 84: Benzo[d]isoxazol-3-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone

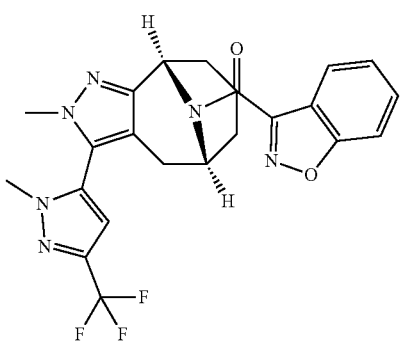

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and benzo[d]isoxazole-3-carboxylic acid instead of 2-methylquinoline-5-carboxylic acid. MS (ESI): mass calcd. for $C_{23}H_{21}F_3N_6O_2$, 470.2; m/z found, 471.2 [M+H]$^+$. $^1$H NMR (500 MHz, DMSO-d$_6$) δ 7.99-7.70 (m, 2H), 7.61-7.35 (m, 1H), 7.27-7.00 (m, 1H), 5.97-5.41 (m, 1H), 5.24-4.58 (m, 1H), 3.88-3.61 (m, 7H), 2.95 (d, J=64.1 Hz, 2H), 2.11-1.09 (m, 6H).

Example 85: (1-Methyl-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone

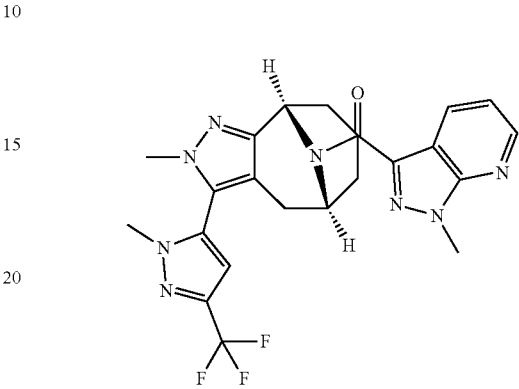

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-pyrazolo[3,4-b]pyridine-3-carboxylic acid instead of 2-methylquinoline-5-carboxylic acid. MS (ESI): mass calcd. for $C_{23}H_{23}F_3N_8O$, 484.2; m/z found, 485.2 [M+H]$^+$. $^1$H NMR (400 MHz, DMSO-d$_6$) δ 8.73-8.57 (m, 1H), 8.48-8.29 (m, 1H), 7.35 (dd, J=7.8, 4.8 Hz, 1H), 7.11 (s, 1H), 6.53-5.63 (m, 1H), 5.52-5.04 (m, 1H), 4.15 (dd, J=23.0, 1.9 Hz, 3H), 3.80 (s, 3H), 3.68 (dd, J=19.9, 1.9 Hz, 3H), 3.50-3.42 (m, 1H), 3.05-2.88 (m, 1H), 2.13-1.42 (m, 6H).

Example 86: (5-Fluoro-1-methyl-1H-indazol-3-yl)((5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazol-10-yl)methanone

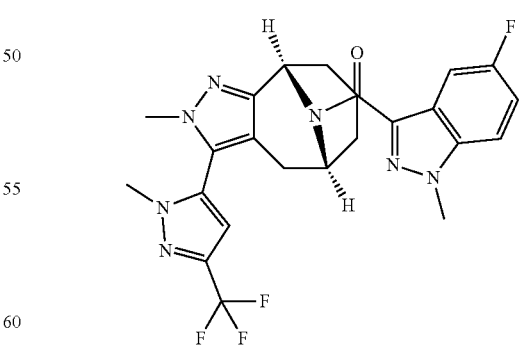

The title compound was prepared in a manner analogous to Example 1, using (5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazole (Intermediate 20) instead of (S)-2,7-dimethyl-3-(1-methyl-3-(trifluoromethyl)-1H- pyrazol-5-yl)-4,5,6,7-tetrahydro-2H-pyrazolo[3,4-c]pyridine and 5-fluoro-1-methyl-1H-indazole-3-carboxylic acid instead of 2-methylquinoline-5-carboxylic acid. MS (ESI): mass calcd. for $C_{24}H_{23}F_4N_7O$, 501.2; m/z found, 502.2 [M+H]$^+$. $^1$H NMR (400 MHz, DMSO-d$_6$) δ 7.90-7.75 (m, 1H), 7.68 (dd, J=9.1, 2.5 Hz, 1H), 7.47-7.31 (m, 1H), 7.19-6.99 (m, 1H), 6.46-5.80 (m, 1H), 5.56-5.07 (m, 1H), 4.15 (dd, J=23.4, 2.0 Hz, 3H), 3.85-3.75 (m, 3H), 3.67 (dd, J=21.6, 2.0 Hz, 3H), 3.06-2.84 (m, 1H), 2.06-1.39 (m, 7H).

Example 87: ((5R,9S)-2-Methyl-3-(1-methyl-5-(trifluoromethyl)-1H-pyrazol-3-yl)-4,5,6,7,8,9-hexahydro-2H-5,9-epiminocycloocta[c]pyrazol-10-yl)(quinolin-6-yl)methanone

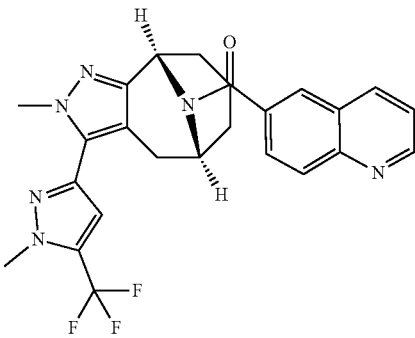

The title compound was prepared in a manner analogous to Example 1, using (5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazole (Intermediate 21) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and quinoline-6-carboxylic acid instead of 2-methylquinoline-5-carboxylic acid. MS (ESI): mass calcd. for $C_{25}H_{23}F_3N_6O$, 480.2; m/z found, 481.2 [M+H]$^+$. $^1$H NMR (400 MHz, DMSO-d$_6$) δ 9.05-8.91 (m, 1H), 8.48 (d, J=8.3 Hz, 1H), 8.16-8.01 (m, 2H), 7.82-7.53 (m, 2H), 7.25 (d, J=13.9 Hz, 1H), 5.76 (s, 1H), 5.13-4.74 (m, 1H), 4.09-3.89 (m, 6H), 3.20-2.99 (m, 1H), 2.68 (dd, J=49.5, 16.6 Hz, 1H), 2.04-1.35 (m, 6H).

Example 88: (6-Fluoro-2-methylquinolin-4-yl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone

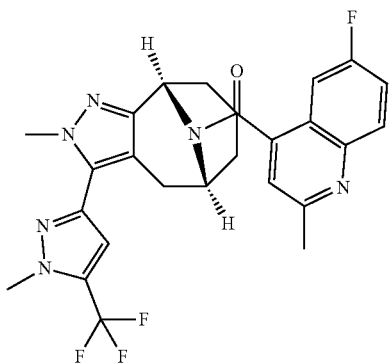

The title compound was prepared in a manner analogous to Example 1, using (5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazole (Intermediate 21) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 6-fluoro-2-methylquinoline-4-carboxylic acid instead of 2-methylquinoline-5-carboxylic acid. MS (ESI): mass calcd. for $C_{26}H_{24}F_4N_6O$, 512.2; m/z found, 513.2 [M+H]$^+$. $^1$H NMR (400 MHz, DMSO-d$_6$) δ 8.07 (d, J=5.7 Hz, 1H), 7.83-7.47 (m, 2H), 7.41-6.77 (m, 2H), 5.96-5.75 (m, 1H), 4.46-4.33 (m, 1H), 4.10-3.74 (m, 7H), 3.14-2.96 (m, 1H), 2.73-2.61 (m, 3H), 2.09-1.35 (m, 6H).

Example 89: (3-Methoxy-2-methylphenyl)((5R,8S)-2-methyl-3-(1-methyl-3-(trifluoromethyl)-1H-pyrazol-5-yl)-2,4,5,6,7,8-hexahydro-5,8-epiminocyclohepta[c]pyrazol-9-yl)methanone

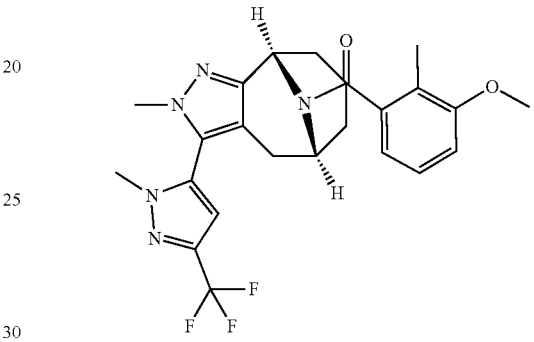

The title compound was prepared in a manner analogous to Example 1, using (5R,8S)-2-methyl-3-(1-methyl-3-(trifluoromethyl)-1H-pyrazol-5-yl)-2,4,5,6,7,8-hexahydro-5,8-epiminocyclohepta[c]pyrazole (Intermediate 24) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 3-methoxy-2-methylbenzoic acid instead of 2-methylquinoline-5-carboxylic acid. MS (ESI): mass calcd. for $C_{23}H_{24}F_3N_5O_2$, 459.2; m/z found, 460.1 [M+H]$^+$. $^1$H NMR (500 MHz, DMSO-d$_6$) δ 7.37-7.13 (m, 1H), 7.17-6.92 (m, 2H), 6.92-6.63 (m, 1H), 5.59-5.45 (m, 1H), 5.01-4.86 (m, 1H), 4.47-4.28 (m, 1H), 3.99-3.85 (m, 1H), 3.85-3.56 (m, 8H), 3.29-2.94 (m, 1H), 2.67-2.53 (m, 1H), 2.36-1.57 (m, 6H).

Examples 96-109, 111, 114-116, 119, 124-131, 136-138 are prophetic compounds which may be made according to methods as described:

Example 90: (S)-(2,7-dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-methylquinolin-6-yl)methanone

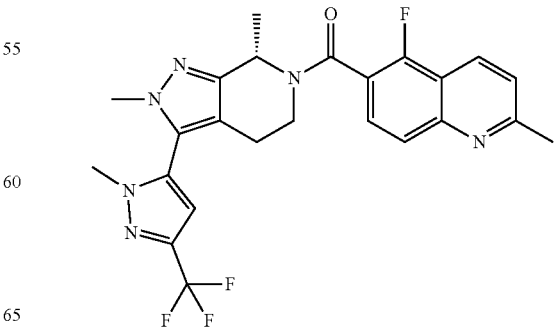

The title compound was prepared in a manner analogous to Example 1, using 5-fluoro-2-methylquinoline-6-carboxylic acid (Intermediate 27) instead of 2-methylquinoline-5-carboxylic acid. MS (ESI): mass calcd. for $C_{24}H_{22}F_4N_6O$, 486.2; m/z found, 487.3 [M+H]$^+$. $^1$H NMR (400 MHz, CDCl$_3$) δ 8.36 (d, J=8.5 Hz, 1H), 7.95-7.86 (m, 1H), 7.68-7.57 (m, 1H), 7.42 (d, J=8.5 Hz, 1H), 6.64-6.59 (m, 1H), 6.02-5.94 (m, 0.66H), 5.01 (dd, J=5.0, 13.1 Hz, 0.41H), 4.91 (q, J=6.6 Hz, 0.41H), 3.85-3.81 (m, 3H), 3.77 (s, 2H), 3.75-3.72 (m, 0.54H), 3.70 (s, 1H), 3.47-3.33 (m, 0.70H), 3.21-3.10 (m, 0.42H), 2.85-2.82 (m, 0.24H), 2.81-2.79 (m, 3H), 2.78-2.75 (m, 0.43H), 2.46 (dd, J=3.1, 15.7 Hz, 0.49H), 2.35-2.26 (m, 0.73H), 1.67 (d, J=6.5 Hz, 2H), 1.51 (d, J=6.3 Hz, 1H).

Example 91: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-6-yl)methanone

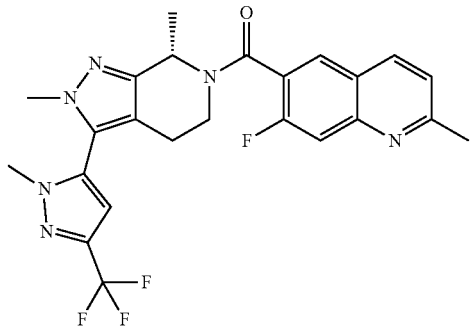

The title compound was prepared in a manner analogous to Example 1, using 7-fluoro-2-methylquinoline-6-carboxylic acid (Intermediate 28) instead of 2-methylquinoline-5-carboxylic acid. MS (ESI): mass calcd. for $C_{24}H_{22}F_4N_6O$, 486.2; m/z found, 487.2 [M+H]$^+$. $^1$H NMR (400 MHz, CDCl$_3$) δ 8.10-8.02 (m, 1H), 7.90-7.78 (m, 1H), 7.72 (d, J=10.7 Hz, 1H), 7.32 (d, J=8.5 Hz, 1H), 6.64-6.58 (m, 1H), 6.02-5.91 (m, 0.64H), 5.00 (dd, J=5.1, 13.1 Hz, 0.35H), 4.87 (q, J=6.8 Hz, 0.35H), 3.85-3.80 (m, 3H), 3.78-3.69 (m, 3H), 3.69-3.65 (m, 0.63H), 3.47-3.31 (m, 0.64H), 3.20-3.09 (m, 0.37H), 2.84-2.78 (m, 1H), 2.78-2.75 (m, 3H), 2.46 (dd, J=2.8, 15.4 Hz, 0.48H), 2.35-2.24 (m, 0.62H), 1.67 (d, J=6.7 Hz, 2H), 1.55-1.44 (m, 1H).

Example 92: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,5-dimethylquinolin-6-yl)methanone

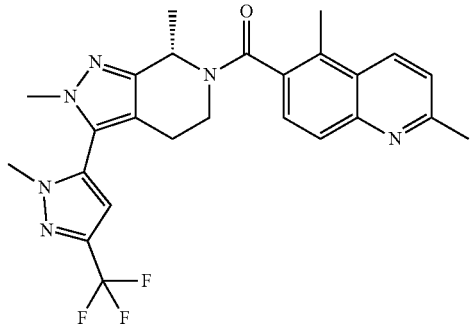

The title compound was prepared in a manner analogous to Example 1, using 2,5-dimethylquinoline-6-carboxylic acid (Intermediate 29) instead of 2-methylquinoline-5-carboxylic acid. MS (ESI): mass calcd. for $C_{25}H_{25}F_3N_6O$, 482.2; m/z found, 483.3 [M+H]$^+$. 1H NMR (400 MHz, CDCl$_3$) δ 8.39-8.13 (m, 1H), 8.02-7.86 (m, 1H), 7.62-7.43 (m, 1H), 7.42-7.33 (m, 1H), 6.67-6.55 (m, 1H), 6.09-5.98 (m, 0.5H), 5.08-5.04 (m, 0.2H), 4.93-4.65 (m, 0.3H), 3.88-3.76 (m, 3H), 3.76-3.67 (m, 3H), 3.59-3.54 (m, 0.2H), 3.33-3.23 (m, 0.5H), 3.14-3.08 (m, 0.3H), 2.86-2.74 (m, 3H), 2.72-2.60 (m, 2H), 2.55-2.48 (m, 0.4H), 2.47-2.36 (m, 1H), 2.32-2.12 (m, 0.6H), 1.70-1.52 (m, 2H), 1.45-1.35 (m, 1H), 1.33-1.19 (m, 2H).

Example 93: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,7-dimethylquinolin-6-yl)methanone

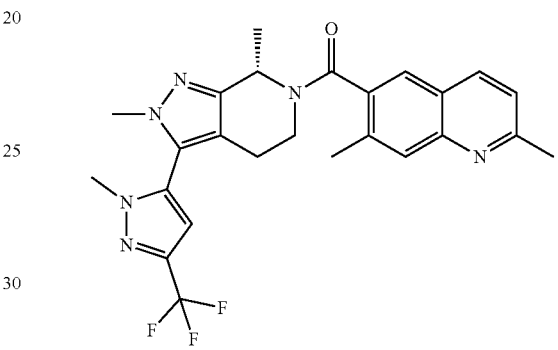

The title compound was prepared in a manner analogous to Example 1, using 2,7-dimethylquinoline-6-carboxylic acid (Intermediate 30) instead of 2-methylquinoline-5-carboxylic acid. MS (ESI): mass calcd. for $C_{25}H_{25}F_3N_6O$, 482.2; m/z found, 483.3 [M+H]$^+$. 1H NMR (400 MHz, CDCl$_3$) δ 8.08-7.95 (m, 1H), 7.95-7.79 (m, 1H), 7.76-7.41 (m, 1H), 7.33-7.27 (m, 1H), 6.61 (d, J=14.9 Hz, 1H), 6.08-5.98 (m, 0.5H), 5.10-4.97 (m, 0.5H), 4.71-4.63 (m, 0.3H), 3.81 (s, 3H), 3.76-3.68 (m, 3H), 3.68-3.48 (m, 0.7H), 3.36-3.04 (m, 1H), 2.78-2.70 (m, 3H), 2.62-2.42 (m, 3H), 2.35-2.19 (m, 1H), 1.68-1.66 (m, 1H), 1.48-1.43 (m, 1H), 1.28-1.20 (m, 2H).

Example 94: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,4-dimethylquinolin-6-yl)methanone. #78625872

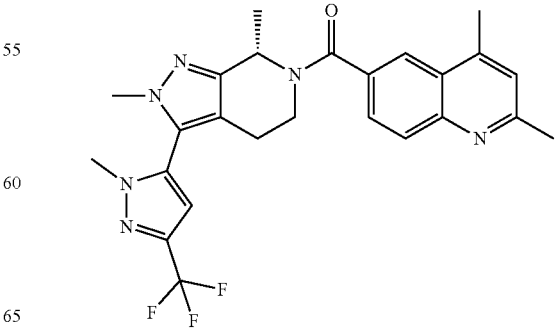

The title compound was prepared in a manner analogous to Example 1, using 2,4-dimethylquinoline-6-carboxylic acid (Intermediate 31) instead of 2-methylquinoline-5-carboxylic acid. MS (ESI): mass calcd. for $C_{25}H_{25}F_3N_6O$, 482.2; m/z found, 483.2 [M+H]$^+$. $^1$H NMR (400 MHz, CDCl$_3$) δ 8.13-8.02 (m, 2H), 7.85-7.57 (m, 1H), 7.21 (s, 1H), 6.61 (s, 1H), 6.15-5.72 (m, 0.5H), 5.26-4.68 (m, 1H), 3.98-3.84 (m, 0.5H), 3.83 (s, 3H), 3.74 (br. s., 3H), 3.47-3.05 (m, 1H), 2.94-2.73 (m, 1H), 2.73 (s, 3H), 2.69 (s, 3H), 2.50-2.25 (m, 1H), 1.86-1.65 (m, 3H).

Example 95: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylquinolin-6-yl)methanone

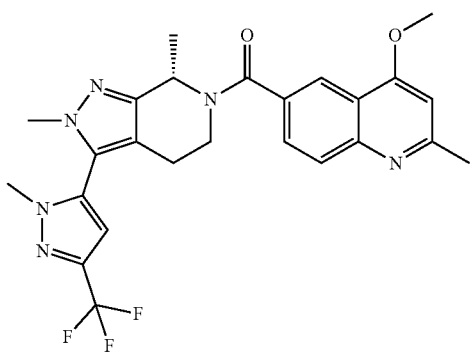

The title compound was prepared in a manner analogous to Example 1, using 4-methoxy-2-methylquinoline-6-carboxylic acid (Intermediate 32) instead of 2-methylquinoline-5-carboxylic acid. MS (ESI): mass calcd. for $C_{25}H_{25}F_3N_6O_2$, 498.2; m/z found, 499.2 [M+H]$^+$. $^1$H NMR (400 MHz, CDCl$_3$) δ 8.50 (s, 1H), 7.80 (s, 1H), 7.58 (d, J=8.7 Hz, 1H), 6.61 (s, 1H), 6.27 (s, 1H), 6.04-5.75 (m, 0.5H), 5.03-4.84 (m, 0.5H), 3.85 (s, 3H), 3.78 (s, 3H), 3.76-3.59 (m, 4H), 3.49-3.17 (m, 1H), 2.81-2.69 (m, 1H), 2.52 (s, 3H), 2.40-2.29 (m, 1H), 1.62-1.56 (m, 3H).

Example 96: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-2-methylquinolin-6-yl)methanone

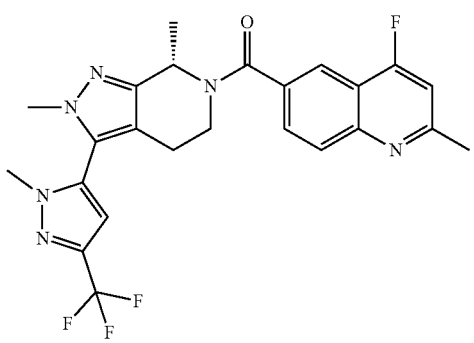

The title compound may be prepared in a manner analogous to Example 1, using 4-fluoro-2-methylquinoline-6-carboxylic acid instead of 2-methylquinoline-5-carboxylic acid. MS (ESI): mass calcd. for $C_{24}H_{22}F_4N_6O$, 486.2.

Example 97: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxyquinolin-6-yl)methanone

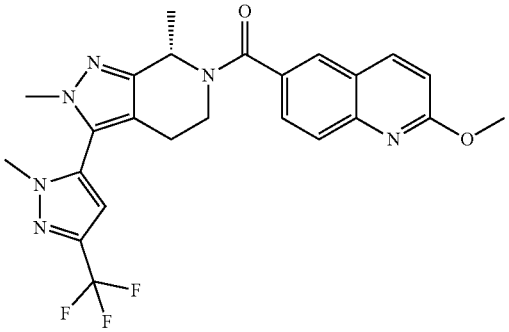

The title compound may be prepared in a manner analogous to Example 1, using 2-methoxyquinoline-6-carboxylic acid instead of 2-methylquinoline-5-carboxylic acid. MS (ESI): mass calcd. for $C_{24}H_{23}F_3N_6O_2$, 484.2.

Example 98: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methoxy-2-methylquinolin-5-yl)methanone

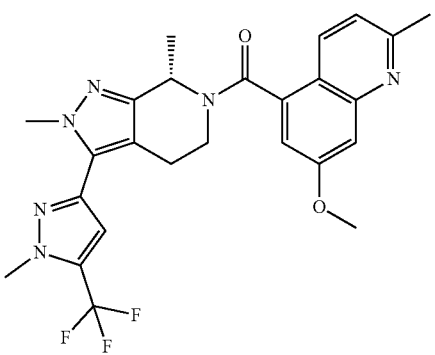

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 7-methoxy-2-methylquinoline-5-carboxylic acid instead of 2-methylquinoline-5-carboxylic acid. MS (ESI): mass calcd. for $C_{25}H_{25}F_3N_6O_2$, 498.2.

Example 99: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-fluoro-8-methoxyquinolin-4-yl)methanone

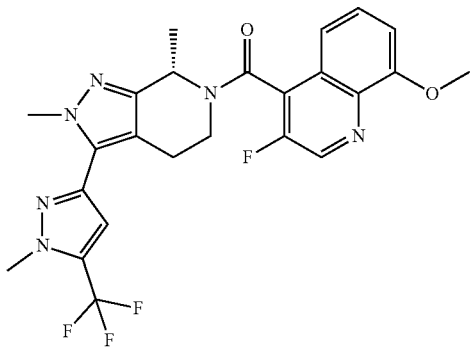

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 3-fluoro-8-methoxyquinoline-4-carboxylic acid instead of 2-methylquinoline-5-carboxylic acid. MS (ESI): mass calcd. for $C_{24}H_{22}F_4N_6O_2$, 502.2.

Example 100: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-fluoro-8-methylquinolin-4-yl)methanone

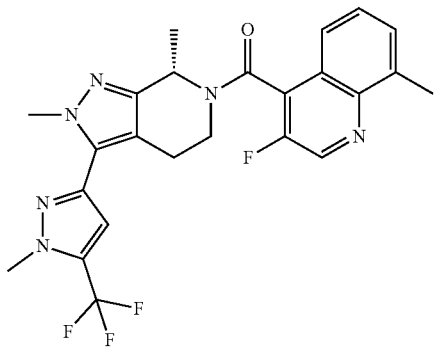

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 3-fluoro-8-methylquinoline-4-carboxylic acid instead of 2-methylquinoline-5-carboxylic acid. MS (ESI): mass calcd. for $C_{24}H_{22}F_4N_6O$, 486.2.

Example 101: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-fluoroisoquinolin-4-yl)methanone

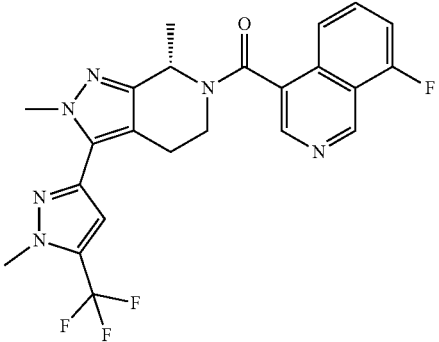 [SMILES: C[C@H]1c2nn(C)c(-c3cc(C(F)(F)F)n(C)n3)c2CCN1C(=O)c1cncc2c(F)cccc12]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 8-fluoroisoquinoline-4-carboxylic acid instead of 2-methylquinoline-5-carboxylic acid. MS (ESI): mass calcd. for $C_{23}H_{20}F_4N_6O$, 472.2.

Example 102: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methoxyquinolin-4-yl)methanone

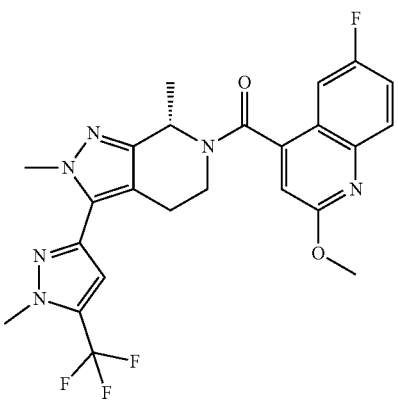 [SMILES: COc1cc(C(=O)N2CCc3c(nn(C)c3-c3cc(C(F)(F)F)n(C)n3)[C@@H]2C)c2cc(F)ccc2n1]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 6-fluoro-2-methoxyquinoline-4-carboxylic acid instead of 2-methylquinoline-5-carboxylic acid. MS (ESI): mass calcd. for $C_{24}H_{22}F_4N_6O$, 502.2.

Example 103: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(5-fluoro-1-methyl-1H-pyrazolo[3,4-b]pyridin-4-yl)methanone

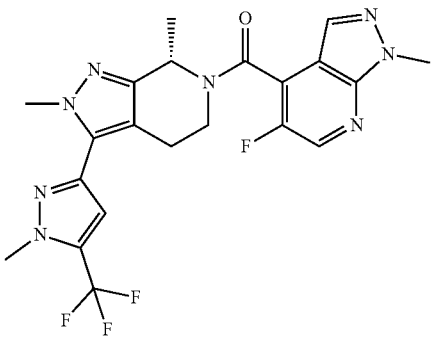

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 5-fluoro-1-methyl-1H-pyrazolo[3,4-b]pyridine-4-carboxylic acid instead of 2-methylquinoline-5-carboxylic acid. MS (ESI): mass calcd. for $C_{21}H_{20}F_4N_8O$, 502.2.

Example 104: (S)-(6-(Difluoromethyl)-1-methyl-1H-pyrazolo[3,4-b]pyridin-4-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone

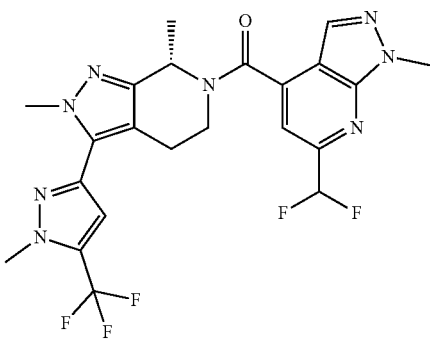

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead (S)-2,7-dimethyl-3-(1-methyl-3-(trifluoromethyl)-1H-pyrazol-5-yl)-4,5,6,7-tetrahydro-2H-pyrazolo[3,4-c]pyridine and using 6-(difluoromethyl)-1-methyl-1H-pyrazolo[3,4-b]pyridine-4-carboxylic acid instead of 2-methylquinoline-5-carboxylic acid. MS (ESI): mass calcd. for $C_{22}H_{21}F_5N_8O$, 508.2.

Example 105: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrazolo[4,3-c]pyridin-4-yl)methanone

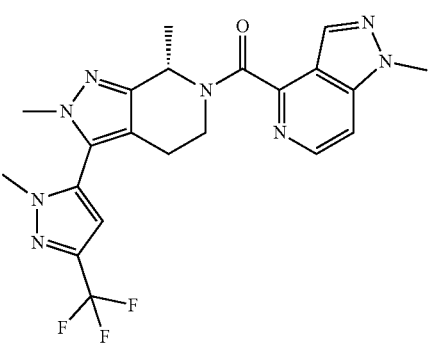

The title compound may be prepared in a manner analogous to Example 1, using 1-methyl-1H-pyrazolo[4,3-c]pyridine-4-carboxylic acid instead of 2-methylquinoline-5-carboxylic acid. MS (ESI): mass calcd. for $C_{21}H_{21}F_3N_8O$, 458.2.

Example 106: (S)-(1,6-Dimethyl-1H-pyrazolo[4,3-c]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

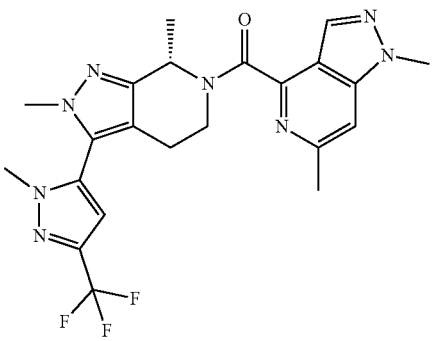

The title compound may be prepared in a manner analogous to Example 1, using 1,6-dimethyl-1H-pyrazolo[4,3-c]pyridine-4-carboxylic acid instead of 2-methylquinoline-5-carboxylic acid. MS (ESI): mass calcd. for $C_{22}H_{23}F_3N_8O$, 472.2.

Example 107: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrazolo[4,3-b]pyridin-5-yl)methanone

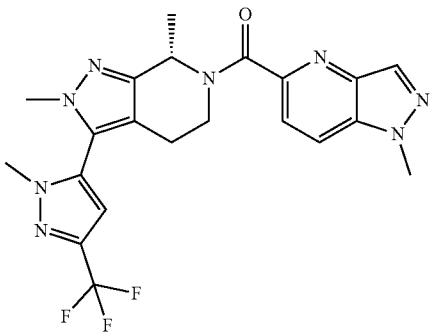 [SMILES: C[C@H]1c2nn(C)c(-c3cc(C(F)(F)F)nn3C)c2CCN1C(=O)c1ccc2c(cnn2C)n1]

The title compound may be prepared in a manner analogous to Example 1, using 1-methyl-1H-pyrazolo[4,3-b]pyridine-5-carboxylic acid instead of 2-methylquinoline-5-carboxylic acid. MS (ESI): mass calcd. for $C_{21}H_{21}F_3N_8O$, 458.2.

Example 108: (S)-(1,6-Dimethyl-1H-pyrazolo[4,3-b]pyridin-5-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

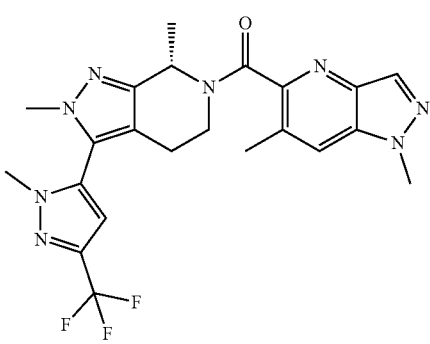 [SMILES: Cc1cc2c(cnn2C)nc1C(=O)N1CCc2c(nn(C)c2-c2cc(C(F)(F)F)nn2C)[C@@H]1C]

The title compound may be prepared in a manner analogous to Example 1, using 1,6-dimethyl-1H-pyrazolo[4,3-b]pyridine-5-carboxylic acid instead of 2-methylquinoline-5-carboxylic acid. MS (ESI): mass calcd. for $C_{22}H_{23}F_3N_8O$, 472.2.

Example 109: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-(trifluoromethoxy)phenyl)methanone

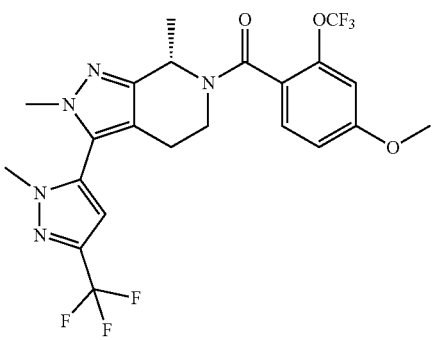

The title compound may be prepared in a manner analogous to Example 1, using 4-methoxy-2-(trifluoromethoxy)benzoic acid instead of 2-methylquinoline-5-carboxylic acid. MS (ESI): mass calcd. for $C_{22}H_{21}F_6N_5O$, 517.2.

Example 110: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methyl-2-(trifluoromethoxy)phenyl)methanone

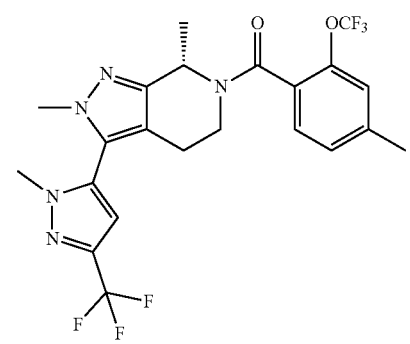

The title compound was prepared in a manner analogous to Example 1, using 4-methyl-2-(trifluoromethoxy)benzoic acid (Intermediate 33) instead of 2-methylquinoline-5-carboxylic acid. MS (ESI): mass calcd. for $C_{22}H_{21}F_6N_5O_2$, 501.2; m/z found, 502.1 [M+H]$^+$. $^1$H NMR (400 MHz, CDCl$_3$) δ 7.38-7.28 (m, 1H), 7.22-7.07 (m, 2H), 6.62-6.58 (m, 1H), 5.98-5.86 (m, 0.64H), 4.99-4.90 (m, 0.42H), 4.82-4.71 (m, 0.41H), 3.82-3.77 (m, 3H), 3.75 (s, 2H), 3.70 (s, 1H), 3.63-3.55 (m, 0.66H), 3.38-3.23 (m, 0.67H), 3.13-3.00 (m, 0.39H), 2.78-2.65 (m, 0.64H), 2.49-2.44 (m, 0.32H), 2.42 (s, 3H), 2.40-2.36 (m, 0.30H), 2.25 (dd, J=2.5, 15.6 Hz, 0.67H), 1.61-1.59 (m, 2H), 1.51-1.42 (m, 1H).

Example 111: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-3-(trifluoromethoxy)phenyl)methanone

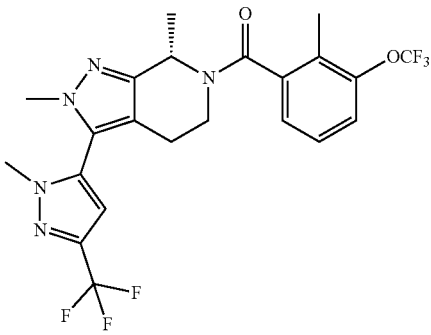 [SMILES: Cc1c(OC(F)(F)F)cccc1C(=O)N1CCc2c(nn(C)c2-c2cc(C(F)(F)F)nn2C)[C@@H]1C]

The title compound may be prepared in a manner analogous to Example 1, using 2-methyl-3-(trifluoromethoxy)benzoic acid instead of 2-methylquinoline-5-carboxylic acid. MS (ESI): mass calcd. for $C_{22}H_{21}F_6N_5O_2$, 501.2.

Example 112: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-fluoro-3-(trifluoromethoxy)phenyl)methanone

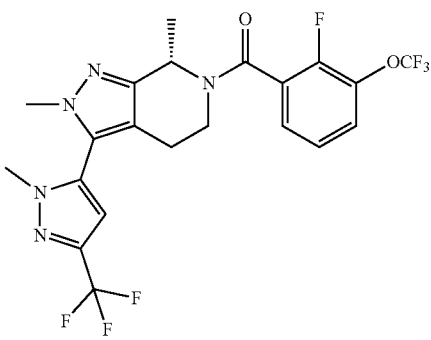 [SMILES: C[C@H]1c2nn(C)c(-c3cc(C(F)(F)F)nn3C)c2CCN1C(=O)c1cccc(OC(F)(F)F)c1F]

The title compound was prepared in a manner analogous to Example 1, using 2-fluoro-3-(trifluoromethoxy)benzoic acid instead of 2-methylquinoline-5-carboxylic acid. MS (ESI): mass calcd. for $C_{21}H_{18}F_7N_5O_2$, 505.1; m/z found, 506.1 [M+H]$^+$. $^1$H NMR (400 MHz, CDCl$_3$) δ 7.43-7.29 (m, 2H), 7.27-7.21 (m, 1H), 6.63-6.59 (m, 1H), 5.97-5.84 (m, 0.65H), 5.00-4.87 (m, 0.40H), 4.83-4.73 (m, 0.40H), 3.84-3.79 (m, 3H), 3.78-3.70 (m, 3H), 3.66-3.57 (m, 0.65H), 3.47-3.31 (m, 0.61H), 3.18-3.06 (m, 0.40H), 2.80-2.69 (m, 0.59H), 2.48-2.40 (m, 0.51H), 2.36-2.24 (m, 0.82H), 2.04-1.98 (m, 0.22H), 1.66-1.48 (m, 3H).

Example 113: (S)-(2-Chloro-4-(trifluoromethoxy)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone

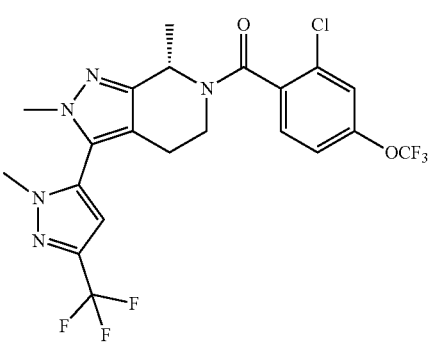 [SMILES: C[C@H]1c2nn(C)c(-c3cc(C(F)(F)F)nn3C)c2CCN1C(=O)c1ccc(OC(F)(F)F)cc1Cl]

The title compound was prepared in a manner analogous to Example 1, using 2-chloro-4-(trifluoromethoxy)benzoic acid instead of 2-methylquinoline-5-carboxylic acid. MS (ESI): mass calcd. for $C_{21}H_{18}ClF_6N_5O_2$, 521.1; m/z found, 522.1 [M+H]$^+$. $^1$H NMR (400 MHz, CDCl$_3$) δ 7.44-7.28 (m, 2H), 7.24-7.15 (m, 1H), 6.64-6.58 (m, 1H), 5.98-5.89 (m, 0.63H), 5.02-4.93 (m, 0.43H), 4.83-4.64 (m, 0.43H), 3.84-3.79 (m, 3H), 3.77-3.71 (m, 3H), 3.58-3.46 (m, 0.68H), 3.46-3.37 (m, 0.41H), 3.34-3.24 (m, 0.24H), 3.18-3.00 (m, 0.48H), 2.82-2.69 (m, 0.72H), 2.49-2.37 (m, 0.87H), 2.33-2.23 (m, 0.72H), 1.67-1.62 (m, 2H), 1.47-1.41 (m, 1H).

Example 114: (S)-(4,6-Difluoro-1-methyl-1H-indazol-3-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone

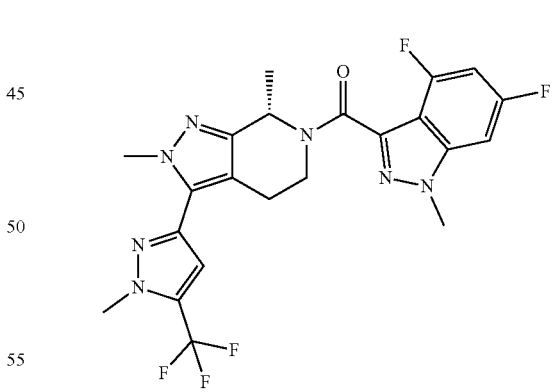

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and lithium 4,6-difluoro-1-methyl-1H-indazole-3-carboxylate (Intermediate 6) instead of 2-methylquinoline-5-carboxylic acid. MS (ESI): mass calcd. for $C_{22}H_{20}F_5N_7O$, 494.2.

Example 115: (S)-(4,6-Difluoro-1H-indazol-3-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone

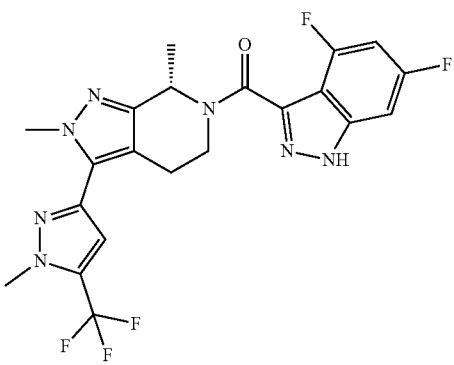 [SMILES: C[C@H]1c2nn(C)c(-c3cc(C(F)(F)F)n(C)n3)c2CCN1C(=O)c1n[nH]c2cc(F)cc(F)c12]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 4,6-difluoro-1H-indazole-3-carboxylic acid instead of 2-methylquinoline-5-carboxylic acid. MS (ESI): mass calcd. for $C_{21}H_{15}F_5N_7O$, 479.15.

Example 116: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-fluoro-4-methylphenyl)methanone

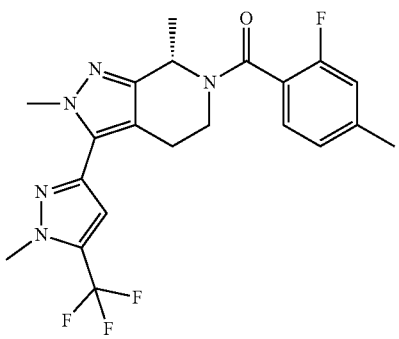

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-fluoro-4-methylbenzoic acid instead of 2-methylquinoline-5-carboxylic acid. MS (ESI): mass calcd. for $C_{21}H_{21}F_4N_5O$, 435.2.

Example 117: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-indazol-7-yl)methanone

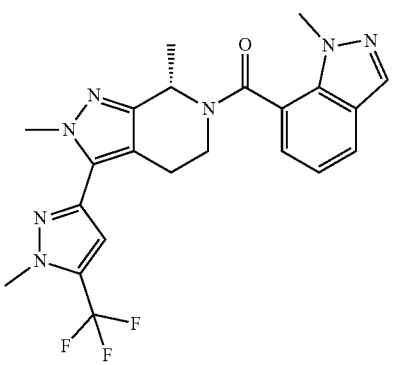 [SMILES: C[C@H]1c2nn(C)c(-c3cc(C(F)(F)F)n(C)n3)c2CCN1C(=O)c1cccc2cnn(C)c12]

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-indazole-7-carboxylic acid instead of 2-methylquinoline-5-carboxylic acid. MS (ESI): mass calcd. for $C_{22}H_{22}F_3N_7O$, 457.2; m/z found, 458.2 $[M+H]^+$. $^1$H NMR (500 MHz, DMSO-$d_6$) δ 8.20-8.09 (m, 1H), 7.94-7.83 (m, 1H), 7.50-7.13 (m, 3H), 5.84-5.57 (m, 1H), 4.95-4.70 (m, 1H), 4.06 (d, J=9.4 Hz, 3H), 4.02-3.81 (m, 6H), 3.72-3.65 (m, 1H), 3.56-3.45 (m, 1H), 2.79 (d, J=15.7 Hz, 1H), 1.63-1.39 (m, 3H).

Example 118: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrazolo[3,4-b]pyridin-4-yl)methanone

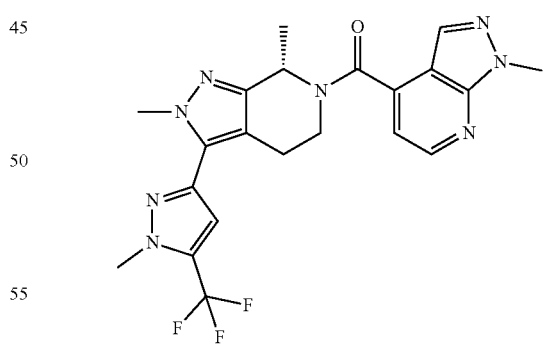

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 1-methyl-1H-pyrazolo[3,4-b]pyridine-4-carboxylic acid instead of 2-methylquinoline-5-carboxylic acid. MS (ESI): mass calcd. for $C_{21}H_{21}F_3N_8O$, 458.2; m/z found, 459.2

[M+H]⁺. ¹H NMR (500 MHz, DMSO-d₆) δ 8.73-8.60 (m, 1H), 8.20-7.90 (m, 1H), 7.22 (d, J=41.2 Hz, 2H), 5.83-5.52 (m, 1H), 4.87-4.48 (m, 1H), 4.13-4.08 (m, 3H), 4.08-3.86 (m, 6H), 3.53-3.43 (m, 1H), 2.93-2.61 (m, 2H), 1.62-1.32 (m, 3H).

Example 119: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2,8-dimethylquinolin-6-yl)methanone

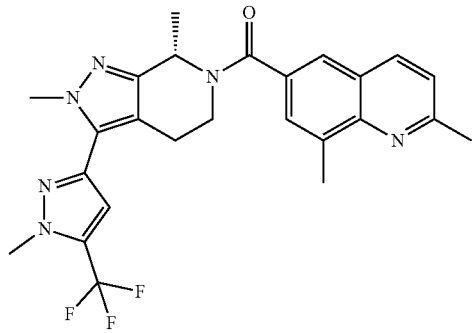

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2,8-dimethylquinoline-6-carboxylic acid instead of 2-methylquinoline-5-carboxylic acid. MS (ESI): mass calcd. for $C_{25}H_{25}F_3N_6O$, 482.2.

Example 120: (S)-Benzo[d]thiazol-6-yl(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone

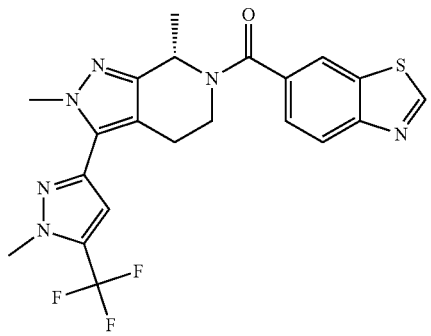 [SMILES: C[C@H]1c2nn(C)c(-c3cc(C(F)(F)F)n(C)n3)c2CCN1C(=O)c1ccc2ncsc2c1]

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and benzo[d]thiazole-6-carboxylic acid instead of 2-methylquinoline-5-carboxylic acid. DMF was used instead of DCM. MS (ESI): mass calcd. for $C_{21}H_{19}F_3N_6OS$, 460.1; m/z found, 461.1 [M+H]⁺. ¹H NMR (500 MHz, CDCl₃) δ 9.08 (s, 1H), 8.18 (d, J=8.4 Hz, 1H), 8.07 (s, 1H), 7.61-7.55 (m, 1H), 6.72 (s, 1H), 5.86 (br s, 0.46H), 5.15-5.74 (m, 0.88H), 4.19-3.73 (m, 6.73H), 3.43-3.08 (m, 1H), 3.01-2.52 (m, 2H), 1.74-1.43 (m, 3H).

Example 121: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxy-3-methylpyridin-4-yl)methanone

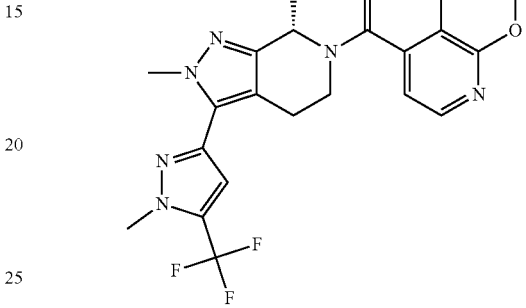

The title compound was prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 2-methoxy-3-methylisonicotinic acid instead of 2-methylquinoline-5-carboxylic acid. DMF was used instead of DCM. MS (ESI): mass calcd. for $C_{21}H_{23}F_3N_6O_2$, 448.2; m/z found, 449.2 [M+H]⁺. ¹H NMR (500 MHz, CDCl₃) δ 8.11-7.95 (m, 1H), 6.81-6.54 (m, 2H), 5.94-5.86 (m, 0.56H), 4.98 (dd, J=13.1, 5.4 Hz, 0.46H), 4.84-4.77 (m, 0.14H), 4.62 (q, J=6.7 Hz, 0.32H), 4.09-3.93 (m, 9H), 3.62-3.49 (m, 0.56H), 3.34-3.24 (m, 0.57H), 3.13-3.03 (m, 0.45H), 2.93-2.81 (m, 0.47H), 2.76-2.49 (m, 1.63H), 2.24-1.91 (m, 3H), 1.57 (s, 3H).

Example 122: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-6-yl)methanone

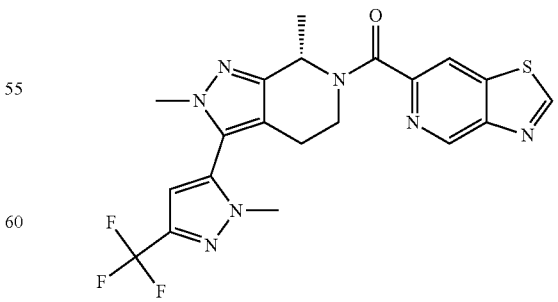

The title compound was prepared in a manner analogous to Example 1, using thiazolo[4,5-c]pyridine-6-carboxylic acid instead of 2-methylquinoline-5-carboxylic acid. MS (ESI): mass calcd. for $C_{20}H_{18}F_3N_7OS$, 461.1; m/z found, 462.1 [M+H]⁺. ¹H NMR (400 MHz, CDCl₃) δ 9.42-9.35 (m, 1H), 9.15 (s, 1H), 8.42-8.35 (m, 1H), 6.61-6.56 (m, 1H), 5.91-5.83 (m, 0.59H), 5.46-5.39 (m, 0.43H), 4.94-4.86 (m, 0.41H), 4.22-4.14 (m, 0.63H), 3.84-3.78 (m, 3H), 3.76-3.65 (m, 3H), 3.36-3.27 (m, 0.62H), 3.22-3.11 (m, 0.44H), 3.01-2.91 (m, 0.67H), 2.84-2.73 (m, 0.50H), 2.46-2.39 (m, 0.50H), 2.35-2.26 (m, 0.72H), 1.38-1.21 (m, 3H).

Example 123: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-6-yl)methanone

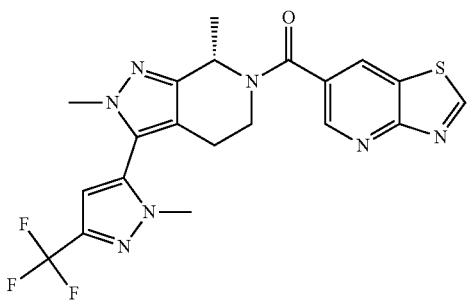 [SMILES: C[C@H]1c2nn(C)c(-c3cc(C(F)(F)F)nn3C)c2CCN1C(=O)c1cnc2ncsc2c1]

The title compound was prepared in a manner analogous to Example 1, using thiazolo[4,5-b]pyridine-6-carboxylic acid instead of 2-methylquinoline-5-carboxylic acid. MS (ESI): mass calcd. for $C_{20}H_{18}F_3N_7OS$, 461.1; m/z found, 462.1 [M+H]⁺. ¹H NMR (400 MHz, DMSO-d₆) δ 9.81 (s, 1H), 8.84-8.82 (m, 1H), 8.82-8.79 (m, 1H), 7.10 (s, 1H), 5.62 (br s, 1H), 5.06-4.38 (m, 1H), 3.82 (s, 3H), 3.73 (s, 3H), 3.70-3.65 (m, 1H), 2.84-2.69 (m, 1H), 2.41-2.27 (m, 1H), 1.53 (d, J=6.4 Hz, 3H).

Example 124: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-7-yl)methanone

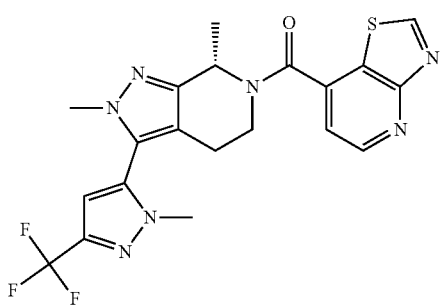 [SMILES: C[C@H]1c2nn(C)c(-c3cc(C(F)(F)F)nn3C)c2CCN1C(=O)c1ccnc2ncsc12]

The title compound may be prepared in a manner analogous to Example 1, using thiazolo[4,5-b]pyridine-7-carboxylic acid instead of 2-methylquinoline-5-carboxylic acid. MS (ESI): mass calcd. for $C_{20}H_{18}F_3N_7OS$, 461.1.

Example 125: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-7-yl)methanone

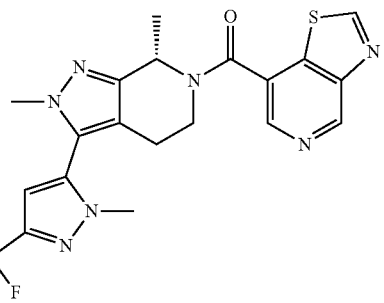

The title compound may be prepared in a manner analogous to Example 1, using thiazolo[4,5-c]pyridine-7-carboxylic acid instead of 2-methylquinoline-5-carboxylic acid. MS (ESI): mass calcd. for $C_{20}H_{18}F_3N_7OS$, 461.1.

Example 126: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[5,4-c]pyridin-4-yl)methanone

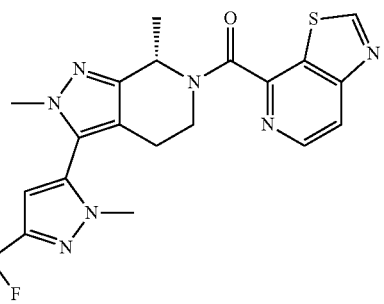

The title compound may be prepared in a manner analogous to Example 1, using thiazolo[5,4-c]pyridine-4-carboxylic acid instead of 2-methylquinoline-5-carboxylic acid. MS (ESI): mass calcd. for $C_{20}H_{18}F_3N_7OS$, 461.1.

Example 127: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-c]pyridin-6-yl)methanone

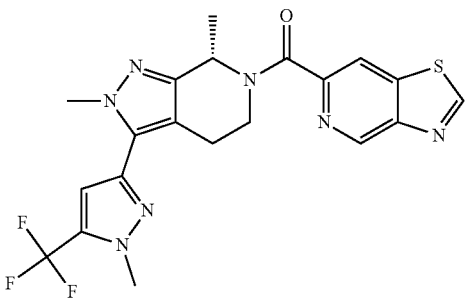

The title compound may be prepare in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and thiazolo[4,5-c]pyridine-6-carboxylic acid instead of 2-methylquinoline-5-carboxylic acid. MS (ESI): mass calcd. for $C_{20}H_{18}F_3N_7OS$, 461.1.

Example 128: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-b]pyridin-6-yl)methanone

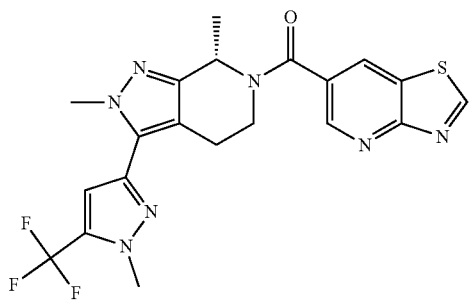 [SMILES: C[C@H]1c2nn(C)c(-c3cc(C(F)(F)F)n(C)n3)c2CCN1C(=O)c1cc2scnc2cn1]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and thiazolo[4,5-b]pyridine-6-carboxylic acid instead of 2-methylquinoline-5-carboxylic acid. MS (ESI): mass calcd. for $C_{20}H_{18}F_3N_7OS$, 461.1.

Example 129: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-b]pyridin-7-yl)methanone

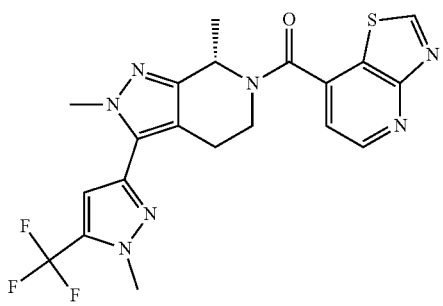 [SMILES: C[C@H]1c2nn(C)c(-c3cc(C(F)(F)F)n(C)n3)c2CCN1C(=O)c1ccnc2ncsc12]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and thiazolo[4,5-b]pyridine-7-carboxylic acid instead of 2-methylquinoline-5-carboxylic acid. MS (ESI): mass calcd. for $C_{20}H_{18}F_3N_7OS$, 461.1.

Example 130: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-c]pyridin-7-yl)methanone

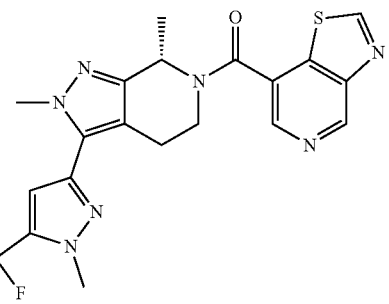

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and thiazolo[4,5-c]pyridine-7-carboxylic acid instead of 2-methylquinoline-5-carboxylic acid. MS (ESI): mass calcd. for $C_{20}H_{18}F_3N_7OS$, 461.1.

Example 131: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[5,4-c]pyridin-4-yl)methanone

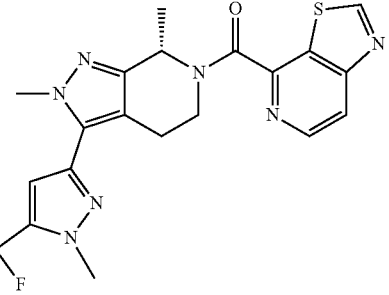

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and thiazolo[5,4-c]pyridine-4-carboxylic acid instead of 2-methylquinoline-5-carboxylic acid. MS (ESI): mass calcd. for $C_{20}H_{18}F_3N_7OS$, 461.1.

Example 132: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(6-fluoro-2-methylquinolin-4-yl)methanone

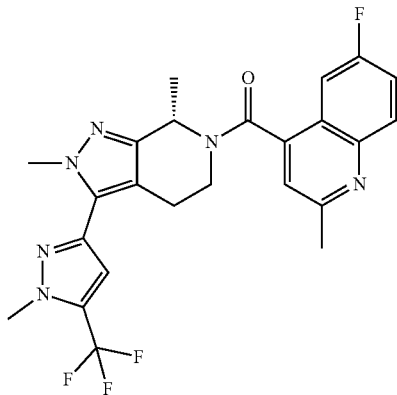 [SMILES: Cc1cc(C(=O)N2CCc3c(nn(C)c3-c3cc(C(F)(F)F)n(C)n3)[C@@H]2C)c2cc(F)ccc2n1]

The title compound is prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 6-fluoro-2-methylquinoline-4-carboxylic acid instead of 2-methylquinoline-5-carboxylic acid. MS (ESI): mass calcd. for $C_{24}H_{22}F_4N_6O$, 486.2; m/z found, 487.2 [M+H]+. 1H NMR (500 MHz, DMSO-d6) δ 8.08 (s, 1H), 7.78-7.43 (m, 2H), 7.39-7.02 (m, 2H), 5.87-5.55 (m, 1H), 4.76 (d, J=93.2 Hz, 2H), 4.17-3.76 (m, 6H), 3.18 (d, J=4.5 Hz, 1H), 2.88-2.62 (m, 3H), 2.50-2.47 (m, 1H), 1.80-1.16 (m, 3H).

Example 132: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methyl-benzo[d]thiazol-6-yl)methanone

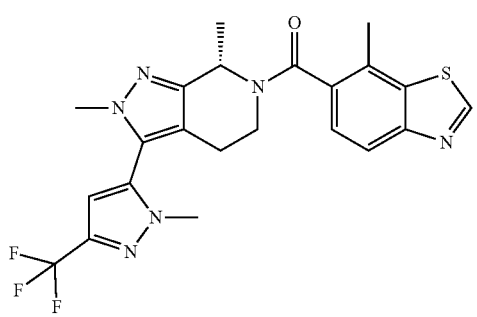 [SMILES: Cc1c(C(=O)N2CCc3c(nn(C)c3-c3cc(C(F)(F)F)nn3C)[C@@H]2C)ccc2ncsc12]

The title compound was prepared in a manner analogous to Example 1, using 7-methylbenzo[d]thiazole-6-carboxylic acid (Intermediate 34) instead of 2-methylquinoline-5-carboxylic acid. MS (ESI): mass calcd. for $C_{22}H_{21}F_3N_6OS$, 474.1; m/z found, 475.3 [M+H]+. 1H NMR (400 MHz, CDCl3) δ 9.07 (s, 1H), 7.88 (s, 1H), 7.38 (s, 1H), 6.61 (s, 1H), 6.05-5.75 (m, 0.52H), 5.14-4.97 (m, 0.41H), 4.95-4.77 (m, 0.41H), 3.98-3.86 (m, 0.47H), 3.83 (s, 3H), 3.73 (s, 3H), 3.40-3.07 (m, 1H), 2.83 (s, 3H), 2.78-2.54 (m, 1H), 2.44-2.29 (m, 1H), 1.62 (s, 3H).

Example 134: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methyl-benzo[d]thiazol-6-yl)methanone

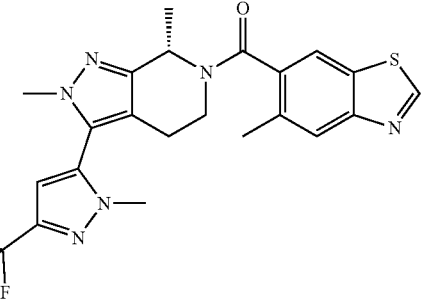

The title compound was prepared in a manner analogous to Example 1, using 5-methylbenzo[d]thiazole-6-carboxylic acid (Intermediate 35) instead of 2-methylquinoline-5-carboxylic acid, and HOBt and EDCI instead of HATU. MS (ESI): mass calcd. for $C_{22}H_{21}F_3N_6OS$, 474.1; m/z found, 475.2 [M+H]+. 1H NMR (400 MHz, CDCl3) δ 9.05 (s, 1H), 8.09-7.96 (m, 1H), 7.90-7.67 (m, 1H), 6.64-6.58 (m, 1H), 6.06-5.96 (m, 0.65H), 5.09-4.92 (m, 0.57H), 4.71-4.62 (m, 0.28H), 3.81 (s, 3H), 3.77 (s, 2H), 3.70 (s, 1H), 3.55 (dd, J=4.5, 13.4 Hz, 0.52H), 3.36-3.25 (m, 0.68H), 3.15-3.05 (m, 0.43H), 2.82-2.70 (m, 0.47H), 2.57 (s, 0.32H), 2.51-2.43 (m, 3H), 2.29 (s, 0.79H), 2.27-2.20 (m, 0.69H), 1.67 (d, J=6.7 Hz, 2H), 1.45 (d, J=5.8 Hz, 1H).

Example 135: (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methyl-benzo[d]thiazol-6-yl)methanone

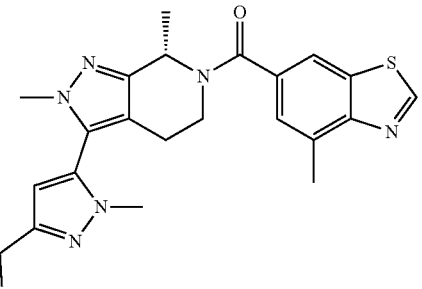

The title compound was prepared in a manner analogous to Example 1, using 4-methylbenzo[d]thiazole-6-carboxylic acid (Intermediate 36) instead of 2-methylquinoline-5-carboxylic acid. MS (ESI): mass calcd. for $C_{22}H_{21}F_3N_6OS$, 474.1; m/z found, 475.3 [M+H]+. 1H NMR (400 MHz, CDCl3) δ 9.07 (s, 1H), 8.11-7.97 (m, 1H), 7.48 (d, J=8.3 Hz, 0.23H), 7.37 (d, J=8.3 Hz, 0.61H), 6.65-6.58 (m, 1H), 6.07-5.96 (m, 0.62H), 5.10-4.89 (m, 0.60H), 4.75-4.65 (m, 0.28H), 3.86-3.79 (m, 3H), 3.77 (s, 2H), 3.69 (s, 1H), 3.58 (dd, J=4.5, 13.6 Hz, 0.37H), 3.34-3.25 (m, 0.63H), 3.12 (dt, J=3.9, 12.7 Hz, 0.44H), 2.83-2.72 (m, 0.43H), 2.70-2.64 (m, 0.33H), 2.63-2.55 (m, 2H), 2.54-2.47 (m, 0.66H), 2.42 (s, 1H), 2.24 (dd, J=2.4, 15.4 Hz, 0.65H), 1.68 (d, J=6.8 Hz, 2H), 1.47 (d, J=6.3 Hz, 1H).

Example 136: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(7-methylbenzo[d]thiazol-6-yl)methanone

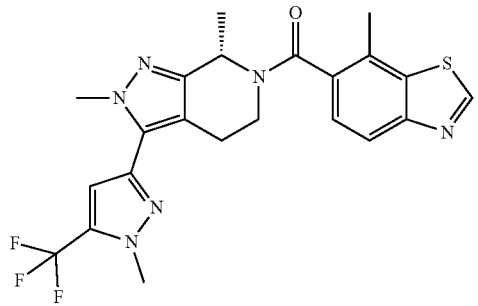 [SMILES: Cc1c(C(=O)N2CCc3c(nn(C)c3-c3cc(C(F)(F)F)n(C)n3)[C@@H]2C)ccc2ncsc12]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 7-methylbenzo[d]thiazole-6-carboxylic acid instead of 2-methylquinoline-5-carboxylic acid. MS (ESI): mass calcd. for $C_{22}H_{21}F_3N_6OS$, 474.1.

Example 137: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(5-methylbenzo[d]thiazol-6-yl)methanone

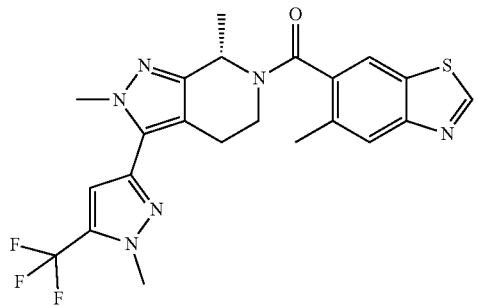 [SMILES: Cc1cc2ncsc2cc1C(=O)N1CCc2c(nn(C)c2-c2cc(C(F)(F)F)n(C)n2)[C@@H]1C]

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 5-methylbenzo[d]thiazole-6-carboxylic acid instead of 2-methylquinoline-5-carboxylic acid. MS (ESI): mass calcd. for $C_{22}H_{21}F_3N_6OS$, 474.1.

Example 138: (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-methylbenzo[d]thiazol-6-yl)methanone

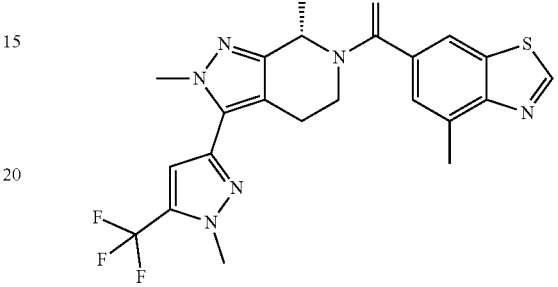

The title compound may be prepared in a manner analogous to Example 1, using (S)-2,7-dimethyl-3-(1-methyl-5-(trifluoromethyl)-1H-pyrazol-3-yl)-4,5,6,7-tetrahydro-2H-pyrazolo[3,4-c]pyridine (Intermediate 14) instead of (S)-2,7-dimethyl-3-(1-methyl-3-(trifluoromethyl)-1H-pyrazol-5-yl)-4,5,6,7-tetrahydro-2H-pyrazolo[3,4-c]pyridine and 4-methylbenzo[d]thiazole-6-carboxylic acid instead of 2-methylquinoline-5-carboxylic acid. MS (ESI): mass calcd. for $C_{22}H_{21}F_3N_6OS$, 474.1.

Biological Data

The assay used to measure the in vitro activity of MGL is adapted from the assay used for another serine hydrolase (FAAH) described in Wilson et al., 2003 (A high-throughput-compatible assay for determining the activity of fatty acid amide hydrolase. Wilson S J, Lovenberg T W, Barbier A J. Anal Biochem. 2003 Jul. 15; 318(2):270-5.). The assay consists of combining endogenously expressed MGL from HeLa cells with test compounds, adding [glycerol-1,3-$^3$H]-oleyl glycerol, incubating for one hour, and then measuring the amount of cleaved [1,3-$^3$H]-glycerol that passes through an activated carbon filter. The amount of cleaved, tritiated glycerol passing through the carbon filter is proportional to the activity of the MGL enzyme in a particular well/test condition.

Standard conditions for this assay combine 300 nM [Glycerol-1,3-$^3$H]-oleyl glycerol with human MGL from HeLa cells and test compounds for one hour, after which the reaction is filtered through activated carbon and tritium is measured in the flow through. The test compound concentration in screening mode is 10 μM, while the highest compound concentration in $IC_{50}$ assays is determined empirically. MGL is the predominant hydrolase in HeLa cells/cell homogenates.

TABLE 6

| Ex # | Compound Name | MGL $IC_{50}$ (nM) |
|---|---|---|
| 1 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-5-yl)methanone; | 35 |

TABLE 6-continued

| Ex # | Compound Name | MGL IC$_{50}$ (nM) |
|---|---|---|
| 2 | (S)-(3-(1,4-Dimethyl-1H-pyrazol-5-yl)-2,7-dimethyl-2,4,5,7-tetrahydro-6H-pyrazolo[3,4-c]pyridin-6-yl)(3-methoxy-2-methylphenyl)methanone; | 10,000 |
| 3 | (S)-(3-(1,5-Dimethyl-3-(trifluoromethyl)-1H-pyrazol-4-yl)-2,7-dimethyl-2,4,5,7-tetrahydro-6H-pyrazolo[3,4-c]pyridin-6-yl)(3-methoxy-2-methylphenyl)methanone; | 6700 |
| 4 | (S)-(2-Chloro-3-(2-oxa-6-azaspiro[3.3]heptan-6-yl)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 20 |
| 5 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-1H-indol-3-yl)methanone; | 37 |
| 6 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indazol-3-yl)methanone; | 37 |
| 7 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylpyrazolo[1,5-a]pyridin-3-yl)methanone; | 50 |
| 8 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylimidazo[1,2-a]pyridin-3-yl)methanone; | 8.9 |
| 9 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-4-yl)methanone; | 12 |
| 10 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methylquinolin-4-yl)methanone; | 18 |
| 11 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoropyrazolo[1,5-a]pyridin-3-yl)methanone; | 6.2 |
| 12 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-(2,2,2-trifluoroethyl)-1H-pyrrolo[2,3-b]pyridin-4-yl)methanone; | 100 |
| 13 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-3-yl)methanone; | 220 |
| 14 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-methoxyquinolin-5-yl)methanone; | 15 |
| 15 | (S)-(1,6-Dimethyl-1H-pyrazolo[3,4-b]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 56 |
| 16 | (S)-(3-(3-Methoxy-1-methyl-1H-pyrazol-4-yl)-2,7-dimethyl-2,4,5,7-tetrahydro-6H-pyrazolo[3,4-c]pyridin-6-yl)(quinolin-6-yl)methanone; | 370 |
| 17 | (S)-(4,6-Difluoropyrazolo[1,5-a]pyridin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 20 |
| 18 | (S)-(5,7-Difluoroquinolin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 360 |
| 19 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-fluoropyrazolo[1,5-a]pyridin-3-yl)methanone; | 19 |
| 20 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxyquinolin-4-yl)methanone; | 8.2 |
| 21 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-1-methyl-1H-indazol-4-yl)methanone; | 5.6 |
| 22 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-indazol-3-yl)methanone; | 30 |
| 23 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-2H-indazol-4-yl)methanone; | 84 |
| 24 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-3-yl)methanone; | 1760 |
| 25 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,6-dimethylquinolin-4-yl)methanone; | 90 |
| 26 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-methoxy-2-methylquinolin-4-yl)methanone; | 880 |
| 27 | (S)-(4,6-Difluoro-1-methyl-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; | 1170 |

TABLE 6-continued

| Ex # | Compound Name | MGL IC$_{50}$ (nM) |
|---|---|---|
| 28 | (S)-(4,6-Difluoro-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; | 2120 |
| 29 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-(trifluoromethyl)phenyl)methanone; | 150 |
| 30 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-fluoro-4-methylphenyl)methanone; | 3070 |
| 31 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-indazol-7-yl)methanone; | 10000 |
| 32 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrazolo[3,4-b]pyridin-4-yl)methanone; | 4560 |
| 33 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2,8-dimethylquinolin-6-yl)methanone; | 6470 |
| 34 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(6-fluoro-2-methylquinolin-4-yl)methanone; | 2190 |
| 35 | (S)-(2-Chloro-3-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 25 |
| 36 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxy-2-methylphenyl)methanone; | 23 |
| 37 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-(1H-pyrazol-1-yl)phenyl)methanone; | 380 |
| 38 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxyphenyl)methanone; | 73 |
| 39 | (S)-(3-Chloro-5-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 38 |
| 40 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylphenyl)methanone; | 230 |
| 41 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxy-4-methylphenyl)methanone; | 62 |
| 42 | (S)-(2-Chloro-4-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 100 |
| 43 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3,4-dimethylphenyl)methanone; | 33 |
| 44 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(isoquinolin-1-yl)methanone; | 19 |
| 45 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indol-4-yl)methanone; | 1.1 |
| 46 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrrolo[2,3-b]pyridin-4-yl)methanone; | 5.7 |
| 47 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-pyrrolo[2,3-b]pyridin-4-yl)methanone. | 0.67 |
| 48 | (S)-(2-Chloro-3-methoxyphenyl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; | 19 |
| 49 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrrolo[2,3-b]pyridin-4-yl)methanone; | 3.2 |
| 50 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(3-methyl-5-(2H-1,2,3-triazol-2-yl)phenyl)methanone; | 23 |
| 51 | (S)-(2-Chloro-3-methoxyphenyl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; | 890 |
| 52 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrrolo[2,3-b]pyridin-4-yl)methanone; | 420 |

TABLE 6-continued

| Ex # | Compound Name | MGL IC$_{50}$ (nM) |
|---|---|---|
| 53 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(3-methyl-5-(2H-1,2,3-triazol-2-yl)phenyl)methanone; | 810 |
| 54 | (S)-Chroman-8-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 16 |
| 55 | (S)-Chroman-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 110 |
| 56 | (S)-Benzo[d]thiazol-6-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 26 |
| 57 | (S)-Benzo[d]thiazol-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 22 |
| 58 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylbenzo[d]thiazol-6-yl)methanone; | 55 |
| 59 | (S)-Benzo[d]thiazol-6-yl(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone; | 2960 |
| 60 | (S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-methoxy-3-methylpyridin-4-yl)methanone; | 4250 |
| 61 | (S)-Chroman-7-yl(2,7-dimethyl-3-(1-methyl-3-(trifluoromethyl)-1H-pyrazol-4-yl)-2,4,5,7-tetrahydro-6H-pyrazolo[3,4-c]pyridin-6-yl)methanone; | 7180 |
| 62 | (S)-(2,7-Dimethyl-3-(1-methyl-1H-pyrazol-4-yl)-2,4,5,7-tetrahydro-6H-pyrazolo[3,4-c]pyridin-6-yl)(quinolin-6-yl)methanone; | 1940 |
| 63 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(quinolin-6-yl)methanone; | 63 |
| 64 | (S)-(2,7-Dimethyl-3-(1-(trifluoromethyl)-1H-pyrazol-4-yl)-2,4,5,7-tetrahydro-6H-pyrazolo[3,4-c]pyridin-6-yl)(quinolin-6-yl)methanone; | 79 |
| 65 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(quinolin-6-yl)methanone; | 39 |
| 66 | (S)-(3-(1-Ethyl-1H-pyrazol-3-yl)-2,7-dimethyl-2,4,5,7-tetrahydro-6H-pyrazolo[3,4-c]pyridin-6-yl)(quinolin-6-yl)methanone; | 4000 |
| 67 | (S)-(3-(1-(Difluoromethyl)-1H-pyrazol-3-yl)-2,7-dimethyl-2,4,5,7-tetrahydro-6H-pyrazolo[3,4-c]pyridin-6-yl)(quinolin-6-yl)methanone; | 1340 |
| 68 | (S)-(3-(1-Cyclopropyl-1H-pyrazol-5-yl)-2,7-dimethyl-2,4,5,7-tetrahydro-6H-pyrazolo[3,4-c]pyridin-6-yl)(quinolin-6-yl)methanone; | 4200 |
| 69 | (S)-(3-(1-(Difluoromethyl)-1H-pyrazol-4-yl)-2,7-dimethyl-2,4,5,7-tetrahydro-6H-pyrazolo[3,4-c]pyridin-6-yl)(quinolin-6-yl)methanone; | 89 |
| 70 | (S)-(2,7-Dimethyl-3-(1-(pyridin-2-yl)-1H-pyrazol-4-yl)-2,4,5,7-tetrahydro-6H-pyrazolo[3,4-c]pyridin-6-yl)(quinolin-6-yl)methanone; | 1230 |
| 71 | (S)-(3-(1-(Cyclopropylmethyl)-1H-pyrazol-5-yl)-2,7-dimethyl-2,4,5,7-tetrahydro-6H-pyrazolo[3,4-c]pyridin-6-yl)(quinolin-6-yl)methanone; | 7300 |
| 72 | ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(2-fluoro-4-methylphenyl)methanone; | 1130 |
| 73 | ((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(3-methoxy-2-methylphenyl)methanone; | 230 |
| 74 | (3-Methoxy-2-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 19 |
| 75 | Chroman-7-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 44 |
| 76 | ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(m-tolyl)methanone; | 68 |
| 77 | (3-Methoxy-5-methylphenyl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 26 |
| 78 | ((5R,9S)-3-(1-Ethyl-3-(trifluoromethyl)-1H-pyrazol-5-yl)-2-methyl-4,5,6,7,8,9-hexahydro-2H-5,9-epiminocycloocta[c]pyrazol-10-yl)(m-tolyl)methanone; | 160 |
| 79 | (3-Methoxy-2-methylphenyl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone; | 16 |
| 80 | ((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(quinolin-6-yl)methanone; | 22 |

TABLE 6-continued

| Ex # | Compound Name | MGL IC$_{50}$ (nM) |
|---|---|---|
| 81 | (5-Fluoro-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 100 |
| 82 | (2-Methyl-1,6-naphthyridin-5-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 74 |
| 83 | (5-Fluoroquinolin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 40 |
| 84 | Benzo[d]isoxazol-3-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 5.1 |
| 85 | (1-Methyl-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 64 |
| 86 | (5-Fluoro-1-methyl-1H-indazol-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone; | 18 |
| 87 | ((5R,9S)-2-Methyl-3-(1-methyl-5-(trifluoromethyl)-1H-pyrazol-3-yl)-4,5,6,7,8,9-hexahydro-2H-5,9-epiminocycloocta[c]pyrazol-10-yl)(quinolin-6-yl)methanone; | 17 |
| 88 | (6-Fluoro-2-methylquinolin-4-yl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone; | 6.6 |
| 89 | (3-Methoxy-2-methylphenyl)((5R,8S)-2-methyl-3-(1-methyl-3-(trifluoromethyl)-1H-pyrazol-5-yl)-2,4,5,6,7,8-hexahydro-5,8-epiminocyclohepta[c]pyrazol-9-yl)methanone; | 66 |
| 90 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-methylquinolin-6-yl)methanone; | 230 |
| 91 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-6-yl)methanone; | 210 |
| 92 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,5-dimethylquinolin-6-yl)methanone; | 380 |
| 93 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,7-dimethylquinolin-6-yl)methanone; | 1210 |
| 94 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,4-dimethylquinolin-6-yl)methanone; | 39 |
| 95 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylquinolin-6-yl)methanone; | 10000 |
| 110 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methyl-2-(trifluoromethoxy)phenyl)methanone; | 650 |
| 112 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-fluoro-3-(trifluoromethoxy)phenyl)methanone; | 86 |
| 113 | (S)-(2-Chloro-4-(trifluoromethoxy)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone; | 9900 |
| 117 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-indazol-7-yl)methanone; | 160 |
| 118 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrazolo[3,4-b]pyridin-4-yl)methanone; | 47 |
| 120 | (S)-Benzo[d]thiazol-6-yl(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone; | 46 |
| 121 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxy-3-methylpyridin-4-yl)methanone; and | 83 |
| 122 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-6-yl)methanone; | 260 |
| 123 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-6-yl)methanone; | 950 |
| 132 | (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(6-fluoro-2-methylquinolin-4-yl)methanone; | 27 |

TABLE 6-continued

| Ex # | Compound Name | MGL IC$_{50}$ (nM) |
|---|---|---|
| 133 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methylbenzo[d]thiazol-6-yl)methanone; | 24 |
| 134 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylbenzo[d]thiazol-6-yl)methanone; | 87 |
| 135 | (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylbenzo[d]thiazol-6-yl)methanone. | 22 |

NT means Not tested.

What is claimed is:

1. A compound of Formula (I):

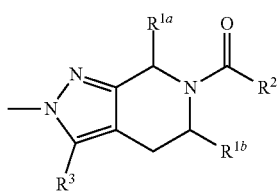

wherein
R$^{1a}$ is C$_{1-4}$alkyl;
R$^{1b}$ is H;
or R$^{1a}$ and R$^{1b}$ taken together form —CH$_2$CH$_2$— or —CH$_2$CH$_2$CH$_2$—;
R$^2$ is selected from:
  (a) phenyl or pyridyl, each optionally substituted with one or two substituents selected from halo, C$_{1-4}$alkyl, C$_{1-4}$haloalkyl, OC$_{1-4}$alkyl, OC$_{1-4}$haloalkyl, N-linked monocyclic or bicyclic heterocycloalkyl, monocyclic heteroaryl, and C$_{3-6}$cycloalkyl, or two adjacent ring substituents taken together with the carbons to which they are attached form a monocyclic cycloalkyl or hetercycloalkyl ring; and
  (b) bicyclic heteroaryl optionally substituted with one or two substituents selected from halo, C$_{1-4}$alkyl, C$_{1-4}$haloalkyl, OC$_{1-4}$alkyl, OC$_{1-4}$haloalkyl, N-linked monocyclic or bicyclic heterocycloalkyl, monocyclic heteroaryl, and C$_{3-6}$cycloalkyl; and
R$^3$ is 1H—C$_{1-4}$alkyl-pyrazolyl, 1H—C$_{1-4}$haloalkyl-pyrazolyl, 1H-pyridyl-pyrazolyl, 1H—(C$_3$-6cycloalkyl)-pyrazolyl, or 1H—(C$_{3-6}$cycloalkyl-methyl)-pyrazolyl, each pyrazolyl optionally substituted with halo, C$_{1-4}$alkyl, C$_{1-4}$haloalkyl, OC$_{1-4}$alkyl, or OC$_{1-4}$haloalkyl;
provided that when R$^2$ is phenyl or pyridyl, each optionally substituted with halo, C$_{1-4}$alkyl, or C$_{1-4}$haloalkyl, then (a) R$^{1a}$ and R$^{1b}$ are taken together form —CH$_2$CH$_2$— or —CH$_2$CH$_2$CH$_2$—;
or (b) R$^3$ is not 1H—C$_{1-4}$alkyl-pyrazol-5-yl

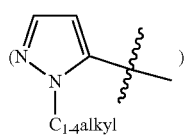

or 1H—C$_{1-4}$haloalkyl-pyrazol-5-yl

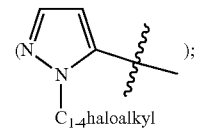

or a pharmaceutically acceptable salt, isotope, N-oxide, solvate, or stereoisomer thereof.

2. The compound of claim 1, wherein R$^2$ is selected from:
(a)

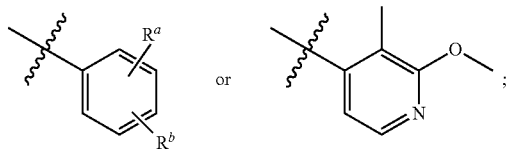

(b) a 5,6-fused or 6,5-fused heteroaryl selected from:

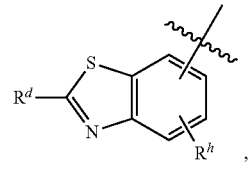

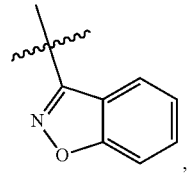

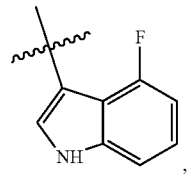

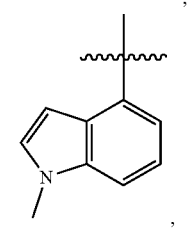

-continued
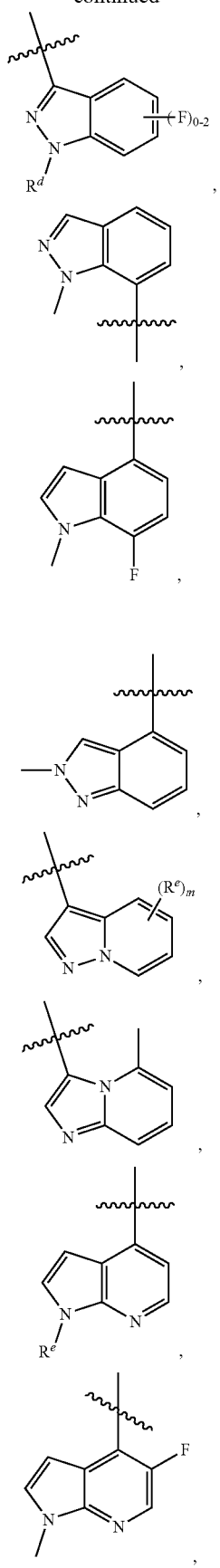
-continued
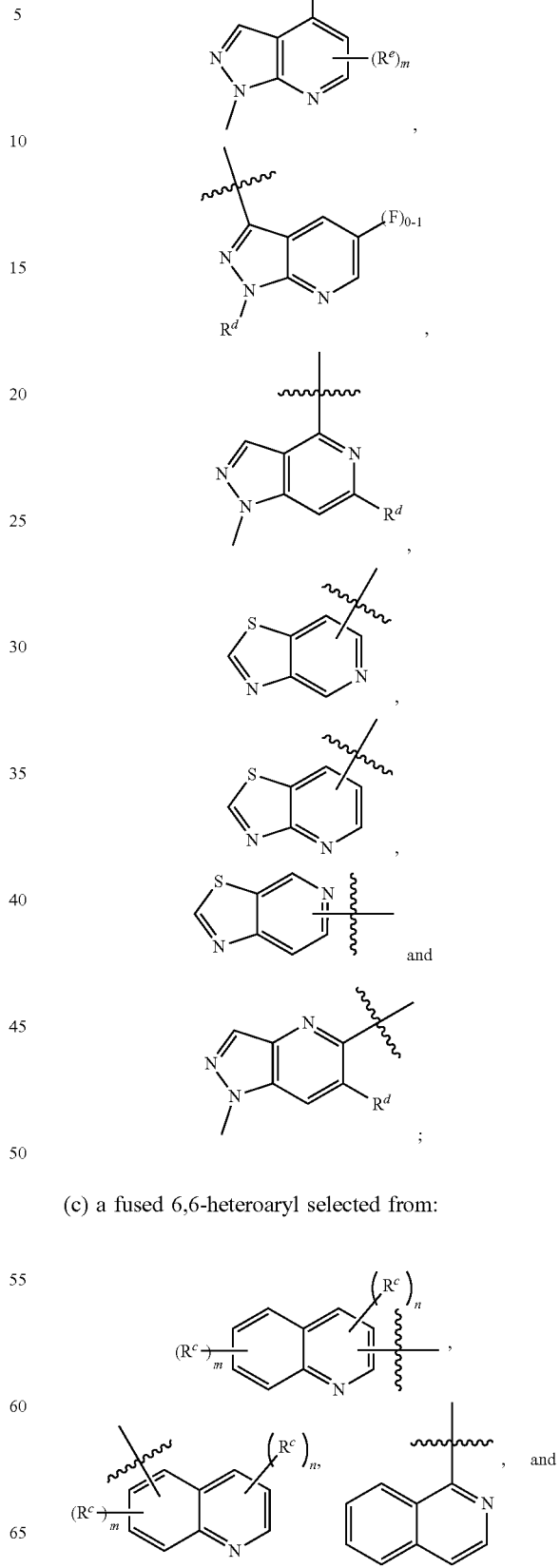
(c) a fused 6,6-heteroaryl selected from:

-continued

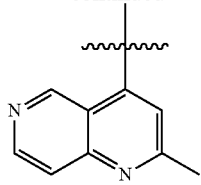

(d)

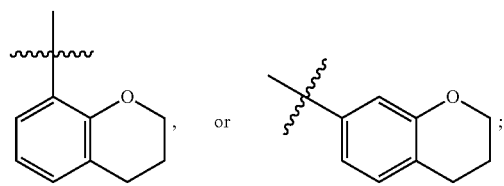 [SMILES: *c1cccc2c1OCCC2 ; *c1ccc2c(c1)OCCC2]

$R^3$ is a 5-membered heteroaryl ring selected from:

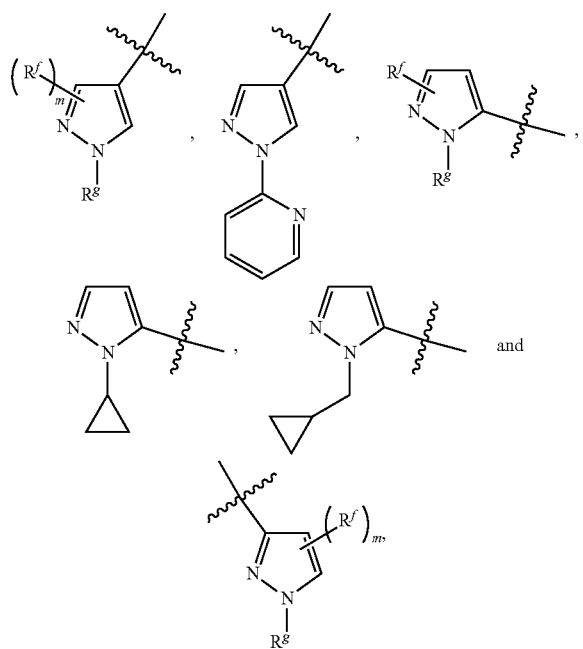

wherein
$R^a$ is selected from: H, halo, $C_{1-4}$alkyl, $C_{1-4}$haloalkyl, and $OC_{1-4}$alkyl;
$R^b$ is selected from: $C_{1-4}$alkyl, $C_{1-4}$haloalkyl, $OC_{1-4}$alkyl, $OC_{1-4}$haloalkyl,

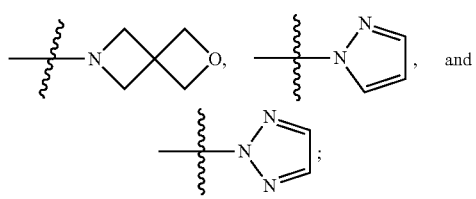

each $R^c$ is independently selected from: halo, $C_{1-4}$alkyl, and $OC_{1-4}$alkyl;

$R^d$ is H or $C_{1-4}$alkyl;
each $R^e$ is independently halo, $C_{1-4}$alkyl, or $C_{1-4}$haloalkyl;
each $R^f$ is independently selected from: $C_{1-4}$alkyl, $C_{1-4}$haloalkyl, and $OC_{1-4}$alkyl;
$R^g$ is $C_{1-4}$alkyl, or $C_{1-4}$haloalkyl; and
$R^h$ is selected from: H, $C_{1-4}$alkyl, $C_{1-4}$haloalkyl, and cycloalkyl;
n is 0, 1, or 2; and
m is 0, 1, or 2.

3. The compound of claim 1, wherein $R^{1a}$ is $CH_3$ and $R^{1b}$ is H.

4. The compound of claim 1, wherein $R^{1a}$ and $R^{1b}$ come together to form —$CH_2CH_2$— or —$CH_2CH_2CH_2$—.

5. The compound of claim 1, wherein $R^2$ is:
(a)

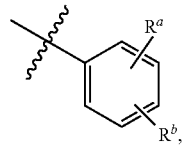

wherein $R^a$ is H, Cl, F, $C_{1-4}$alkyl or $C_{1-4}$haloalkyl; and $R^b$ is $C_{1-4}$alkyl, $C_{1-4}$haloalkyl, $OC_{1-4}$alkyl, or $OC_{1-4}$haloalkyl;

(b)

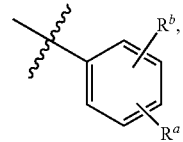

wherein $R^a$ is Cl, F, or $C_{1-4}$alkyl; and $R^b$ is

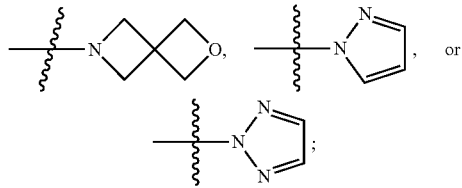

or (c)

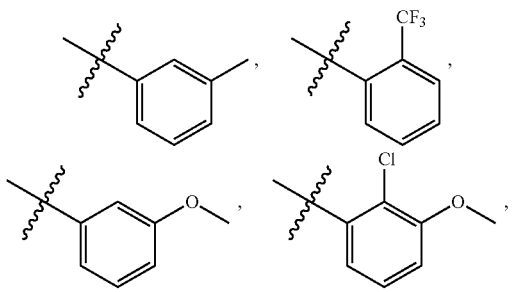

-continued
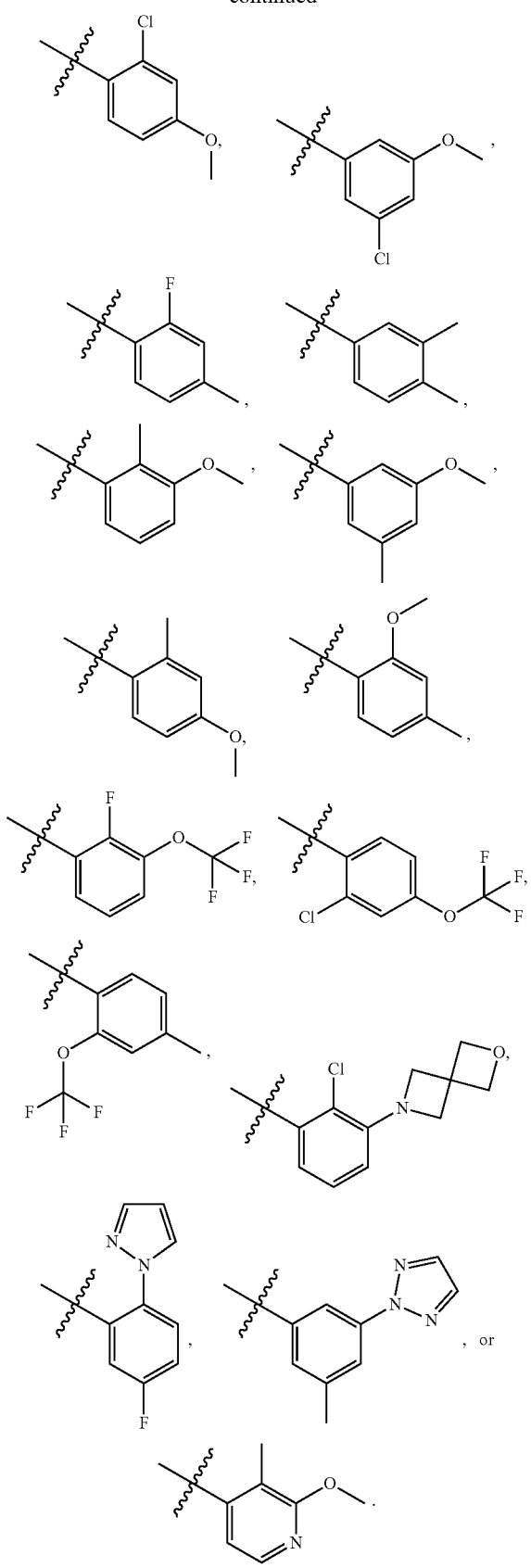
6. The compound of claim 5, wherein $R^{1a}$ is $CH_3$ and $R^2$ is
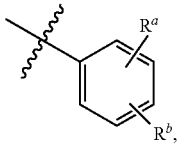
wherein $R^a$ is Cl or F, and $R^b$ is $OC_{1-4}$alkyl.
7. The compound of claim 1, wherein $R^2$ is:
(a)
(b)
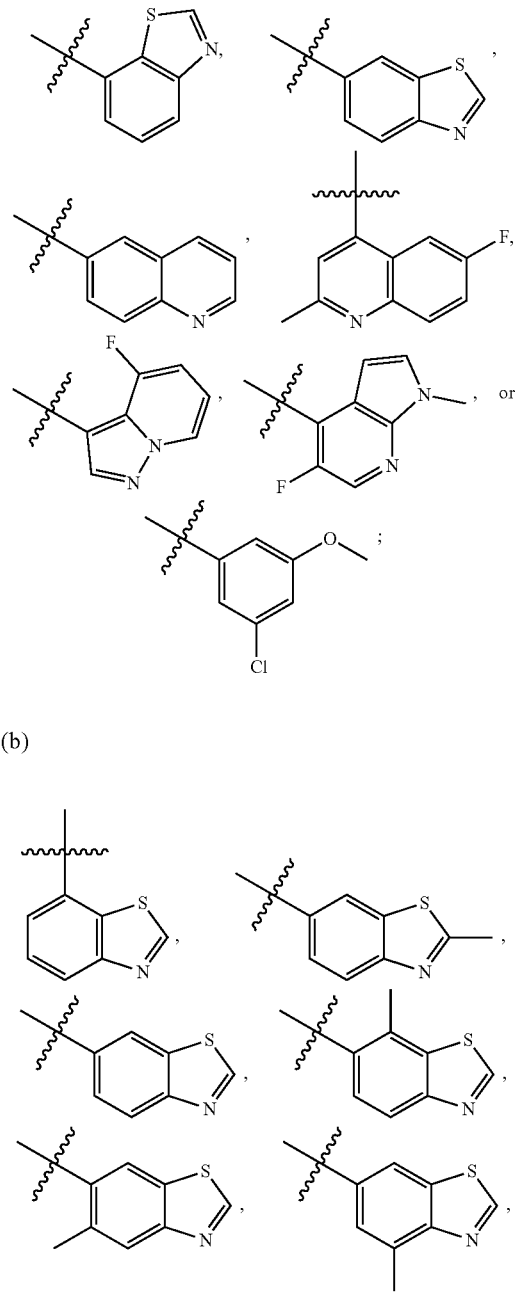

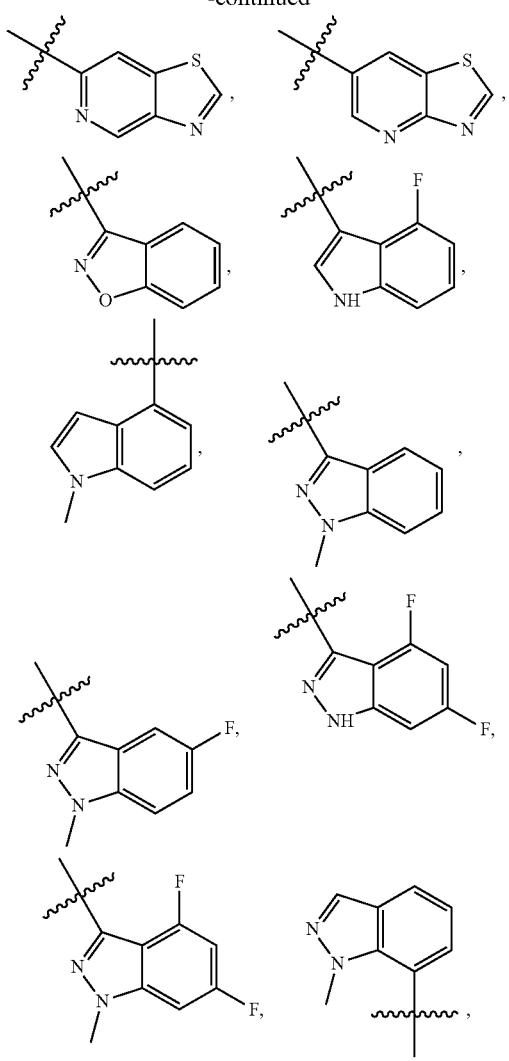
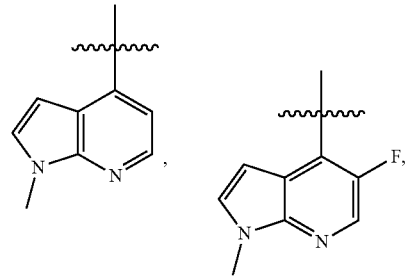
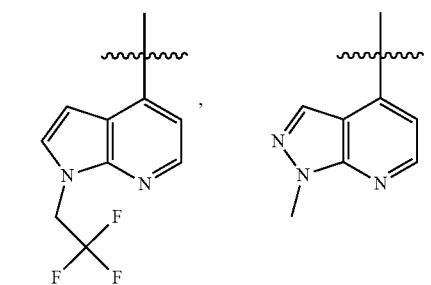
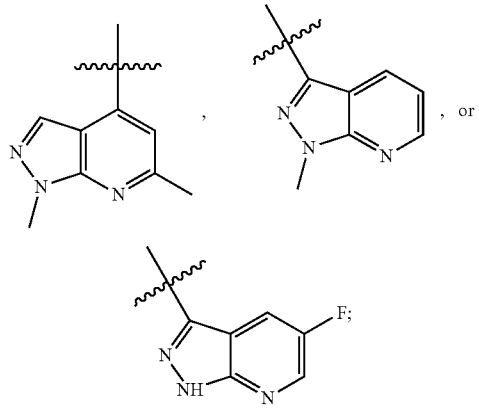
or
(c)
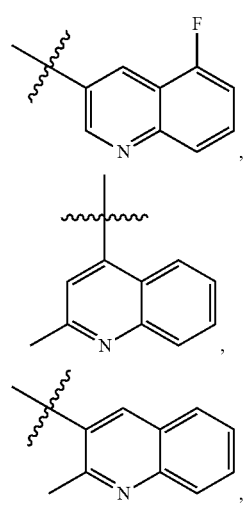

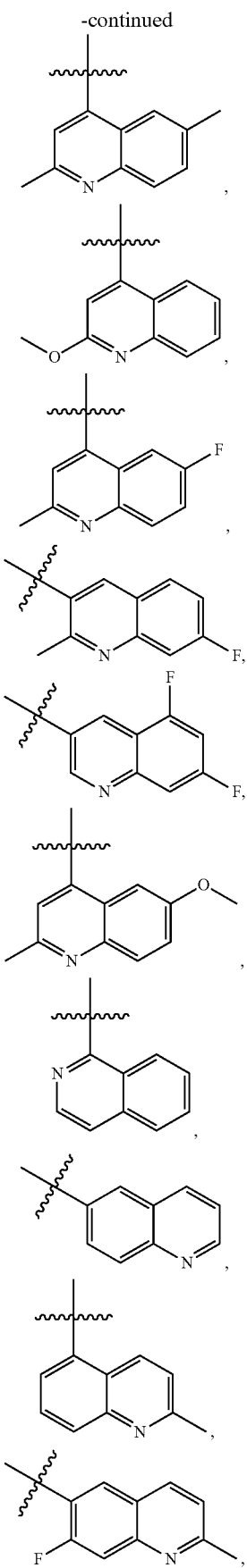
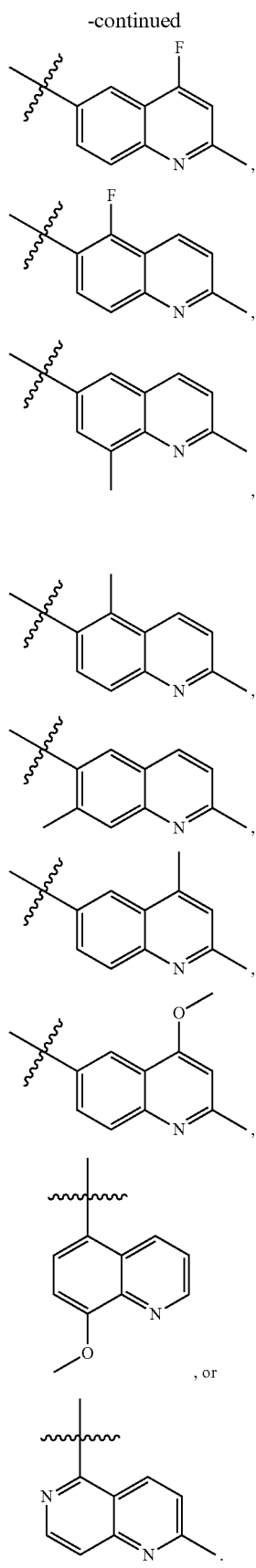

8. The compound of claim 1, wherein $R^2$ is

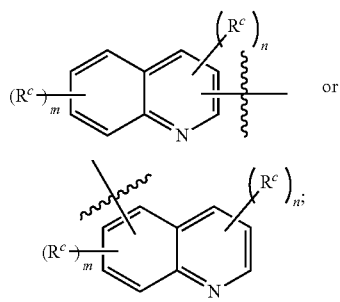

wherein each $R^c$ is independently selected from: F, $CH_3$, and $OCH_3$; and m and n are each independently 0 or 1.

9. The compound of claim 1, wherein (a) $R^{1a}$ is $C_{1-4}$alkyl or $R^{1a}$ and $R^{1b}$ come together to form —$CH_2CH_2CH_2$—, and (b) $R^2$ is

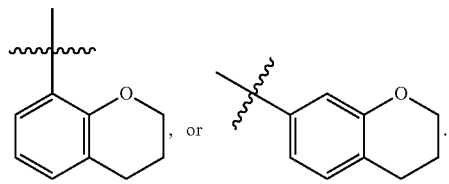 [SMILES: *c1cccc2c1OCCC2 ; *c1ccc2c(c1)OCCC2]

10. The compound as claimed in claim 1 or claim 2, wherein $R^3$ is

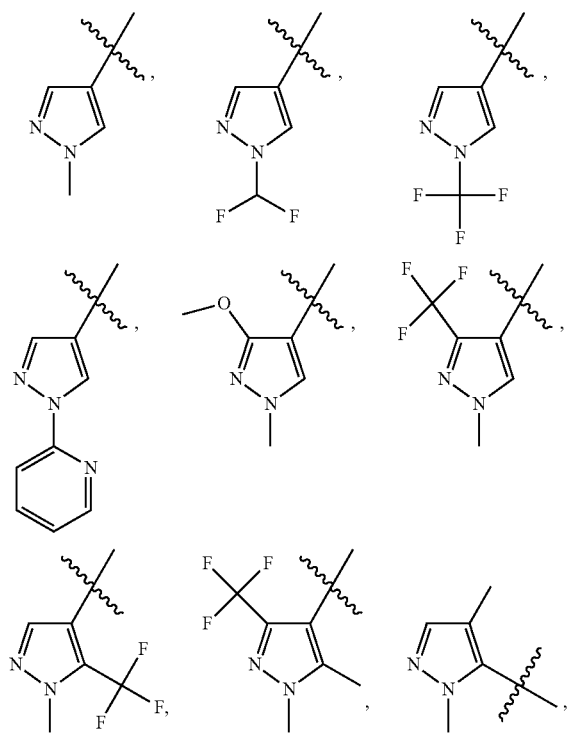

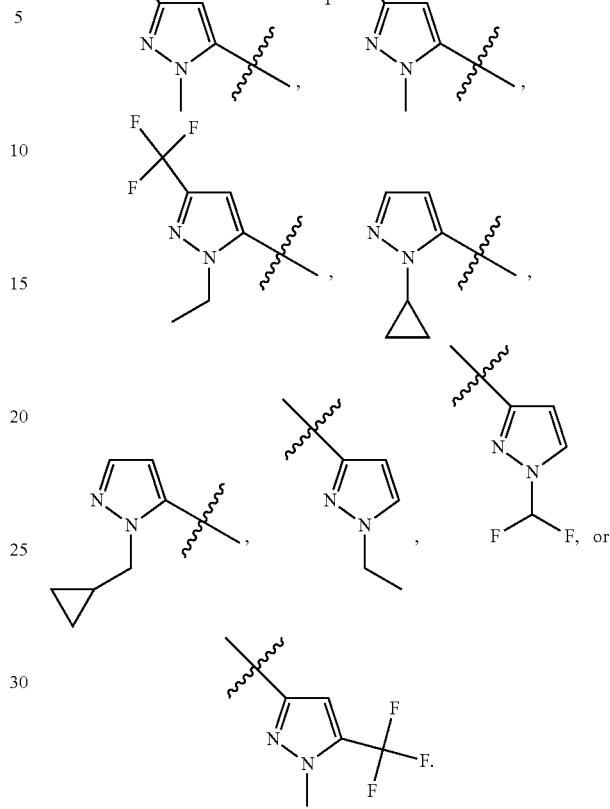

11. The compound of claim 2, wherein (a) m is 1 or 2; (b) n is 1 or 2; or (c) m and n are each 1.

12. The compound of claim 1, wherein the compound is selected from:
- (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-5-yl)methanone;
- (S)-(3-(1,4-Dimethyl-1H-pyrazol-5-yl)-2,7-dimethyl-2,4,5,7-tetrahydro-6H-pyrazolo[3,4-c]pyridin-6-yl)(3-methoxy-2-methylphenyl)methanone;
- (S)-(3-(1,5-Dimethyl-3-(trifluoromethyl)-1H-pyrazol-4-yl)-2,7-dimethyl-2,4,5,7-tetrahydro-6H-pyrazolo[3,4-c]pyridin-6-yl)(3-methoxy-2-methylphenyl)methanone;
- (S)-(2-Chloro-3-(2-oxa-6-azaspiro[3.3]heptan-6-yl)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;
- (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-1H-indol-3-yl)methanone;
- (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indazol-3-yl)methanone;
- (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylpyrazolo[1,5-a]pyridin-3-yl)methanone;
- (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylimidazo[1,2-a]pyridin-3-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methylquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoropyrazolo[1,5-a]pyridin-3-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-(2,2,2-trifluoroethyl)-1H-pyrrolo[2,3-b]pyridin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylquinolin-3-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-methoxyquinolin-5-yl)methanone;

(S)-(1,6-Dimethyl-1H-pyrazolo[3,4-b]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(3-(3-Methoxy-1-methyl-1H-pyrazol-4-yl)-2,7-dimethyl-2,4,5,7-tetrahydro-6H-pyrazolo[3,4-c]pyridin-6-yl)(quinolin-6-yl)methanone;

(S)-(4,6-Difluoropyrazolo[1,5-a]pyridin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(5,7-Difluoroquinolin-3-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-fluoropyrazolo[1,5-a]pyridin-3-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxyquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-1-methyl-1H-indazol-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-indazol-3-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-2H-indazol-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-3-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,6-dimethylquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-methoxy-2-methylquinolin-4-yl)methanone;

(S)-(4,6-Difluoro-1-methyl-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone;

(S)-(4,6-Difluoro-1H-indazol-3-yl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-(trifluoromethyl)phenyl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-fluoro-4-methylphenyl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-indazol-7-yl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrazolo[3,4-b]pyridin-4-yl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2,8-dimethylquinolin-6-yl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(6-fluoro-2-methylquinolin-4-yl)methanone;

(S)-(2-Chloro-3-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxy-2-methylphenyl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-(1H-pyrazol-1-yl)phenyl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-methoxyphenyl)methanone;

(S)-(3-Chloro-5-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylphenyl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxy-4-methylphenyl)methanone;

(S)-(2-Chloro-4-methoxyphenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3,4-dimethylphenyl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(isoquinolin-1-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-indol-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrrolo[2,3-b]pyridin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-1-methyl-1H-pyrrolo[2,3-b]pyridin-4-yl)methanone;

(S)-(2-Chloro-3-methoxyphenyl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrrolo[2,3-b]pyridin-4-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(3-methyl-5-(2H-1,2,3-triazol-2-yl)phenyl)methanone;

(S)-(2-Chloro-3-methoxyphenyl)(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(1-methyl-1H-pyrrolo[2,3-b]pyridin-4-yl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(3-methyl-5-(2H-1,2,3-triazol-2-yl)phenyl)methanone;

(S)-Chroman-8-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-Chroman-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-Benzo[d]thiazol-6-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-Benzo[d]thiazol-7-yl(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methylbenzo[d]thiazol-6-yl)methanone;

(S)-Benzo[d]thiazol-6-yl(2,7-dimethyl-3-(1-methyl-5-(trifluoromethyl)-1H-pyrazol-4-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-4-yl)-2,4,5,7-tetrahydro-6H-pyrazolo[3,4-c]pyridin-6-yl)(2-methoxy-3-methylpyridin-4-yl)methanone;

(S)-Chroman-7-yl(2,7-dimethyl-3-(1-methyl-3-(trifluoromethyl)-1H-pyrazol-4-yl)-2,4,5,7-tetrahydro-6H-pyrazolo[3,4-c]pyridin-6-yl)methanone;

(S)-(2,7-Dimethyl-3-(1-methyl-1H-pyrazol-4-yl)-2,4,5,7-tetrahydro-6H-pyrazolo[3,4-c]pyridin-6-yl)(quinolin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(quinolin-6-yl)methanone;

(S)-(2,7-Dimethyl-3-(1-(trifluoromethyl)-1H-pyrazol-4-yl)-2,4,5,7-tetrahydro-6H-pyrazolo[3,4-c]pyridin-6-yl)(quinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(quinolin-6-yl)methanone;

(S)-(3-(1-Ethyl-1H-pyrazol-3-yl)-2,7-dimethyl-2,4,5,7-tetrahydro-6H-pyrazolo[3,4-c]pyridin-6-yl)(quinolin-6-yl)methanone;

(S)-(3-(1-(Difluoromethyl)-1H-pyrazol-3-yl)-2,7-dimethyl-2,4,5,7-tetrahydro-6H-pyrazolo[3,4-c]pyridin-6-yl)(quinolin-6-yl)methanone;

(S)-(3-(1-Cyclopropyl-1H-pyrazol-5-yl)-2,7-dimethyl-2,4,5,7-tetrahydro-6H-pyrazolo[3,4-c]pyridin-6-yl)(quinolin-6-yl)methanone;

(S)-(3-(1-(Difluoromethyl)-1H-pyrazol-4-yl)-2,7-dimethyl-2,4,5,7-tetrahydro-6H-pyrazolo[3,4-c]pyridin-6-yl)(quinolin-6-yl)methanone;

(S)-(2,7-Dimethyl-3-(1-(pyridin-2-yl)-1H-pyrazol-4-yl)-2,4,5,7-tetrahydro-6H-pyrazolo[3,4-c]pyridin-6-yl)(quinolin-6-yl)methanone;

(S)-(3-(1-(Cyclopropylmethyl)-1H-pyrazol-5-yl)-2,7-dimethyl-2,4,5,7-tetrahydro-6H-pyrazolo[3,4-c]pyridin-6-yl)(quinolin-6-yl)methanone;

((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(2-fluoro-4-methylphenyl)methanone;

((5R,9S)-3-(1,3-Dimethyl-1H-pyrazol-5-yl)-2-methyl-4,5,6,7,8,9-hexahydro-2H-5,9-epiminocycloocta[c]pyrazol-10-yl)(3-methoxy-2-methylphenyl)methanone;

(3-Methoxy-2-methylphenyl)((5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazol-10-yl)methanone;

Chroman-7-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(m-tolyl)methanone;

(3-Methoxy-5-methylphenyl)((5R,9S)-2-methyl-3-(1-methyl-3-(trifluoromethyl)-1H-pyrazol-5-yl)-4,5,6,7,8,9-hexahydro-2H-5, 9-epiminocycloocta[c]pyrazol-10-yl)methanone;

((5R,9S)-3-(1-Ethyl-3-(trifluoromethyl)-1H-pyrazol-5-yl)-2-methyl-4,5,6,7,8,9-hexahydro-2H-5,9-epiminocycloocta[c]pyrazol-10-yl)(m-tolyl)methanone;

(3-Methoxy-2-methylphenyl)((5R,9S)-2-methyl-3-(1-methyl-5-(trifluoromethyl)-1H-pyrazol-3-yl)-4,5,6,7,8, 9-hexahydro-2H-5, 9-epiminocycloocta[c]pyrazol-10-yl)methanone;

((5R,9S)-2-Methyl-3-(1-methyl-3-(trifluoromethyl)-1H-pyrazol-5-yl)-4,5,6,7,8,9-hexahydro-2H-5,9-epiminocycloocta[c]pyrazol-10-yl)(quinolin-6-yl)methanone;

(5-Fluoro-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

(2-Methyl-1,6-naphthyridin-5-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

(5-Fluoroquinolin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

Benzo[d]isoxazol-3-yl((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

(1-Methyl-1H-pyrazolo[3,4-b]pyridin-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

(5-Fluoro-1-methyl-1H-indazol-3-yl)((5R,9S)-2-methyl-3-(1-methyl-3-(trifluoromethyl)-1H-pyrazol-5-yl)-4,5,6,7,8,9-hexahydro-2H-5,9-epiminocycloocta[c]pyrazol-10-yl)methanone;

((5R,9S)-2-Methyl-3-(1-methyl-5-(trifluoromethyl)-1H-pyrazol-3-yl)-4,5,6,7,8,9-hexahydro-2H-5,9-epiminocycloocta[c]pyrazol-10-yl)(quinolin-6-yl)methanone;

(6-Fluoro-2-methylquinolin-4-yl)((5R,9S)-2-methyl-3-(1-methyl-5-(trifluoromethyl)-1H-pyrazol-3-yl)-4,5,6,7,8,9-hexahydro-2H-5,9-epiminocycloocta[c]pyrazol-10-yl)methanone;

(3-Methoxy-2-methylphenyl)((5R,8S)-2-methyl-3-(1-methyl-3-(trifluoromethyl)-1H-pyrazol-5-yl)-2,4,5,6,7,8-hexahydro-5,8-epiminocyclohepta[c]pyrazol-9-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-fluoro-2-methylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-fluoro-2-methylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,5-dimethylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,7-dimethylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2,4-dimethylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-methylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methyl-2-(trifluoromethoxy)phenyl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-fluoro-3-(trifluoromethoxy)phenyl)methanone;

(S)-(2-Chloro-4-(trifluoromethoxy)phenyl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(1-methyl-1H-pyrazolo[3,4-b]pyridin-4-yl)methanone;

(S)-Benzo[d]thiazol-6-yl(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-methoxy-3-methylpyridin-4-yl)methanone; and (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(6-fluoro-2-methylquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methylbenzo[d]thiazol-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(5-methylbenzo[d]thiazol-6-yl)methanone; and (S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methylbenzo[d]thiazol-6-yl)methanone;

and pharmaceutically acceptable salts, isotopes, N-oxides, solvates, and stereoisomers thereof.

13. The compound of claim 1, wherein the compound is selected from:

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-fluoro-2-methylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methoxyquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(7-methoxy-2-methylquinolin-5-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-fluoro-8-methoxyquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(3-fluoro-8-methylquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(8-fluoroisoquinolin-4-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(6-fluoro-2-methoxyquinolin-4-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(5-fluoro-1-methyl-1H-pyrazolo[3,4-b]pyridin-4-yl)methanone;

(S)-(6-(Difluoromethyl)-1-methyl-1H-pyrazolo[3,4-b]pyridin-4-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrazolo[4,3-c]pyridin-4-yl)methanone;

(S)-(1,6-Dimethyl-1H-pyrazolo[4,3-c]pyridin-4-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(1-methyl-1H-pyrazolo[4,3-b]pyridin-5-yl)methanone;

(S)-(1,6-Dimethyl-1H-pyrazolo[4,3-b]pyridin-5-yl)(2,7-dimethyl-3-(1-methyl-3-(trifluoromethyl)-1H-pyrazol-5-yl)-2,4,5,7-tetrahydro-6H-pyrazolo[3,4-c]pyridin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(4-methoxy-2-(trifluoromethoxy)phenyl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(2-methyl-3-(trifluoromethoxy)phenyl)methanone;

(S)-(4,6-Difluoro-1-methyl-1H-indazol-3-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone;

(S)-(4,6-Difluoro-1H-indazol-3-yl)(2,7-dimethyl-3-(1-methyl-5-(trifluoromethyl)-1H-pyrazol-3-yl)-2,4,5,7-tetrahydro-6H-pyrazolo[3,4-c]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2-fluoro-4-methylphenyl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(2,8-dimethylquinolin-6-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-b]pyridin-7-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[4,5-c]pyridin-7-yl)methanone;

(S)-(2,7-Dimethyl-3-(1-methyl-3-(trifluoromethyl)-1H-pyrazol-5-yl)-2,4,5,7-tetrahydro-6H-pyrazolo[3,4-c]pyridin-6-yl)(thiazolo[5,4-c]pyridin-4-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-c]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-b]pyridin-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-b]pyridin-7-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[4,5-c]pyridin-7-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(thiazolo[5,4-c]pyridin-4-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(7-methylbenzo[d]thiazol-6-yl)methanone;

(S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(5-methylbenzo[d]thiazol-6-yl)methanone; and (S)-(2,7-Dimethyl-3-(1-methyl-5-(trifluoromethyl)-1H-pyrazol-3-yl)-2,4,5,7-tetrahydro-6H-pyrazolo[3,4-c]pyridin-6-yl)(4-methylbenzo[d]thiazol-6-yl)methanone;

and pharmaceutically acceptable salts, isotopes, N-oxides, solvates, and stereoisomers thereof.

14. The compound of claim 1, wherein the compound is selected from:

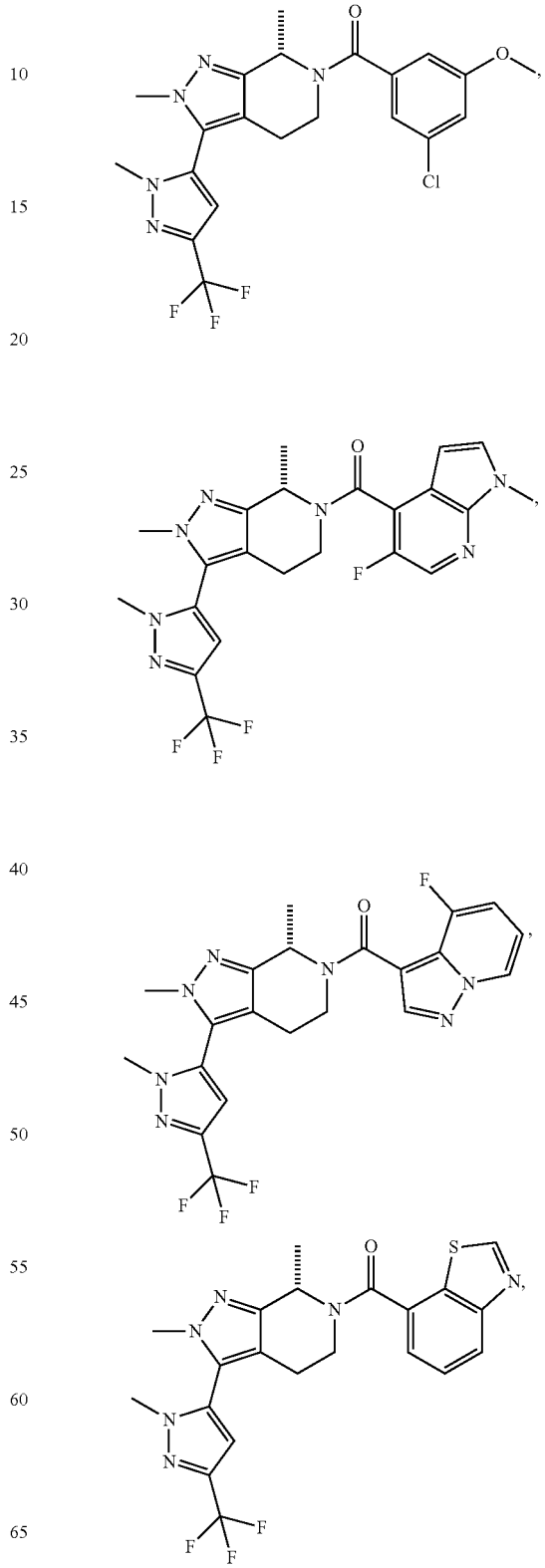

-continued
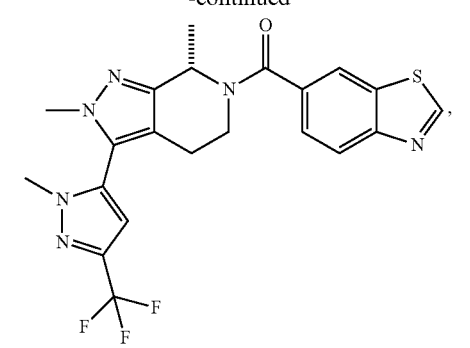
,
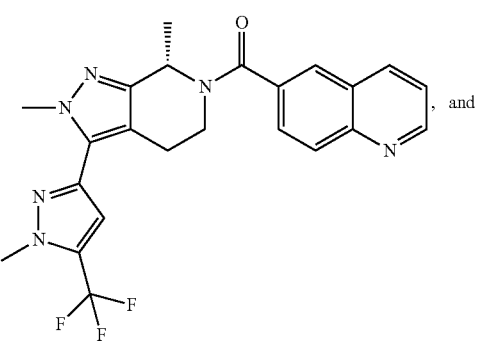
, and
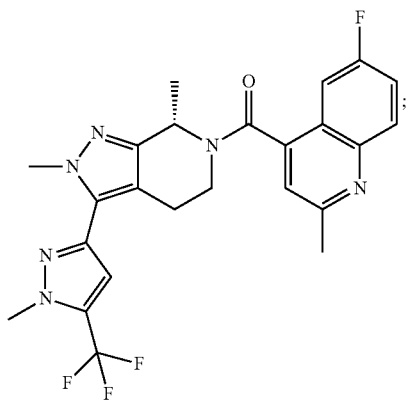
;
and pharmaceutically acceptable salts, isotopes, N-oxides, solvates, and stereoisomers thereof.
15. The compound of claim 1, having the structure of Formula (IA):
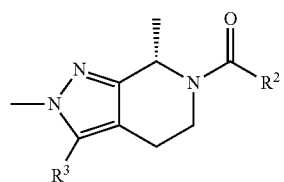
(IA)
wherein
R² is selected from:
(a)
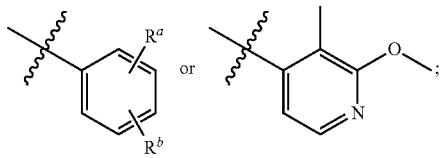
(b) a 5,6-fused or 6,5-fused heteroaryl selected from:
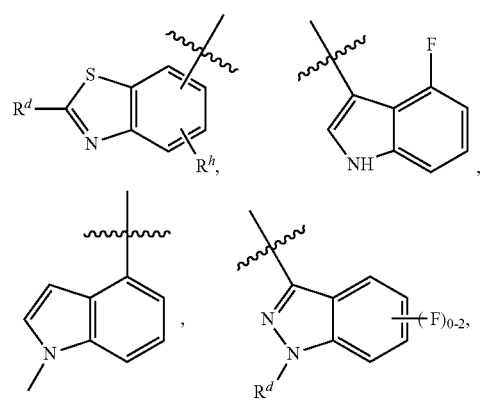
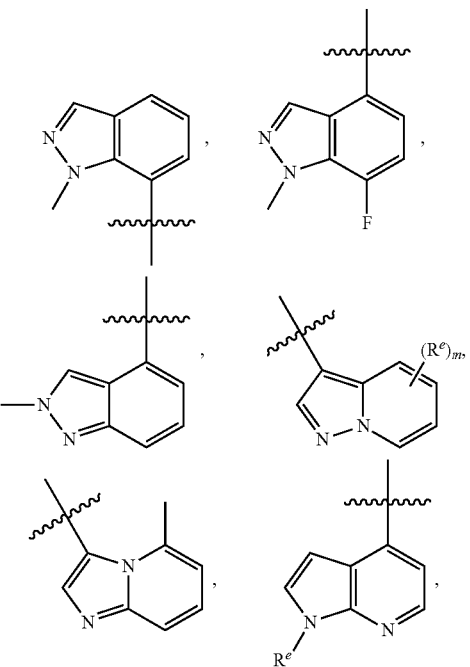
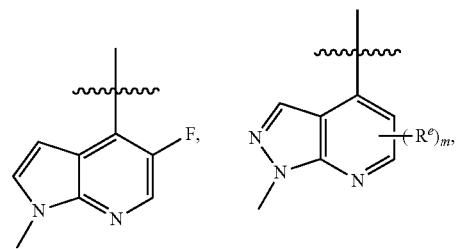

-continued

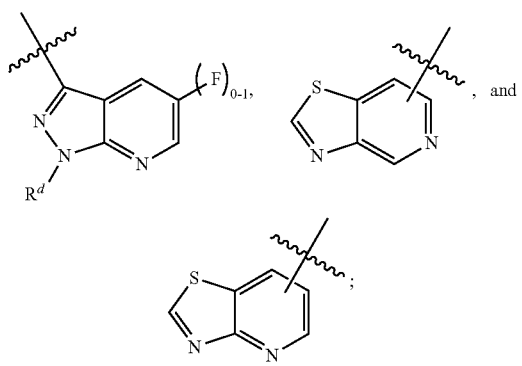

(c) a fused 6,6-heteroaryl selected from:

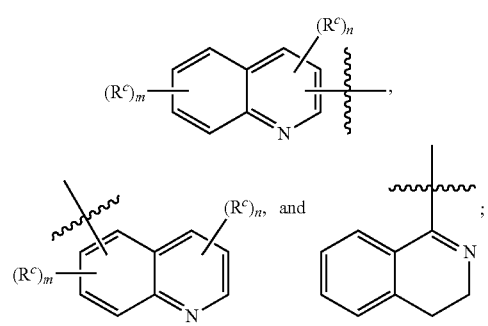

and
(d)

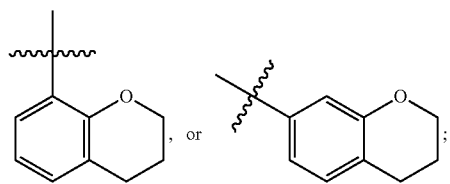 [SMILES: *c1cccc2c1OCCC2 ; *c1ccc2c(c1)OCCC2]

$R^3$ is a 5-membered heteroaryl ring selected from:

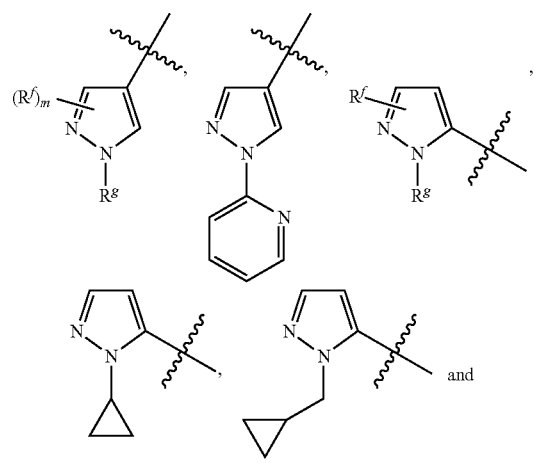

-continued

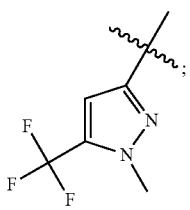

or wherein $R^3$ is

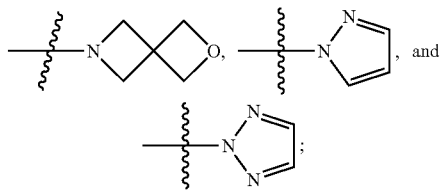

wherein
$R^a$ is selected from: H, Cl, F, $C_{1-4}$alkyl, and $C_{1-4}$haloalkyl;
$R^b$ is selected from: $C_{1-4}$alkyl, $C_{1-4}$haloalkyl, $OC_{1-4}$alkyl,

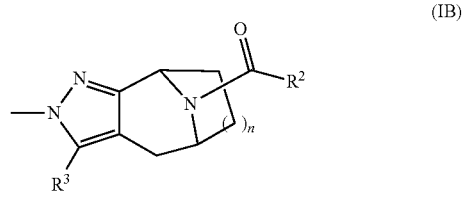

each $R^c$ is independently selected from: halo, $C_{1-4}$alkyl, and $OCH_3$;
$R^d$ is H or $CH_3$;
each $R^e$ is independently F, $C_{1-4}$alkyl, or $C_{1-4}$haloalkyl;
each $R^f$ is independently selected from: $C_{1-4}$alkyl, $C_{1-4}$haloalkyl, and $OCH_3$; and
$R^g$ is $C_{1-4}$alkyl or $C_{1-4}$haloalkyl;
$R^h$ is selected from: H, $C_{1-4}$alkyl, $C_{1-4}$haloalkyl, and cycloalkyl:
n is 0, 1, or 2; and
m is 0, 1, or 2;
or a pharmaceutically acceptable salt, isotope, N-oxide, solvate, or stereoisomer thereof.

16. The compound of claim 1, having the structure of Formula (IB):

(IB)

wherein
n is 1 or 2;
$R^2$ is selected from:
(a)

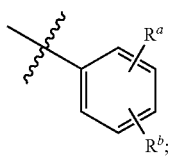

(b)

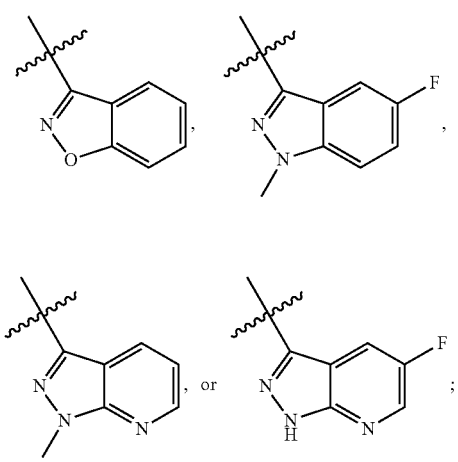

(c)

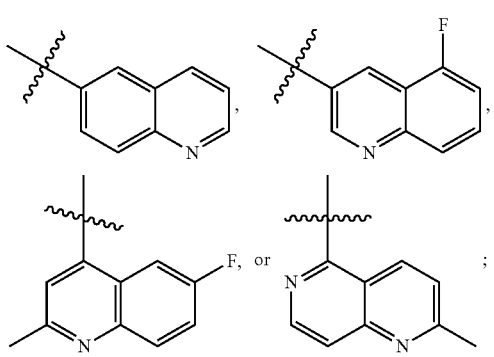

and
(d)

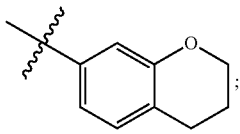 [SMILES: *c1ccc2c(c1)OCCC2]

and
$R^3$ is

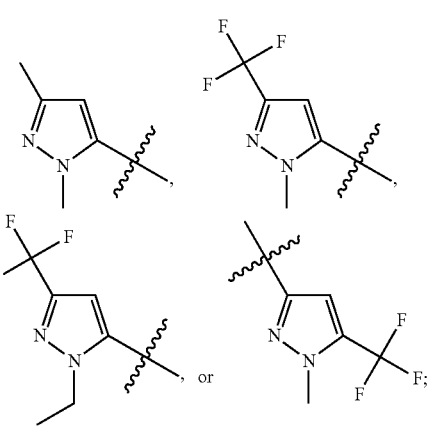

wherein
$R^a$ is H, halo, or $C_{1-4}$alkyl; and
$R^b$ is $C_{1-4}$alkyl or $OC_{1-4}$alkyl;
or a pharmaceutically acceptable salt, isotope, N-oxide, solvate, or stereoisomer thereof.

17. A pharmaceutical composition comprising:
(A) a therapeutically effective amount of at least one compound of claim 1, or a pharmaceutically acceptable salt, isotope, N-oxide, solvate, or stereoisomer thereof; and
(B) at least one pharmaceutically acceptable excipient.

18. A method of treating a subject suffering from or diagnosed with a disease, disorder, or condition mediated by MGL receptor activity, comprising administering to a subject in need of such treatment a therapeutically effective amount of at least one compound of claim 1, or a pharmaceutically acceptable salt, isotope, N-oxide, solvate, or stereoisomer thereof.

19. The method of claim 18, wherein the MGL receptor mediated disease, disorder, or condition is selected from: (a) pain, psychiatric conditions, neurological conditions, cancers, and eye conditions; (b) major depressive disorder, treatment resistant depression, anxious depression, autism spectrum disorders, Asperger syndrome, and bipolar disorder; and (c) inflammatory pain.

* * * * *